US009012446B2

(12) United States Patent  
Chen et al.

(10) Patent No.: US 9,012,446 B2
(45) Date of Patent: Apr. 21, 2015

(54) AMINO-OXAZINES AND AMINO-DIHYDROTHIAZINE COMPOUNDS AS BETA-SECRETASE MODULATORS AND METHODS OF USE

(71) Applicant: Amgen Inc., Thousand Oaks, CA (US)

(72) Inventors: Jian Chen, Camarillo, CA (US); Wenge Zhong, Thousand Oaks, CA (US); Patricia Lopez, West Hills, CA (US); Ryan White, Somerville, CA (US); Matthew Weiss, Boston, MA (US); Ted Judd, Granada Hills, CA (US); Timothy Powers, Malibu, CA (US); Yuan Cheng, Newbury Park, CA (US); Thomas Dineen, Somerville, MA (US); Jonathan D. Low, Tarzana, CA (US); Isaac E. Marx, Cambridge, MA (US); Ana Elena Minatti, Santa Monica, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/929,483

(22) Filed: Jun. 27, 2013

(65) Prior Publication Data

US 2014/0045828 A1 Feb. 13, 2014

Related U.S. Application Data

(62) Division of application No. 13/047,693, filed on Mar. 14, 2011, now Pat. No. 8,497,264.

(60) Provisional application No. 61/314,024, filed on Mar. 15, 2010.

(51) Int. Cl.
| | | |
|---|---|---|
| *C07D 498/10* | (2006.01) | |
| *C07D 498/20* | (2006.01) | |
| *C07D 513/20* | (2006.01) | |
| *C07D 513/10* | (2006.01) | |

(52) U.S. Cl.
CPC ............ *C07D 513/10* (2013.01); *C07D 498/10* (2013.01); *C07D 498/20* (2013.01); *C07D 513/20* (2013.01)

(58) Field of Classification Search
USPC .......................................... 544/71; 514/228.8
See application file for complete search history.

(56) References Cited

U.S. PATENT DOCUMENTS

| | | | |
|---|---|---|---|
| 2,683,718 A | 7/1954 | Clinton et al. | |
| 3,185,696 A | 5/1965 | Tien et al. | |
| 5,441,870 A | 8/1995 | Seubert et al. | |
| 5,712,130 A | 1/1998 | Hajko et al. | |
| 5,942,400 A | 8/1999 | Anderson et al. | |
| 6,835,565 B1 | 12/2004 | Gurney et al. | |
| 6,864,290 B2 | 3/2005 | Schostarez et al. | |
| 6,962,934 B2 | 11/2005 | Warpehoski et al. | |
| 6,982,264 B2 | 1/2006 | John et al. | |
| 6,992,103 B2 | 1/2006 | Faller et al. | |
| 7,034,182 B2 | 4/2006 | Fang et al. | |
| 7,067,542 B2 | 6/2006 | Schostarez et al. | |
| 7,074,799 B2 | 7/2006 | Bakthavatchalam et al. | |
| 7,109,217 B2 | 9/2006 | Coburn et al. | |
| 7,115,652 B2 | 10/2006 | Yang et al. | |
| 7,132,568 B2 | 11/2006 | Yang et al. | |
| 7,176,242 B2 | 2/2007 | John et al. | |
| 7,223,774 B2 | 5/2007 | Aquino et al. | |
| 7,244,725 B2 | 7/2007 | John et al. | |
| 7,244,755 B2 | 7/2007 | Fisher et al. | |

(Continued)

FOREIGN PATENT DOCUMENTS

| | | |
|---|---|---|
| EP | 01942105 A1 | 9/2008 |
| EP | 02305672 A1 | 6/2011 |

(Continued)

OTHER PUBLICATIONS

Joachim et al., *Alz. Dis. Assoc. Dis.*, 6:7-34 (1992).

(Continued)

*Primary Examiner* — Kahsay Habte
(74) *Attorney, Agent, or Firm* — G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I

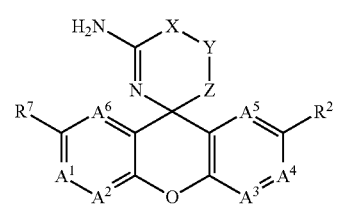

wherein $A^1, A^2, A^3, A^4, A^5, A^6, R^2, R^7, X, Y$ and $Z$ of Formula I are defined herein. The invention also includes use of these compounds in pharmaceutical compositions for treatment, prophylactic or therapeutic, of disorders and conditions related to the activity of beta-secretase protein. Such disorders include, for example, Alzheimer's Disease, cognitive deficits, cognitive impairment, schizophrenia and other central nervous system conditions related to and/or caused by the formation and/or deposition of plaque on the brain. The invention also comprises further embodiments of Formula I, intermediates and processes useful for the preparation of compounds of Formula I.

20 Claims, No Drawings

(56) References Cited

U.S. PATENT DOCUMENTS

| | | |
|---|---|---|
| 7,253,198 B2 | 8/2007 | Demont et al. |
| 7,291,620 B2 | 11/2007 | Coburn et al. |
| 7,312,360 B2 | 12/2007 | TenBrink et al. |
| 7,348,448 B2 | 3/2008 | Nantermet et al. |
| 7,371,853 B2 | 5/2008 | Coburn et al. |
| 7,592,348 B2 | 9/2009 | Zhu et al. |
| 2003/0109559 A1 | 6/2003 | Gailunas et al. |
| 2005/0038019 A1 | 2/2005 | Beck |
| 2005/0054690 A1 | 3/2005 | Aquino et al. |
| 2005/0282825 A1 | 12/2005 | Malamas et al. |
| 2006/0111370 A1 | 5/2006 | Zhu et al. |
| 2006/0211740 A1 | 9/2006 | Demont et al. |
| 2006/0241133 A1 | 10/2006 | Shearman et al. |
| 2006/0287297 A1 | 12/2006 | DeCorte et al. |
| 2007/0004786 A1 | 1/2007 | Malamas et al. |
| 2007/0027199 A1 | 2/2007 | Malamas et al. |
| 2007/0072925 A1 | 3/2007 | Malamas et al. |
| 2007/0203116 A1 | 8/2007 | Quagliato et al. |
| 2007/0287692 A1 | 12/2007 | Wu et al. |
| 2008/0200445 A1 | 8/2008 | Zhu et al. |
| 2009/0082560 A1 | 3/2009 | Kobayashi et al. |
| 2009/0209529 A1 | 8/2009 | Andreini et al. |
| 2009/0209755 A1 | 8/2009 | Suzuki et al. |
| 2009/0306047 A1 | 12/2009 | Zhu et al. |
| 2010/0075957 A1 | 3/2010 | Malamas et al. |
| 2010/0160290 A1 | 6/2010 | Kobayashi et al. |

FOREIGN PATENT DOCUMENTS

| | | |
|---|---|---|
| WO | 01/70671 A2 | 9/2001 |
| WO | 03/002518 A1 | 1/2003 |
| WO | 03/030886 A2 | 4/2003 |
| WO | 2004/000821 A1 | 12/2003 |
| WO | 2004/099376 A2 | 11/2004 |
| WO | 2005058311 A1 | 6/2005 |
| WO | 2005097767 A1 | 10/2005 |
| WO | 2006041404 A1 | 4/2006 |
| WO | 2006076284 A2 | 7/2006 |
| WO | 2006138230 A2 | 12/2006 |
| WO | 2006138265 A2 | 12/2006 |
| WO | 2007011810 A1 | 1/2007 |
| WO | 2007011833 A1 | 1/2007 |
| WO | 2007038271 A1 | 4/2007 |
| WO | 2007114771 A1 | 10/2007 |
| WO | 2007120096 A1 | 10/2007 |
| WO | 2007145571 A1 | 12/2007 |
| WO | 2007149033 A1 | 12/2007 |
| WO | 2008054698 A1 | 5/2008 |
| WO | 2008076045 A1 | 6/2008 |
| WO | 2008076046 A1 | 6/2008 |
| WO | 2008092785 A1 | 8/2008 |
| WO | 2008103351 A2 | 8/2008 |
| WO | 2008118379 A2 | 10/2008 |
| WO | 2008150217 A1 | 12/2008 |
| WO | 2009131974 A1 | 10/2009 |
| WO | 2009131975 A1 | 10/2009 |
| WO | 2009134617 A1 | 11/2009 |
| WO | 2010010014 A1 | 1/2010 |
| WO | 2010030954 A1 | 3/2010 |

OTHER PUBLICATIONS

Selkoe, Neuron, 6:487 (1991).
Seubert et al., Nature, 359:325-327 (1992).
Citron, Trends in Pharmacological Sciences, 25(2):92-97 (2004).
Nature Medicine (Jun. 22, 2008).
Nature, 402:537-554 (1999) (p510).
Sabbagh, M. et al., Alz. Dis. Rev. 3:1-19 (1997).
Cole, S.L., Vasser, R., Molecular Degeneration 2:22, 2007.
Luo et al., Nature Neuroscience, 4:231-232 (2001).
Bioorganic & Medicinal Chemistry Letters 20 (2010) 2068-2073.
J. Med. Chem. 2009.
Alzheimer's Research & Therapy 2009.
Expert Opin. Emerging Drugs (2008) 13(2):255-271.
J. Med. Chem. 2008, 51, 6259-6262.
Chem. Soc. Rev., 2009, 38, 2698-2715.
Sabbagh_ClinicalDev_2009.
J. Neurosci., Oct. 14, 2009 • 29(41):12787-12794.
Zhou_et_al_ARKIVOC_2010_vi_84-88.
Nowak_Bioorganic_Medicinal_Chemistry_Letters_2009.
Malamas_Bioorganic_Medicinal_Chemistry_Letters_2009.
Zhou_Bioorganic_Medicinal_Chemistry_Letters_2010.
Malamas_JMedChem_2009.

AMINO-OXAZINES AND AMINO-DIHYDROTHIAZINE COMPOUNDS AS BETA-SECRETASE MODULATORS AND METHODS OF USE

RELATED APPLICATIONS

This application is a divisional patent application of and claims a priority benefit to U.S. patent application Ser. No. 13/047,693, filed Mar. 14, 2011 and granted as U.S. Pat. No. 8,497,264, which in turn claims the benefit of U.S. Provisional Application No. 61/314,024, filed March 15, 2010, both specifications of which are hereby incorporated herein by reference in their entireties.

FIELD OF THE INVENTION

The invention relates generally to pharmaceutically active compounds, pharmaceutical compositions and methods of use thereof, to treat Beta-Secretase mediated diseases and conditions, including, without limitation, Alzheimer's disease, plaque formation on the brain and related disorders.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shankar, G. M., *Nature Medicine* (Jun. 22, 2008) online doi 10:1038 nm 1782.

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942, 400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 09/091,016, WO 08/108,378, WO 09/134,617, WO 05/097767, WO 08/092,785, WO 06/138265, WO 08/103,351, WO 06/138230, WO 08/200,445, WO 06/111370, WO 07/287,692, WO 05/058311, EP 01942105, WO 08/133,273, WO 08/133,274, WO 07/049,532, US20070027199, WO 07/038,271, US20070072925, US20070203116, WO 08/118,379, WO 06/076284, US20070004786, WO 06/083760, WO 07/011,810, WO 07/011,833, WO11/009,943 and WO 08/054,698, describe inhibitors of BACE, useful for treating AD and other beta-secretase mediated disorders.

BRIEF DESCRIPTION OF THE INVENTION

The present invention provides a new class of compounds useful for the modulation of beta secretase activity. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

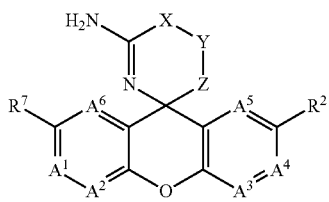

wherein $A^1, A^2, A^3, A^4, A^5, A^6, R^2, R^7, X, Y$ and $Z$ of Formula I are described below. The invention also provides procedures for making compounds of sub-Formulas thereof, as well as intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts thereof, are generally defined by the compound of Formula I:

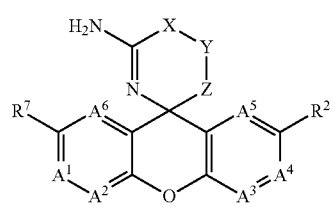

or a stereoisomer, tautomer, hydrate, solvate or pharmaceutically acceptable salt thereof, wherein $A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1, A^2, A^3, A^4, A^5$ and $A^6$ is N;

each of $R^1, R^4, R^5$ and $R^8$, independently, is H, F, Cl, Br, $CF_3$, $OCF_3$, $C_{1-6}$-alkyl, CN, OH, —$OC_{1-6}$-alkyl, —$S(O)_o C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_o C_{1-6}$-alkyl, —$NHC_{1-6}$-alkyl and —$C(O)C_{1-6}$-alkyl are optionally substituted with 1-3 substituents of F, oxo or OH;

each of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl)$_2$, —NH-phenyl, —NH-benzyl and ring are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_o C_{1-6}$-alkyl, $NHC_{1-6}$-alkyl or $C(O)C_{1-6}$-alkyl;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CR^{10}R^{10}$—, —O— or —S—, wherein each $R^{10}$, independently, is H, halo, haloalkyl, $C_{1-6}$alkyl, $C_{2-6}$alkenyl, $C_{2-6}$alkynyl, $C_{3-6}$cycloalkyl or a ring selected from the group consisting of morpholinyl, piperidinyl, piperizinyl, tetrahydrofuranyl, furanyl, thienyl, phenyl, pyrdinyl, pyrimidinyl, pyridazinyl, pyrazinyl, pyranyl, dihydropyranyl, tetrahydropyranyl, pyrrolyl, dihydropyrrolyl, tetrahydropyrrolyl and oxetanyl;

Y is —O—, —S— or —$CH_2$—, provided that (1) when X is —O— or —S—, then Y is —$CH_2$—, or (2) when X is —$CR^{10}R^{10}$—, then Y is —O— or —S—; and Z is $CH_2$, CHF, $CF_2$, $CH(CH_3)$, $C(CH_3)_2$ or $CH(CF_3)$.

In another embodiment of the present invention, the compounds, and solvates, tautomers, stereoisomers and pharmaceutically acceptable salts thereof, are defined by Formula II

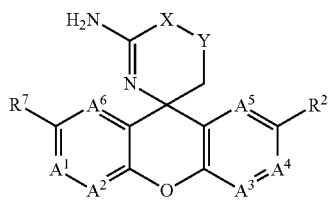

II wherein
$A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N, provided that no more than one of $A^1$, $A^2$, $A^3$, $A^4$, $A^5$ and $A^6$ is N;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$ $C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl or cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl and cyclohexyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CH_2$—, O or S; and
Y is —O—, S or —$CH_2$—, provided that (1) when X is either —O— or —S—, then Y is —$CH_2$— or (2) when X is —$CH_2$—, then Y is —O— or —S—.

In another embodiment of the present invention, the compounds, and solvates, tautomers, stereoisomers and pharmaceutically acceptable salts thereof, are defined by Formula I-A

I-A

[Structure of Formula I-A showing a spiro compound with H₂N, X, Y, Z, R¹, R², R⁵, R⁷, R⁸, A¹, A³, A⁴ substituents]

wherein each of $A^1$, $A^3$, $A^4$, $R^1$, $R^2$, $R^5$, $R^7$, $R^8$, X, Y and Z is as defined above with respect to Formula I.

In another embodiment of the present invention, the compounds, and solvates, tautomers, stereoisomers and pharmaceutically acceptable salts thereof, are defined by Formula I-A wherein $A^1$ is $CR^6$;

$A^3$ is $CR^4$ or N;

$A^4$ is $CR^3$ or N, provided that no more than one of $A^3$ and $A^4$ is N;

each of $R^1$, $R^3$, $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-azabicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl —NH-benzyl, phenyl, pyridyl, pyrimidyl or thienyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidinyl and thienyl are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CH_2$—, —O— or —S—;

Y is —O—, —S— or —$CH_2$—, provided that (1) when X is —O— or —S—, then Y is —$CH_2$—, or (2) when X is —$CH_2$, then Y is —O— or —S—; and Z is $CH_2$, $CF_2$ or $CH(CH_3)$.

In another embodiment of the present invention, the compounds, and solvates, tautomers, stereoisomers and pharmaceutically acceptable salts thereof, are defined by Formula I-A, wherein $A^1$ is $CR^6$;

$A^3$ is CH, CF or N;

$A^4$ is CH, CF or N, provided that no more than one of $A^3$ and $A^4$ is N; and each of $R^1$, $R^3$, $R^4$, $R^5$, $R^6$ and $R^8$, independently, is H, F, $CF_3$, methyl or CN.

In another embodiment of the present invention, the compounds, and solvates, tautomers, stereoisomers and pharmaceutically acceptable salts thereof, are defined by Formula II-A

II-A

[Structure of Formula II-A showing spiro compound with H₂N, X, R², R⁷, A¹, A², A³, A⁴, A⁵, A⁶ substituents]

wherein $A^1$ is CH or CF;

$A^2$ is CH or CF;

$A^3$ is CH, CF or N;

$A^4$ is CH, CF or N;

$A^5$ is CH;

$A^6$ is CH or CF, provided that no more than one of $A^3$ and $A^4$ is N;

each of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-azabicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and X is —O— or —S—.

In another embodiment of the present invention, the compounds, and solvates, tautomers, stereoisomers and pharmaceutically acceptable salts thereof, are defined by Formula II-A, wherein $A^1$ is CH or CF;
$A^2$ is CH;
$A^3$ is CH, CF or N;
$A^4$ is CH, CF or N, provided that no more than one of $A^3$ and $A^4$ is N;
$A^5$ is CH;
$A^6$ is CH;
$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;
$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$; and
each $R^9$, independently, is F, $CF_3$, CN, $CH_3$, —$OCH_3$, —$SCH_3$, —$NHCH_3$, oxetanyl or $C_{2-3}$alkynyl.

In another embodiment of the present invention, the compounds, and solvates, tautomers, stereoisomers and pharmaceutically acceptable salts thereof, are defined by Formula II-A, wherein each of $A^1$, $A^2$, $A^5$ and $A^6$, independently, is CH;
$A^3$ is CH, CF or N;
$A^4$ is CH, CF or N, provided that no more than one of $A^3$ and $A^4$ is N;
$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methylpropoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$;
$R^7$ is a ring selected from the group consisting of phenyl, pyridyl, pyrimidyl, pyridazinyl, pyrazinyl, triazinyl and thienyl, said ring optionally substituted, independently, with 1-3 substituents of $R^9$; and
X is —O— or —S—.

In another embodiment of the present invention, the compounds, and solvates, tautomers, stereoisomers and pharmaceutically acceptable salts thereof, are defined by Formula II-B

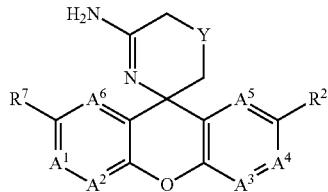

wherein $A^1$ is CH or CF;
$A^2$ is CH or CF;
$A^3$ is CH, CF or N;
$A^4$ is CH, CF or N;
$A^5$ is CH;
$A^6$ is CH or CF, provided that no more than one of $A^3$ and $A^4$ is N;
each of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;
each $R^9$, independently, is halo, haloalkyl, CN, OH, $NO_2$, $NH_2$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl; and Y is —O— or —S—.

In another embodiment of the present invention, the compounds, and solvates, tautomers, stereoisomers and pharmaceutically acceptable salts thereof, are defined by Formula II-B, wherein $A^1$ is CH or CF;
$A^2$ is CH;
$A^3$ is CH, CF or N;
$A^4$ is CH, CF or N, provided that no more than one of $A^3$ and $A^4$ is N;
$A^5$ is CH;
$A^6$ is CH;
$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$; and each $R^9$, independently, is F, $CF_3$, CN, $CH_3$, —$OCH_3$, —$SCH_3$, —$NHCH_3$, oxetanyl or $C_{2-3}$alkynyl.

In another embodiment of the present invention, the compounds, and solvates, tautomers, stereoisomers and pharmaceutically acceptable salts thereof, are defined by Formula II-B, wherein each of $A^1$, $A^2$, $A^5$ and $A^6$, independently, is CH;

$A^3$ is CH, CF or N;

$A^4$ is CH, CF or N, provided that no more than one of $A^3$ and $A^4$ is N;

$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methylpropoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyridazinyl, pyrazinyl, triazinyl and thienyl, said ring optionally substituted, independently, with 1-3 substituents of $R^9$; and Y is —O— or —S—.

In another embodiment of the invention, the compounds, including stereoisomers, tautomers, solvates, pharmaceutically acceptable salts, are generally defined by Formula I-A-1, wherein

I-A-1 each of $R^1$, $R^5$ and $R^8$, independently, is H;

$A^1$ is CH, CF or N;

$A^3$ is CH, CF or N;

$A^4$ is CH, CF or N, provided that no more than one of $A^1$, $A^3$ and $A^4$ is N;

$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl or oxetanyl;

X is —$CH_2$—, —O— or —S—; and

Y is —O—, —S— or —$CH_2$—, provided that (1) when X is —O— or —S—, then Y is —$CH_2$—, or (2) when X is —$CH_2$, then Y is —O— or —S—.

In another embodiment of the invention, the compounds, including stereoisomers, tautomers, solvates, pharmaceutically acceptable salts, are generally defined by Formula I-A-1, wherein each of $R^1$, $R^5$ and $R^8$, independently, is H;

$A^1$ is CH;

$A^3$ is CH, CF or N;

$A^4$ is CH, CF or N, provided that no more than one of $A^3$ and $A^4$ is N;

$R^2$ is 2-fluoro-4-pyridyl, 2-methyl-4-pyridyl, 5-fluoro-3-pyridyl, 4-pyridyl, 2-fluoro-2-methylpropoxyl, 3-fluoro-pyrrolidin-1-yl, 4,4-difluoro-1-piperidinyl, 3-methyl-3-oxetanyl-ethyn-1-yl, 3,3-dimethyl-butyn-1-yl, 4-methylphenyl, 4-fluorophenyl, 5,6-dihydro-2H-pyran-3-yl, 3,6-dihydro-2H-pyran-4-yl, 3,4-difluorophenyl, 2,2-dimethylpropoxyl, 2,2-dimethyl-2-cyano-propoxyl, 3,3-difluoro-1-pyrrolidinyl or 4-morpholinyl;

$R^7$ is 2-fluoro-3-pyridyl, 3-pyridyl, 5-fluoro-3-pyridyl, 2,5-difluorophenyl or 3-fluorophenyl;

X is —$CH_2$—, —O— or —S—; and

Y is —O—, —S— or —$CH_2$—, provided that (1) when X is —O— or —S—, then Y is —$CH_2$—, or (2) when X is —$CH_2$, then Y is —O— or —S—.

In another embodiment of the invention, the compounds, including stereoisomers, and pharmaceutically acceptable salts, are generally defined by Formula I-A-1, wherein each of $R^1$, $R^5$ and $R^8$, independently, is H;

$A^1$ is CH;

$A^3$ is CH, CF or N;

$A^4$ is CH, CF or N, provided that no more than one of $A^3$ and $A^4$ is N;

$R^2$ is a ring selected from the group consisting of pyridine, pyrrolidine, piperidine, phenyl, dihydropyran, and morpholine or $R^2$ is —O—$C_{1-6}$alkyl, $C_{1-6}$alkynyl, wherein the ring, —O—$C_{1-6}$allyl and $C_{1-6}$alkynyl are optionally substituted independently with 1-5 substituents of $R^9$;

$R^7$ is a ring selected from the group consisting of pyridine and phenyl, wherein the ring is optionally substituted independently with 1-3 substituents of $R^9$;

each $R^9$ is, independently, F, Cl, Br, $C_{1-6}$alkyl, $C_{1-6}$alkenyl, $C_{1-6}$alkynyl, —$OC_{1-6}$alkyl, CN, $CF_3$, —$OCF_3$ or spiro-oxetanyl;

X is —$CH_2$—, —O— or —S—; and

Y is —O—, —S— or —$CH_2$—, provided that (1) when X is —O— or —S—, then Y is —$CH_2$—, or (2) when X is —$CH_2$—, then Y is —O— or —S—.

In another embodiment of the invention, the compounds, including stereoisomers, tautomers, solvates, pharmaceutically acceptable salts, are generally defined by Formula I-A-2

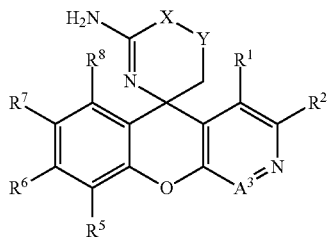

I-A-2 wherein each of $R^1$, $R^5$, $R^6$ and $R^8$, independently, is H;

$A^3$ is CH or CF;

$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CH_2$—, —O— or —S—; and

Y is —O—, —S— or —$CH_2$—, provided that (1) when X is —O— or —S—, then Y is —$CH_2$—, or (2) when X is —$CH_2$—, then Y is —O— or —S—.

In another embodiment of the invention, the compounds, including stereoisomers, tautomers, solvates, pharmaceutically acceptable salts, are generally defined by Formula I-A-3

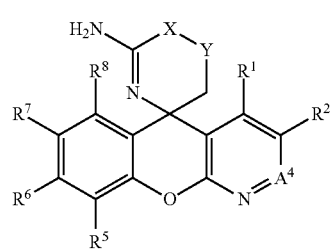

I-A-3 wherein each of $R^1$, $R^5$, $R^6$ and $R^8$, independently, is H;

$A^4$ is CH or CF;

$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CH_2$—, —O— or —S—; and

Y is —O—, —S— or —$CH_2$—, provided that (1) when X is —O— or —S—, then Y is —$CH_2$—, or (2) when X is —$CH_2$—, then Y is —O— or —S—.

In another embodiment of the invention, the compounds, including stereoisomers, tautomers, solvates, pharmaceutically acceptable salts, are generally defined by Formula I-A-4, wherein

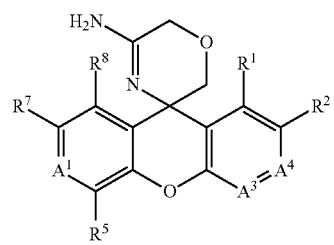

I-A-4 wherein each of $R^1$, $R^5$ and $R^8$, independently, is H;

$A^1$ is CH or CF;

$A^3$ is CH, CF or N;

$A^4$ is CH, CF or N, provided no more than one of $A^3$ and $A^4$ is N;

$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$; and each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl.

In another embodiment of the invention, the compounds, including stereoisomers, tautomers, solvates, pharmaceutically acceptable salts, are generally defined by Formula I-A-5, wherein

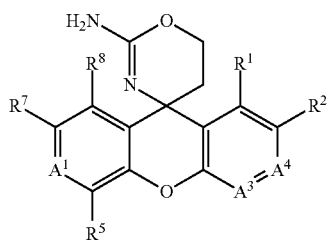

I-A-5 wherein each of $R^1$, $R^5$ and $R^8$, independently, is H;

$A^1$ is CH or CF;

$A^3$ is CH, CF or N;

$A^4$ is CH, CF or N, provided no more than one of $A^3$ and $A^4$ is N;

$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$; and each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl.

In another embodiment of the invention, the compounds, including stereoisomers, tautomers, solvates, pharmaceutically acceptable salts, are generally defined by Formula I-A-6, wherein

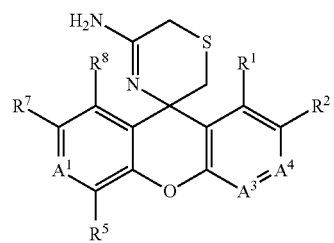

I-A-6 wherein each of $R^1$, $R^5$ and $R^8$, independently, is H;

$A^1$ is CH or CF;

$A^3$ is CH, CF or N;

$A^4$ is CH, CF or N, provided no more than one of $A^3$ and $A^4$ is N;

$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;

$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$; and each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl.

In another embodiment of the invention, the compounds, including stereoisomers, tautomers, solvates, pharmaceutically acceptable salts, are generally defined by Formula I-A-7, wherein

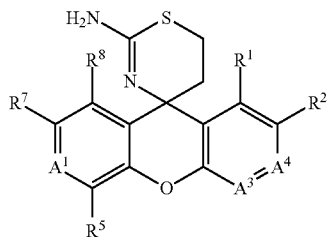

I-A-7 wherein each of $R^1$, $R^5$ and $R^8$, independently, is H;
$A^1$ is CH or CF;
$A^3$ is CH, CF or N;
$A^4$ is CH, CF or N, provided no more than one of $A^3$ and $A^4$ is N;
$R^2$ is $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$OC_{1-6}$alkyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl, are optionally substituted, independently, with 1-3 substituents of $R^9$;
$R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$; and
each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperidinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl.

In another embodiment of the invention, the compounds, including stereoisomers, tautomers, solvates, pharmaceutically acceptable salts thereof, are generally defined by the compound of Formula I-B:

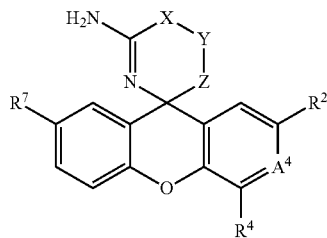

I-B wherein
$A^4$ is CH, CF or N;
$R^4$ is H or F;
one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —N($C_{1-3}$alkyl)$_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-azabicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —N($C_{1-3}$alkyl)$_2$, —NH-phenyl, —NH-benzyl and ring are optionally substituted, independently, with 1-3 substituents of $R^9$;
the other of $R^2$ and $R^7$, independently, is $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —N($C_{1-3}$alkyl)$_2$, —NH-phenyl or —NH-benzyl, phenyl, pyridyl, pyrimidyl or thienyl, wherein the $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —N($C_{1-3}$alkyl)$_2$, —NH-phenyl, —NH-benzyl, phenyl, pyridyl, pyrimidinyl and thienyl are optionally substituted, independently, with 1-3 substituents of $R^9$;
each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;
X is —$CH_2$—, —O— or —S—;
Y is —O—, —S— or —$CH_2$—, provided that (1) when X is —O— or —S—, then Y is —$CH_2$—, or (2) when X is —$CH_2$—, then Y is —O— or —S—; and
Z is $CH_2$, $CF_2$ or CH($CH_3$).

In another embodiment of the invention, the compounds, including stereoisomers, tautomers, solvates, pharmaceutically acceptable salts thereof, are generally defined by the compound of Formula I-B, wherein $A^4$ is CH, CF or N;

$R^4$ is H or F;

$R^2$ is 2-fluoro-4-pyridyl, 2-methyl-4-pyridyl, 5-fluoro-3-pyridyl, 4-pyridyl, 2-fluoro-2-methylpropoxyl, 3-fluoro-pyrrolidin-1-yl, 4,4-difluoro-1-piperidinyl, 3-methyl-3-oxetanyl-ethyn-1-yl, 3,3-dimethyl-butyn-1-yl, 4-methylphenyl, 4-fluorophenyl, 5,6-dihydro-2H-pyran-3-yl, 3,6-dihydro-2H-pyran-4-yl, 3,4-difluorophenyl, 2,2-dimethylpropoxyl, 2,2-dimethyl-2-cyano-propoxyl, 3,3-difluoro-1-pyrrolidinyl or 4-morpholinyl;

$R^7$ is 2-fluoro-3-pyridyl, 3-pyridyl, 5-fluoro-3-pyridyl, 2,5-difluorophenyl or 3-fluorophenyl;

X is —CH$_2$—, —O— or —S—;

Y is —O—, —S— or —CH$_2$—, provided that (1) when X is —O— or —S—, then Y is —CH$_2$—, or (2) when X is —CH$_2$, then Y is —O— or —S—; and Z is —CH$_2$ or CH(CH$_3$).

In another embodiment of the invention, the compounds, including stereoisomers, tautomers, solvates, pharmaceutically acceptable salts thereof, are generally defined by the compound of Formula I-B, wherein $A^4$ is CH, CF or N;

$R^4$ is H or F;

$R^2$ is a ring selected from the group consisting of pyridine, pyrrolidine, piperidine, phenyl, dihydropyran and morpholine or $R^2$ is —O—C$_{1-6}$allyl, C$_{1-6}$alkynyl, wherein the ring, —O—C$_{1-6}$alkyl and C$_{1-6}$alkynyl are optionally substituted independently with 1-5 substituents of $R^9$;

$R^7$ is a ring selected from the group consisting of pyridine and phenyl, wherein the ring is optionally substituted independently with 1-3 substituents of $R^9$;

each $R^9$ is, independently, F, Cl, Br, C$_{1-6}$alkyl, C$_{1-6}$alkenyl, C$_{1-6}$alkynyl, —OC$_{1-6}$alkyl, CN, CF3, —OCF$_3$ or spiro-oxetanyl;

X is —CH$_2$—, —O— or —S—;

Y is —O—, —S— or —CH$_2$—, provided that (1) when X is —O— or —S—, then Y is —CH$_2$—, or (2) when X is —CH$_2$, then Y is —O— or —S—; and Z is —CH$_2$ or CH(CH$_3$).

In another embodiment of the invention, the compounds of the invention include compounds wherein X is O or S when Y and Z are each —CH$_2$—, in conjunction with any of the above or below embodiments.

In another embodiment of the invention, the compounds of the invention include compounds wherein Y is O or S when X and Z are each —CH$_2$—, in conjunction with any of the above or below embodiments.

In another embodiment of the invention, the compounds of the invention include compounds wherein X is O, and Y and Z are each CH$_2$, in conjunction with any of the above or below embodiments.

In another embodiment of the invention, the compounds of the invention include compounds wherein X is S, and Y and Z are each CH$_2$, in conjunction with any of the above or below embodiments.

In another embodiment of the invention, the compounds of the invention include compounds wherein X and Z are each —CH$_2$— and Y is O, in conjunction with any of the above or below embodiments.

In another embodiment of the invention, the compounds of the invention include compounds wherein X and Z are each —CH$_2$— and Y is S, in conjunction with any of the above or below embodiments.

In another embodiment of the invention, the compounds of the invention include compounds wherein Z is CH$_2$, CHF, CF$_2$, CH(CH$_3$), C(CH$_3$)$_2$ or CH(CF$_3$), in conjunction with any of the above or below embodiments.

In another embodiment of the invention, the compounds of the invention include compounds wherein Z is CH$_2$, CF$_2$ or C(HCH$_3$), in conjunction with any of the above or below embodiments.

In another embodiment of the invention, the compounds of the invention include compounds wherein Z is CH$_2$ or C(CH$_3$), in conjunction with any of the above or below embodiments.

In another embodiment of the invention, the compounds of the invention include compounds wherein Z is CH$_2$, in conjunction with any of the above or below embodiments.

The present invention contemplates that the various different embodiments below of each individual variable $A^1$, $A^2$, $A^3$, $A^4$, $A^5$, $A^6$, $R^2$, $R^7$, X, Y and Z, as described below, may be applied "in conjunction with any of the other {above and below} embodiments" to create various embodiments of general Formulas I and II, and each sub-formula thereof, described hereinabove, which are not literally described herein.

In another embodiment, the invention includes compounds wherein $A^1$ is CH, CF or N, in conjunction with any of the above or below embodiments.

In another embodiment, the invention includes compounds wherein $A^1$ is CH, in conjunction with any of the above or below embodiments.

In another embodiment, the invention includes compounds wherein $A^1$ is CF, in conjunction with any of the above or below embodiments.

In another embodiment, the invention includes compounds wherein $A^1$ is N, in conjunction with any of the above or below embodiments.

In another embodiment, the invention includes compounds wherein $A^2$ is CH, CF or N, in conjunction with any of the above or below embodiments.

In another embodiment, the invention includes compounds wherein $A^2$ is CH, in conjunction with any of the above or below embodiments.

In another embodiment, the invention includes compounds wherein $A^2$ is CF, in conjunction with any of the above or below embodiments.

In another embodiment, the invention includes compounds wherein $A^2$ is N, in conjunction with any of the above or below embodiments.

In another embodiment, the invention includes compounds wherein $A^3$ is CH, CF or N, in conjunction with any of the above or below embodiments.

In another embodiment, the invention includes compounds wherein $A^3$ is CH, in conjunction with any of the above or below embodiments.

In another embodiment, the invention includes compounds wherein $A^3$ is CF, in conjunction with any of the above or below embodiments.

In another embodiment, the invention includes compounds wherein $A^3$ is N, in conjunction with any of the above or below embodiments.

In another embodiment, the invention includes compounds wherein $A^4$ is CH, CF or N, in conjunction with any of the above or below embodiments.

In another embodiment, the invention includes compounds wherein $A^4$ is CH, in conjunction with any of the above or below embodiments.

In another embodiment, the invention includes compounds wherein $A^4$ is CF, in conjunction with any of the above or below embodiments.

In another embodiment, the invention includes compounds wherein $A^4$ is N, in conjunction with any of the above or below embodiments.

In another embodiment, the invention includes compounds wherein $A^5$ is CH, $CR^1$ wherein $R^1$ is F, Br or

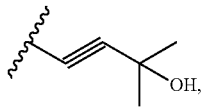 [SMILES: *C#CC(C)(C)O]

or $A^5$ is N, in conjunction with any of the above or below embodiments.

In another embodiment, the invention includes compounds wherein $A^5$ is CH, in conjunction with any of the above or below embodiments.

In another embodiment, the invention includes compounds wherein $A^5$ is $CR^1$ wherein $R^1$ is F, Br or

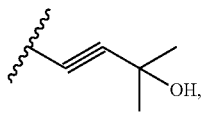

in conjunction with any of the above or below embodiments.

In another embodiment, the invention includes compounds wherein $A^5$ is N, in conjunction with any of the above or below embodiments.

In another embodiment, the invention includes compounds wherein $A^6$ is CH, CF or N, in conjunction with any of the above or below embodiments.

In another embodiment, the invention includes compounds wherein $A^6$ is CH, in conjunction with any of the above or below embodiments.

In another embodiment, the invention includes compounds wherein $A^6$ is CF, in conjunction with any of the above or below embodiments.

In another embodiment, the invention includes compounds wherein $A^6$ is N, in conjunction with any of the above or below embodiments.

In another embodiment, the invention includes compounds wherein $R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —Si(CH$_3$)$_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$, in conjunction with any of the above or below embodiments.

In another embodiment, the invention includes compounds wherein $R^2$ is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$, in conjunction with any of the above or below embodiments.

In another embodiment, the invention includes compounds wherein $R^2$ is $C_{3-6}$-alkyl, $C_{2-4}$alkynyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl or 8-oxo-3-aza-bicyclo[3.2.1]oct-3-yl, wherein the $C_{3-6}$-alkyl, $C_{2-4}$alkynyl, —$SC_{1-6}$alkyl, phenyl, pyridyl, pyrimidyl, pyrazinyl, pyridazinyl, dihydropyranyl, tetrahydropyranyl, pyrrolidinyl, piperidinyl, morpholinyl and 8-oxo-3-aza-bicyclo[3.2.1]oct-3-yl are optionally substituted, independently, with 1-3 substituents of $R^9$, in conjunction with any of the above or below embodiments.

In another embodiment, the invention includes compounds wherein $R^2$ is $C_{2-4}$alkynyl, —$OC_{1-6}$alkyl, pyridyl, pyrimidyl, dihydropyranyl, tetrahydropyranyl, pyrrolidinyl or piperidinyl, wherein the $C_{2-4}$alkynyl, —$OC_{1-6}$alkyl, pyridyl, pyrimidyl, dihydropyranyl, tetrahydropyranyl, pyrrolidinyl and piperidinyl are optionally substituted, independently, with 1-3 substituents of $R^9$, in conjunction with any of the above or below embodiments.

In another embodiment, the invention includes compounds wherein $R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_{2-4}$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of $R^9$, in conjunction with any of the above or below embodiments.

In another embodiment, the invention includes compounds wherein $R^2$ is 2-fluoro-4-pyridyl, 2-methyl-4-pyridyl, 5-fluoro-3-pyridyl, 4-pyridyl, 2-fluoro-2-methylpropoxyl, 3-fluoro-pyrrolidin-1-yl, 4,4-difluoro-1-piperidinyl, 3-methyl-3-oxetanyl-ethyn-1-yl, 3,3-dimethyl-butyn-1-yl, 4-methylphenyl, 4-fluorophenyl, 5,6-dihydro-2H-pyran-3-yl, 3,6-dihydro-2H-pyran-4-yl, 3,4-difluorophenyl, 2,2-dimethylpropoxyl, 2,2-dimethyl-2-cyano-propoxyl, 3,3-difluoro-1-pyrrolidinyl or 4-morpholinyl, in conjunction with any of the above or below embodiments.

In another embodiment, the invention includes compounds wherein $R^2$ is a ring selected from the group consisting of pyridine, pyrrolidine, piperidine, phenyl, dihydropyran and morpholine or $R^2$ is —O—$C_{1-6}$alkyl, $C_{1-6}$alkynyl, wherein the ring, —O—$C_{1-6}$alkyl and $C_{1-6}$alkynyl are optionally substituted independently with 1-5 substituents of $R^9$, in conjunction with any of the above or below embodiments.

In another embodiment, the invention includes compounds wherein $R^7$ is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl)$_2$, —NH-phenyl, —NH-benzyl, —$Si(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl)$_2$, —NH-phenyl, —NH-benzyl and ring are optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, phenyl, pyridyl, pyrimidyl, pyrazinyl or pyridazinyl, wherein the $C_{2-4}$alkynyl, —$OC_{1-6}$alkyl, pyridyl, pyrimidyl, pyrazinyl and pyridazinyl are optionally substituted, independently, with 1-3 substituents of $R^9$, in conjunction with any of the above or below embodiments.

In another embodiment, the invention includes compounds wherein $R^7$ is $C_{2-4}$alkynyl, —$OC_{1-6}$alkyl, phenyl, 3-pyridyl, 5-pyrimidyl, pyrazinyl or 2-pyridazinyl, wherein the $C_{2-4}$alkynyl, —$OC_{1-6}$alkyl, 3-pyridyl, 5-pyrimidyl, pyrazinyl and 2-pyridazinyl are optionally substituted, independently, with 1-3 substituents of $R^9$, in conjunction with any of the above or below embodiments.

In another embodiment, the invention includes compounds wherein $R^7$ is a ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl and morpholinyl, said ring optionally substituted, independently, with 1-3 substituents of R, in conjunction with any of the above or below embodiments.

In another embodiment, the invention includes compounds wherein $R^7$ is a ring selected from phenyl, 3-pyridyl, 5-pyrimidyl or 2-pyridazinyl, said ring optionally substituted, independently, with 1-5 substituents of $R^9$, in conjunction with any of the above or below embodiments.

In another embodiment, the invention includes compounds wherein $R^7$ is phenyl, 3-pyridyl, 5-pyrimidyl or 2-pyridazinyl, each of which is optionally substituted with 1-5 substituents of F, Cl, Br, I, CN, $CF_3$, $C_2F_5$, haloalkoxyl, $C_{1-6}$-alkyl, CN, OH, $OC_{1-6}$-alkyl, $SC_{1-6}$-alkyl, oxetanyl or $C_{2-3}$alkynyl, in conjunction with any of the above or below embodiments.

In another embodiment, the invention includes compounds wherein $R^7$ is 3-pyridyl, 2-fluoro-3-pyridyl, 2,5-difluorophenyl, 3,3-dimethyl-1-butynyl, 3-cyanophenyl, 5-fluoro-3-pyridyl, 3,4-difluorophenyl, in conjunction with any of the above or below embodiments.

In another embodiment, the invention includes compounds wherein $R^7$ is 2-fluoro-3-pyridyl, 3-pyridyl, 5-fluoro-3-pyridyl, 2,5-difluorophenyl or 3-fluorophenyl, in conjunction with any of the above or below embodiments.

In another embodiment, the invention includes compounds wherein $R^7$ is a ring selected from the group consisting of pyridine and phenyl, wherein the ring is optionally substituted independently with 1-3 substituents of $R^9$, in conjunction with any of the above or below embodiments.

In another embodiment, the invention includes compounds wherein $R^2$ is halo, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, wherein the $C_{1-6}$-alkyl, $C_{2-4}$alkenyl, $C_{2-4}$alkynyl and $C_{3-8}$-cycloalkyl are optionally substituted, independently, with 1-3 substituents of $R^9$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from the group consisting of phenyl, pyridyl, pyrimidyl, pyridazinyl, pyrazinyl, triazinyl and thienyl, said ring optionally substituted, independently, with 1-3 substituents of $R^9$;

each $R^9$, independently, is halo, haloalkyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl, spiro-oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CH_2$—, —O— or —S—;

Y is —O—, —S— or —$CH_2$—, provided that (1) when X is —O— or —S—, then Y is —$CH_2$—, or (2) when X is —$CH_2$—, then Y is —O— or —S—; and Z is $CH_2$.

In another embodiment, the invention includes compounds wherein each $R^8$, independently, is F, Cl, $CF_3$, $OCF_3$, methyl, CN, OH, $OCH_3$, $SCH_3$, $NHCH_3$, oxetanyl or $C_{2-3}$alkynyl, in conjunction with any of the above or below embodiments.

In another embodiment, the invention includes compounds wherein each $R^9$, independently, is F, methyl, CN, OH, spiro-oxetanyl or $C_{2-3}$alkynyl, in conjunction with any of the above or below embodiments.

In another embodiment, the invention includes compounds wherein each $R^9$, independently, is F, $CF_3$, CN, $CH_3$, —$OCH_3$, —$SCH_3$, —$NHCH_3$, spiro-oxetanyl or $C_{2-3}$alkynyl, in conjunction with any of the above or below embodiments.

In another embodiment, the invention includes compounds wherein each $R^9$ is, independently, F, Cl, Br, $C_{1-6}$alkyl, $C_{1-6}$alkenyl, $C_{1-6}$alkynyl, —$OC_{1-6}$alkyl, CN, $CF_3$, —$OCF_3$ or spiro-oxetanyl, in conjunction with any of the above or below embodiments.

In another embodiment, the invention provides the compound of Formula I, or a pharmaceutically acceptable salt thereof, selected from list the individual compounds described in Table 1 herein.

In another embodiment, the invention provides the compound of Formula I, or a stereoisomer or pharmaceutically acceptable salt thereof, selected from (5S)-7-(2-fluoro-3-pyridinyl)-3-(2-fluoro-4-pyridinyl)-6'H-spiro[chromeno[2,3-c]pyridine-5,3'-[1,4]oxazin]-5'-amine;

(5S)-3-(5,6-dihydro-2H-pyran-3-yl)-7-(2-fluoro-3-pyridinyl)-6'H-spiro[chromeno[2,3-c]pyridine-5,3'-[1,4]oxazin]-5'-amine;

(5S)-3-(3,4-difluorophenyl)-7-(2-fluoro-3-pyridinyl)-6'H-spiro[chromeno[2,3-c]pyridine-5,3'-[1,4]oxazin]-5'-amine;

(5S)-3-(3,3-difluoro-1-pyrrolidinyl)-7-(2-fluoro-3-pyridinyl)-6'H-spiro[chromeno[2,3-c]pyridine-5,3'-[1,4]oxazin]-5'-amine;

(5S)-3-(4,4-difluoro-1-piperidinyl)-7-(2-fluoro-3-pyridinyl)-6'H-spiro[chromeno[2,3-c]pyridine-5,3'-[1,4]oxazin]-5'-amine;

(5S)-3-(2,2-dimethylpropoxy)-7-(2-fluoro-3-pyridinyl)-6'H-spiro[chromeno[2,3-c]pyridine-5,3'-[1,4]oxazin]-5'-amine;

(3S)-4'-fluoro-7'-(2-fluoro-3-pyridinyl)-2'-(2-fluoro-4-pyridinyl)-6H-spiro[1,4-oxazine-3,9'-xanthen]-5-amine;

(3S)-4'-fluoro-2'-(2-fluoro-2-methylpropoxy)-7'-(2-fluoro-3-pyridinyl)-6H-spiro[1,4-oxazine-3,9'-xanthen]-5-amine;

(3R)-4'-fluoro-7'-(2-fluoro-3-pyridinyl)-2'-((3R)-3-fluoro-1-pyrrolidinyl)-6H-spiro[1,4-oxazine-3,9'-xanthen]-5-amine;

(3R)-2'-(4,4-difluoro-1-piperidinyl)-4'-fluoro-7'-(2-fluoro-3-pyridinyl)-6H-spiro[1,4-oxazine-3,9'-xanthen]-5-amine;

(5S)-3-(3,3-dimethyl-1-butyn-1-yl)-7-(2-fluoro-3-pyridinyl)-6'H-spiro[chromeno[2,3-b]pyridine-5,3'-[1,4]oxazin]-5'-amine;

(5S)-7-(2-fluoro-3-pyridinyl)-3-(4-methylphenyl)-6'H-spiro[chromeno[2,3-b]pyridine-5,3'-[1,4]oxazin]-5'-amine;

(5S)-3-(4-fluorophenyl)-7-(2-fluoro-3-pyridinyl)-6'H-spiro[chromeno[2,3-b]pyridine-5,3'-[1,4]oxazin]-5'-amine;

(5S)-1-fluoro-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine;

(5S)-3-(5,6-dihydro-2H-pyran-3-yl)-1-fluoro-7-(2-fluoro-3-pyridinyl)-5',6'-dihydrospiro[chromeno[2,3-c]pyridine-5,4'-[1,3]oxazin]-2'-amine;

(5S)-3-(3,6-dihydro-2H-pyran-4-yl)-7-(2-fluoro-3-pyridinyl)-5',6'-dihydrospiro[chromeno[2,3-c]pyridine-5,4'-[1,3]oxazin]-2'-amine;

(5S)-3-(3,4-difluorophenyl)-7-(5-fluoro-3-pyridinyl)-6'H-spiro[chromeno[2,3-c]pyridine-5,3'-[1,4]oxazin]-5'-amine;

(5S)-3-(3,4-difluorophenyl)-7-(3-pyridinyl)-6'H-spiro[chromeno[2,3-c]pyridine-5,3'-[1,4]oxazin]-5'-amine;

(5S)-3-(2,2-dimethylpropoxy)-7-(3-pyridinyl)-6'H-spiro[chromeno[2,3-c]pyridine-5,3'-[1,4]oxazin]-5'-amine;

(5S)-3-(2,2-dimethylpropoxy)-7-(5-fluoro-3-pyridinyl)-6'H-spiro[chromeno[2,3-c]pyridine-5,3'-[1,4]oxazin]-5'-amine;

(5S)-3-(3,3-difluoro-1-pyrrolidinyl)-7-(5-fluoro-3-pyridinyl)-6'H-spiro[chromeno[2,3-c]pyridine-5,3'-[1,4]oxazin]-5'-amine;

3-(((5S)-5'-amino-7-(3-fluorophenyl)-6'H-spiro[chromeno[2,3-c]pyridine-5,3'-[1,4]oxazin]-3-yl)oxy)-2,2-dimethylpropanenitrile;

(3R)-2'-(2-fluoro-3-pyridinyl)-7'-(2-fluoro-4-pyridinyl)-6H-spiro[1,4-oxazine-3,9'-xanthen]-5-amine;

(3R)-2'-(3,6-dihydro-2H-pyran-4-yl)-7'-(2-fluoro-3-pyridinyl)-6H-spiro[1,4-oxazine-3,9'-xanthen]-5-amine;

(3S)-2'-(3,6-dihydro-2H-pyran-4-yl)-4'-fluoro-7'-(2-fluoro-3-pyridinyl)-6H-spiro[1,4-oxazine-3,9'-xanthen]-5-amine;

(3S)-4'-fluoro-7'-(2-fluoro-3-pyridinyl)-2'-((3-methyl-3-oxetanyl)ethynyl)-6H-spiro[1,4-oxazine-3,9'-xanthen]-5-amine;

(3S)-2'-(5,6-dihydro-2H-pyran-3-yl)-4'-fluoro-7'-(2-fluoro-3-pyridinyl)-6H-spiro[1,4-oxazine-3,9'-xanthen]-5-amine;

(3S)-2'-(5,6-dihydro-2H-pyran-3-yl)-4'-fluoro-7'-(3-pyridinyl)-6H-spiro[1,4-oxazine-3,9'-xanthen]-5-amine;

(5S)-3-(2-fluoro-4-pyridinyl)-7-(5-fluoro-3-pyridinyl)-5',6'-dihydrospiro[chromeno[2,3-c]pyridine-5,4'-[1,3]oxazin]-2'-amine;

(5S)-3-(5,6-dihydro-2H-pyran-3-yl)-7-(5-fluoro-3-pyridinyl)-5',6'-dihydrospiro[chromeno[2,3-c]pyridine-5,4'-[1,3]oxazin]-2'-amine;

(5S)-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine;

(5S)-3-(5,6-dihydro-2H-pyran-3-yl)-7-(2-fluoro-3-pyridinyl)-5',6'-dihydrospiro[chromeno[2,3-c]pyridine-5,4'-[1,3]oxazin]-2'-amine;

(5S)-3-(3,3-dimethyl-1-butyn-1-yl)-7-(2-fluoro-3-pyridinyl)-5',6'-dihydrospiro[chromeno[2,3-c]pyridine-5,4'-[1,3]oxazin]-2'-amine;

(5S)-7-(2-fluoro-3-pyridinyl)-3-(5-fluoro-3-pyridinyl)-5',6'-dihydrospiro[chromeno[2,3-c]pyridine-5,4'-[1,3]oxazin]-2'-amine;

(4S)-2'-(3,6-dihydro-2H-pyran-4-yl)-4'-fluoro-7'-(3-pyridinyl)-5,6-dihydrospiro[1,3-oxazine-4,9'-xanthen]-2-amine;

(4S)-2'-(3,6-dihydro-2H-pyran-4-yl)-4'-fluoro-7'-(2-fluoro-3-pyridinyl)-5,6-dihydrospiro[1,3-oxazine-4,9'-xanthen]-2-amine;

(4S)-2'-(5,6-dihydro-2H-pyran-3-yl)-4'-fluoro-7'-(3-pyridinyl)-5,6-dihydrospiro[1,3-oxazine-4,9'-xanthen]-2-amine;

(4S)-4'-fluoro-7'-(2-fluoro-3-pyridinyl)-2'-((3-methyl-3-oxetanyl)ethynyl)-5,6-dihydrospiro[1,3-oxazine-4,9'-xanthen]-2-amine;

(4S)-4'-fluoro-7'-(2-fluoro-3-pyridinyl)-2'-(4-pyridinyl)-5,6-dihydrospiro[1,3-oxazine-4,9'-xanthen]-2-amine;

(4S)-4'-fluoro-7'-(2-fluoro-3-pyridinyl)-2'-(3-pyridinyl)-5,6-dihydrospiro[1,3-oxazine-4,9'-xanthen]-2-amine;

(4S)-2'-(5,6-dihydro-2H-pyran-3-yl)-4'-fluoro-7'-(2-fluoro-3-pyridinyl)-5,6-dihydrospiro[1,3-oxazine-4,9'-xanthen]-2-amine;

(4S)-4'-fluoro-2'-(2-fluoro-2-methylpropoxy)-7'-(3-pyridinyl)-5,6-dihydrospiro[1,3-oxazine-4,9'-xanthen]-2-amine;

(4S)-4'-fluoro-7'-(2-fluoro-3-pyridinyl)-2'-((3R)-3-fluoro-1-pyrrolidinyl)-5,6-dihydrospiro[1,3-oxazine-4,9'-xanthen]-2-amine;

(4S)-4'-fluoro-2'-(2-fluoro-2-methylpropoxy)-7'-(2-fluoro-3-pyridinyl)-5,6-dihydrospiro[1,3-oxazine-4,9'-xanthen]-2-amine;

(4S)-2'-(4,4-difluoro-1-piperidinyl)-4'-fluoro-7'-(2-fluoro-3-pyridinyl)-5,6-dihydrospiro[1,3-oxazine-4,9'-xanthen]-2-amine;

(4S)-2'-(5,6-dihydro-2H-pyran-3-yl)-4'-fluoro-7'-(2-fluoro-3-pyridinyl)-5,6-dihydrospiro[1,3-thiazine-4,9'-xanthen]-2-amine;

(4S)-4'-fluoro-2'-(2-fluoro-2-methylpropoxy)-7'-(2-fluoro-3-pyridinyl)-5,6-dihydrospiro[1,3-thiazine-4,9'-xanthen]-2-amine;

(5S)-7-(2,5-difluorophenyl)-3-(2-fluoro-4-pyridinyl)-6'H-spiro[chromeno[2,3-b]pyridine-5,3'-[1,4]oxazin]-5'-amine;

(5S)-3-(2,2-dimethylpropoxy)-7-(2-fluoro-3-pyridinyl)-6'H-spiro[chromeno[2,3-b]pyridine-5,3'-[1,4]oxazin]-5'-amine;

(5S)-1-fluoro-3-(2-fluoro-4-pyridinyl)-7-(5-fluoro-3-pyridinyl)-5',6'-dihydrospiro[chromeno[2,3-c]pyridine-5,4'-[1,3]oxazin]-2'-amine;

(5S)-1-fluoro-3-(2-fluoro-4-pyridinyl)-7-(3-pyridinyl)-5',6'-dihydrospiro[chromeno[2,3-c]pyridine-5,4'-[1,3]oxazin]-2'-amine;

(5S)-1-fluoro-7-(2-fluoro-3-pyridinyl)-3-(3-pyridinyl)-5',6'-dihydrospiro[chromeno[2,3-c]pyridine-5,4'-[1,3]oxazin]-2'-amine;

(5S)-1-fluoro-7-(2-fluoro-3-pyridinyl)-3-(2-methyl-4-pyridinyl)-6'H-spiro[chromeno[2,3-c]pyridine-5,3'-[1,4]oxazin]-5'-amine;

(5S)-3-(5,6-dihydro-2H-pyran-3-yl)-1-fluoro-7-(2-fluoro-3-pyridinyl)-6'H-spiro[chromeno[2,3-c]pyridine-5,3'-[1,4]oxazin]-5'-amine;

(5S)-3-(2,2-dimethylpropoxy)-1-fluoro-7-(2-fluoro-3-pyridinyl)-6'H-Spiro[chromeno[2,3-c]pyridine-5,3'-[1,4]oxazin]-5'-amine;

(5S)-7-(2-fluoro-3-pyridinyl)-3-(2-fluoro-4-pyridinyl)-5',6'-dihydrospiro[chromeno[2,3-b]pyridine-5,4'-[1,3]oxazin]-2'-amine;

(5S)-7-(2-fluoro-3-pyridinyl)-3-((3-methyl-3-oxetanyl)ethynyl)-5',6'-dihydrospiro[chromeno[2,3-b]pyridine-5,4'-[1,3]oxazin]-2'-amine; and (5S)-3-(3,3-dimethyl-1-butyn-1-yl)-7-(2-fluoro-3-pyridinyl)-5',6'-dihydrospiro[chromeno[2,3-b]pyridine-5,4'-[1,3]oxazin]-2'-amine.

All of the possible embodiments described herein for various of the R groups of the compounds of Formula I may be applied, as appropriate, to compounds of Formulas II, III and IV and any sub-formulas thereof.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the invention described herein.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxyl" radicals or with other substitution. Examples of such radicals include fluoromethoxy, chloromethoxy, trifluoromethoxy (—OCF$_3$), trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl" or, when used alone or in combination, means a partially or fully saturated ring moiety containing one ("monocyclic"), two ("bicyclic") or even three ("tricyclic") rings wherein such rings may be attached together in a fused manner and formed from carbon atoms. The term "$C_{\alpha-\beta}$cycloalkyl" means cycloalkyl radicals each having α to β number of carbon atoms. Examples of saturated carbocyclic radicals include saturated 3 to 6-membered monocyclic groups such as cyclopropane, cyclobutane, cyclopentane and cyclohexane. Carbocycilc may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

Thus, the term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring sytems as well as spiro-fused rings. This phrase encompasses carbocyclics, heterocyclics, aryl and heteroaryl rings.

The phrase "a saturated or partially or fully unsaturated" when referring to a 3-8 membered monocyclic or a 6-12 membered bicyclic ring system is intended to include both aromatic and non-aromatic rings. The non-aromatic rings may be partially or fully saturated in nature.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine (F), chlorine (Cl), bromine (Br) or iodine (I) atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl (—$CF_3$), chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "compounds of the invention" are intended to encompass compounds of Formula I, which in turn encompasses compounds of Formula II, as well as compounds of any sub-formulas thereof, such as Formulas I-A, I-A-1, I-A-2, I-A-3, I-A-4, I-A-5, I-A-6, I-A-7, I-B, II-A and II-B.

The term "pharmaceutically-acceptable" when used with reference to a compound of Formulas I-II, and sub-formulas thereof, is intended to refer to a form of the compound that is safe for administration. For example, a salt form, a solvate, a hydrate, a prodrug or derivative form of a compound of Formulas I-II, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-II, Formulas I-II, and sub-formulas thereof, are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-II, and sub-formulas thereof, may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, diisopropylethylamine and trimethylamine. All of these salts may be prepared by conventional means from the corresponding compound of the invention by reacting, for example, the appropriate acid or base with the compound of Formulas I-IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Multiple counter-ions may form the salts of the compounds of the invention. Thus, hemi-, mono-, di, tri- and poly-salt forms of the compounds of the present invention are also contemplated herein. For example, the salt may be a mono-ionic salt, di-ionic salt or tri-ionic salt, such as mono- or di-hydrochloride salt, bis-methansulfonate salt or a monofumarate salt. Similarly, hemi-, mono-, di, tri- and polyhydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-II. A "pharmaceutically-acceptable prodrug" as used herein, denotes a prodrug which is pharmaceutically acceptable. Pharmaceutically acceptable modifications to the compounds of Formula I-IV are readily appreciated by those of ordinary skill in the art.

The compound(s) of Formulas I-II, and sub-formulas thereof, may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-II, and sub-formulas thereof. The compounds of Formulas I-II can be synthesized according to the procedures described in the following Schemes 1 and 2, wherein the substituents are as defined for Formulas I-II above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DCE—dichloroethane
DIBAL—diisobutylaluminumhydride
DIC—1,3-diisopropylcarbodiimide
DIEA, DIPEA—diisopropylethylamine
DIPA—diisopropylamine
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol N₂—nitrogen
NaCNBH₃—sodium cyanoborohydride
Na₂CO₃—sodium carbonate
NaHCO₃—sodium bicarbonate
NaH—sodium hydride
NaI—sodium iodide
NaBH₄—sodium borohydride TBAF—Tetrabutylammonium flouride
TBTU—O-benzotriazol-1-yl-N,N,N,N'-tetramethyluronium tetrafluoroborate
TEA, Et₃N—triethylamine
TFA—trifluoroacetic acid
THF—tetrahydrofuran
UV—ultraviolet light

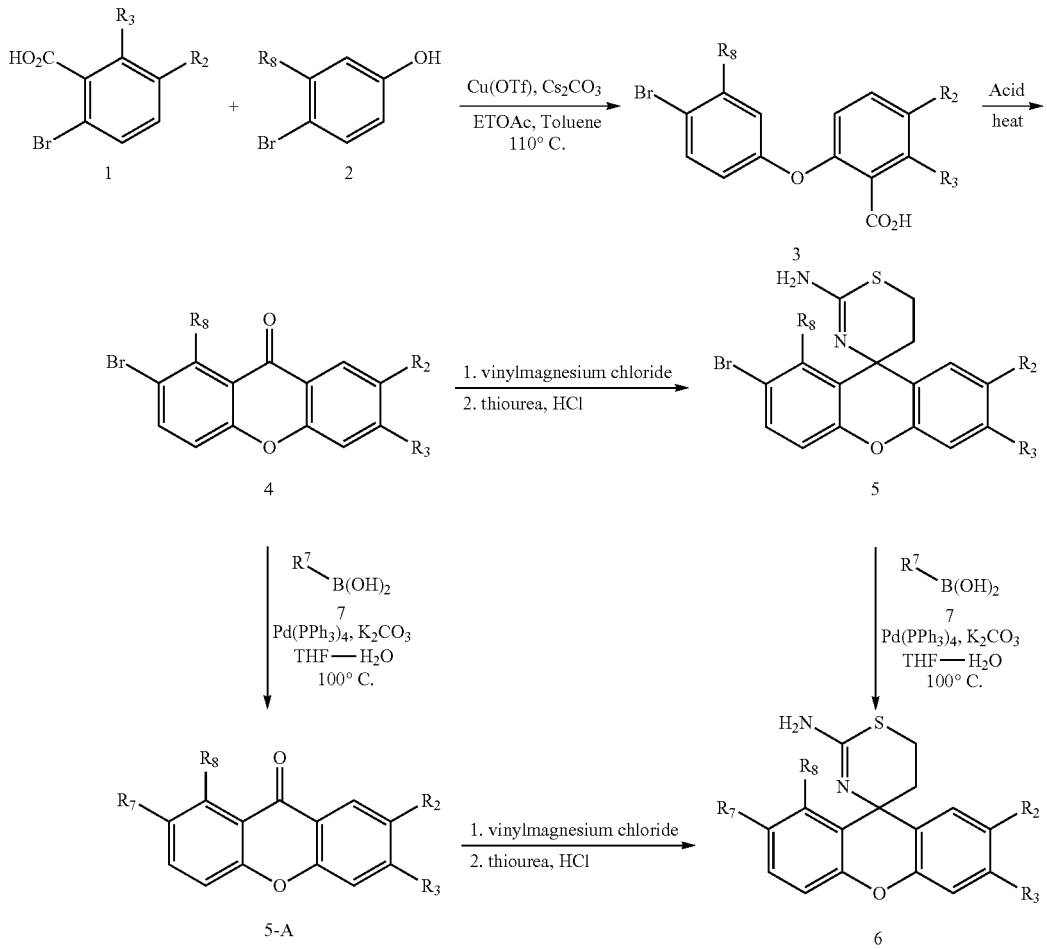

NaOH—sodium hydroxide
Na₂SO₄—sodium sulfate
NH₄Cl—ammonium chloride
NH₄OH—ammonium hydroxide
P(t-bu)₃—tri(tert-butyl)phosphine
PBS—phosphate buffered saline
Pd/C—palladium on carbon
Pd(PPh₃)₄—palladium(0)triphenylphosphine tetrakis
Pd(dppf)Cl₂—palladium(1,1-bisdiphenylphosphinoferrocene) II chloride
Pd(PhCN)₂Cl₂—palladium di-cyanophenyl dichloride
Pd(OAc)₂—palladium acetate
Pd₂(dba)₃—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography Scheme 1 describes an exemplary method for preparing compounds 6 of Formulas I-IV, wherein X is S, Y is CH₂, A¹ is CR⁶ and R¹, R⁴, R⁵, R⁶ and R⁸ are each H, respectively. As shown, a bromo-benzoic acid 1 can be coupled to a bromo-phenol 2 using a copper reagent in conjunction with a suitable base, such cesium carbonate, under suitable conditions. The coupled ether 3 can then be treated with an acid, such as sulfuric acid, to effect ring closure to the corresponding bromo-xanthene 4. The ketone of xanthene 4 can be converted to the corresponding spiro amino-thiazine 5 as shown under suitable conditions, such as using vinyl magnesium chloride and thiourea in the presence of an acid, such as HCl. Bromo-intermediate 5 (where R² is a desired group, such as methoxy) can be converted to desired compounds 6 via coupling at the site of the bromide, such as by a Suzuki or Suzuki-like aromatic-halogen exchange, which reaction generally employs a boronic acid moiety, a palladium catalyst reagent and a base.

Alternatively, the ketone intermediate 4 may be functionalized with the desired R⁷ group via a Suzuki or Suzuki-like coupling reaction, as discussed further herein, to provide intermediate 5-A. The ketone of intermediate 5-A may then be converted to the corresponding amino dihydrothiazine product 6 using the conditions discussed above.

The boronic ester intermediates 7 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be purchased commercially in catalogs, or specially made by the vendor or by persons skilled in the art.

The Suzuki method is a reaction using a borane reagent, such as a boronic acid 7 or ester such as a dioxaborolane (not shown), and a suitable leaving group containing reagent, such as the Br-xanthene 5 (Br is a suitable halogen leaving group "LG"). As appreciated to one of ordinary skill in the art, Suzuki reactions also utilize a palladium catalyst. Suitable palladium catalysts include, without limitation, Pd(PPh$_3$)$_4$, Pd(OAc)$_2$ or Pd(dppf)Cl$_2$. Where LG is a halide, the halide may be an iodide, a bromide or even a chloride. Chloropyridyl rings (where A¹=N) undergo Suzuki reactions in the presence of Pd catalysts. Other LGs are also suitable. For example, Suzuki couplings are known to occur with a sulfonate, such as trifluoromethanesulfonate, as the leaving group. The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular bromide 5 and/or boronic acid or ester 7, as appreciated by those skilled in the art. In addition, where the bromide is an aromatic moiety, such as phenyl, the reaction may be complete in a short period of time with heat.

Other coupling methods are known. For example metal catalyzed coupling chemistry, such Stille, Kumada, Negishi coupling methods, and the like, may be employed to the xanthene cores 5 to prepare desired cyclic products 6. In addition, for compounds wherein X is S, the free amino group may need to be protected for effective coupling reactions to install either R² or R⁷ groups, and later deprotected to afford the final desired compounds 6, as appreciated by persons of ordinary skill in the art.

Scheme 2

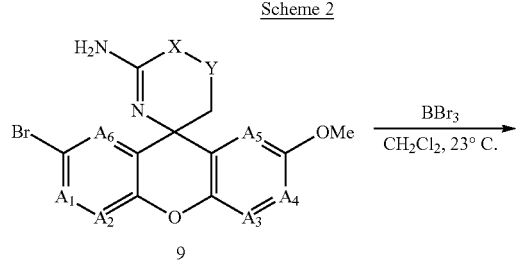

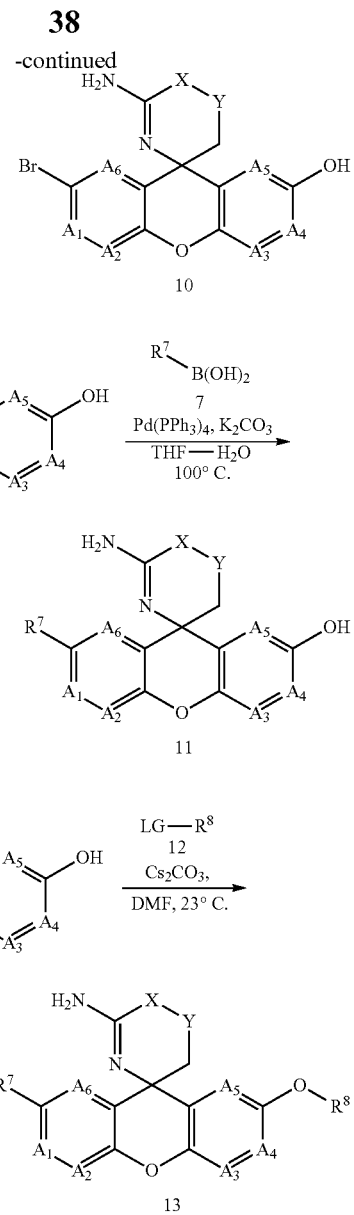

Desired compounds 13 of Formula I, and sub-formulas of II, III and IV, wherein the R² group is —OR⁸ may be made as generally described in Scheme 2. As shown, bromo-methoxy intermediate 9 can be O-d-methylate using known reagents, such as borontribromide to afford the alcohol product 10. The bromide of alcohol 10 can be coupled as described above in scheme 1 to provide the desired R⁷ group intermediate 11. The alcohol of intermediate 11 can be functionalized as desired, such as by alkylation as shown, by reaction with an alkyl halide in the presence of a suitable base, such as cesium carbonate as shown, in suitable solvents to afford the finally desired product 13.

"LG" in this instance is a "leaving group" which may be a halide such as an iodide, bromide, chloride or fluoride. LG may also be a non-halide moiety such as an alkylsulfonate or other known groups which generally form an electrophilic species (E⁺). Coupling reactions generally occur more readily in one or a combination of solvents and a base. Suitable solvents include, without limitation, generally non-nucleophilic, anhydrous solvents such as toluene, CH$_2$Cl$_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

EXAMPLES

The Examples, described herein below, represent various exemplary starting materials, intermediates and compounds of Formulas I-II, which should assist in a better understanding and appreciation of the scope of the present invention and of the various methods which may be used to synthesize compounds of Formulas I-II. Starting materials and intermediates used in the Examples herein may also be prepared using the procedures described in co-pending U.S. patent application Ser. No. 12/558,426, filed Sep. 11, 2009, which specification and disclosure is hereby incorporated herein by reference in its entirety. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material orconcentrate through an ISCO brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a suitable solvent gradient, such as 0% to 40% EtOAc in hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1H$ NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an $(M+H^+)$ molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 8.0 software, available in Chem Office, or (2) by the ISIS database software (Advanced Chemistry Design Labs or ACD software).

Example 1

Procedure A

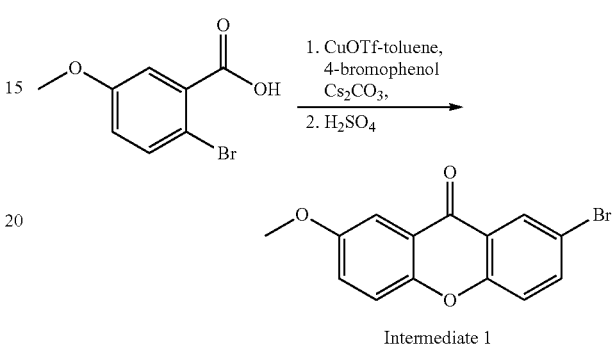

Intermediate 1

Synthesis of Intermediate 1

Step 1: A RBF equipped with a reflux condenser was charged with 2-bromo-5-methoxy benzoic acid (430 g, 1.8614 mol), 4-bromo phenol (322 g, 1.8614 mol), potassium carbonate (514.5 g, 3.7 228 mol) and CuOTf-toluene complex (24.08 g, 0.04653 mol). EtOAc (9.0 ml 0.09679 mol, 0.052) and toluene (1.3 L) were carefully added portion wise. After stirring at RT for 10 min, the mixture was heated to 50° C. for 30 min and then to 110° C. for 20 hrs. The reaction mixture was cooled to RT and diluted with water and acidified with 2N HCl. The reaction mixture was extracted with EtOAc (3.0×2 L) and filtered through a pad of celite. The combined extracts were dried over sodium sulfate and concentrated to provide 590 g of a brown solid that was carried on without further purification.

Step 2: Sulfuric acid (1.6 L) was added to 2-(4-bromophenoxy)-5-methoxybenzoic acid (530 g, 1.6401 mol) at RT. The resulting dark mixture was heated to 60° C. for 1 hour. The brown solution was cooled to RT and poured onto ice while stirring. The resulting tan precipitate was collected by filtration, washed sequentially with water (2 L), 1N NaOH (2.0 L) and ethanol (800 mL). The derived solid was suspended in 2 L of acetone and stiffed vigorously for 1 hour. The mixture was filtered and dried under a vacuum to afford 1.3 kg of 2-bromo-7-methoxy-9H-xanthen-9-one as a white solid.

Example 2

Procedure B

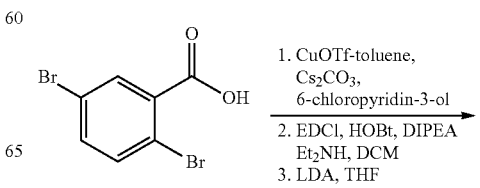

41
-continued

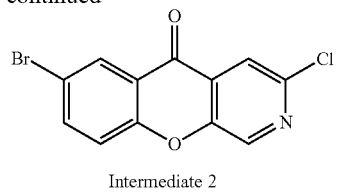

Intermediate 2

Synthesis of Intermediate 2

Step 1: A mixture of 2,5-dibromobenzoic acid (1244 g, 4.44 mol), 5-hydroxy-2-chloropyridine (663.3 g, 5.12 mol) and cesium carbonate (2893.3 g, 8.88 mol) was stirred for 20 minutes under a nitrogen atmosphere. To this slurry were added copper (I) trifloromethanesulfonate toluene complex (59.7 g, 0.115 mol), toluene (9 L) and EtOAc (39 mL). The resulting suspension was heated to 105° C. and stirred for 2 h before being cooled to RT. The toluene was decanted, and water (8 L) and EtOAc (8 L) were added. The resulting mixture was stirred until the solid was completely dissolved. The EtOAc layer was separated and the pH of the aqueous layer was adjusted to pH 2~3 with 6N HCl. The aqueous layer was extracted with EtOAc (3×5 L). The combined organic layers were dried over $Na_2SO_4$, filtered and concentrated to give 1.28 Kg of 5-bromo-2-(6-chloropyridin-3-yloxy)benzoic acid as brown solid. This material was used in next step without further purification.

Step 2: A mixture of compound 5-bromo-2-(6-chloropyridin-3-yloxy)benzoic acid (1.28 Kg, 4.44 mol), DEA (461 mL, 4.44 mol), HOBT (600 g, 4.44 mol), DIPEA (1.547 L, 8.88 mol) in anhydrous DCM (8 L) was cooled to 0° C. and EDCI (851.2 g, 4.44 mol, 1 eq) was added. The mixture was stirred at 0° C. for 30 minutes and then at RT overnight. The reaction mixture was washed with an aqueous, saturated solution of $NaHCO_3$, brine and water. The organic phase was separated, dried over $MgSO_4$ and concentrated under reduced pressure. The resulting crude mixture was purified by silica gel chromatography (5 to 20% ethyl acetate in hexane) to afford 950 g of 5-bromo-2-(6-chloropyridin-3-yloxy)-N,N-diethylbenzamide as a yellow oil.

Step 3: 5-Bromo-2-(6-chloropyridin-3-yloxy)-N,N-diethylbenzamide (457.5 g, 1.23 mol, 1 eq) was dissolved in anhydrous THF (3 L) and cooled to −78° C. To this solution was added a solution of LDA (2M in heptane/THF/ethyl benzene, 2.25 L, 4.5 mol, 3.65 eq) maintaining the temperature below −70° C. After the addition was complete, the solution was stirred for additional 30 min at −78° C. The acetone-dry ice bath was removed and the reaction was quenched with a saturated aqueous solution of $NH_4Cl$ (1 L), maintaining the temperature below 10° C. Another batch of 5-bromo-2-(6-chloropyridin-3-yloxy)-N,N-diethylbenzamide (457.5 g) was processed using the same protocol. The crude reaction mixtures from both reactions were combined and the layers were separated. The aqueous layer was extracted with ethyl acetate (3×5 L). The combined organic layers were dried and passed through a pad of silica gel. The filtrate was evaporated, and the residue was triturated with DCM to give 70 g of 7-bromo-3-chloro-5H-chromeno[2,3-c]pyridin-5-one. The mother liquor was evaporated and the solid thus obtained was purified by recrystallization using DCM/hexanes to give 180 g of 7-bromo-3-chloro-5H-chromeno[2,3-c]pyridin-5-one.

Example 3

Procedure C

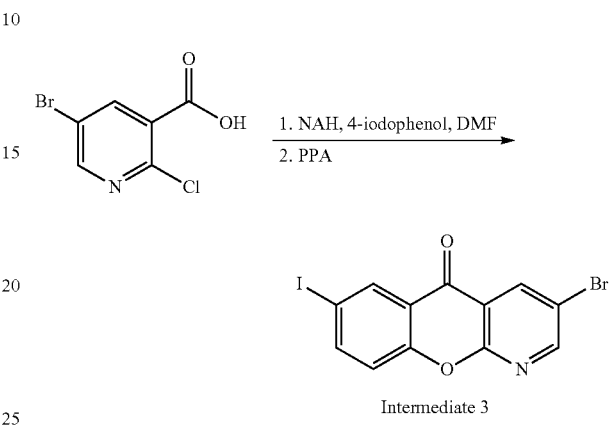

Intermediate 3

Synthesis of Intermediate 3

Step 1: A 3-neck 12 L flask equipped with an overhead stirrer, thermometer, condenser and nitrogen inlet was charged with NaH (186.1 g, 4.653 mol) and DMF (1500 mL). The slurry was cooled to 0° C. and a solution of 4-iodophenol (488.6 g, 2.221 mol) in DMF (1500 mL) and added. The temperature of the reaction mixture was maintained below 25-30° C. during this addition. After complete addition, the cooling bath was promptly removed and the mixture continued to stir at RT for 1 h. 5-Bromo-2-chloronicotinic acid (500 g, 2.115 mol) was then added to the slurry portion wise. The reaction mixture was heated to 115° C. overnight. The dark brown reaction mixture was cooled to 20° C. and diluted with water (2 L). The reaction mixture was acidified using HOAc (845 ml). The black homogenous solution (pH=5) was allowed to stir for 1 h at RT and poured slowly onto ice-water (20 L). The slurry was filtered at RT, washed with water (2×2 L) and dried in air to give 765 g of 5-Bromo-2-(4-iodophenoxy)-nicotinic acid as light orange solid.

Step 2: A 5 L 3-neck flask equipped with an overhead stirrer, a thermometer and nitrogen inlet was charged with PPA (4 Kg, 1942 mL) (115% $H_3PO_4$) and heated to 115-120° C. 5-Bromo-2-(4-iodophenoxy)nicotinic acid (400 g, 952 mmol) was charged portion wise to the hot PPA. The viscous mixture was then allowed to stir overnight (16-18 h) at 115-120° C. The dark viscous mixture was cooled to 60-65° C. and poured slowly onto a mixture of ice (3000 g) and water (2000 mL) under mechanical stirring. The light brown slurry was allowed to stir overnight and filtered at RT. The wet cake was washed with water (2×1000 mL) followed by IPA (1500 mL) and hexane (2×1000 mL). The solid was dried to obtain 326.4 g of 3-Bromo-7-iodo-5H-chromeno[2,3-b]pyridine-5-one as a grey solid.

Example 4

Procedure D

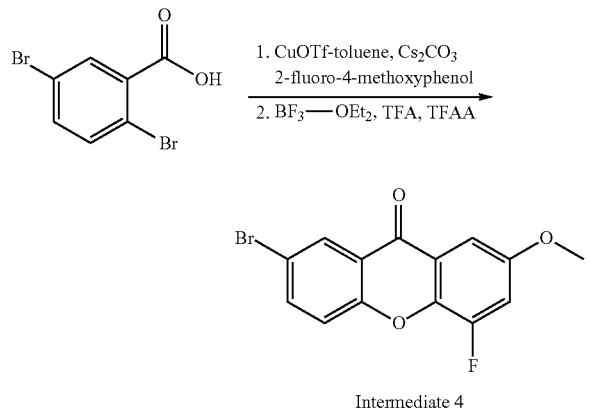

Intermediate 4

Synthesis of Intermediate 4

Step 1: A dry 100 L glass jacketed reactor equipped with an addition funnel, reflux condenser, solids addition system and temperature probe was charged with 2,5-dibromobenzoic acid (2685 g, 9.6 mol) and copper (I) triflate toluene complex (2:1, 50.0 g, 0.2 mol). Toluene (30 L) and EtOAc (20 mL) were then charged, followed by 2-methoxy-4-fluorophenol (1500 g, 10.6 mol). With vigorous stirring cesium carbonate (6258 g, 19.2 mol) was added in portions. The mixture was heated to 90° C. for 4 hours. The mixture was cooled to 35° C. and water (15 L) was added. After 15 minutes of stirring the phases were separated and the aqueous phase was washed with toluene (7.5 L). With stirring, EtOAc (15.0 L) was added to the aqueous phase, followed by 6 M HCl (5.6 L) keeping the internal temperature below 30° C. The layers were separated and the organics were dried over magnesium sulfate. Filtration through a pad of celite and concentration provided a solid that was reslurried in 915 mL of EtAOc and 9.2 L of heptanes. Stirring was continued for 1 hour before the solids were filtered and washed with heptanes. Drying provided 2560 g of 5-bromo-2-(2-fluoro-4-methoxyphenoxy)benzoic acid as a cream colored solid.

Step 2: A dry 100 L glass jacketed reactor equipped with an addition funnel, reflux condenser and temperature probe was charged with 5-bromo-2-(2-fluoro-4-methoxyphenoxy)benzoic acid (2340 g, 6.9 mol). TFA (11.7 L) was carefully added followed by TFAA (1144 mL). Boron trifluoride diethyl etherate (85 mL, 0.68 mol) was then carefully added. Stirring was continued to 4 hours at which point the reaction was transferred to another 100 L glass reactor containing 35.1 L of water cooled to 0° C. The resulting slurry was allowed to warm to RT and stir for 1 hour. The solids were filtered and washed with water (4.7 L) and 3 N NaOH (2×3.5 L) and water (7 L). The solids were transferred into a 22 L reactor and acetone (4.7 L) was added. The solids were slurried for 1.5 hour and the filtered, washing well with acetone (4.7 L). An additional slurry with acetone (6.4 L@45° C.) provided 1310 g of 7-bromo-4-fluoro-2-methoxy-9H-xanthen-9-one as an off white solid.

Example 5

Procedure E

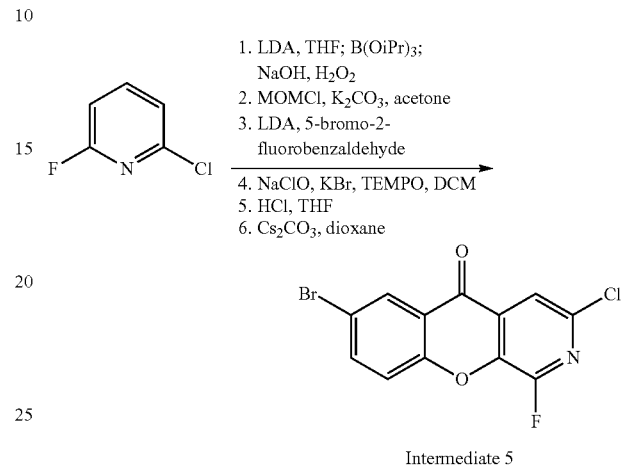

Intermediate 5

Synthesis of Intermediate 5

Step 1: A solution of i-Pr$_2$NH (828 mL, 5.85 mol) in anhydrous THF (1.3 L) was cooled to −10° C. n-BuLi (1.6 M in hexanes, 3660 mL, 5.85 mol) was added and the solution was stirred for 10 min at 0° C. The reaction mixture was cooled to −78° C. and a solution of 2-chloro-6-fluoropyridine (700 g, 5.32 mol) in anhydrous THF (1.3 L) was slowly added keeping the internal temperature below −60° C. After the addition was complete, the reaction mixture was stirred for an additional hour and then a solution of triisopropyl borate (1221 mL, 5.32 mol) in anhydrous THF (620 mL) was added drop wise keeping the internal temperature below −60° C. After the addition, the reaction mixture was warmed to RT and stirred over night. Water (3 L) was added and the mixture was stirred vigorously. The reaction mixture was concentrated under reduced pressure. The residue was treated with a cold aqueous solution of NaOH (10 M, 1610 mL, 16.0 mol) and 50% H$_2$O$_2$ (392 mL, 6.92 mol) and stirred over night (Note: the internal temperature increased slowly from 5 to 60° C.). The reaction mixture was quenched with ice and 4N HCl until pH of the mixture was ~5. EtOAc (5 L) was added and stirred well. After phase separation, the aqueous layer was extracted with EtOAc (1.5 L×2). The combined organic layers were washed with brine, dried over anhydrous Na$_2$SO$_4$, and concentrated under reduced pressure to provide 6-chloro-2-fluoropyridin-3-ol as an off white solid.

Step 2: A solution of 6-chloro-2-fluoropyridin-3-ol (1.4 Kg, 9.49 mol) was dissolved in acetone (13 L), and treated with K$_2$CO$_3$ (1574 g, 11.39 mol, 1.2 eq) and MOMCl (840 g, 10.44 mol, 1.1 eq). The mixture was heated at 60° C. for 2 hrs. After cooling to RT, the reaction mixture was filtered to remove inorganic salts. The filtrate was concentrated under reduced pressure. The residue was purified by flash column chromatography (0-10% EtOAc/hexanes), affording 6-chloro-2-fluoro-3-(methoxymethoxy)pyridine (1496 g) as a colorless oil in 80% yield over two steps.

Step 3: A solution of i-Pr$_2$NH (1100 mL, 7.72 mol) in anhydrous THF (3.5 L) was cooled to −10° C. n-BuLi (2.5 M in hexanes, 3087 mL, 7.72 mol) was added drop wise and the solution was stirred for 10 min at 0° C. The reaction mixture was cooled to −78° C. and a solution of 6-chloro-2-fluoro-3-(methoxymethoxy)pyridine (1344 g, 7.02 mol) in anhydrous THF (2 L) was added slowly, keeping the internal temperature below −60° C. The resulting solution was stirred at −75° C. for 1 hr. A solution of 5-bromo-2-fluorobenzaldehyde (1430 g, 7.02 mol) in THF (1.7 L) was added drowise. After the addition was complete, the reaction mixture was stirred at −75° C. for 30 min. The reaction mixture was warmed to RT and quenched with saturated aqueous NH$_4$Cl solution (3 L). EtOAc (5 L) was added and the mixture was stirred vigorously. After phase separation, the aqueous layer was extracted with EtOAc (3 L×2). The combined organics were washed with brine and dried over anhydrous Na$_2$SO$_4$. The solvent was removed under reduced pressure and the residue was purified by column chromatography (0-10% EtOAc/hexanes) to provide 2128 g of (5-bromo-2-fluorophenyl)(6-chloro-2-fluoro-3-(methoxymethoxy)pyridin-4-yl)methanol as a light yellow solid.

Step 4: A solution of KBr (65.1 g, 0.55 mol) in water (5.9 L) was added to a solution of (5-bromo-2-fluorophenyl)(6-chloro-2-fluoro-3-(methoxymethoxy)pyridin-4-yl)methanol (2157 g, 5.47 mol) in DCM (5.9 L). The resulting biphasic mixture was cooled to 5° C. TEMPO (8.6 g, 0.055 mol) was added and the reaction mixture was stirred for 5 min. A solution of NaHCO$_3$ (106 g, 1.26 mol, 0.23 eq) in bleach (6170 mL, 6.01 mol, 1.1 eq) was added slowly keeping the internal temperature below 10° C. After the addition was completed, the organic phase was separated. The aqueous layer was extracted with DCM (4 L×2). The combined organic layers were washed with 5% aqueous solution of sodium metabisulfite (6 L×1), brine (3 L×1) and dried over anhydrous Na$_2$SO$_4$. The solution was concentrated under reduced pressure to give 2200 g of (5-bromo-2-fluorophenyl)(6-chloro-2-fluoro-3-(methoxymethoxy)pyridin-4-yl)methanone as a yellow solid.

Step 5: To a solution of (5-bromo-2-fluorophenyl)(6-chloro-2-fluoro-3-(methoxymethoxy)pyridin-4-yl)methanone (1200 g, 3.06 mol) in THF (4.8 L) was added 6 N aqueous HCl solution (1600 mL, 9.17 mol) and the reaction mixture was heated to 60° C. for 5 hours. The reaction mixture was cooled to RT, and then water (3 L) and EtOAc (3 L) were added. After the phases were separated, the aqueous layer was extracted with EtOAc (3 L×2). The combined organic layers was washed with brine (2 L×1) and dried over Na$_2$SO$_4$. The solution was concentrated under reduced pressure. The residue was dissolved in hot MTBE (~700 mL). The solution was triturated with hexanes until a solid began to precipitate. The slurry was cooled to RT overnight. The solid was filtered, washed with hexanes (500 mL×2), and dried to give 821 g of (5-bromo-2-fluorophenyl)(6-chloro-2-fluoro-3-hydroxypyridin-4-yl)methanone as a yellow solid.

Step 6: A solution of (5-bromo-2-fluorophenyl)(6-chloro-2-fluoro-3-hydroxypyridin-4-yl)methanone (730 g, 2.10 mol) in dioxane (6 L) was treated with Cs$_2$CO$_3$ (1024 g, 3.14 mol). The reaction mixture was heated to 100° C. for 5 hours and then cooled to RT. Water (9 L) was added and the mixture was stirred vigorously. The resulting solids were filtered, washed with water (1 L×2), hexanes (1 L×1), and EtOAc (700 mL) to provide 602 g of 7-bromo-3-chloro-1-fluoro-5H-chromeno[2,3-c]pyridin-5-one as a light yellow solid.

Example 6

Procedure F

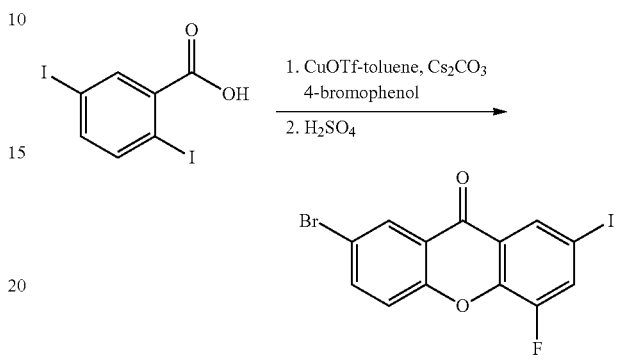

Synthesis of Intermediate 6

Step 1: A RBF equipped with a reflux condenser was charged with 4-bromophenol (15.5 g, 89.4 mmol), 2,5-diiodobenzoic acid (25.700 g, 68.7 mmol), EtOAc (0.337 ml, 3.44 mmol), and toluene (100 mL). Cs$_2$CO$_3$ (44.8 g, 137 mmol) was carefully added portion-wise. After stirring at RT for 1 min, the mixture was heated to 50° C. for 40 min and then heated to 100° C. for 20 hrs. The reaction mixture was allowed to cool to RT. The mixture was filtered through Celite and the solids were washed with EtOAc. The filtrate was diluted with water (200 mL), acidified with 2N HCl (300 mL), and extracted with EtOAc (4×500 mL). The organic extract was washed with brine and dried over sodium sulfate. The organic fraction was concentrated under reduced pressure to afford crude 2-(4-bromophenoxy)-5-iodobenzoic acid (31.1 g) as a tan oil that solidified upon standing.

Step 2: H$_2$SO$_4$ (73.3 ml, 1375 mmol) was added to 2-(4-bromophenoxy)-5-iodobenzoic acid (28.800 g, 68.7 mmol) at rt. The resulting dark mixture was heated to 60° C. for 45 minutes. The brown solution was poured slowly onto ice-water (1 L) with stirring. The resulting tan precipitant was collected by filtration, washed with water a 1 N solution of NaOH, again with water, and dried under reduced pressure to afford 2-bromo-7-iodo-9H-xanthen-9-one (23.4 g) as a tan solid that was used without further purification.

Example 7

Procedure G

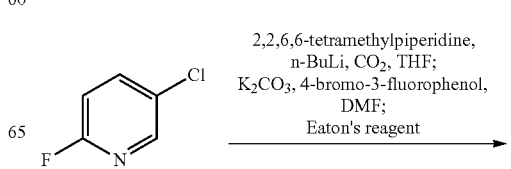

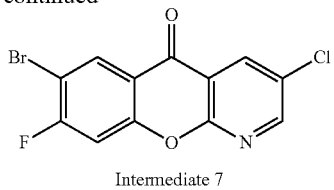

Intermediate 7

Synthesis of Intermediate 7

A solution of n-butyllithium (2.7N in heptanes; 165 mL, 445 mmol) in THF (300 mL) was cooled to −78° C. and treated with 2,2,6,6-tetramethylpiperidine (77 mL, 456 mmol). The reaction mixture was allowed to stir for 30 minutes. A solution of 5-chloro-2-fluoropyridine (50.0 g, 380 mmol) in THF (200 mL) was added dropwise over 30 minutes. After stirring for an additional 30 minutes, the reaction mixture was quenched by bubbling $CO_2$ through the reaction mixture for 10 minutes. The reaction mixture was allowed to warm to RT, and $CO_2$ was bubbled through for an additional 30 minutes. The reaction mixture was then concentrated under reduced pressure and dissolved in DMF (400 mL). 4-Bromo-3-fluorophenol (72.6 g, 380 mmol) was added, followed by potassium carbonate (68.3 g, 494 mmol). The reaction mixture was heated to 120° C. overnight. The reaction mixture was diluted with EtOAc and washed with 4N HCl. The organic layer was separated, washed with water and dried over $MgSO_4$. The solvent was removed under reduced pressure. The crude residue was dissolved in Eaton's Reagent (700 mL, 54.0 g, 380 mmol) and the reaction mixture was heated to 120° C. overnight. The reaction mixture was poured onto a mixture of ice and MeOH. The resulting solid was filtered off and washed with water. The solid was suspended in a mixture of MeOH (100 mL) and cyclopropyl methyl ether (200 mL) and filtered off. The grey solid was washed with hexanes and dried yielding 7-bromo-3-chloro-8-fluoro-5H-chromeno[2,3-b]pyridin-5-one (53.76 g, 164 mmol, 43.0% yield) as a ~4:1 mixture of isomers.

Example 8

Procedure H

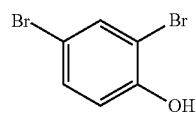

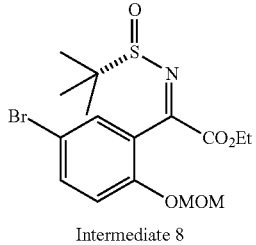

Intermediate 8

Synthesis of Intermediate 8

Step 1: A flask was charged with 2,4-dibromophenol (50.4 g, 200 mmol), potassium carbonate (69.1 g, 500 mmol) and acetone (500 mL). The suspension was stirred at RT for 30 minutes and then treated dropwise with chloromethyl ethyl ether (19 mL, 213 mmol). After 3 h at RT the mixture was filtered and the filtrate was partitioned between EtOAc and water. The organic phase was separated, washed with water, aqueous saturated $NaHCO_3$ and brine. The organic phase was dried over $MgSO_4$ and the solvent was removed under reduced pressure to afford 54.2 g 2,4-dibromo-1-(methoxymethoxy)benzene, which was used in the next step without further purification.

Step 2: A solution of 2,4-dibromo-1-(methoxymethoxy)benzene (40.5 g, 137 mmol) in $Et_2O$ (140 mL) was cooled to −78° C. and treated with n-BuLi (2.5M in hexanes; 60.2 mL, 151 mmol) under nitrogen atmosphere. After 30 minutes a solution of diethyl oxalate (27.9 mL, 205 mmol) in $Et_2O$ (20 mL) was added dropwise. The reaction mixture was stirred for 45 minutes at that temperature then quenched cold with saturated ammonium chloride solution. The mixture was partitioned between $Et_2O$ and water. The organic phase was separated, washed with water, brine, then dried over $MgSO_4$. The solvent was removed under reduced pressure to afford 49 g of ethyl 2-(5-bromo-2-(methoxymethoxy)phenyl)-2-oxoacetate, which was used in the next step without further purification.

Step 3: A flask was charged with (S)-2-methylpropane-2-sulfinamide (0.764 g, 6.31 mmol) and neopentylzinc(II) iodide (0.5 M in THF, 10.0 mL, 5.00 mmol) was added under nitrogen atmosphere. The mixture was stirred at RT for 15 minutes and ethyl 2-(5-bromo-2-(methoxymethoxy)phenyl)-2-oxoacetate (1.00 g, 3.15 mmol) was added in one portion. The reaction mixture was quenched with saturated aqueous ammonium chloride after 8 h. The reaction was partitioned between EtOAc and water. The organic phase was separated, washed with $NH_4Cl$, water and brine. The organic phase was dried over $MgSO_4$ and the solvent was removed under reduced pressure. The crude material was purified by silica gel chromatography (10-30% EtOAc/hexane) to provide 0.675 g (S)-ethyl 2-(5-bromo-2-(methoxymethoxy)phenyl)-2-(tert-butylsulfinylimino)acetate.

Example 9

Procedure I

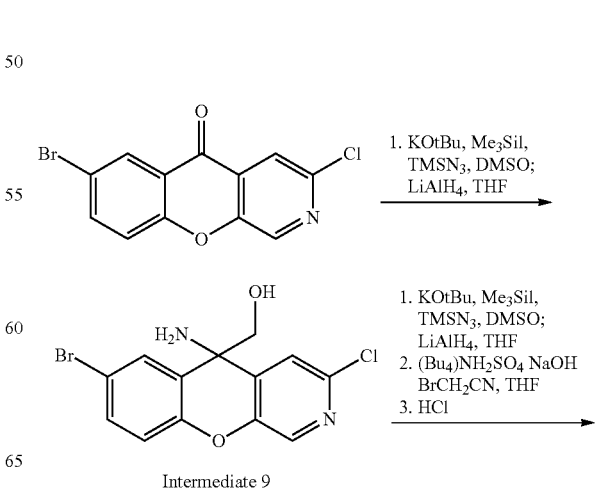

Intermediate 9

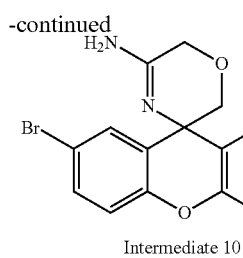

Intermediate 10

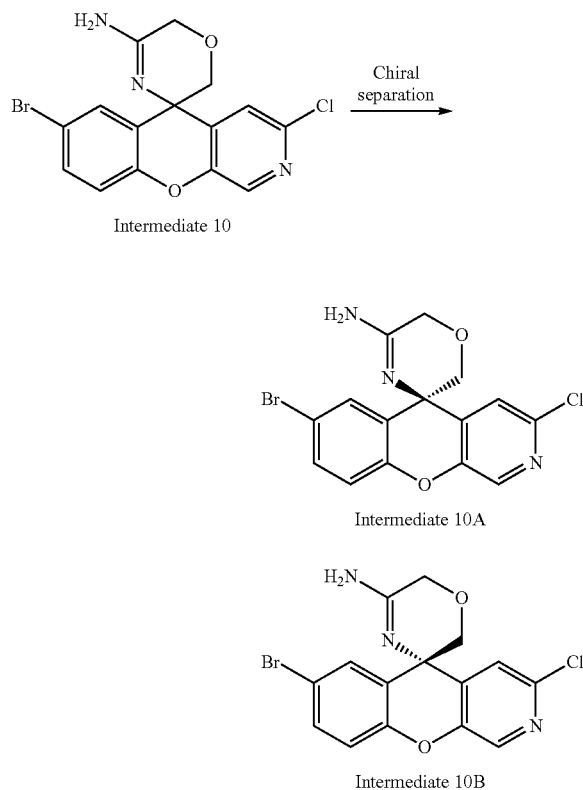

Synthesis of Intermediates 9, 10, 10A and 10B

Step 1: A 500-mL RBF was charged with 7-bromo-3-chloro-5H-chromeno[2,3-c]pyridin-5-one (12.3789 g, 39.9 mmol), trimethylsulfonium iodide (8.95 g, 43.9 mmol), and DMSO (199 mL). The resulting slurry was stirred vigorously for 5 minutes leading to a tan slurry before potassium 2-methylpropan-2-olate (4.92 g, 43.9 mmol) was added in one portion. The resulting reddish orange solution was maintained at rt for 2 hours at which time azidotrimethylsilane (10.49 mL, 80 mmol) was added in one portion. The heterogeneous mixture became homogeneous after 2-3 hours. The solution was maintained at RT overnight before being diluted with EtOAc and transferred to a separatory funnel containing saturated NaHCO$_3$ (500 mL). The layers were separated and the aqueous layer was extracted with EtOAc (3×250 mL). The combined organic layers were sequentially washed with water and brine and dried over sodium sulfate. The solution was concentrated in vacuo to provide an orange oil that was evaporated from DCM (3×250 mL) to provide 5-azido-7-bromo-3-chloro-5-((trimethylsilyloxy)methyl)-5H-chromeno[2,3-c]pyridine which was carried on without further purification. A solution of the derived foam in THF (250 mL) was cooled to 0° C. and LAH (2M in THF) (39.9 mL, 80 mmol) was. The reaction was maintained at 0° C. for 2 hours then allowed to warm to RT for 30 minutes. The reaction was diluted with 150 mL of THF and quenched by the addition of sodium sulfate decahydrate (38.5 g, 120 mmol). After the addition was complete the slurry was stirred at RT for 1.5 hours before being filtered through a pad of celite. The filter pad was washed with THF. The filtrate was concentrated under vacuum to give a brown foam. The foam was concentrated from DCM twice and left under vacuum overnight. The solid was taken up in DCM (75 mL) and heated to boiling for 1 minute. The mixture was cooled to RT, and then placed in the fridge for 1 hour. The solid was filtered, washed with DCM (50 mL) and dried to provide (5-amino-7-bromo-3-chloro-5H-chromeno[2,3-c]pyridin-5-yl)methanol (8.94 g) as a light orange solid.

Step 2: A 4-neck 3000-mL RBF with a mechanical stirrer was charged with (5-amino-7-bromo-3-chloro-5H-chromeno[2,3-c]pyridin-5-yl)methanol (29.43 g, 86 mmol), tetrabutylammonium hydrogen sulfate (5.85 g, 17.23 mmol), THF (431 mL), and bromoacetonitrile (30.0 mL, 431 mmol) to give a clear, brown solution. The resulting solution was stirred vigorously for 5 min, then a 2N aq. solution of NaOH (431 mL, 862 mmol) was added in one portion. The mixture was stirred overnight and concentrated under vacuum. The remaining material was partitioned between EtOAc (500 mL) and water (500 mL). The layers were separated and the aqueous layer was extracted with EtOAc (2×250 mL). The combined organic layers were washed with brine and dried over magnesium sulfate. The solvent was removed under reduced pressure. The residue was taken up in DCM and filtered through a short pad of silica gel. The filtrate was concentrated and purified by silica gel chromatography (0.5% MeOH/DCM) to provide 2-((5-amino-7-bromo-3-chloro-5H-chromeno[2,3-c]pyridin-5-yl)methoxy)acetonitrile.

Step 3: A flask was charged with 2-((5-amino-7-bromo-3-chloro-5H-chromeno[2,3-c]pyridin-5-yl)methoxy)acetonitrile (21 g, 55.2 mmol), dioxane (460 mL) and HCl (4M in dioxane) (55.2 mL, 221 mmol) under nitrogen atmosphere. The reaction mixture was heated to 100° C. overnight. The mixture was cooled to RT and filtered. The filter cake was washed sequentially with dioxane and ether. The collected material was dried to give 15.72 g of a cream-colored solid, which was dissolved in DCM (100 mL) and saturated aqueous sodium bicarbonate (750 mL). The mixture was extracted with DCM (2×250 mL) and EtOAc (2×250 mL). The combined organic extracts were dried over sodium sulfate and concentrated to give 7-bromo-3-chloro-2',6'-dihydrospiro[chromeno[2,3-c]pyridine-5,3'-[1,4]oxazin]-5'-amine (Intermediate 1, 14.63 g) as an off-white solid.

Step 4: 7-Bromo-3-chloro-2',6'-dihydrospiro[chromeno[2,3-c]pyridine-5,3'-[1,4]oxazin]-5'-amine was chromatographed using supercritical CO$_2$ (additives 25% MeOH with 0.2% DEA) on a Chiralpak AD-H column (50×150 mm, 5 μm) eluting at a flow rate 300 ml/min (100 bar pressure, 40° C. column temperature). The first peak (retention time=1.6 min) provided (R)-7-bromo-3-chloro-2',6'-dihydrospiro[chromeno[2,3-c]pyridine-5,3'-[1,4]oxazin]-5'-amine (example 9B; intermediate 10A; >99% ee), and the second peak (retention time=2.4 min) provided (S)-7-bromo-3-chloro-2',6'-dihydrospiro[chromeno[2,3-c]pyridine-5,3'-[1,4]oxazin]-5'-amine (example 9A; intermediate 10B; >99% ee).

Example 10

Procedure J

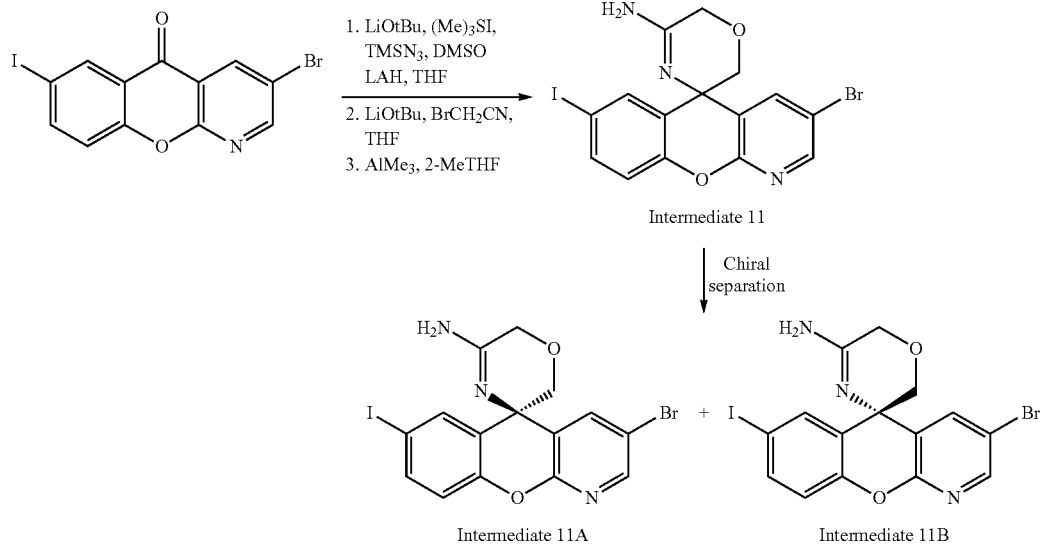

Intermediate 11

Intermediate 11A  Intermediate 11B

Synthesis of Intermediates 11, 11A and 11B

Step 1: To a suspension of 3-bromo-7-iodo-5H-chromeno[2,3-b]pyridin-5-one (20.00 g, 49.8 mmol) and trimethylsulfonium iodide (11.17 g, 54.7 mmol) in 250 mL DMSO under nitrogen atmosphere was added lithium tert-butoxide [1N in heptane (54.7 mL, 54.7 mmol)] drop wise over 40 minutes. After stirring for an additional 30 minutes, trimethylsilylazide (13.21 mL, 100 mmol) was added. After stirring for an additional hour, the reaction mixture was concentrated under reduced pressure. The remaining solution was diluted with water. The resulting solid was filtered off and washed with water. The solid was dissolved in 2-MeTHF, dried over MgSO$_4$ and concentrated. The crude residue was dissolved in 200 mL THF, cooled to 0° C. and treated with LAH (1.888 g, 49.8 mmol). After stirring for 30 minutes, the cooling bath was removed, and the reaction mixture was allowed to stir for an additional 30 minutes. The reaction mixture was then cooled to 0° C. and quenched with sodium sulfate decahydrate (32.1 g, 100 mmol). The reaction mixture was vigorously stirred for one hour, filtered through a plug of celite and concentrated. Purification of the crude residue by column chromatography [0-80% (95:5 EtOAc/MeOH)/DCM] gave (5-amino-3-bromo-7-iodo-5H-chromeno[2,3-b]pyridin-5-yl)methanol (8.80 g, 20.32 mmol, 40.8% yield).

Step 2: A solution of (5-amino-3-bromo-7-iodo-5H-chromeno[2,3-b]pyridin-5-yl)methanol (10.00 g, 23.09 mmol) and bromoacetonitrile (12.06 mL, 173 mmol) in 25 mL THF was heated to 40° C. Lithium tert-butoxide [1N in THF (173 mL, 173 mmol)] was added drop wise via addition funnel over 5 hours. After completed addition, the reaction mixture was concentrated. The residue was purified by column chromatography [0-80% (95:5 EtOAc/MeOH)/heptane] to yield 2-((5-amino-3-bromo-7-iodo-5H-chromeno[2,3-b]pyridin-5-yl)methoxy)acetonitrile (5.58 g, 11.82 mmol, 51.2% yield).

Step 3: A solution of 2-((5-amino-3-bromo-7-iodo-5H-chromeno[2,3-b]pyridin-5-yl)methoxy)acetonitrile (5.58 g, 11.82 mmol) in 100 mL 2-MeTHF under nitrogen atmosphere was treated with trimethylaluminum [2N in heptane (7.98 mL, 15.96 mmol)]. After stirring for 10 minutes at RT, the reaction mixture was heated to 80° C. for 90 minutes. The reaction mixture was cooled to RT and quenched with MeOH. The reaction mixture was treated with saturated Rochelle's salt solution and vigorously stirred for an additional hour. The organic layer was separated, washed with brine, dried over MgSO$_4$ and concentrated under reduced pressure. Purification of the crude residue by column chromatography [0-80% (90:10:1 DCM/MeOH/NH$_4$OH)/DCM] gave 3-bromo-7-iodo-2',6'-dihydrospiro[chromeno[2,3-b]pyridine-5,3'-[1,4]oxazin]-5'-amine (Intermediate 2, 2.97 g).

Step 4: Intermediates (R)-3-bromo-7-iodo-2',6'-dihydrospiro[chromeno[2,3-b]pyridine-5,3'-[1,4]oxazin]-5'-amine (11A) and (S)-3-bromo-7-iodo-2',6'-dihydrospiro[chromeno[2,3-b]pyridine-5,3'-[1,4]oxazin]-5'-amine (11B) were obtained form racemic 3-bromo-7-iodo-2',6'-dihydrospiro[chromeno[2,3-b]pyridine-5,3'-[1,4]oxazin]-5'-amine using similar chiral separation conditions as described herein for intermediate 10.

Example 11

Procedure K

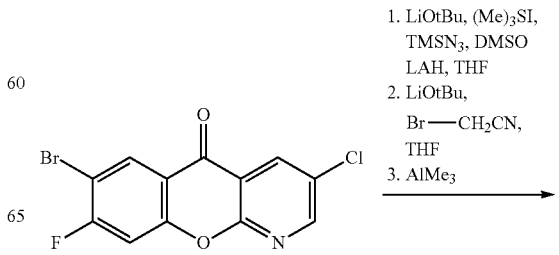

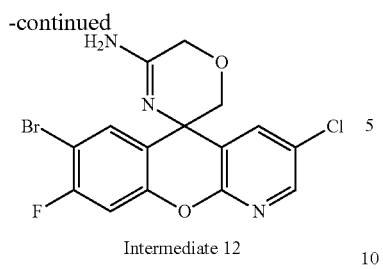

Intermediate 12

Synthesis of Intermediate 12

Step 1: A solution of 7-bromo-3-chloro-8-fluoro-5H-chromeno[2,3-b]pyridin-5-one (10.00 g, 30.4 mmol) and trimethylsulfonium iodide (6.83 g, 33.5 mmol) in 150 mL DMSO under argon atmosphere was treated with potassium tert-butoxide (3.76 g, 33.5 mmol) at rt. After 75 minutes, trimethylsilylazide (8.08 mL, 60.9 mmol) was added, and the reaction mixture was allowed to stir overnight. The reaction mixture was then diluted with EtOAc and washed with water. The suspension was filtered, and the filtrate was dried over $MgSO_4$ and concentrated under reduced pressure. The crude residue was taken up in 100 mL THF and cooled to 0° C. LAH (1.155 g, 30.4 mmol) was added, and the reaction mixture was allowed to stir for 30 minutes. The ice bath was removed, and the reaction mixture was allowed to stir for an additional 30 minutes. The reaction mixture was then cooled back to 0° C. and quenched with sodium sulfate decahydrate (9.81 g, 30.4 mmol). After stirring for one hour, the reaction mixture was filtered through celite and concentrated under reduced pressure. Purification of the crude residue by column chromatography [0-80% (95:5 EtOAc/MeOH)/DCM] gave (5-amino-7-bromo-3-chloro-8-fluoro-5H-chromeno[2,3-b]pyridin-5-yl)methanol (2.83 g, 7.87 mmol, 25.9% yield).

Step 2: A solution of (5-amino-7-bromo-3-chloro-8-fluoro-5H-chromeno[2,3-b]pyridin-5-yl)methanol (2.83 g, 7.87 mmol) and bromoacetonitrile (5.48 mL, 79 mmol) in 16 mL THF was heated to 40° C. and treated drop wise with lithium tert-butoxide [1N in THF (79 mL, 79 mmol)] over a time period of 4 hours. After completed addition the reaction mixture was concentrated under reduced pressure. Purification of the crude residue by column chromatography [0-40% (95:5 EtOAc/MeOH)/DCM] gave 2-((5-amino-7-bromo-3-chloro-8-fluoro-5H-chromeno[2,3-b]pyridin-5-yl)methoxy)acetonitrile (1.362 g, 3.42 mmol, 43.4% yield).

Step 3: To a solution of 2-((5-amino-7-bromo-3-chloro-8-fluoro-5H-chromeno[2,3-b]pyridin-5-yl)methoxy)acetonitrile (1.363 g, 3.42 mmol) in 10 mL 2-MeTHF under nitrogen atmosphere was added trimethylaluminum [2N in heptane (3.42 mL, 6.84 mmol)]. After stirring for 10 minutes, the reaction mixture was heated to 80° C. overnight. The reaction mixture was then allowed to cool to RT, and quenched with MeOH. Saturated Rochelle's salt solution was added, and the reaction mixture was vigorously stirred for an additional hour. The organic layer was separated, washed with brine, dried over $MgSO_4$ and concentrated under reduced pressure. Purification of the crude residue by column chromatography [0-80% (90:10:1 DCM/MeOH/NH4OH)/DCM] gave 7-bromo-3-chloro-8-fluoro-2',6'-dihydrospiro[chromeno[2,3-b]pyridine-5,3'-[1,4]oxazin]-5'-amine (0.422 g, 1.059 mmol, 31.0% yield).

Example 12

Procedure L

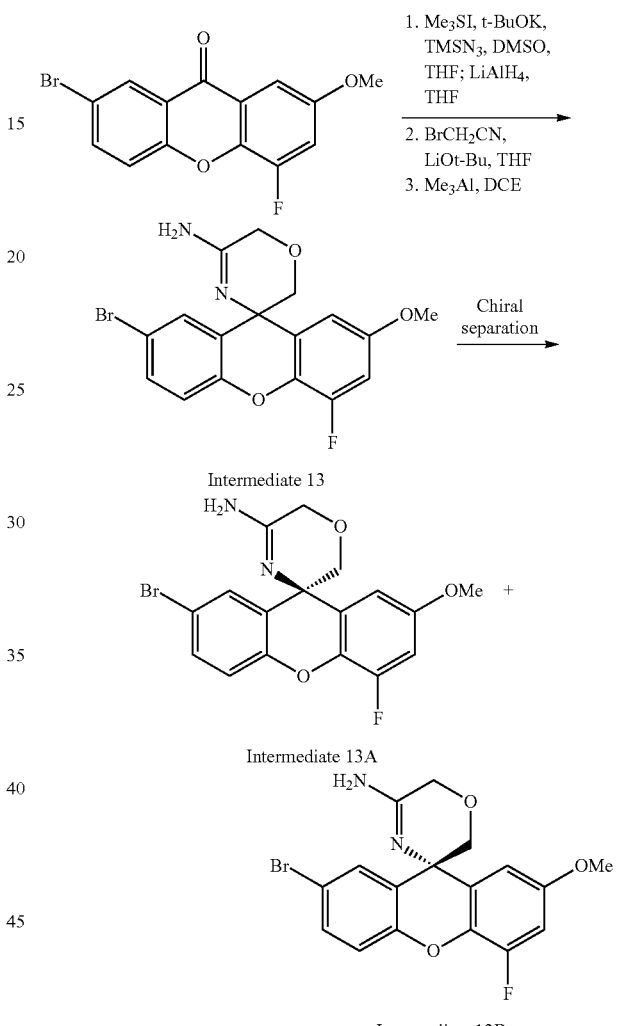

Synthesis of Intermediates 13, 13A and 13B

Step 1: To a suspension of 7-bromo-4-fluoro-2-methoxy-9H-xanthen-9-one (25.00 g, 77 mmol) and trimethylsulfonium iodide (23.68 g, 116 mmol) in DMSO (130 mL)/THF (130 mL) was added drop wise potassium tert-butoxide (1M in THF) (116 mL, 116 mmol). After 15 min at RT trimethylsilyl azide (20.54 mL, 155 mmol) was added. The reaction mixture was stirred for additional 40 minutes and then quenched by addition of 100 ml of saturated aqueous sodium bicarbonate. After stirring for 10 minutes EtOAc (100 ml) and water (100 ml) were added and the layers were separated. The organic layer was washed with water (3×100 ml), brine (100 ml) and dried over $MgSO_4$. The solvent was removed under reduced pressure to obtain a yellow residue which was dissolved in 250 ml THF. The solution was cooled to 0° C. and LAH (1 M in THF, 108 mL, 108 mmol) was added drop wise. After 5 minutes at 0° C. the reaction mixture was allowed to warm to RT. The reaction mixture was cooled again to 0° C. and sodium sulfate decahydrate (21.98 g, 155 mmol) was added portion wise. The mixture was stirred for 5 minutes and diluted with 100 ml EtOAc. The reaction mixture was filtered through a pad of Celite and the filter cake was washed with EtOAc (100 ml). The filtrate was concentrated under reduced pressure to obtain a yellow foam which was re-crystallized from DCM to afford (9-amino-7-bromo-4-fluoro-2-methoxy-9H-xanthen-9-yl)methanol as a white solid.

Step 2: A solution of (9-amino-7-bromo-4-fluoro-2-methoxy-9H-xanthen-9-yl)methanol (9.83 g, 27.8 mmol) in THF (46.3 mL) was sequentially treated with lithium t-butoxide (1 M in THF) (30.5 mL, 30.5 mmol) and 2-bromoacetonitrile (2.90 mL, 41.6 mmol) at RT. After 2.5 hours reaction time, additional 0.5 equivalent lithium t-butoxide and 2-bromoacetonitrile (1.5 mL) were added. After 4 hours reaction time, an additional 0.25 equivalent lithium t-butoxide and bromoacetonitrile (0.75 mL) were added. After 5 hours reaction time another 0.25 equivalent of lithium t-butoxide and bromoacetonitrile (0.75 mL) were added to the mixture. Water (100 ml) was added and solvents were removed under reduced pressure. The aqueous residue was filtered, the solid was washed twice with water, dried under reduced pressure and re-suspended in ethanol. The solid was filtered off, washed with ethanol and dried under reduced pressure to afford 2-((9-amino-7-bromo-4-fluoro-2-methoxy-9H-xanthen-9-yl)methoxy)acetonitrile.

Step 3: To a solution of 2-((9-amino-7-bromo-4-fluoro-2-methoxy-9H-xanthen-9-yl)methoxy)acetonitrile (7.72 g, 19.63 mmol) in DCE (115 mL) was added trimethylaluminum (2M in toluene) (19.63 mL, 39.3 mmol) at RT. The reaction mixture was stirred for 10 min at RT and then heated to 75° C. for 1 hour. The reaction mixture was cooled to RT and quenched with sodium sulfate decahydrate. The reaction mixture was vigorously stirred for 30 minutes, diluted with EtOAc and stirred overnight. The mixture was filtered through a pad of celite and filter cake was washed with EtOAc. The solvent was removed under reduced pressure to obtain an oily residue which crystallized to give 7'-bromo-4'-fluoro-2'-methoxy-2,6-dihydrospiro[[1,4]oxazine-3,9'-xanthen]-5-amine (7.49 g, 19.05 mmol, 97% yield) as a cream-colored solid.

Step 4: Intermediates (R)-7'-bromo-4'-fluoro-2'-methoxy-2,6-dihydrospiro[[1,4]oxazine-3,9'-xanthen]-5-amine (13A) and (S)-7'-bromo-4'-fluoro-2'-methoxy-2,6-dihydrospiro[[1,4]oxazine-3,9'-xanthen]-5-amine (13B) were obtained from racemic product, 7'-bromo-4'-fluoro-2'-methoxy-2,6-dihydrospiro[[1,4]oxazine-3,9'-xanthen]-5-amine (Intermediate 13) using similar chiral separation conditions as described herein for intermediate 10.

Example 13

Procedure M

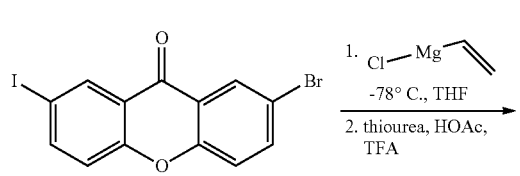

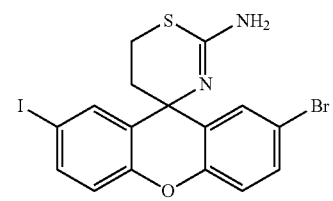

Intermediate 14

Synthesis of Intermediate 14

Step 1: To a solution of vinylmagnesium chloride (6.86 mL, 10.97 mmol) at −78° C. under nitrogen atmosphere was added drop wise a solution of 2-bromo-7-iodo-9H-xanthen-9-one (2.00 g, 4.99 mmol) in THF (30 mL). The reaction mixture was allowed to slowly warm to −10° C., then the reaction was quenched with saturated NH$_4$Cl. The mixture was extracted with EtOAc followed by a solvent mixture of CHCl$_3$:i-PrOH (3:1). The combined organic layers were dried over Na$_2$SO$_4$ and concentrated under reduced pressure. The crude material was purified by filtration over silica gel (10% EtOAc/hexane) to give 2.14 g of 2-bromo-7-iodo-9-vinyl-9H-xanthen-9-ol as a white solid.

Step 2: To a solution of 2-bromo-7-iodo-9-vinyl-9H-xanthen-9-ol (0.50 g, 1.16 mmol) and thiourea (0.18 g, 2.33 mmol) in acetic acid (2.00 mL) was added TFA (4.00 mL). The reaction mixture was stirred at RT overnight. The reaction mixture was concentrated under reduced pressure and extracted with EtOAc, followed by a solvent mixture of CHCl$_3$:i-PrOH (3:1). The combined organic layers were dried over Na$_2$SO$_4$ and concentrated in vacuo. The residue was purified by chromatography (10%-100% EtOAc/hexane) to provide 0.36 g of 2'-bromo-7'-iodo-5,6-dihydrospiro[[1,3]thiazine-4,9'-xanthen]-2-amine as a light yellow solid.

Example 14

Procedure N

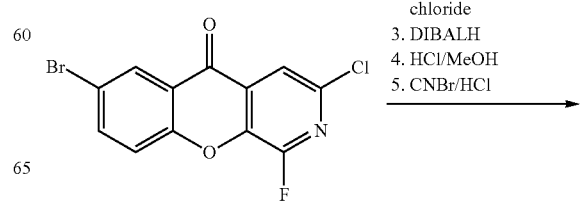

1. Ti(OEt)$_4$
   (R)-2-methy-2-propanesulfinamide
2. (2-tert-butoxy-2-oxoethyl)zinc(II) chloride
3. DIBALH
4. HCl/MeOH
5. CNBr/HCl

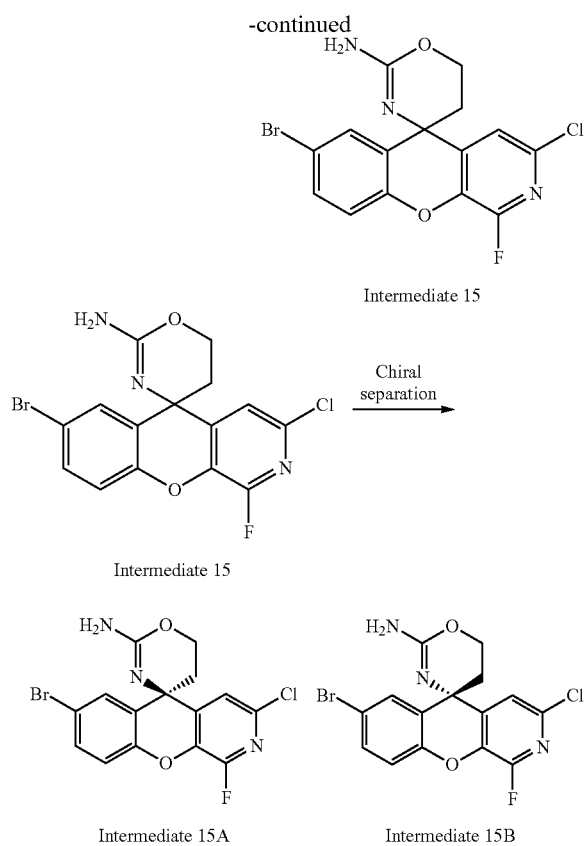

Synthesis of Intermediates 15, 15A and 15B

Step 1: A suspension of 7-bromo-3-chloro-1-fluoro-5H-chromeno[2,3-c]pyridin-5-one (20 g, 60.9 mmol), (R)-2-methyl-2-propanesulfinamide (14.76 g, 122 mmol), and titanium (IV) ethoxide (25.2 mL, 122 mmol) in THF (250 mL) was heated to 70° C. for 24 h. Additional (R)-2-methyl-2-propanesulfinamide (1.0 equiv) and titanium (IV) ethoxide (1.0 equiv) were added and the reaction mixture was heated for additional 24 h. Additional (R)-2-methyl-2-propanesulfinamide (1.0 equiv) and titanium (IV) ethoxide (1.0 equiv) were added and the reaction mixture was heated for additional 8 h. The reaction mixture was quenched with brine (150 mL). The resulting suspension was filtered through celite, and the filter cake was washed with EtOAc. The filtrate was washed with brine, dried over $Na_2SO_4$ and concentrated under reduced pressure. The residue was purified by chromatography (100% hexanes) to afford racemic N-(7-bromo-3-chloro-1-fluoro-5H-chromeno[2,3-c]pyridin-5-ylidene)-2-methyl-propane-2-sulfinamide as an orange solid (15 g, 34.7 mmol, 57.1% yield).

Step 2: A solution of (2-tert-butoxy-2-oxoethyl)zinc(II) chloride (0.5M in $Et_2O$; 116 mL, 57.9 mmol) was cooled to 0° C. and a solution of (Z)—N-(7-bromo-3-chloro-1-fluoro-5H-chromeno[2,3-c]pyridin-5-ylidene)-2-methylpropane-2-sulfinamide (10 g, 23.16 mmol) in THF (100 mL) was added drop wise. The resulting mixture was stirred at for 1 hour 0° C. The reaction mixture was diluted with EtOAc and washed with aqueous saturated solution of $NH_4Cl$, followed by brine. The organic layer was dried over $Na_2SO_4$, and concentrated under reduced pressure. The obtained residue was purified by chromatography (0-20% EtOAc/hexanes) to afford tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol, 59.1% yield) as a yellow solid.

Step 3: A solution of tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol) in dry THF (25 mL) was cooled to −78° C. and diisobutylaluminum hydride (54.8 mL, 54.8 mmol) was added drop wise. The mixture was warmed to 0° C. and kept at this temperature for 1 h. The reaction mixture was quenched with a aqueous, saturated solution of Rochelle's salt and vigorously stirred for 15 h. The organic layer was separated and the aqueous phase was extracted with EtOAc. The combined organic layers were washed with brine and dried over $Na_2SO_4$. The solution was concentrated under reduced pressure. The residue was purified by chromatography (0-30% EtOAc/hexanes) to afford N-(7-bromo-3-chloro-1-fluoro-5-(2-hydroxyethyl)-5H-chromeno[2,3-c]pyridin-5-yl)-2-methylpropane-2-sulfinamide (5.8 g, 89% yield) as a light yellow solid.

Step 4: To a solution of N-(7-bromo-3-chloro-1-fluoro-5-(2-hydroxyethyl)-5H-chromeno[2,3-c]pyridin-5-yl)-2-methylpropane-2-sulfinamide (5.8 g, 12.14 mmol) in dry MeOH (100 mL) at −20° C. was added a mixture of MeOH (80 mL)/acetylchloride (20 ml). The resulting reaction mixture was stirred at −20° C. for 30 min and then quenched with 10% aqueous solution of $Na_2CO_3$. DCM was added, the organic phase was separated and dried over $Na_2SO_4$. The solution concentrated under reduced pressure and the residue was purified by chromatography (0-50% EtOAc/hexanes) to afford 2-(5-amino-7-bromo-3-chloro-1-fluoro-5H-chromeno[2,3-c]pyridin-5-yl)ethanol (4.0 g, 10.71 mmol, 88% yield) as a light yellow solid-foam.

Step 5: To a solution of 2-(5-amino-7-bromo-3-chloro-1-fluoro-5H-chromeno[2,3-c]pyridin-5-yl)ethanol (4.2 g, 11.24 mmol) in MeOH (40 mL) was added potassium acetate (2.207 g, 22.48 mmol) followed by the drop wise addition of cyanogen bromide (3.0 m solution in DCM; 4.50 mL, 13.49 mmol). The resulting reaction mixture was stirred at RT for 17 h. The reaction mixture was concentrated under reduced pressure, followed by the addition of 4.0 M HCl in dioxane (15 mL). The reaction mixture was stirred at RT for 2 h. The reaction mixture was concentrated under reduced pressure, The residue was dissolved in DCM, washed with aqueous, saturated $NaHCO_3$ solution and brine. The solution was dried over $Na_2SO_4$ and concentrated under reduced pressure. The residue was purified by chromatography (0-100% EtOAc/hexanes) to afford 7-bromo-3-chloro-1-fluoro-5',6'-dihydrospiro[chromeno[2,3-c]pyridine-5,4'-[1,3]oxazin]-2'-amine (Intermediate 11, 1.3 g, 3.26 mmol, 29.0% yield) as a yellow solid.

Step 6: Intermediates (R)-7-bromo-3-chloro-1-fluoro-5',6'-dihydrospiro[chromeno[2,3-c]pyridine-5,4'-[1,3]oxazin]-2'-amine (15A) and (S)-7-bromo-3-chloro-1-fluoro-5',6'-dihydrospiro[chromeno[2,3-c]pyridine-5,4'-[1,3]oxazin]-2'-amine (15B) were obtained from racemic 7-bromo-3-chloro-1-fluoro-5',6'-dihydrospiro[chromeno[2,3-c]pyridine-5,4'-

Example 15

Procedure O

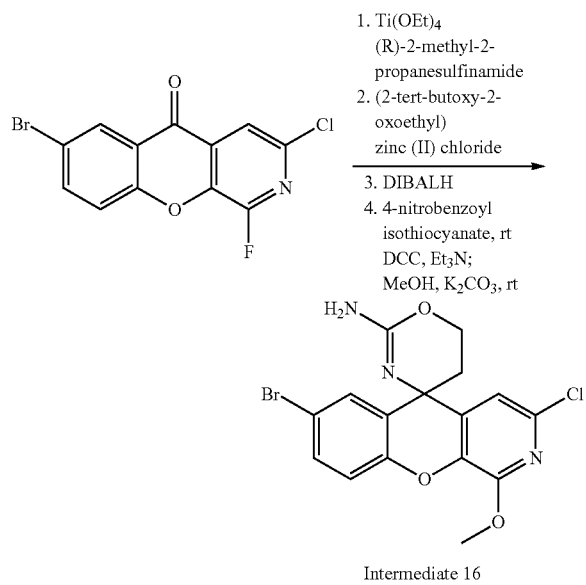

Intermediate 16

Synthesis of Intermediate 16

Step 1: A suspension of 7-bromo-3-chloro-1-fluoro-5H-chromeno[2,3-c]pyridin-5-one (20 g, 60.9 mmol), (R)-2-methyl-2-propanesulfinamide (14.76 g, 122 mmol), and titanium (IV) ethoxide (25.2 mL, 122 mmol) in THF (250 mL) was heated to 70° C. for 24 h. Additional (R)-2-methyl-2-propanesulfinamide (1.0 equiv) and titanium (IV) ethoxide (1.0 equiv) were added and the reaction mixture was heated for additional 24 h. Additional (R)-2-methyl-2-propanesulfinamide (1.0 equiv) and titanium (IV) ethoxide (1.0 equiv) were added and the reaction mixture was heated for additional 8 h. The reaction mixture was quenched with brine (150 mL). The resulting suspension was filtered through celite, and the filter cake was washed with EtOAc. The filtrate was washed with brine, dried over $Na_2SO_4$ and concentrated under reduced pressure. The residue was purified by chromatography (100% hexanes) to afford racemic N-(7-bromo-3-chloro-1-fluoro-5H-chromeno[2,3-c]pyridin-5-ylidene)-2-methylpropane-2-sulfinamide as an orange solid (15 g, 34.7 mmol, 57.1% yield).

Step 2: A solution of (2-tert-butoxy-2-oxoethyl)zinc(II) chloride (0.5M in $Et_2O$; 116 mL, 57.9 mmol) was cooled to 0° C. and a solution of (Z)—N-(7-bromo-3-chloro-1-fluoro-5H-chromeno[2,3-c]pyridin-5-ylidene)-2-methylpropane-2-sulfinamide (10 g, 23.16 mmol) in THF (100 mL) was added drop wise. The resulting mixture was stirred at for 1 hour 0° C. The reaction mixture was diluted with EtOAc and washed with aqueous saturated solution of $NH_4Cl$, followed by brine. The organic layer was dried over $Na_2SO_4$, and concentrated under reduced pressure. The obtained residue was purified by chromatography (0-20% EtOAc/hexanes) to afford tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol, 59.1% yield) as a yellow solid.

Step 3: A solution of tert-butyl 2-(7-bromo-3-chloro-5-(1,1-dimethylethylsulfinamido)-1-fluoro-5H-chromeno[2,3-c]pyridin-5-yl)acetate (7.5 g, 13.69 mmol) in dry THF (25 mL) was cooled to −78° C. and diisobutylaluminum hydride (54.8 mL, 54.8 mmol) was added drop wise. The mixture was warmed to 0° C. and kept at this temperature for 1 h. The reaction mixture was quenched with a aqueous, saturated solution of Rochelle's salt and vigorously stirred for 15 h. The organic layer was separated and the aqueous phase was extracted with EtOAc. The combined organic layers were washed with brine and dried over $Na_2SO_4$. The solution was concentrated under reduced pressure. The residue was purified by chromatography (0-30% EtOAc/hexanes) to afford N-(7-bromo-3-chloro-1-fluoro-5-(2-hydroxyethyl)-5H-chromeno[2,3-c]pyridin-5-yl)-2-methylpropane-2-sulfinamide (5.8 g, 89% yield) as a light yellow solid.

Step 4: To a solution of 2-(5-amino-7-bromo-3-chloro-1-fluoro-5H-chromeno[2,3-c]pyridin-5-yl)ethanol (0.50 g, 1.338 mmol) in THF (10 mL) was added 4-nitrobenzoyl isothiocyanate (0.306 g, 1.472 mmol) and the reaction mixture was stirred at RT for 25 min. TEA (0.019 mL, 0.134 mmol) and 1,3-dicyclohexylcarbodiimide (0.304 g, 1.472 mmol) were added and the reaction mixture was heated at 70° C. for 1.5 h. The reaction mixture was allowed to warm to RT and concentrated under reduced pressure. The residue was dissolved in MeOH (15 mL) and potassium carbonate (0.555 g, 4.01 mmol) was added. The resulting mixture was stirred at rt overnight. The reaction mixture was concentrated under reduced pressure, washed with water and extracted with DCM. The combined organic layers were dried over $Na_2SO_4$ and the solvent was removed under reduced pressure. The residue was purified by chromatography (0-40% EtOAc/hexanes) to afford 7-bromo-3-chloro-1-methoxy-5',6'-dihydrospiro[chromeno[2,3-c]pyridine-5,4'-[1,3]oxazin]-2'-amine (0.45 g, 1.096 mmol, 82% yield) as a yellow solid.

Example 16

Procedure P

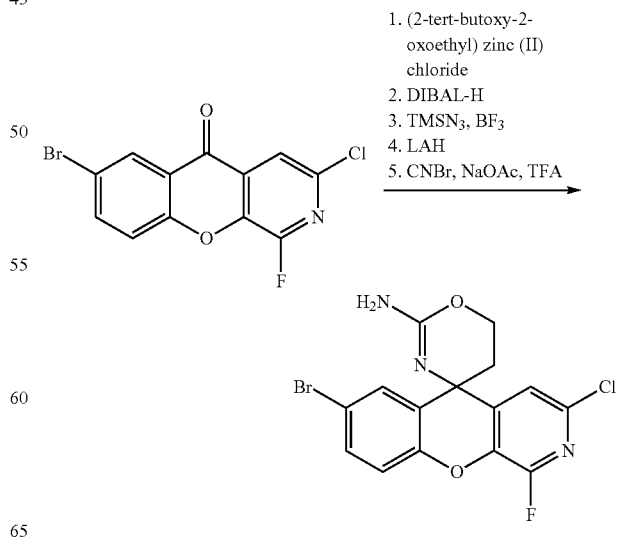

Intermediate 15

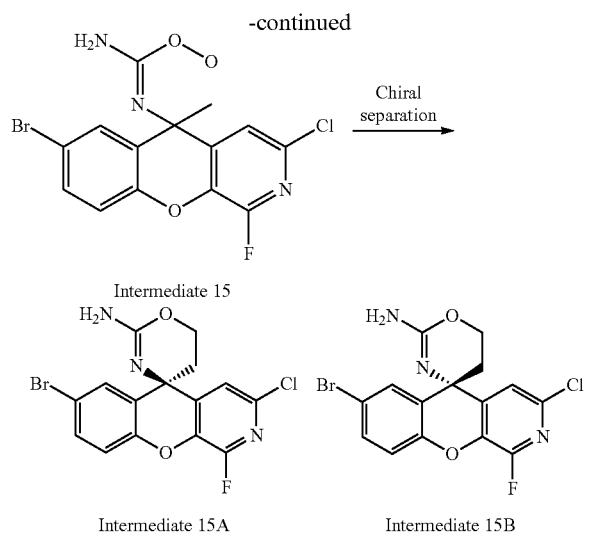

Alternative Methods for Synthesis of Intermediates 15, 15A and 15B

Step 1: To a solution of (2-tert-butoxy-2-oxoethyl)zinc(II) chloride (0.5M in Et₂O; 670 ml, 335 mmol) at 0° C. was added drop wise a solution of 7-bromo-3-chloro-1-fluoro-5H-chromeno[2,3-c]pyridin-5-one (55 g, 167 mmol) in THF (30 mL). The resulting reaction mixture was stirred at 0° C. for 1 h. The reaction mixture was quenched with aqueous, saturated NH₄Cl solution and extracted with EtOAc. The organic extracts were dried over Na₂SO₄ and concentrated under reduced pressure to afford tert-butyl 2-(7-bromo-3-chloro-1-fluoro-5-hydroxy-5H-chromeno[2,3-c]pyridin-5-yl)acetate (66.0 g, 148 mmol, 89% yield) as a yellow solid.

Step 2: A solution of tert-butyl 2-(7-bromo-3-chloro-1-fluoro-5-hydroxy-5H-chromeno[2,3-c]pyridin-5-yl)acetate (66 g, 148 mmol) in THF (200 mL) was cooled to −78° C. followed by the drop wise addition of diisobutylaluminum hydride (1.0 M solution in THF; 180 ml, 180 mmol). The resulting reaction mixture was cooled to 0° C. and stirred for 2 h. The reaction mixture was quenched with aqueous, saturated NH₄Cl solutionand extracted with EtOAc. The combined organics were dried over Na₂SO₄ and concentrated under reduced pressure. The obtained residue was purified by chromatography (0-50% EtOAc/hexanes) to afford 7-bromo-3-chloro-1-fluoro-5-(2-hydroxyethyl)-5H-chromeno[2,3-c]pyridin-5-ol (48 g, 128 mmol, 86% yield) as a light yellow solid.

Step 3: To a solution of 7-bromo-3-chloro-1-fluoro-5-(2-hydroxyethyl)-5H-chromeno[2,3-c]pyridin-5-ol (48 g, 128 mmol) in THF (58 mL) were added azidotrimethylsilane (34.0 ml, 256 mmol) and boron trifluoride diethyl etherate (31.6 ml, 256 mmol). The reaction mixture was heated to 60° C. for 15 h. Additional azidotrimethylsilane (34.0 ml, 256 mmol) and boron trifluoride diethyl etherate (31.6 ml, 256 mmol) were added and heating was continued for 3 h. The reaction mixture was quenched with aqueous, saturated NaHCO₃ solution and extracted with EtOAc. The organic phase was separated, dried over Na₂SO₄ and concentrated under reduced pressure. The residue was purified by chromatography (0-30% EtOAc/hexanes) to afford 2-(5-azido-7-bromo-3-chloro-1-fluoro-5H-chromeno[2,3-c]pyridin-5-yl)ethanol (41 g, 103 mmol, 80% yield) as a pale yellow solid-foam.

Step 4: To a solution of LAH (1.0 M solution in tetrahydrafuran; 90 ml, 90 mmol) in THF (50 mL) at rt was added drop wise a solution of 2-(5-azido-7-bromo-3-chloro-1-fluoro-5H-chromeno[2,3-c]pyridin-5-yl)ethanol (24 g, 60.1 mmol) in THF (150 mL). The resulting mixture was stirred at RT for 1 h. The reaction mixture was quenched with sodiumsulfate decahydrate and stirred for 30 min. The mixture was filtered, the filtrate was concentrated under reduced pressure and the residue was purified by chromatography (0-50% EtOAc/hexanes) to afford 2-(5-amino-7-bromo-3-chloro-1-fluoro-5H-chromeno[2,3-c]pyridin-5-yl)ethanol (16.5 g, 44.2 mmol) as a colorless oil.

Step 5: To a solution of 2-(5-amino-7-bromo-3-chloro-1-fluoro-5H-chromeno[2,3-c]pyridin-5-yl)ethanol (13 g, 34.8 mmol) in EtOH (50 mL) was added sodium acetate (5.71 g, 69.6 mmol) followed by the dropwise addition of cyanogen bromide (3.0M solution in DCM; 13.92 ml, 41.8 mmol). The resulting mixture was stirred at RT for 5 days. The reaction mixture was concentrated under reduced pressure, washed with water extracted with DCM. The combined organic layers were dried over Na₂SO₄, concentrated under reduced pressure and azeotropically dried with toluene. The obtained residue was dissolved in DCM and TFA (40 mL) was added to the solution. The resulting mixture was stirred at RT for 30 min. The mixture was carefully quenched with aqueous, saturated NaHCO₃ solution and extracted with DCM. The combined organics were dried over Na₂SO₄ and concentrated under reduced pressure. The obtained residue was purified by chromatogrpahy (0-3% MeOH/DCM) to afford 7-bromo-3-chloro-1-fluoro-5',6'-dihydrospiro[chromeno[2,3-c]pyridine-5,4'-[1,3]oxazin]-2'-amine (6.2 g, 15.55 mmol, 44.7% yield) as a light yellow solid.

Step 6: Intermediates (R)-7-bromo-3-chloro-1-fluoro-5',6'-dihydrospiro[chromeno[2,3-c]pyridine-5,4'-[1,3]oxazin]-2'-amine (15A) and (S)-7-bromo-3-chloro-1-fluoro-5',6'-dihydrospiro[chromeno[2,3-c]pyridine-5,4'-[1,3]oxazin]-2'-amine (15B) were obtained from racemic 7-bromo-3-chloro-1-fluoro-5',6'-dihydrospiro[chromeno[2,3-c]pyridine-5,4'-[1,3]oxazin]-2'-amine using similar chiral separation conditions as described herein for intermediate 10.

Example 17

Procedure Q

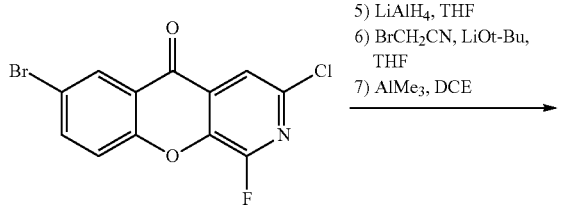

-continued

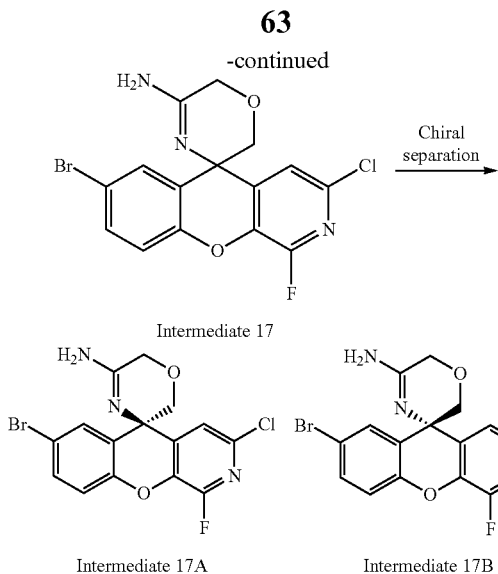

Synthesis of Intermediates 17, 17A and 17B

Step 1: A suspension of 7-bromo-3-chloro-1-fluoro-5H-chromeno[2,3-c]pyridin-5-one (35 g, 107 mmol) in dry THF (210 mL) under nitrogen atmosphere was cooled to 0° C. and a solution of methylmagnesium bromide (3.0M solution in diethyl ether; 107 mL, 320 mmol) in dry THF (70 mL) was added over 10 minutes via an addition funnel. After complete addition a saturated aqueous solution of $NH_4Cl$ (125 mL) was added slowly to the stirring reaction mixture, keeping the internal temperature below 30° C. Water was added and the mixture was extracted twice with EtOAc. The combined organic layers were dried over sodium sulfate before concentrating under reduced pressure to afford 7-bromo-3-chloro-1-fluoro-5-methyl-5H-chromeno[2,3-c]pyridin-5-ol (34.33 g, 100 mmol).

Step 2: To a solution of 7-bromo-3-chloro-1-fluoro-5-methyl-5H-chromeno[2,3-c]pyridin-5-ol (50 g, 145 mmol) in THF (300 mL) was added HCl in dioxane (4M, 19.95 mL, 80 mmol). The reaction was heated to 50° C. for 16 hours. The reaction was cooled to RT and $K_2CO_3$ (30.1 g, 218 mmol) was added. The reaction mixture was stirred for 30 minutes before filtering. The filtrate was concentrated under reduced pressure and the resulting crude material was washed with DCM. The solid was collected by filtration to afford 7-bromo-3-chloro-1-fluoro-5-methylene-5H-chromeno[2,3-c]pyridine (33.0 g, 101 mmol, 69.6% yield).

Step 3: To a solution of 7-bromo-3-chloro-1-fluoro-5-methylene-5H-chromeno[2,3-c]pyridine (33 g, 101 mmol) in THF (450 mL) were added successively water (69.2 mL), iodine (51.3 g, 202 mmol) and silver(II) oxide (46.8 g, 202 mmol) at RT. The reaction mixture was stirred at RT for 10 minutes before adding $K_2CO_3$ (41.9 g, 303 mmol). After 30 minutes, the reaction mixture was diluted with EtOAc and filtered through a pad of celite. The filter cake was washed with additional EtOAc. The combined filtrate was concentrated under reduced pressure upon which a white solid precipitated. The solid was filtered off. The filtrate was further concentrated under reduced pressure to obtain a residue which was triturated with ether to afford a white precipitate. The solid was filtered off, combined with the first solid and dried under reduced pressure to afford 7-bromo-3-chloro-1-fluorospiro[chromeno[2,3-c]pyridine-5,2'-oxirane] (23.56 g, 68.8 mmol).

Step 4: To a solution of 7-bromo-3-chloro-1-fluorospiro[chromeno[2,3-c]pyridine-5,2'-oxirane] (23.5 g, 68.6 mmol) in DMF (600 mL) was added azidotrimethylsilane (54.6 mL, 412 mmol). The reaction mixture was stirred at RT for 6 hours. Additional azidotrimethylsilane (54.6 mL, 412 mmol) was added and the reaction was stirred at RT for 18 hours. The reaction mixture was diluted with EtOAc and water. The organic layer was separated, washed sequentially with a saturated aqueous LiCl solution and brine before drying over sodium sulfate. The solution was concentrated under reduced pressure to afford (5-azido-7-bromo-3-chloro-1-fluoro-5H-chromeno[2,3-c]pyridin-5-yl)methanol (26.12 g, 67.7 mmol, 99% yield).

Step 5: A solution of (5-azido-7-bromo-3-chloro-1-fluoro-5H-chromeno[2,3-c]pyridin-5-yl)methanol (25.1 g, 65.1 mmol) in THF (500 mL) was cooled to −10° C. and a solution of LAH (1.0 M in THF; 65.1 mL, 65.1 mmol) was added drop wise via an addition funnel over a time period of 1.5 hours. Upon complete addition, the reaction mixture was stirred additional 20 min at −10° C. The reaction mixture was quenched with the drop wise addition of saturated aqueous potassium sodium tartarate solution (60 mL). The reaction was diluted with water and EtOAc. The organic layer was separated, washed with brine and dried over sodium sulfate. The solvent was removed under reduced pressure to afford (5-amino-7-bromo-3-chloro-1-fluoro-5H-chromeno[2,3-c]pyridin-5-yl)methanol (21.74 g, 60.5 mmol, 93% yield).

Step 6: A 3-neck RBF was charged with (5-amino-7-bromo-3-chloro-1-fluoro-5H-chromeno[2,3-c]pyridin-5-yl)methanol (20.7 g, 57.6 mmol) and THF (10 mL). The flask was equipped with two addition funnels which were charged with lithium tert-butoxide solution (1.0M in THF; 98 mL, 98 mmol) and a solution of bromoacetonitrile (6.82 mL, 98 mmol) in THF (10 mL), respectively. The two solutions were added simultaneously to the stirring solution at ambient temperature over a time period of 3 hours. Upon complete addition, the addition funnels were recharged with lithium tert-butoxide solution, 1.0 M in THF (98 mL, 98 mmol) and a solution of bromoacetonitrile (6.82 mL, 98 mmol) in THF (10 mL), respectively. The two solutions were added simultaneously to the stirring solution at ambient temperature over a time period of 3 hours. The reaction was quenched with saturated aqueous ammonium chloride solution and stirred for 16 hours. The reaction was diluted with water and EtOAc. The organic layer was separated and the aqueous layer was extracted twice with EtOAc. The combined organic layers were washed with brine and dried over sodium sulfate. The solution was concentrated under reduced pressure, and the resulting black solid was triturated with ether and filtered to afford a brown precipitate. The filtrate was further concentrated and purified by chromatography (50-100% EtOAc/hexanes). The solids obtained through trituration and purification by chromatography were combined to afford 2-((5-amino-7-bromo-3-chloro-1-fluoro-5H-chromeno[2,3-c]pyridin-5-yl)methoxy)acetonitrile (17.9 g, 44.9 mmol).

Step 7: A solution of trimethylaluminum solution (2.0 M in toluene; 7.32 ml, 14.64 mmol) was added drop wise to a suspension of 2-((5-amino-7-bromo-3-chloro-1-fluoro-5H-chromeno[2,3-c]pyridin-5-yl)methoxy)acetonitrile (3.89 g, 9.76 mmol) in DCE (14.00 ml) at RT under an atmosphere of nitrogen. Upon complete addition, the reaction mixture was heated to 70° C. for 10 minutes. The reaction mixture was cooled to RT quenched with a saturated aqueous potassium sodium tartarate solution. The reaction mixture was vigorously stirred for one hour before diluting with EtOAc and water. The organic layer was separated, and the aqueous layer was washed twice with additional EtOAc. The combined organic layers were washed with brine, dried over sodium sulfate and concentrated under reduced pressure. DCM and EtOAc were added to the residue and the resulting solution was filtered. The filtrate was concentrated under reduced pressure and purified by chromatography (20-70% EtOAc/ hexanes) to afford 7-bromo-3-chloro-1-fluoro-2',6'-dihydrospiro[chromeno[2,3-c]pyridine-5,3'-[1,4]oxazin]-5'-amine (Intermediate 7, 1.539 g, 3.86 mmol, 37%).

Step 8: Intermediates (R)-7-bromo-3-chloro-1-fluoro-2',6'-dihydrospiro[chromeno[2,3-c]pyridine-5,3'-[1,4]oxazin]-5'-amine (17B) and (S)-7-bromo-3-chloro-1-fluoro-2',6'-dihydrospiro[chromeno[2,3-c]pyridine-5,3'-[1,4]oxazin]-5'-amine (17A) were obtained from racemic 7-bromo-3-chloro-1-fluoro-2',6'-dihydrospiro[chromeno[2,3-c]pyridine-5,3'-[1,4]oxazin]-5'-amine using similar chiral separation conditions as described herein for intermediate 10.

Example 18

Procedure R

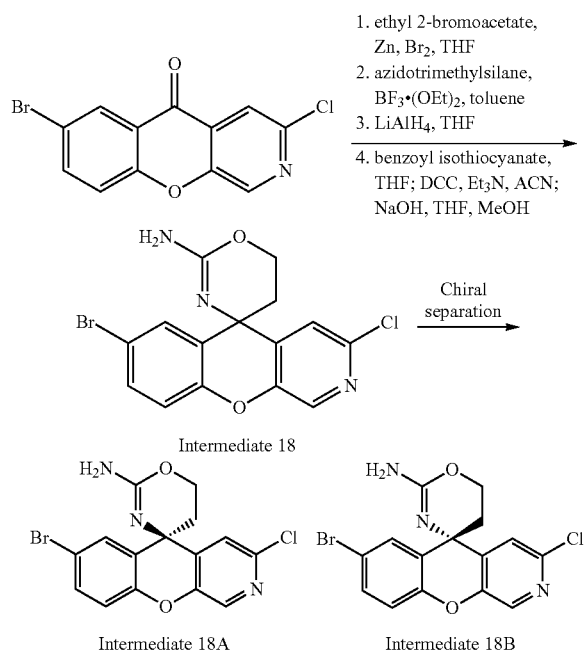

Synthesis of Intermediates 18, 18A and 18B

Step 1: A 3-neck RBF equipped with an addition funnel and reflux condenser was charged with zinc dust (37.9 g, 580 mmol) and diethyl ether (300 ml). Bromine (1.544 ml, 29.0 mmol) was added drop wise to the stirring suspension at RT. After 5 minutes, ethyl 2-bromoacetate (32.3 ml, 290 mmol) was added drop wise via addition funnel over the time period of 1 hour. The reaction mixture was heated to reflux for one hour. 7-Bromo-3-chloro-5H-chromeno[2,3-c]pyridin-5-one (30 g, 97 mmol) was added in one portion followed by THF (200 ml). After stirring at 40° C. for 10 minutes, the reaction mixture was cooled to RT and quenched with saturated aqueous ammonium chloride solution (250 mL). The reaction mixture was stirred for 1 hour before diluting with EtOAc and filtering through a pad of celite. The organic layer was separated, washed with brine and dried over MgSO$_4$. The solution was concentrated under reduced pressure to afford ethyl 2-(7-bromo-3-chloro-5-hydroxy-5H-chromeno[2,3-c]pyridin-5-yl)acetate (40.3 g) which was used in the next step without further purification.

Step 2: To a solution of ethyl 2-(7-bromo-3-chloro-5-hydroxy-5H-chromeno[2,3-c]pyridin-5-yl)acetate (38.5 g, 97 mmol) in toluene (400 ml) was added azidotrimethylsilane (38.4 ml, 290 mmol) followed by (diethyloxonio)trifluoroborate (24.48 ml, 193 mmol) under an atmosphere of nitrogen. The reaction mixture was stirred at RT for 16 hours. The reaction mixture was quenched with MeOH (200 mL) and diluted with EtOAc. The organic phase was separated, washed with saturated aqueous sodium bicarbonate solution and brine. The organic layer was dried over magnesium sulfate and concentrated under reduced pressure to afford ethyl 2-(5-azido-7-bromo-3-chloro-5H-chromeno[2,3-c]pyridin-5-yl)acetate (40.82 g) which was used in the next step without further purification.

Step 3: A solution of ethyl 2-(5-azido-7-bromo-3-chloro-5H-chromeno[2,3-c]pyridin-5-yl)acetate (40.82 g, 96 mmol) in THF (400 ml) was cooled to 0° C. under nitrogen atmosphere. A solution of LAH (1.0M solution in THF; 116 ml, 116 mmol) was added drop wise at 0° C. over a time period of 90 minutes. Upon complete addition, the reaction mixture was warmed to RT and stirred for additional 10 minutes. The reaction mixture was quenched with sodium sulfate decahydrate (50 g) and stirred for 20 minutes at RT. Celite was added to the reaction mixture and the suspension was filtered. The filtrate was concentrated under reduced pressure and the crude residue was purified by chromatography [1-2% (2M ammonia in MeOH)/DCM] to afford 2-(5-amino-7-bromo-3-chloro-5H-chromeno[2,3-c]pyridin-5-yl)ethanol (17.3 g, 48.6 mmol, 50.5% yield).

Step 4: To a solution of 2-(5-amino-7-bromo-3-chloro-5H-chromeno[2,3-c]pyridin-5-yl)ethanol (0.782 g, 2.199 mmol) in THF (15.27 ml) was added benzoyl isothiocyanate (0.325 ml, 2.419 mmol) at RT. The reaction mixture was stirred for 30 minutes after which the reaction was concentrated to dryness under reduced pressure. The residue was dissolved in ACN (15.27 ml) and triethylamine (0.031 ml, 0.220 mmol) and dicyclohexylcarbodiimide (0.476 g, 2.309 mmol) were added consecutively. The reaction mixture was heated to 80° C. for 2 hours. The reaction mixture was cooled to RT and concentrated to dryness under reduced pressure. The resulting residue was suspended in MeOH (15.27 ml) and THF (3.05 ml). A solution of NaOH (1.0M in water; 10.67 ml, 11.0 mmol) was added and the reaction mixture was heated to 70° C. for 3 hours. The reaction mixture was cooled to RT and concentrated under reduced pressure. The resulting residue was dissolved in EtOAc and washed with water and brine. The organic layer was dried over magnesium sulfate and concentrated under reduced pressure. The residue was purified chromatography [1-5% (2M ammonia in MeOH)/DCM] to afford 7-bromo-3-chloro-5',6'-dihydrospiro[chromeno[2,3-c]pyridine-5,4'-[1,3]oxazin]-2'-amine (Intermediate 10, 0.492 g, 1.293 mmol, 58.8% yield).

Step 5: Intermediates (R)-7-bromo-3-chloro-5',6'-dihydrospiro[chromeno[2,3-c]pyridine-5,4'-[1,3]oxazin]-2'-amine (18A) and (S)-7-bromo-3-chloro-5',6'-dihydrospiro[chromeno[2,3-c]pyridine-5,4'-[1,3]oxazin]-2'-amine (18B) were obtained from racemic 7-bromo-3-chloro-5',6'-dihydrospiro[chromeno[2,3-c]pyridine-5,4'-[1,3]oxazin]-2'-amine using similar chiral separation conditions as described herein for intermediate 10.

Example 19

Procedure S

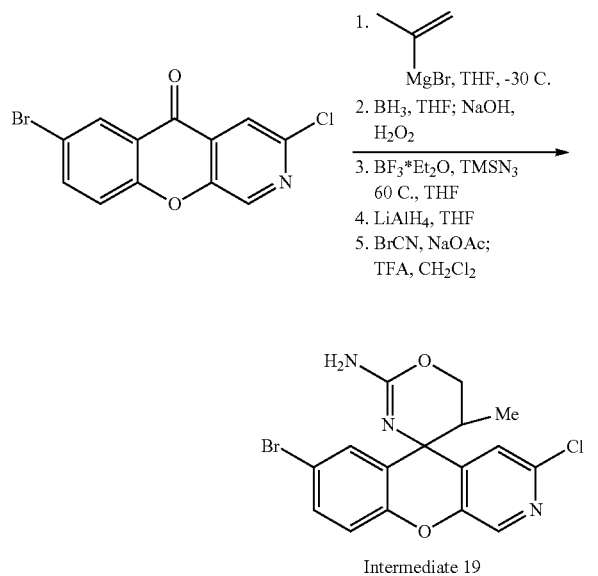

Intermediate 19

Synthesis of Intermediate 19

Step 1: A solution of 7-bromo-3-chloro-5H-chromeno[2,3-c]pyridin-5-one (3000 mg, 9.66 mmol) in THF (70 mL) was cooled to −30° C. under nitrogen atmosphere. Isopropenylmagnesium bromide, (0.5m solution in THF; 48.3 mL, 24.15 mmol) was added dropwise. The reaction mixture was stirred for 30 min at −30° C. Aqueous saturated ammoniumchloride solution was added, followed by EtOAc. The organic phase was separated and dried over MgSO$_4$. The solvent was removed under reduced pressure to yield the product as a light-yellow solid (3.2 g). The product was taken onto the next reaction step without further purification.

Step 2: To a solution of 7-bromo-3-chloro-5-(prop-1-en-2-yl)-5H-chromeno[2,3-c]pyridin-5-ol (3.2 g, 9.08 mmol) in THF (80 mL) was added a solution of borane-THF complex (1.0M in THF; 72.6 mL, 72.6 mmol) at RT under nitrogen atmosphere. The reaction mixture was allowed to stir at RT overnight. Water (10 mL) was added, followed by 2 M NaOH (15 mL). Then hydrogen peroxide (35 wt. % solution in H$_2$O; 22.25 mL, 726 mmol) was added slowly. Et$_2$O was added, followed by water. The organic phase was separated, washed with brine and dried over MgSO$_4$. The solvent was removed under reduced pressure and the residue was purified by flash chromatography (5-30% EtOAc/hexanes). The desired product 7-bromo-3-chloro-5-(1-hydroxypropan-2-yl)-5H-chromeno[2,3-c]pyridin-5-ol (2.53 g, 6.83 mmol, 75% yield) was isolated as a white solid (1:1 mixture of diastereoisomers).

Step 3: Azidotrimethylsilane (1.432 mL, 10.79 mmol) and borontriflouride etherate (1.368 mL, 10.79 mmol) were added sequentially to a solution of 7-bromo-3-chloro-5-(1-hydroxypropan-2-yl)-5H-chromeno[2,3-c]pyridin-5-ol (2000 mg, 5.40 mmol) in THF (50 mL). The reaction mixture was heated to 66° C. After 12 h reaction time, additional azidotrimethylsilane (1.432 mL, 10.79 mmol) and borontriflouride etherate (1.368 mL, 10.79 mmol) were added and the reaction mixture was continued to be heated to 65° C. After 24 h reaction time, additional azidotrimethylsilane (1.432 mL, 10.79 mmol) and borontriflouride etherate (1.368 mL, 10.79 mmol) were added and the reaction mixture was continued to be heated to 65° C. After 32 h reaction time, the reaction mixture was cooled to rt and aqueous saturated bicarbonate solution was added carefully, followed by EtOAc. The organic phase was separated and dried over MgSO$_4$. The solvent was removed under reduced pressure and the residue was purified by flash chromatography (10-55% EtOAc/hexanes). 2-(5-azido-7-bromo-3-chloro-5H-chromeno[2,3-c]pyridin-5-yl)propan-1-ol (1.32 g, 85% purity) was isolated of a white solid and taken onto the next step without further purification.

Step 4: A solution of 2-(5-azido-7-bromo-3-chloro-5H-chromeno[2,3-c]pyridin-5-yl)propan-1-ol (1300 mg, 3.29 mmol, 85% purity) in THF (10 mL) was cooled to 0° C. under nitrogen atmosphere. LAH (1.0M solution in THF; 3.61 mL, 3.61 mmol) was added dropwise. A mixture of celite and Na$_2$SO$_4$*10H$_2$O was added. The reaction mixture was filtered, the solvent was removed under reduced pressure and the residue was purified by flash chromatography (10-50% EtOAc/hexanes) to afford the desired product 2-(5-amino-7-bromo-3-chloro-5H-chromeno[2,3-c]pyridin-5-yl)propan-1-ol (0.85 g, 2.300 mmol, 70.0% yield) as a white solid.

Step 5: To a suspension of 2-(5-amino-7-bromo-3-chloro-5H-chromeno[2,3-c]pyridin-5-yl)propan-1-ol (0.85 g, 2.300 mmol) in EtOH (10 mL) was added anhydrous sodium acetate (0.377 g, 4.60 mmol) followed by the drop wise addition of cyanogen bromide (3.0M in CH$_2$Cl$_2$; 0.920 mL, 2.76 mmol). The suspension was stirred at RT for 48 h. Additional cyanogen bromide (0.8 mL, 0.6 eq) and NaOAc (180 mg, 1.0 eq) were added. The reaction mixture was allowed to stir for 3 days at RT. The reaction mixture was concentrated under reduced pressure, washed with water and extracted with DCM. The combined organic layers were dried over MgSO$_4$ and azeotropically dried with toluene. A white solid was obtained which was suspended in DCM (15 mL). Upon dropwise addition of TFA (2 mL) the reaction mixture turned clear and yellow. The resulting mixture was stirred at RT for 20 min. The solvent was removed under reduced pressure and aqueous saturated NaHCO$_3$ solution and CH$_2$Cl$_2$ were added. The suspension was filtered and 7-bromo-3-chloro-5'-methyl-5',6'-dihydrospiro[chromeno[2,3-c]pyridine-5,4'-[1,3]oxazin]-2'-amine was obtained as a white solid (305 mg). The filtrate was transferred into a separatory funnel. The organic phase was separated and dried over MgSO$_4$. The solvent was removed under reduced pressure and the residue was purfied by flash chromatography to obtain additional 7-bromo-3- chloro-5'-methyl-5',6'-dihydrospiro[chromeno[2,3-c]pyridine-5,4'-[1,3]oxazin]-2'-amine (300 mg).

Example 20

Procedure T

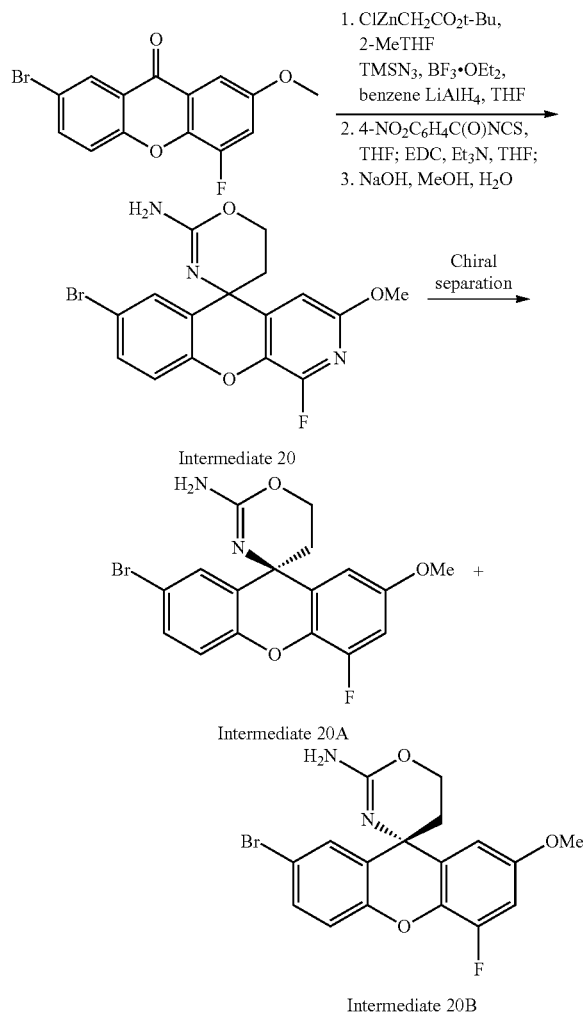

Synthesis of Intermediates 20, 20A and 20B

Step 1: To a suspension of 7-bromo-4-fluoro-2-methoxy-9H-xanthen-9-one (20 g, 61.9 mmol) in 2-methyl-THF (300 mL) a solution of (2-tert-butoxy-2-oxoethyl)zinc(II) chloride (0.5 M in Et$_2$O; 186 mL, 93 mmol) was added at RT. The mixture was stirred for 10 min at RT, and then heated to 45° C. for 1 hour. The reaction mixture was cooled to RT and quenched with aqueous, saturated NH$_4$Cl (150 mL) and water (100 mL). The organic layer was separated, washed with brine and filtered through the pad of Celite. The solvent was removed under reduced pressure to yield as a yellowish solid which was dissolved in of benzene (200 mL). Azidotrimethylsilane (12.30 mL, 93 mmol) was added and the reaction mixture was cooled to 5° C. Borontrifluoride etherate (7.84 mL, 61.9 mmol) was added drop wise. The reaction mixture was quenched by the addition of MeOH (5 mL) and aqueous, saturated NaHCO$_3$ solution (100 ml). The organic layer was separated, washed with brine, filtered through Celite and concentrated under reduced pressure to afford a yellow residue, which was dissolved in THF (300 mL). The solution was cooled to 0° C. and LAH (1M in THF; 93 mL, 93 mmol) was added drop wise at this temperature. The reaction mixture was allowed to warm to RT and quenched by the addition of sodium sulfate decahydrate (20 g). The reaction mixture was stirred for 2 hrs at RT, then filtered through celite. The filter cake was washed twice with EtOAc. The filtrate was concentrated under reduced pressure and the residue was purified by chromatography [5-50% DCM/MeOH/NH$_4$OH (90:10:1)] in DCM to afford 2-(9-amino-7-bromo-4-fluoro-2-methoxy-9H-xanthen-9-yl)ethanol (10.99 g, 29.8 mmol).

Step 2: To a solution of 2-(9-amino-7-bromo-4-fluoro-2-methoxy-9H-xanthen-9-yl)ethanol (7.17 g, 19.47 mmol) in THF (100 mL) was added 4-nitrobenzoyl isothiocyanate (4.26 g, 20.45 mmol). The reaction mixture was stirred for 30 min at RT. EDC (5.60 g, 29.2 mmol) and TEA (0.543 ml, 3.89 mmol) were added sequentially and the reaction mixture was heated to 70° C. for 1 hr. The reaction mixture was cooled to RT and water (50 ml) was added. The reaction mixture was stirred for 1 hr, upon which a precipitate formed, which was filtered off and washed with water and MeOH. The solid was dried to afford N-(7'-bromo-4'-fluoro-2'-methoxy-5,6-dihydrospiro[[1,3]oxazine-4,9'-xanthene]-2-yl)-4-nitrobenzamide (6.0 g, 11.06 mmol, 56.8% yield).

Step 3: A suspension of N-(7'-bromo-4'-fluoro-2'-methoxy-5,6-dihydrospiro[[1,3]oxazine-4,9'-xanthene]-2-yl)-4-nitrobenzamide (6.0 g, 11.06 mmol) in methanol (60 mL) was heated to 65° C. NaOH (2 M solution) (48.7 ml, 97 mmol) was added and the resulting mixture was heated to 65° C. for 4 hrs. The reaction mixture was concentrated under reduced pressure, the precipitate was filtered off, washed twice with water and dried to afford 7'-bromo-4'-fluoro-2'-methoxy-5,6-dihydrospiro[[1,3]oxazine-4,9'-xanthen]-2-amine (3.90 g, 9.92 mmol, 50.9% yield) as white solid.

Step 4: Intermediates (R)-7'-bromo-4'-fluoro-2'-methoxy-5,6-dihydrospiro[[1,3]oxazine-4,9'-xanthen]-2-amine (20A) and (S)-7'-bromo-4'-fluoro-2'-methoxy-5,6-dihydrospiro[[1,3]oxazine-4,9'-xanthen]-2-amine (20B) were obtained from racemic 7'-bromo-4'-fluoro-2'-methoxy-5,6-dihydrospiro[[1,3]oxazine-4,9'-xanthen]-2-amine using similar chiral separation conditions as described herein for intermediate 10.

Example 21

Procedure U

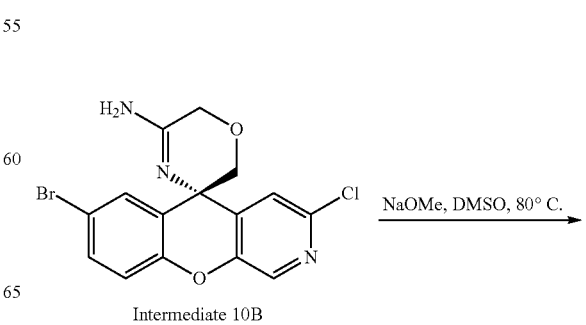

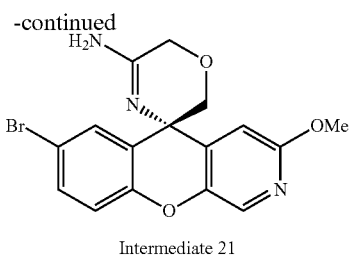

Intermediate 21

Synthesis of Intermediate 21

A vial was charged with (S)-7-bromo-3-chloro-2',6'-dihydrospiro[chromeno[2,3-c]pyridine-5,3'-[1,4]oxazin]-5'-amine (Intermediate 1B, 1.0 g, 2.63 mmol) and DMSO (13.14 mL). Sodium methoxide (0.710 g, 13.14 mmol) was added and the reaction mixture was heated to 80° C. for 2.5 hours. The reaction mixture was cooled to RT and quenched with aqueous, saturated ammonium chloride solution. Water and EtOAc were added, and the organic layer was separated and the aqueous layer was extracted with EtOAc. The combined organic layers were washed with brine, dried over sodium sulfate and concentrated under reduced pressure. The residue was purified via column chromatography (0-100% EtOAc/hexanes) to afford (S)-7-bromo-3-methoxy-2',6'-dihydrospiro[chromeno[2,3-c]pyridine-5,3'-[1,4]oxazin]-5'-amine (Example 21A; 0.611 g, 1.624 mmol, 61.8% yield) as a yellow solid.

Example 22

Procedure V

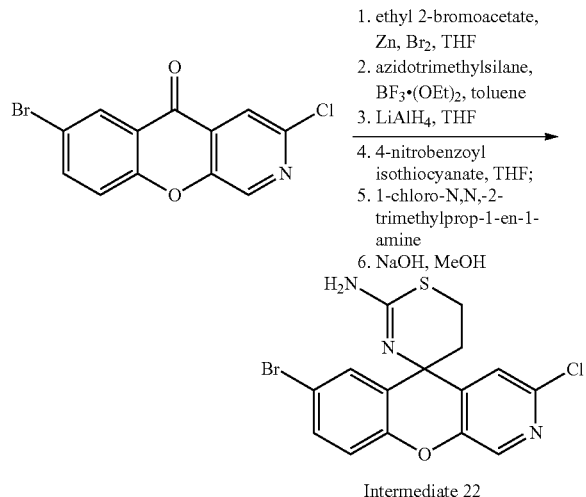

Intermediate 22

Synthesis of Intermediate 22

Step 1: Bromine (0.072 ml, 1.4 mmol) was added to a suspension of zinc dust (1.41 g, 21.57 mmol) in diethyl ether (25 ml) at RT. After 5 minutes, ethyl 2-bromoacetate (1.202 ml, 10.8 mmol) was added drop wise over a time period of 10 minutes and the reaction mixture was heated to reflux for 2 hours. 7-Bromo-3-chloro-5H-chromeno[2,3-c]pyridin-5-one (2 g, 6.44 mmol) was added in one portion, followed by THF (25.00 ml) and the reaction mixture was heated to reflux for 30 minutes. The reaction mixture was quenched with aqueous saturated NH$_4$Cl solution (20 mL) and water (20 mL) and stirred 30 min at RT. The solution was filtered and the organic phase was separated. The solvent was removed under educed pressure to afford ethyl 2-(7-bromo-3-chloro-5-hydroxy-5H-chromeno[2,3-c]pyridin-5-yl)acetate (2.5 g, 6.27 mmol, 97% yield).

Step 2: To a solution of ethyl 2-(7-bromo-3-chloro-5-hydroxy-5H-chromeno[2,3-c]pyridin-5-yl)acetate (20 g, 50.2 mmol) in toluene (300 ml) was added azidotrimethylsilane (19.93 ml, 151 mmol(, followed by (diethyloxonio)trifluoroborate (12.72 ml, 100 mmol). The mixture was stirred overnight at RT. The reaction mixture was quenched with MeOH (200 mL) and diluted with EtOAc. The organic phase was separated, washed with saturated aqueous sodium bicarbonate solution and brine. The organic layer was dried over magnesium sulfate and concentrated under reduced pressure to afford ethyl 2-(5-azido-7-bromo-3-chloro-5H-chromeno[2,3-c]pyridin-5-yBacetate (21 g, 49.6 mmol, 99% yield).

Step 3: A solution of ethyl 2-(5-azido-7-bromo-3-chloro-5H-chromeno[2,3-c]pyridin-5-yl)acetate (47 g, 111 mmol) in THF (600 ml) was cooled to 0° C. under nitrogen atmosphere. A solution of LAH (1.0M in THF; 133 ml, 133 mmol) was added drop wise at 0° C. Upon complete addition, the reaction mixture was warmed to RT and stirred for additional 10 minutes. The reaction mixture was quenched with sodium sulfate decahydrate (50 g) and stirred for 1 hour at room temperature. The suspension was filtered over celite. The filtrate was concentrated under reduced pressure and the crude residue was purified by by recrystallization from cold DCM with heptane to afford 2-(5-amino-7-bromo-3-chloro-5H-chromeno[2,3-c]pyridin-5-yl)ethanol (16 g, 45.0 mmol, 40.6% yield).

Step 4: A reaction mixture of 2-(5-amino-7-bromo-3-chloro-5H-chromeno[2,3-c]pyridin-5-yl)ethanol (2.8 g, 7.87 mmol) and 4-nitrobenzoyl isothiocyanate (1.639 g, 7.87 mmol) in THF (100 mL) was stirred at RT for 1 hour. The reaction mixture was then concentrated under reduced pressure to afford N-(7-bromo-3-chloro-5-(2-hydroxyethyl)-5H-chromeno[2,3-c]pyridin-5-ylcarbamothioyl)-4-nitrobenzamide (5 g, 8.87 mmol).

Step 5: 1-Chloro-N,N,2-trimethylprop-1-en-1-amine (2.84 ml, 21.28 mmol) was added to a solution of N-((7-bromo-3-chloro-5-(2-hydroxyethyl)-5H-chromeno[2,3-c]pyridin-5-yl)carbamothioyl)-4-nitrobenzamide (12 g, 21.28 mmol) in DCM (200 ml). The reaction mixture was stirred at RT for 8 hours and then concentrated under reduced pressure to 50% of its original volume. A precipitate formed upon cooling which was filtered off, washed with DCM and then dried under reduced pressure to afford N-(7-bromo-3-chloro-5',6'-dihydrospiro[chromeno[2,3-c]pyridine-5,4'-[1,3]thiazin]-2'-yl)-4-nitrobenzamide hydrochloride (10.5 g, 18.03 mmol, 85% yield) as an off white solid.

Step 6: A 2 N NaOH solution (24.47 ml, 48.9 mmol) was added to a solution of N-(7-bromo-3-chloro-5',6'-dihydrospiro[chromeno[2,3-c]pyridine-5,4'-[1,3]thiazin]-2'-yl)-4-nitrobenzamide hydrochloride (9.5 g, 16.32 mmol) in MeOH (250 ml). The reaction mixture was heated to 65° C. for 3 hours. The reaction mixture was diluted with water (300 mL), stirred for 10 min, and then filtered. The solid was washed with water and dried under reduced pressure to afford 7-bromo-3-chloro-5',6'-dihydrospiro[chromeno[2,3-c]pyridine-5,4'-[1,3]thiazin]-2'-amine (3.9 g, 9.83 mmol, 60.3% yield).

Example 23

Procedure W

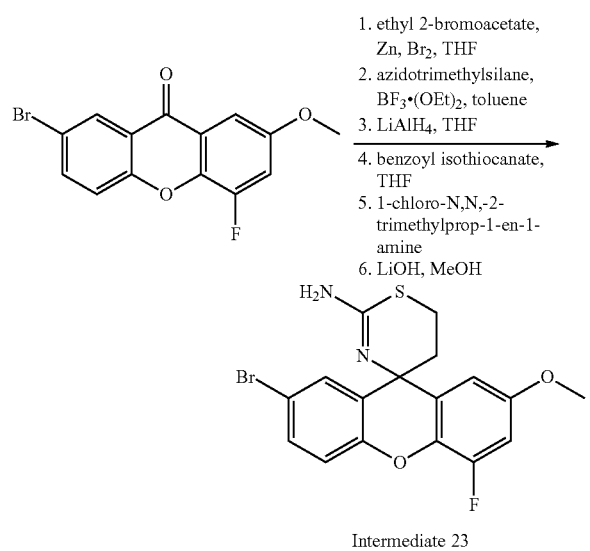

Intermediate 23

Synthesis of Intermediate 23

Step 1: Bromine (0.797 ml, 15.47 mmol) was added to a suspension of zinc dust (8.09 g, 124 mmol in diethyl ether (150 ml) at RT. After 5 minutes, ethyl 2-bromoacetate (6.86 ml, 61.9 mmol) was added drop wise over a time period of 20 minutes and the reaction mixture was heated to reflux for 2 hours. 7-bromo-4-fluoro-2-methoxy-9H-xanthen-9-one (10 g, 30.9 mmol) was added in one portion, followed by THF (100 ml) and the reaction mixture was heated to reflux for 3 hours. The reaction mixture was quenched with aqueous saturated $NH_4Cl$ solution (100 mL) and EtOAc (100 mL) and stirred 2 hours at RT. The solution was filtered and the organic phase was separated. The solvent was removed under educed pressure to afford ethyl 2-(7-bromo-4-fluoro-9-hydroxy-2-methoxy-9H-xanthen-9-yl)acetate (12.7 g, 30.9 mmol, 100% yield).

Step 2: To a solution of ethyl 2-(7-bromo-4-fluoro-9-hydroxy-2-methoxy-9H-xanthen-9-yl) acetate (1.0 g, 2.432 mmol) in toluene (25 ml) was added azidotrimethylsilane (0.560 g, 4.86 mmol). The solution was cooled to 0° C. and (diethyloxonio)trifluoroborate (0.308 ml, 2.432 mmol) was added drop wise. The mixture was stirred overnight at RT. The solution was quenched with MeOH (10 ml) and diluted with EtOAc. The organic phase was separated, washed with saturated aqueous sodium bicarbonate solution and brine, and then concentrated to afford crude ethyl 2-(9-azido-7-bromo-4-fluoro-2-methoxy-9H-xanthen-9-yl)acetate (1 g, 2.292 mmol, 94% yield).

Step 3: A solution of ethyl 2-(5-azido-7-bromo-3-chloro-5H-chromeno[2,3-c]pyridin-5-yl)acetate (13.5 g, 30.9 mmol) in THF (200 ml) was cooled to 0° C. under nitrogen atmosphere. A solution of LAH (1.0M in THF; 37.1 ml, 37.1 mmol) was added drop wise at 0° C. After 10 min, the reaction mixture was quenched with sodium sulfate decahydrate (20 g) and stirred for 5 min at RT. The suspension was filtered. The filtrate was concentrated under reduced pressure and the crude residue was purified by column chromatography [10-100% 90/10/1 (DCM/MeOH/ammonia) in DCM] to afford 2-(9-amino-7-bromo-4-fluoro-2-methoxy-9H-xanthen-9-yl) ethanol (8.8 g, 23.90 mmol).

Step 4: A reaction mixture of 2-(9-amino-7-bromo-4-fluoro-2-methoxy-9H-xanthen-9-yl) ethanol (8.8 g, 23.90 mmol) and benzoyl isothiocyanate (3.22 ml, 23.90 mmol) in THF (200 ml) was stirred at RT for 1 hour. The reaction mixture was then concentrated under reduced pressure to afford N-((7-bromo-4-fluoro-9-(2-hydroxyethyl)-2-methoxy-9H-xanthen-9-yl)carbamothioyl)benzamide (12.7 g, 23.90 mmol).

Step 5: 1-Chloro-N,N,2-trimethylprop-1-en-1-amine (2.012 ml, 15.05 mmol) was added to a solution of N-((7-bromo-4-fluoro-9-(2-hydroxyethyl)-2-methoxy-9H-xanthen-9-yl)carbamothioyl)-benzamide (8 g, 15.05 mmol) in DCM (3 ml). The reaction mixture was stirred at RT for 8 hours. The reaction mixture was quenched with aqueous, saturated sodium carbonate solution and stirred for 10 minutes. The organic layer was separated and concentrated under reduced pressure to afford crude N-(7'-bromo-4'-fluoro-2'-methoxy-5,6-dihydrospiro[[1,3]thiazine-4,9'-xanthen]-2-yl)benzamide (7.7 g, 15.00 mmol, 100% yield).

Step 6: A 2 N solution of lithium hydroxide (22.50 ml, 45.0 mmol) was added to a solution of N-(7'-bromo-4'-fluoro-2'-methoxy-5,6-dihydrospiro[[1,3]thiazine-4,9'-xanthen]-2-yl) benzamide (7.7 g, 15.00 mmol) in MeOH (250 ml). The reaction mixture was heated to 65° C. for 3 hours. The reaction mixture was diluted with water and extracted with EtOAc. The combined organic extracts were concentrated under reduced pressure. The residue was purified via column chromatography [0-70% 90/10/1 (DCM/MeOH/ammonia) in DCM] to afford 7'-bromo-4'-fluoro-2'-methoxy-5,6-dihydrospiro[[1,3]thiazine-4,9'-xanthen]-2-amine as a racemic mixture (2 g, 2.443 mmol, 32% yield).

Example 24

Procedure X

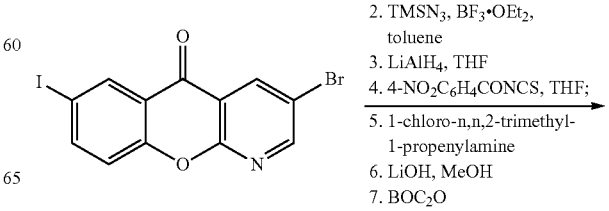

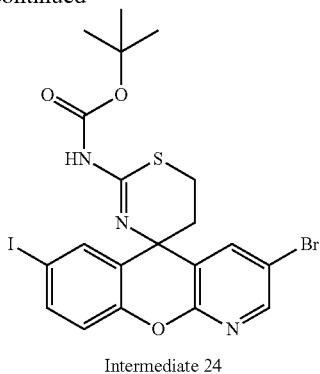

Intermediate 24

Synthesis of Intermediate 24

Step 1: To a suspension of tetraethoxytitanium (3.40 g, 14.93 mmol) in THF (16.58 ml) was added 3-bromo-7-iodo-5H-chromeno[2,3-b]pyridin-5-one (2.00 g, 4.98 mmol). The suspension was cooled to 0° C. and (2-ethoxy-2-oxoethyl)zinc (II) bromide (149 ml, 14.93 mmol) was added drop wise. The reaction mixture was allowed to warm to RT and stirred 1 h. The reaction mixture was quenched with aqueous, half-saturated NaHCO₃ solution (20 mL) and stirred for 30 min. The solution was filtered through a pad of celite and the filter cake was rinsed with EtOAc. The organic layer was separated and concentrated under reduced pressure to afford ethyl 2-(3-bromo-5-hydroxy-7-iodo-5H-chromeno[2,3-b]pyridin-5-yl)acetate as a yellowish solid.

Step 2: Azidotrimethylsilane (1.102 ml, 8.32 mmol) was added to a suspension of ethyl 2-(3-bromo-5-hydroxy-7-iodo-5H-chromeno[2,3-b]pyridin-5-yl)acetate (2.33 g, 4.75 mmol) in toluene (31.7 ml). The reaction mixture was cooled to 0° C. and (diethyloxonio)trifluoroborate (0.753 ml, 5.94 mmol) was added slowly. The reaction mixture was allowed to warm to RT. After 30 min, the reaction mixture was quenched with MeOH (5 mL) followed by aqueous, saturated NaHCO₃ solution (10 mL). The reaction mixture was extracted twice with EtOAc. The combined organic phases were washed with brine and dried over sodium sulfate. The solvent was removed under reduced pressure to afford ethyl 2-(5-azido-3-bromo-7-iodo-5H-chromeno[2,3-b]pyridin-5-yl)acetate as a yellow solid.

Step 3: LAH (1M in THF; 6.12 ml, 6.12 mmol) was added slowly to a −78 C cooled solution of ethyl 2-(5-azido-3-bromo-7-iodo-5H-chromeno[2,3-b]pyridin-5-yl)acetate (2.10 g, 4.08 mmol) in THF (40.8 ml). The reaction mixture was stirred at 78° C. for 15 min, and the reaction mixture was allowed to warm to RT and stirred for additional 30 min. The reaction mixture was cooled to 0° C., quenched with sodium sulfate decahydrate (2.90 g, 20.38 mmol) and allowed to stir 20 min. The solution was filtered through a pad of celite, the filter cake was eluted with 10% MeOH/DCM and the filtrate was concentrated. The residue was purified via flash chromatography (0-25% EtOAc/CH₂Cl₂) to afford 2-(5-amino-3-bromo-7-iodo-5H-chromeno[2,3-b]pyridin-5-yl)ethanol as a yellow solid.

Step 4: A solution of 2-(5-amino-3-bromo-7-iodo-5H-chromeno[2,3-b]pyridin-5-yl)ethanol (0.930 g, 2.080 mmol) in THF (20.80 ml) was added cooled to 0° C. and solid 4-nitrobenzoyl isothiocyanate (0.442 g, 2.122 mmol) was added. The reaction mixture was stirred at 0° C. for 20 min. The reaction mixture was concentrated under reduced pressure to yield N-((3-bromo-5-(2-hydroxyethyl)-7-iodo-5H-chromeno[2,3-b]pyridin-5-yl)carbamothioyl)-4-nitrobenzamide as a yellow solid.

Step 5: 1-Chloro-n,n,2-trimethyl-1-propenylamine (0.556 ml, 4.16 mmol) was added to a solution of N-((3-bromo-5-(2-hydroxyethyl)-7-iodo-5H-chromeno[2,3-b]pyridin-5-yl)carbamothioyl)-4-nitrobenzamide (1.363 g, 2.080 mmol) in CH₂Cl₂ (7 ml) at 0° C. The reaction mixture was allowed to warm to RT and stir for 2 h. The reaction mixture was quenched with aqueous, saturated NaHCO₃ solution (5 mL), and was further diluted with 10% MeOH/DCM and 5 mL water and N-(3-bromo-7-iodo-5',6'-dihydrospiro[chromeno[2,3-b]pyridine-5,4'-[1,3]thiazin]-2'-yl)-4-nitrobenzamide collected as a pink solid.

Step 6: A suspension of N-(3-bromo-7-iodo-5',6'-dihydrospiro[chromeno[2,3-b]pyridine-5,4'-[1,3]thiazin]-2'-yl)-4-nitrobenzamide (0.906 g, 1.422 mmol) and lithium hydroxide hydrate (0.179 g, 4.27 mmol) in MeOH (28.4 ml) was heated to reflux for 3 hours. The solvent was removed under reduced pressure to afford 3-bromo-7-iodo-5',6'-dihydrospiro[chromeno[2,3-b]pyridine-5,4'-[1,3]thiazin]-2'-amine as a pink solid.

Step 7: Aqueous, saturated NaHCO₃ solution (7.6 ml, 7.11 mmol) and boc anhydride (3.3 ml, 14.22 mmol) were added to a stirred suspension of 3-bromo-7-iodo-5',6'-dihydrospiro[chromeno[2,3-b]pyridine-5,4'-[1,3]thiazin]-2'-amine (694 mg, 1.422 mmol) in dioxane (7 ml). The reaction mixture was stirred for 16 h at RT. The reaction mixture was partitioned between EtOAc (50 mL) and water (20 ml). The aqueous layer was separated and extracted with EtOAc (1×10 mL). The combined organic extracts were washed with brine, dried over Na₂SO₄ and concentrated under reduced pressure. The residue was purified via flash chromatography (0-25% EtOAc/CH₂Cl₂) to afford tert-butyl (3-bromo-7-iodo-5',6'-dihydrospiro[chromeno[2,3-b]pyridine-5,4'-[1,3]thiazin]-2'-yl)carbamate a yellow solid.

Example 25

Procedure Y

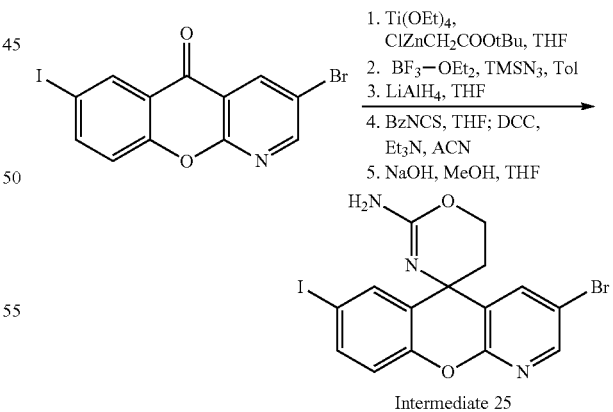

Intermediate 25

Synthesis of Intermediate 25

Step 1: 3-Bromo-7-iodo-5H-chromeno[2,3-b]pyridin-5-one (6.0 g, 14.93 mmol) was taken up in THF (150 mL). Neat tetraethoxytitanium (9.29 mL, 44.8 mmol) was added. An ether solution of (2-tert-butoxy-2-oxoethyl)zinc(II) chloride (0.5 M, 62.7 mL, 31.3 mmol) was added via cannula. The reaction was stirred at 0° C. for 30 min, then was warmed to rt and stirred 30 min. Excess organozinc reagent was quenched at 0° C. with 250 mL of half-saturated brine. The mixture was filtered through Celite, rinsing the solid with EtOAc (700 mL). The resulting filtrate's organic layer was separated and extracted further with saturated brine (50 mL), then was dried over sodium sulfate and concentrated. The crude tert-butyl 2-(3-bromo-5-hydroxy-7-iodo-5H-chromeno[2,3-b]pyridin-5-yl)acetate (7.8 g) was used in the next step without further purification.

Step 2: In a 1-L flask, the tert-butyl 2-(3-bromo-5-hydroxy-7-iodo-5H-chromeno[2,3-b]pyridin-5-yl)acetate (7.8 g, 15.05 mmol) was suspended in toluene (100 mL). Neat azidotrimethylsilane (2.99 mL, 22.58 mmol) was added. The mixture was cooled to 0° C., and BF$_3$-etherate (2.098 mL, 16.56 mmol) was added. The mixture was allowed to warm naturally in the ice bath. After two hours, the mixture was quenched with MeOH (3 mL), then with half-saturated aqueous NaHCO$_3$ (100 mL). The residue was extracted with 10% MeOH-EtOAc (3×200 mL). The organics were combined, washed with saturated brine (50 mL), dried over sodium sulfate and concentrated. The crude tert-butyl 2-(5-azido-3-bromo-7-iodo-5H-chromeno[2,3-b]pyridin-5-yl)acetate was used in the next step without further purification (7.27 g).

Step 3: In a 1-L flask, the tert-butyl 2-(5-azido-3-bromo-7-iodo-5H-chromeno[2,3-b]pyridin-5-yl)acetate (7.27 g, 13.38 mmol) was suspended in THF (100 mL) and the suspension was cooled to 0° C. A THF solution of LAH (1 M, 20.08 mL, 20.08 mmol) was added. After 30 min, the reaction mixture was quenched with careful addition of water (0.75 mL), 4 M aqueous NaOH (2.2 mL), and water (0.75 mL). The mixture was filtered through Celite, rinsing with THF (60 mL), then with EtOAc (150 mL). The combined filtrate was concentrated. The residue was purified through silica gel (400 mL) which had been deactivated with Et$_3$N (40 mL), using 100:100:1 EtOAc-hexane-Et$_3$N, to afford 2-(5-amino-3-bromo-7-iodo-5H-chromeno[2,3-b]pyridin-5-yl)ethanol (2.24 g).

Step 4: In a 250-mL flask, the 2-(5-amino-3-bromo-7-iodo-5H-chromeno[2,3-b]pyridin-5-yl)ethanol (2.24 g, 5.01 mmol) was dissolved in THF (30 mL). Benzoyl isothiocyanate (0.607 mL, 4.51 mmol) was added. After 1 h, the mixture was concentrated. The residue was taken up in ACN (30 mL), and catalytic TEA (0.069 mL, 0.501 mmol) was added, followed by DCC (1.137 g, 5.51 mmol). A water-cooled condenser was affixed, and the solution was stirred in an 80° C. oil bath for 2 h. The reaction was then concentrated. The residue was used directly in the next step without further purification.

Step 5: In a 150-mL resealable vessel, the crude N-(3-bromo-7-iodo-5',6'-dihydrospiro[chromeno[2,3-b]pyridine-5,4'-[1,3]oxazine]-2'-yl)benzamide from the above procedure was dissolved in 1:1 THF-MeOH (12 mL). Aqueous NaOH (12.04 mL, 30.1 mmol) was added. The vessel was sealed and heated in a 90° C. oil bath. After 2 h, the reaction was concentrated to remove most of the THF and MeOH. The aqueous residue was diluted with water (35 mL), and the aqueous layer was extracted with 5% MeOH-dcm (3×100 mL). The organics were combined, washed with dilute brine (35 mL), dried over sodium sulfate and concentrated. The residue was purified through silica gel (300 mL) using 3% MeOH-dcm, to afford intermediate 25 (3-bromo-7-iodo-5',6'-dihydrospiro [chromeno[2,3-b]pyridine-5,4'-[1,3]oxazin]-2'-amine) (1.99 g). MS (m/z) 472/474 (M+H)$^+$.

Example 26

Procedure Z

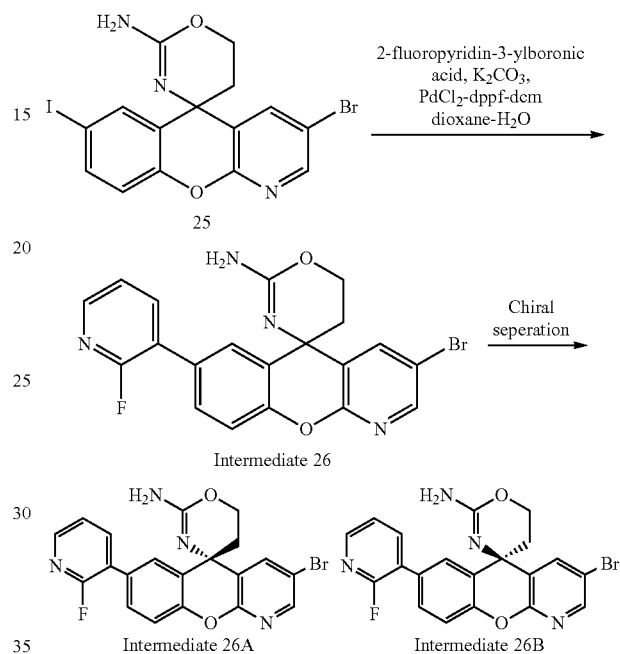

Synthesis of Intermediates 26, 26A and 26B

Step 1: In a 150-mL resealable flask, potassium carbonate (1.557 g, 11.27 mmol 3-bromo-7-iodo-5',6'-dihydrospiro [chromeno[2,3-b]pyridine-5,4'-[1,3]oxazin]-2'-amine (intermediate 25 1.97 g, 4.17 mmol), 2-fluoropyridin-3-ylboronic acid (0.441 g, 3.13 mmol), and PdCl$_2$-dppf-dcm (0.225 g, 0.275 mmol) were suspended in dioxane (18 mL) and water (6 mL). Argon was blown through the vessel, which was sealed and heated in an 85° C. oil bath for 2 h. The reaction was concentrated to remove most of the dioxane. The aqueous residue was diluted further with dilute brine (50 mL), and the aqueous phase was extracted with 10% MeOH-DCM (3×100 mL). The organics were combined, washed with dilute brine (30 mL), dried over sodium sulfate and concentrated. The residue was purified by chromatography (4% MeOH/DCM), to afford (3-bromo-7-(2-fluoropyridin-3-yl)-5',6'-dihydrospiro[chromeno[2,3-b]pyridine-5,4'-[1,3]oxazin]-2'-amine) (1.03 g). MS (m/z) 441/443 (M+H)$^+$.

Step 2: Intermediates ((S)-3-bromo-7-(2-fluoropyridin-3-yl)-5',6'-dihydrospiro[chromeno[2,3-b]pyridine-5,4'-[1,3]oxazin]-2'-amine) (intermediate 26A, 350 mg), and its enantiomer ((R)-3-bromo-7-(2-fluoropyridin-3-yl)-5',6'-dihydrospiro[chromeno[2,3-b]pyridine-5,4'-[1,3]oxazin]-2'-amine (intermediate 26 B, 500 mg) were obtained from racemic (3-bromo-7-(2-fluoropyridin-3-yl)-5',6'-dihydrospiro[chromeno[2,3-b]pyridine-5,4'-[1,3]oxazin]-2'- amine) using similar chiral separation conditions as described herein for intermediate 10. MS (m/z) 441/443 (M+H)+.

Example 27

Procedure ZZ

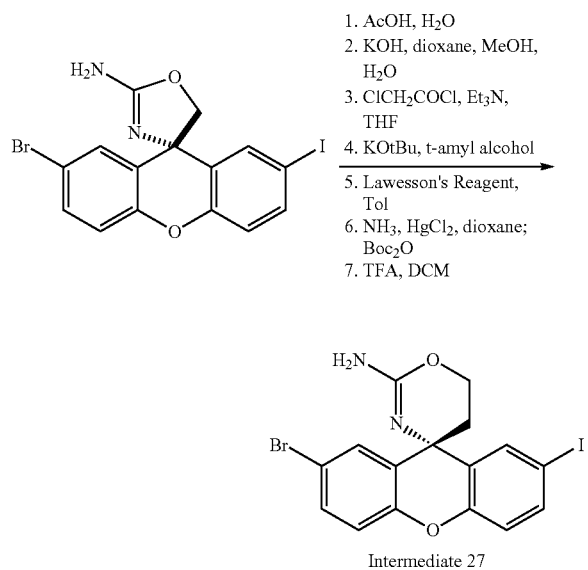

Synthesis of Intermediate 27

Step 1: In a 350-mL resealable vessel the (S)-2'-bromo-7'-iodo-5H-spiro[oxazole-4,9'-xanthen]-2-amine (11.5 g, 25.2 mmol) was taken up in AcOH (125 mL) and water (31 mL). The vessel was sealed and heated in a 140° C. oil bath for 14 h. The reaction was concentrated to remove most of the AcOH. The reaction residue was neutralized with 1M aqueous $Na_2CO_3$ (250 mL). The residue was filtered through Celite, rinsing with 5% MeOH-DCM (800 mL). The filtrate's organic layer was separated, dried over sodium sulfate and concentrated. The crude (S)-2'-bromo-7'-iodospiro[oxazolidine-4,9'-xanthen]-2-one was used in the next step without further purification.

Step 2: In a 350-mL resealable vessel, the (S)-2'-bromo-7'-iodospiro[oxazolidine-4,9'-xanthen]-2-one (11 g, 24.02 mmol) was dissolved in 1:1 MeOH-dioxane (160 mL). Aqueous KOH (5 M, 48.0 mL, 240 mmol) was added. The vessel was sealed and placed in a 105° C. oil bath. After 24 h, the reaction was concentrated to remove the MeOH and most of the dioxane. The residue was diluted with water (200 mL) and the aqueous phase was extracted with 5% MeOH-DCM (4×200 mL). The organics were combined, washed with dilute brine (35 mL), dried over sodium sulfate and concentrated. The residue was purified by chromatography (1.5% MeOH/DCM) to afford (S)-(9-amino-2-bromo-7-iodo-9H-xanthen-9-yl)methanol (3.84 g, 8.89 mmol).

Step 3: The (S)-(9-amino-2-bromo-7-iodo-9H-xanthen-9-yl)methanol (3.84 g, 8.89 mmol) was dissolved in THF (200 mL). The solution was cooled to 0° C., and TEA (1.425 mL, 10.22 mmol) and 2-chloroacetyl chloride (0.707 mL, 9.07 mmol) were added. The reaction was allowed to warm naturally to RT. After 14 h, the reaction was concentrated. The residue was taken up in aqueous 1 M $Na_2CO_3$ (50 mL) and the aqueous phase was extracted with 7.5% MeOH-DCM (3×133 mL). The organics were combined, washed with aqueous 1 M $Na_2CO_3$ (30 mL), dried over sodium sulfate and concentrated. The residue was dissolved in THF (100 mL) and aqueous 1 M $Na_2CO_3$ (15 mL) was added. The reaction was concentrated. The residue was taken up in 5% MeOH-dcm (400 mL) and the organic phase was washed with dilute brine (40 mL), dried over sodium sulfate and concentrated to afford crude (S)—N-(2-bromo-9-(hydroxymethyl)-7-iodo-9H-xanthen-9-yl)-2-chloroacetamide, which was used in the next step without further purification.

Step 4: In a 500-mL flask (S)—N-(2-bromo-9-(hydroxymethyl)-7-iodo-9H-xanthen-9-yl)-2-chloroacetamide (4.52 g, 8.89 mmol) was dissolved in t-amyl alcohol (125 mL). Potassium t-butoxide (2.244 g, 20.00 mmol) was added. After 14 h, the reaction was concentrated. The residue was taken up in dilute aqueous $NH_4Cl$ (50 mL) and the aqueous phase was extracted with 5% MeOH-DCM (3×133 mL). The organics were combined, washed with dilute brine (25 mL), dried over sodium sulfate and concentrated. The material was purified through silica gel (500 mL) using 30% EtOAc-hexane to afford (S)-2'-bromo-7'-iodospiro[morpholine-3,9'-xanthen]-5-one (1.92 g, 4.07 mmol).

Step 5: In a 250-mL flask, the (S)-2'-bromo-7'-iodospiro[morpholine-3,9'-xanthen]-5-one (1.483 g, 3.14 mmol) was suspended in toluene (30 mL). Lawesson's reagent (0.794 g, 1.963 mmol) was added. An air-cooled condenser was affixed, and the reaction vessel was placed in a 90° C. oil bath After 7 h, the reaction was concentrated. Without working it up, the residue was purified by chromatography (15% EtOAc/hexanes) to afford (S)-2'-bromo-7'-iodospiro[morpholine-3,9'-xanthene]-5-thione (1.25 g, 2.56 mmol).

Step 6: In a 350-mL resealable vessel, the (S)-2'-bromo-7'-iodospiro[morpholine-3,9'-xanthene]-5-thione (1.25 g, 2.56 mmol) was dissolved in a dioxane solution of ammonia (0.5 M, 61.5 mL, 30.7 mmol). After the solid had dissolved, mercury(II) chloride (1.043 g, 3.84 mmol) was added. The vessel was sealed and placed in a 55° C. oil bath overnight. The reaction was filtered through Celite, rinsing with DCM (50 mL). The mixture was concentrated to remove the DCM, and $Boc_2O$ (0.84 g, 3.84 mmol) and $Et_3N$ (0.535 mL, 3.84 mmol) were added. After 1.5 h, the mixture was concentrated, and the residue was purified by chromatography (15% EtOAc/hexanes) to afford impure (S)-tert-butyl 2'-bromo-7'-iodo-2,6-dihydrospiro[[1,4]oxazine-3,9'-xanthene]-5-ylcarbamate.

Step 7: In a 150-mL resealable vessel, the (S)-tert-butyl 2'-bromo-7'-iodo-2,6-dihydrospiro[[1,4]oxazine-3,9'-xanthene]-5-ylcarbamate (1.475 g, 2.58 mmol) was dissolved in dcm (10 mL), and 2,2,2-trifluoroacetic acid (1.989 mL, 25.8 mmol) was added. The vessel was sealed and placed in a 50° C. oil bath. After 2 h, the reaction was concentrated and the mixture was neutralized with 0.5 M aqueous $Na_2CO_3$ (15 mL) and the aqueous phase was extracted with 5% MeOH-dcm (3×33 mL). The organics were combined, washed with dilute brine (10 mL), dried over sodium sulfate and concentrated. The residue was purified by chromatography (5.5% MeOH/DCM) to afford (S)-2'-bromo-7'-iodo-2,6-dihydrospiro[[1,4]oxazine-3,9'-xanthen]-5-amine (151 mg, 0.321 mmol). MS (m/z) 471/473 (M+H)+.

Example 28

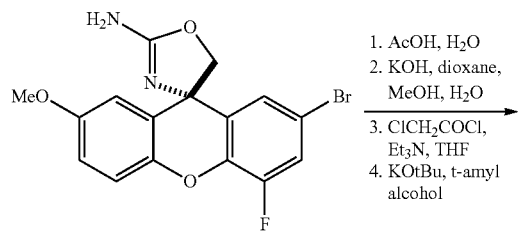

1. AcOH, H₂O
2. KOH, dioxane, MeOH, H₂O
3. ClCH₂COCl, Et₃N, THF
4. KOtBu, t-amyl alcohol

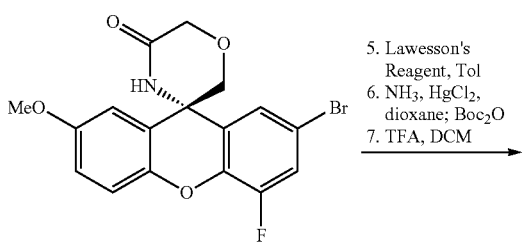

Intermediate 28

5. Lawesson's Reagent, Tol
6. NH₃, HgCl₂, dioxane; Boc₂O
7. TFA, DCM

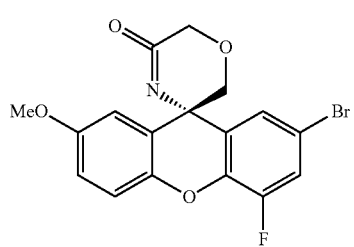

Intermediate 29

Synthesis of Intermediates 28 and 29

Step 1: The same reagents and reaction conditions in Steps 1-4 of Procedure ZZ were used to convert (S)-2'-bromo-4'-fluoro-7'-methoxy-5H-spiro[oxazole-4,9'-xanthen]-2-amine to (S)-2'-bromo-4'-fluoro-7'-methoxyspiro[morpholine-3,9'-xanthen]-5-one. MS (m/z) 394/396 (M+H)⁺.

Step 2: The same reagents and reaction conditions in Steps 5-7 of Procedure ZZ were used to convert (S)-2'-bromo-4'-fluoro-7'-methoxyspiro[morpholine-3,9'-xanthen]-5-one to (S)-2'-bromo-4'-fluoro-7'-methoxy-2,6-dihydrospiro[[1,4]oxazine-3,9'-xanthen]-5-amine. MS (m/z) 393/395 (M+H)⁺.

Example 29

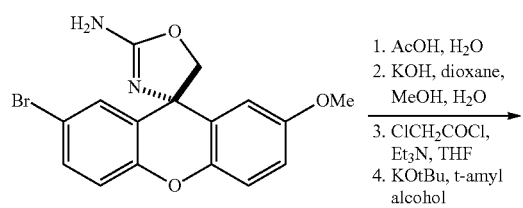

1. AcOH, H₂O
2. KOH, dioxane, MeOH, H₂O
3. ClCH₂COCl, Et₃N, THF
4. KOtBu, t-amyl alcohol

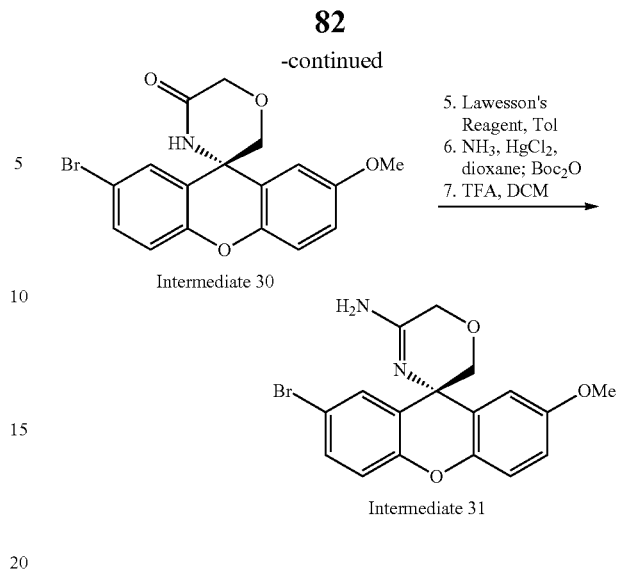

Intermediate 30

5. Lawesson's Reagent, Tol
6. NH₃, HgCl₂, dioxane; Boc₂O
7. TFA, DCM

Intermediate 31

Synthesis of Intermediates 30 and 31

Step 1: The same reagents and conditions in Steps 1-4 in Procedure ZZ were used to convert (S)-2'-bromo-7'-methoxy-5H-spiro[oxazole-4,9'-xanthen]-2-amine to (S)-2'-bromo-7'-methoxyspiro[morpholine-3,9'-xanthen]-5-one.

Step 2: The same reagents and conditions in Steps 5-7 of Procedure ZZ were used to convert (S)-2'-bromo-7'-methoxyspiro[morpholine-3,9'-xanthen]-5-one to (S)-2'-bromo-7'-methoxy-2,6-dihydrospiro[[1,4]oxazine-3,9'-xanthen]-5-amine. MS (m/z) 375/377 (M+H)⁺.

Example 30

Method A1

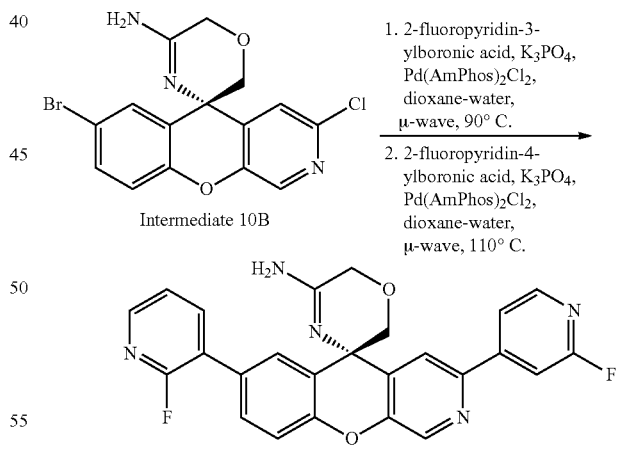

Intermediate 10B 1. 2-fluoropyridin-3-ylboronic acid, K₃PO₄, Pd(AmPhos)₂Cl₂, dioxane-water, μ-wave, 90° C.
2. 2-fluoropyridin-4-ylboronic acid, K₃PO₄, Pd(AmPhos)₂Cl₂, dioxane-water, μ-wave, 110° C.

Synthesis of (S)-7-(2-fluoropyridin-3-yl)-3-(2-fluoropyridin-4-yl)-2',6'-dihydrospiro[chromeno[2,3-c]pyridine-5,3'-[1,4]oxazin]-5'-amine Step 1: A vial was charged with (S)-7-bromo-3-chloro-2',6'-dihydrospiro[chromeno[2,3-c]pyridine-5,3'-[1,4]oxazin]-5'-amine (546.36 mg, 1.435 mmol), 2-fluoropyridin-3-ylboronic acid (303 mg, 2.153 mmol), potassium phosphate (914 mg, 4.31 mmol), and bis[di-tert-butyl(4-dimethylaminophenyl)phosphine]dichloropalladium(II) (50.8 mg, 0.072 mmol). The vial was flushed with Argon, and then dioxane (5383 µL) and water (1794 µL) were added. The vial was sealed and heated in a Biotage Initiator microwave reactor for 20 min at 90° C. The reaction mixture was diluted with water and extracted with EtOAc (3×). The combined organic extracts were dried over sodium sulfate, concentrated under reduced pressure. The residue was purified by chromatography (0-100% EtOAc/Hexane) to give (S)-3-chloro-7-(2-fluoropyridin-3-yl)-2',6'-dihydrospiro[chromeno[2,3-c]pyridine-5,3'-[1,4]oxazin]-5'-amine (510.4 mg, 95% purity) as an off-white solid.

Step 2: A vial was charged with (S)-3-chloro-7-(2-fluoropyridin-3-yl)-2',6'-dihydrospiro[chromeno[2,3-c]pyridine-5,3'-[1,4]oxazin]-5'-amine (104.72 mg, 0.264 mmol), 2-fluoropyridin-4-ylboronic acid (74.4 mg, 0.528 mmol), potassium phosphate (168 mg, 0.792 mmol), and bis[di-tert-butyl(4-dimethylaminophenyl)phosphine]dichloropalladium(II) (9.34 mg, 0.013 mmol). The vial was flushed with Argon, then dioxane (990 µL) and water (330 µL) were added. The vial was sealed and heated in a Biotage Initiator microwave reactor for 30 min at 110° C. The mixture was extracted with EtOAc (3×), and the combined organic extracts were concentrated under reduced pressure. The residue was purified by chromatography (30-60% of a 90:10:1 mixture of DCM/MeOH/NH$_4$OH in DCM) to give (S)-7-(2-fluoropyridin-3-yl)-3-(2-fluoropyridin-4-yl)-2',6'-dihydrospiro[chromeno[2,3-c]pyridine-5,3'-[1,4]oxazin]-5'-amine (90 mg) as a light-yellow solid. MS m/z=458.2 [M+H]$^+$.

$^1$H NMR (400 MHz, DMSO-d$_6$) δ=8.72 (s, 1 H), 8.38 (d, J=5.3 Hz, 1 H), 8.26 (td, J=1.4, 3.2 Hz, 1 H), 8.11 (ddd, J=2.0, 7.7, 10.1 Hz, 1 H), 8.00-7.87 (m, 2 H), 7.75 (s, 1 H), 7.64 (td, J=1.6, 8.7 Hz, 1 H), 7.57-7.47 (m, 2 H), 7.41 (d, J=8.4 Hz, 1 H), 6.29 (br. s., 2 H), 4.45-4.20 (m, 2 H), 3.68-3.47 (m, 2 H).

Example 31

Method A2

3-b]pyridine-5,3'-[1,4]oxazin]-5'-amine, and potassium carbonate (0.293 g, 2.118 mmol) was treated with 2.5 mL dioxane and 1 mL water. The vial was then flushed with argon, sealed and heated to 80° C. for 1 hr. The reaction mixture was diluted with EtOAc, dried over MgSO$_4$ and concentrated under reduced pressure to yield 3-bromo-7-(2-fluoropyridin-3-yl)-2',6'-dihydrospiro[chromeno[2,3-b]pyridine-5,3'-[1,4]oxazin]-5'-amine (0.309 g, 0.700 mmol, 132% yield). This material was used without further purification.

Step 2: A vial charged with Pd(PPh$_3$)$_4$ (0.079 g, 0.068 mmol), copper(I) iodide (0.013 g, 0.068 mmol), 18-crown-6 (0.045 g, 0.170 mmol), potassium fluoride (0.118 g, 2.040 mmol), trimethyl((3-methyloxetan-3-yl)ethynyl)silane (0.229 g, 1.360 mmol), and 3-bromo-7-(2-fluoropyridin-3-yl)-2',6'-dihydrospiro[chromeno[2,3-b]pyridine-5,3'-[1,4]oxazin]-5'-amine (0.300 g, 0.680 mmol) was treated with 3 mL DMF, sealed under argon, and heated to 110° C. overnight. The reaction mixture was then poured onto water (10 mL) and extracted with EtOAc (3×10 mL). The combined organic layers were dried over MgSO$_4$ and concentrated under reduced pressure. Purification of the crude residue by column chromatography [0-50% (9:1 DCM/MeOH)/DCM] gave (S)-7-(2-fluoropyridin-3-yl)-3-((3-methyloxetan-3-yl)ethynyl)-2',6'-dihydrospiro[chromeno[2,3-b]pyridine-5,3'-[1,4]oxazin]-5'-amine (0.079 g, 0.094 mmol, 25.46% yield).

Example 32

Method A3

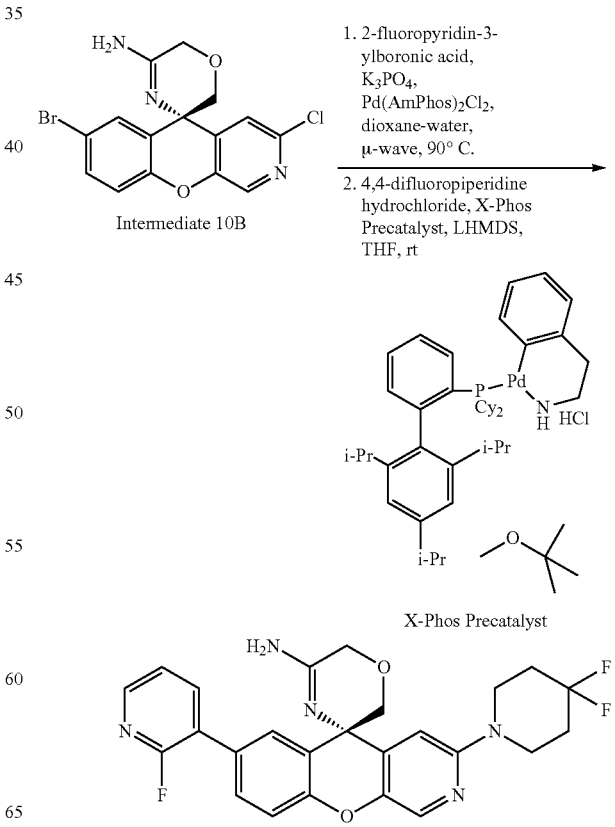

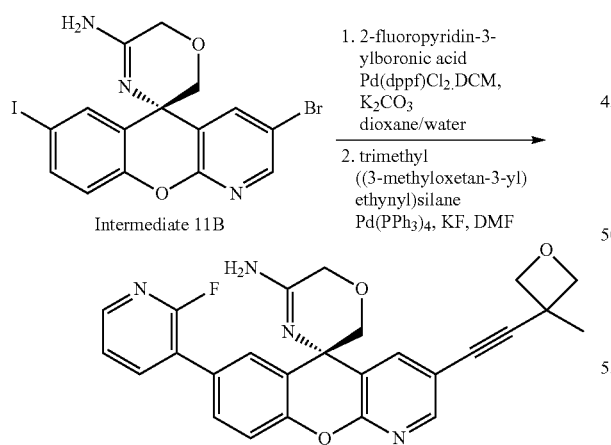

Synthesis of (S)-7-(2-fluoropyridin-3-yl)-3-((3-methyloxetan-3-yl)ethynyl)-2',6'-dihydrospiro[chromeno[2,3-b]pyridine-5,3'-[1,4]oxazin]-5'-amine Step 1: A vial charged with 2-fluoropyridin-3-ylboronic acid (0.078 g, 0.556 mmol), PdCl$_2$(dppf)-CH$_2$Cl$_2$ (0.022 g, 0.026 mmol), (S)-3-bromo-7-iodo-2',6'-dihydrospiro[chromeno[2,

Synthesis of (S)-3-(4,4-difluoropiperidin-1-yl)-7-(2-fluoropyridin-3-yl)-2',6'-dihydrospiro[chromeno[2,3-c]pyridine-5,3'-[1,4]oxazin]-5'-amine Step 1: A vial was charged with (S)-7-bromo-3-chloro-2',6'-dihydrospiro[chromeno[2,3-c]pyridine-5,3'-[1,4]oxazin]-5'-amine (546.36 mg, 1.435 mmol), 2-fluoropyridin-3-ylboronic acid (303 mg, 2.153 mmol), potassium phosphate (914 mg, 4.31 mmol), and bis[di-tert-butyl(4-dimethylaminophenyl)phosphine]dichloropalladium(II) (50.8 mg, 0.072 mmol). The vial was flushed with Ar (g), then dioxane (5383 µL) and water (1794 µL) were added in sequence. The vial was sealed and heated in a Biotage Initiator microwave reactor for 20 min at 90° C. The mixture was diluted with water and extracted with EtOAc (3x). The combined organic extracts were dried over sodium sulfate, filtered, and concentrated. The residue was purified by chromatography (0-100% EtOAc/Hexane) to give (S)-3-chloro-7-(2-fluoropyridin-3-yl)-2',6'-dihydrospiro[chromeno[2,3-c]pyridine-5,3'-[1,4]oxazin]-5'-amine (510.4 mg, 95% purity) as an off-white solid.

Step 2: A vial was charged with (S)-3-chloro-7-(2-fluoropyridin-3-yl)-2',6'-dihydrospiro[chromeno[2,3-c]pyridine-5,3'-[1,4]oxazin]-5'-amine (60.4 mg, 0.152 mmol), 4,4-difluoropiperidine hydrochloride (27.7 mg, 0.228 mmol), and X-Phos Precatalyst (25.2 mg, 0.030 mmol). The vial was flushed with Ar (g), then capped with a septum. Lithium bis(trimethylsilyl)amide (1M in THF) (533 µL, 0.533 mmol) was added in one portion at rt. After 30 min. the reaction mixture was diluted with saturated aq. ammonium chloride solution and extracted with EtOAc (3x). The combined organic extracts were dried over sodium sulfate, filtered, and concentrated. The residue was purified by chromatography (30% of a 90:10:1 mixture of DCM/MeOH/NH$_4$OH in DCM) to give 43 mg of an oil. The oil was further purified by reverse-phase HPLC (15-90% CH$_3$CN/H$_2$O with 0.1% TFA). Fractions containing product were combined and washed with saturated aq. sodium bicarbonate solution. The mixture was extracted with DCM (3x). The combined organic extracts were dried over sodium sulfate, and concentrated to give (S)-3-(4,4-difluoropiperidin-1-yl)-7-(2-fluoropyridin-3-yl)-2',6'-dihydrospiro[chromeno[2,3-c]pyridine-5,3'-[1,4]oxazin]-5'-amine as a white solid. MS m/z=482.1 [M+H]$^+$.

$^1$H NMR (400 MHz, DMSO-d$_6$) δ=8.23 (td, J=1.5, 4.8 Hz, 1 H), 8.14 (d, J=0.4 Hz, 1 H), 8.07 (ddd, J=1.9, 7.5, 10.3 Hz, 1 H), 7.59-7.54 (m, 1 H), 7.51-7.43 (m, 2 H), 7.29 (d, J=8.5 Hz, 1 H), 6.72 (s, 1 H), 6.14 (br. s., 2 H), 4.27-4.14 (m, 2 H), 3.60 (t, J=5.7 Hz, 4 H), 3.47-3.38 (m, 2 H), 2.09-1.96 (m, 4 H).

Example 33

Method A4

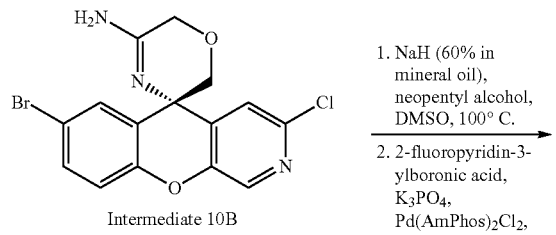

1. NaH (60% in mineral oil), neopentyl alcohol, DMSO, 100° C.
2. 2-fluoropyridin-3-ylboronic acid, K$_3$PO$_4$, Pd(AmPhos)$_2$Cl$_2$, dioxane-water, µ-wave, 90° C.

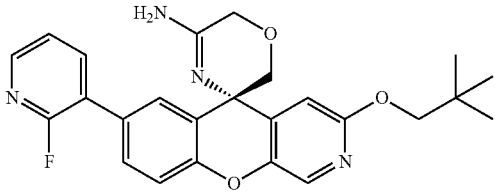

Synthesis of (S)-7-(2-fluoropyridin-3-yl)-3-(neopentyloxy)-2',6'-dihydrospiro[chromeno[2,3-c]pyridine-5,3'-[1,4]oxazin]-5'-amine Step 1: A vial was charged with 2,2-dimethylpropan-1-ol (100 mg, 1.130 mmol) and DMSO (1130 µL). Sodium hydride (60% in mineral oil; 45.2 mg, 1.130 mmol) was added. The vial was placed in a 100° C. oil bath for 5 min. the reaction mixture was cooled to room temperature and (S)-7-bromo-3-chloro-2',6'-dihydrospiro[chromeno[2,3-c]pyridine-5,3'-[1,4]oxazin]-5'-amine (86 mg, 0.226 mmol) was added in one portion. The vial was sealed and heated in a 100° C. oil bath for 2 h. The mixture was cooled to room temperature, then diluted with water and EtOAc. Brine was added, and the layers were separated. The aq. layer was extracted with EtOAc (2x). The combined organic extracts were dried over sodium sulfate, and concentrated. The residue was purified by chromatography (0-100% EtOAc/Hexane) to give (S)-7-bromo-3-(neopentyloxy)-2',6'-dihydrospiro[chromeno[2,3-c]pyridine-5,3'-[1,4]oxazin]-5'-amine as a light-yellow solid.

Step 2: A vial was charged with (S)-7-bromo-3-(neopentyloxy)-2',6'-dihydrospiro[chromeno[2,3-c]pyridine-5,3'-[1,4]oxazin]-5'-amine (51 mg, 0.118 mmol), 2-fluoropyridin-3-ylboronic acid (33.2 mg, 0.236 mmol), potassium phosphate (75 mg, 0.354 mmol), and bis[di-tert-butyl(4-dimethylaminophenyl)phosphine]dichloropalladium(II) (4.18 mg, 5.90 µmol). The vial was flushed with Ar (g), then dioxane (442 µL) and water (147 µL) were added in sequence. The vial was sealed and heated in a Biotage Initiator microwave reactor for 20 min at 90° C. The mixture was extracted with EtOAc (3x), and the combined organic extracts were concentrated. The residue was purified by chromatography (30% of a 90:10:1 mixture of DCM/MeOH/NH$_4$OH in DCM) to give (S)-7-(2-fluoropyridin-3-yl)-3-(neopentyloxy)-2',6'-dihydrospiro[chromeno[2,3-c]pyridine-5,3'-[1,4]oxazin]-5'-amine (46.23 mg) as an off-white solid. MS m/z=449.2 [M+H]$^+$.

$^1$H NMR (400 MHz, DMSO-d$_6$) δ=8.23 (td, J=1.5, 4.8 Hz, 1 H), 8.14-8.01 (m, 2 H), 7.65-7.54 (m, 1 H), 7.53-7.43 (m, 2 H), 7.31 (d, J=8.4 Hz, 1 H), 6.64 (s, 1 H), 6.16 (br. s., 2 H), 4.33-4.13 (m, 2 H), 3.99-3.84 (m, 2 H), 3.53-3.36 (m, 2 H), 1.02 (br. s., 9 H).

Example 34

Method A5

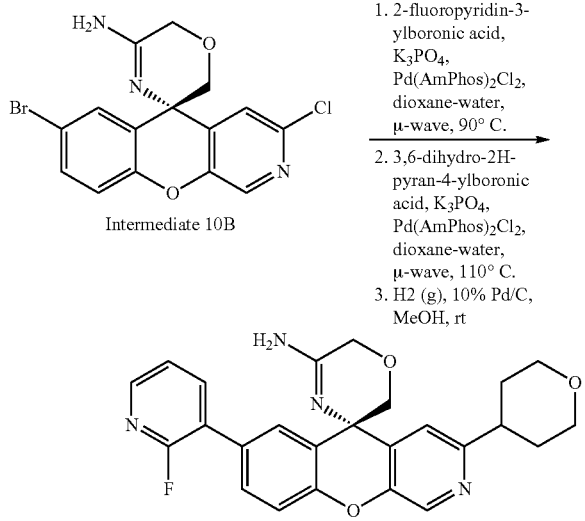

Synthesis of (S)-7-(2-fluoropyridin-3-yl)-3-(tetrahydro-2H-pyran-4-yl)-2',6'-dihydrospiro[chromeno[2,3-c]pyridine-5,3'-[1,4]oxazin]-5'-amine Step 1: A vial was charged with (S)-7-bromo-3-chloro-2',6'-dihydrospiro[chromeno[2,3-c]pyridine-5,3'-[1,4]oxazin]-5'-amine (546.36 mg, 1.435 mmol), 2-fluoropyridin-3-ylboronic acid (303 mg, 2.153 mmol), potassium phosphate (914 mg, 4.31 mmol), and bis[di-tert-butyl(4-dimethylaminophenyl)phosphine]dichloropalladium(II) (50.8 mg, 0.072 mmol). The vial was flushed with Ar (g), then dioxane (5383 μL) and water (1794 μL) were added in sequence. The vial was sealed and heated in a Biotage Initiator microwave reactor for 20 min at 90° C. The mixture was diluted with water and extracted with EtOAc (3×). The combined organic extracts were dried over sodium sulfate, filtered, and concentrated. The residue was purified by chromatography on silica gel (0-100% EtOAc/Hexane) to give (S)-3-chloro-7-(2-fluoropyridin-3-yl)-2',6'-dihydrospiro[chromeno[2,3-c]pyridine-5,3'-[1,4]oxazin]-5'-amine (510.4 mg) as an off-white solid containing ca. 5% of the bis-coupled byproduct.

Step 2: A vial was charged with and (S)-3-chloro-7-(2-fluoropyridin-3-yl)-2',6'-dihydrospiro[chromeno[2,3-c]pyridine-5,3'-[1,4]oxazin]-5'-amine (79.05 mg, 0.199 mmol), 3,6-dihydro-2H-pyran-4-ylboronic acid (76 mg, 0.598 mmol), bis[di-tert-butyl(4-dimethylaminophenyl)phosphine]dichloropalladium(II) (7.05 mg, 9.96 μmol), and potassium phosphate (127 mg, 0.598 mmol). Dioxane (747 μL) and water (249 μL) were added, and the vial was sealed and heated in a Biotage Initiator microwave reactor for 30 min at 110° C. The mixture was extracted with EtOAc (3×), and the combined organic extracts were concentrated. The residue was purified by chromatography on silica gel (0-10% MeOH/DCM) to give (S)-3-(3,6-dihydro-2H-pyran-4-yl)-7-(2-fluoropyridin-3-yl)-2',6'-dihydrospiro[chromeno[2,3-c]pyridine-5,3'-[1,4]oxazin]-5'-amine (82.18 mg) as a yellow solid.

Step 3: A 10-mL round-bottom flask was charged with (S)-3-(3,6-dihydro-2H-pyran-4-yl)-7-(2-fluoropyridin-3-yl)-2',6'-dihydrospiro[chromeno[2,3-c]pyridine-5,3'-[1,4]oxazin]-5'-amine (82.8 mg, 0.186 mmol) and MeOH (2.5 mL). The flask was flushed with Ar (g), then 10% Pd/C (ca. 35 mg) was added. H₂ (g) was bubbled through the mixture for 1 min, then the reaction mixture was stirred under an H₂ (g) atmosphere overnight. An additional portion of 10% Pd/C (21 mg) was added, and H₂ (g) was bubbled through for 1 min. After stirring overnight, the mixture was filtered through celite, and the filter cake was washed with methanol. The filtrate was concentrated, and the residue was purified by chromatography (10-40% of a 90:10:1 mixture of DCM/MeOH/NH₄OH in DCM) to give (S)-7-(2-fluoropyridin-3-yl)-3-(tetrahydro-2H-pyran-4-yl)-2',6'-dihydrospiro[chromeno[2,3-c]pyridine-5,3'-[1,4]oxazin]-5'-amine (72 mg) as an off-white solid. [M+H]+=447.2.

Example 35A

Method A6

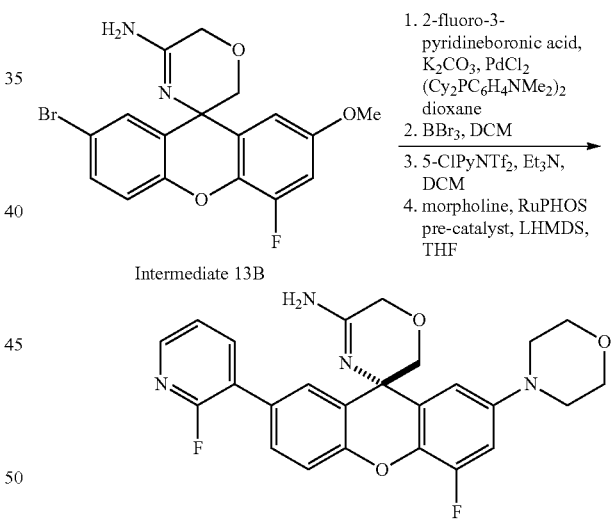

Synthesis of (S)-4'-fluoro-7'-(2-fluoropyridin-3-yl)-2'-morpholino-2,6-dihydrospiro[[1,4]oxazine-3,9'-xanthen]-5-amine Step 1: A 250 ml RBF was charged with 7'-bromo-4'-fluoro-2'-methoxy-2,6-dihydrospiro[[1,4]oxazine-3,9'-xanthen]-5-amine (2.73 g, 6.94 mmol), bis(di-tert-butyl(4-dimethylaminophenyl)phosphine)dichloropalladium(II) (0.492 g, 0.694 mmol) and 2-fluoropyridin-3-ylboronic acid (1.467 g, 10.41 mmol). Dioxane (40 mL) and potassium carbonate (1M in water; 20.83 mL, 20.83 mmol) were added and the mixture was flushed with argon and heated at 85° C. for 30 minutes.

The mixture was cooled to RT, diluted with EtOAc and the organic layer was separated and concentrated in vacuo to give a yellow residue. After triturating with 10 ml of ethanol the solid was filtered off, washed with EtOH (2×1 ml) and dried on air overnight to afford 4'-fluoro-7'-(2-fluoropyridin-3-yl)-2'-methoxy-2,6-dihydrospiro[[1,4]oxazine-3,9'-xanthen]-5-amine (2.11 g, 5.15 mmol).

Step 2: To a suspension of 4'-fluoro-7'-(2-fluoropyridin-3-yl)-2'-methoxy-2,6-dihydrospiro[[1,4]oxazine-3,9'-xanthen]-5-amine (1.668 g, 4.07 mmol) in DCM (12 ml) was added boron tribromide (0.963 mL, 10.19 mmol) at 0° C. The reaction mixture was stirred for 45 hrs at 0° C. The reaction mixture was allowed to warm to RT and was stirred for additional 2 hrs. The reaction mixture was cooled to 0° C. and quenched by addition of saturated aqueous NaHCO₃ solution (~10 mL). The solvent was removed in vacuo, the mixture was diluted with water and filtered. The solid was washed with water and dried under reduced pressure to afford 5-amino-4'-fluoro-7'-(2-fluoropyridin-3-yl)-2,6-dihydrospiro[[1,4]oxazine-3,9'-xanthen]-2'-ol (1.53 g, 3.87 mmol, 95% yield).

Step 3: To a suspension of 5-amino-4'-fluoro-7'-(2-fluoropyridin-3-yl)-2,6-dihydrospiro[[1,4]oxazine-3,9'-xanthen]-2'-ol (1.01 g, 2.55 mmol) in DCM (12.77 mL) were added TEA (1.424 mL, 10.22 mmol) and N-(5-chloropyridin-2-yl)-1,1,1-trifluoro-N-(trifluoromethylsulfonyl)methanesulfonamide (1.103 g, 2.81 mmol). After stirring for 2 hours the reaction mixture was washed 3× with 2N NaOH solution followed by brine. The solution was then concentrated. The yellow residue was diluted with DCM (5 ml) and the white precipitate was filtered, washed with DCM and dried under a stream of air to afford 355 mg (26%) of pure product. The filtrate was purified by chromatography (5-40% DCM/MeOH/NH₄OH in DCM) to afford 5-amino-5'-fluoro-2'-(2-fluoropyridin-3-yl)-2,6-dihydrospiro[[1,4]oxazine-3,9'-xanthene]-7'-yl trifluoromethanesulfonate (880 mg, 1.668 mmol, 65.3% yield) as a white foam. Total isolated 5-amino-5'-fluoro-2'-(2-fluoropyridin-3-yl)-2,6-dihydrospiro[[1,4]oxazine-3,9'-xanthene]-7'-yl trifluoromethanesulfonate (1235 mg, 2.342 mmol, 92% yield).

Step 4: A re-sealable vial was charged with 5-amino-5'-fluoro-2'-(2-fluoropyridin-3-yl)-2,6-dihydrospiro[[1,4]oxazine-3,9'-xanthene]-7'-yl trifluoromethanesulfonate (200 mg, 0.379 mmol), chloro(2-dicyclohexylphosphino-2',6'-diisopropoxy-1,1'-biphenyl)[2-(2-aminoethylphenyl)]palladium(II) 1 (27.6 mg, 0.038 mmol) and 0.5 ml of THF. The mixture was stirred at RT until all solids were dissolved. Morpholine (66.1 µL, 0.758 mmol) and LiHMDS (1M in THF) (1138 µL, 1.138 mmol) were added and the vial was sealed and stirred at RT for 20 minutes. The reaction was quenched by addition of water (1 ml) and diluted with EtOAc (2 ml). The organic layer was separated, and the aqueous layer was extracted with EtOAc (2×2 ml). The combined organic fractions were concentrated and purified by chromatography (10-80% DCM/MeOH/NH₄OH in DCM) to provide racemic 4'-fluoro-7'-(2-fluoropyridin-3-yl)-2'-morpholino-2,6-dihydrospiro[[1,4]oxazine-3,9'-xanthen]-5-amine (97 mg, 0.209 mmol, 55.1% yield).

Step 5: The final compound (S)-4'-fluoro-7'-(2-fluoropyridin-3-yl)-2'-morpholino-2,6-dihydrospiro[[1,4]oxazine-3,9'-xanthen]-5-amine was obtained from racemic 4'-fluoro-7'-(2-fluoropyridin-3-yl)-2'-morpholino-2,6-dihydrospiro[[1,4]oxazine-3,9'-xanthen]-5-amine using similar chiral separation conditions as described herein for intermediate 10.

Example 36A

Method A7

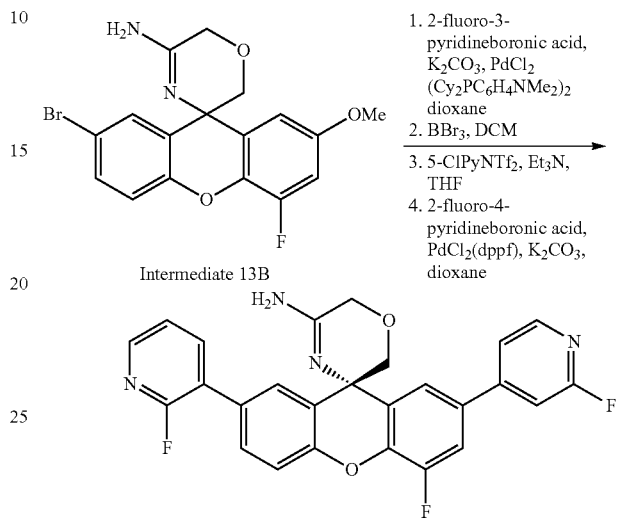

Synthesis of (S)-4'-fluoro-7'-(2-fluoropyridin-3-yl)-2'-(2-fluoropyridin-4-yl)-2,6-dihydrospiro[[1,4]oxazine-3,9'-xanthen]-5-amine Step 1: A 250 ml RBF was charged with 7'-bromo-4'-fluoro-2'-methoxy-2,6-dihydrospiro[[1,4]oxazine-3,9'-xanthen]-5-amine (2.73 g, 6.94 mmol), bis(di-tert-butyl(4-dimethylaminophenyl)phosphine)dichloropalladium(II) (0.492 g, 0.694 mmol) and 2-fluoropyridin-3-ylboronic acid (1.467 g, 10.41 mmol). Dioxane (40 mL) and potassium carbonate (1M solution) (20.83 mL, 20.83 mmol) were added and the mixture was flushed with argon and heated at 85° C. for 30 minutes. The mixture was cooled to RT, diluted with EtOAc and the organic layer was separated and concentrated in vacuo to give a yellow semisolid. After trituration with 10 ml of EtOH the solid was filtered, washed with EtOH (2×1 ml) and dried on air overnight to afford 4'-fluoro-7'-(2-fluoropyridin-3-yl)-2'-methoxy-2,6-dihydrospiro[[1,4]oxazine-3,9'-xanthen]-5-amine (2.11 g, 5.15 mmol).

Step 2: To a suspension of 4'-fluoro-7'-(2-fluoropyridin-3-yl)-2'-methoxy-2,6-dihydrospiro[[1,4]oxazine-3,9'-xanthen]-5-amine (1.668 g, 4.07 mmol) in DCM (12 ml) was added boron tribromide (0.963 mL, 10.19 mmol). Stirring was continued for 45 hrs at 0° C. at which point the mixture was removed from the bath and stirred for 2 hrs at RT. The reaction mixture was recooled to 0° C. and quenched by careful addition of saturated aqueous NaHCO₃ solution (~10 mL). The mixture became colorless with a white precipitate. The solvent was removed in vacuo, the mixture was diluted with water and filtered. The solid was washed with water and dried on air for 2 hrs, then for 2 hrs in high vacuum at RT to afford 5-amino-4'-fluoro-7'-(2-fluoropyridin-3-yl)-2,6-dihydrospiro[[1,4]oxazine-3,9'-xanthen]-2'-ol (1.53 g, 3.87 mmol, 95% yield).

Step 3: To a suspension of 5-amino-4'-fluoro-7'-(2-fluoropyridin-3-yl)-2,6-dihydrospiro[[1,4]oxazine-3,9'-xanthen]-2'- ol (1.01 g, 2.55 mmol) in DCM (12.77 mL) were added TEA (1.424 mL, 10.22 mmol) and N-(5-chloropyridin-2-yl)-1,1,1-trifluoro-N-(trifluoromethylsulfonyl)methanesulfonamide (1.103 g, 2.81 mmol). After stirring for 2 hours the reaction mixture was washed 3× with 2N NaOH solution followed by brine. The solution was then concentrated. The yellow residue was diluted with DCM (5 ml) and the white precipitate was filtered, washed with DCM and dried under a stream of air to afford 355 mg (26%) of pure product. The filtrate was purified by chromatography (5-40% DCM/MeOH/NH4OH in DCM) to afford 5-amino-5'-fluoro-2'-(2-fluoropyridin-3-yl)-2,6-dihydrospiro[[1,4]oxazine-3,9'-xanthene]-7'-yl trifluoromethanesulfonate (880 mg, 1.668 mmol, 65.3% yield) as a white foam. Total isolated 5-amino-5'-fluoro-2'-(2-fluoropyridin-3-yl)-2,6-dihydrospiro[[1,4]oxazine-3,9'-xanthene]-7'-yl trifluoromethanesulfonate (1235 mg, 2.342 mmol, 92% yield).

Step 4: A 10 ml resealable tube was charged with 5-amino-5'-fluoro-2'-(2-fluoropyridin-3-yl)-2,6-dihydrospiro[[1,4]oxazine-3,9'-xanthene]-7'-yl trifluoromethanesulfonate (385 mg, 0.730 mmol), 2-fluoropyridin-4-ylboronic acid (165 mg, 1.168 mmol), PdCl$_2$(dppf)-DCM adduct (59.6 mg, 0.073 mmol), dioxane (3650 µL) and potassium carbonate (1M solution) (2190 µL, 2.190 mmol). The mixture was flushed with argon, sealed and heated at 85° C. for 1 hr. The mixture was diluted with EtOAc, organic layer was filtered through Celite and concentrated. The brown residue was purified by chromatography (10-80% DCM/MeOH/NH$_4$OH in DCM) to afford 4'-fluoro-7'-(2-fluoropyridin-3-yl)-2'-(2-fluoropyridin-4-yl)-2,6-dihydrospiro[[1,4]oxazine-3,9'-xanthen]-5-amine (294 mg, 85% yield) as off-white solid.

Step 5: The final compound (S)-4'-fluoro-7'-(2-fluoropyridin-3-yl)-2'-(2-fluoropyridin-4-yl)-2,6-dihydrospiro[[1,4]oxazine-3,9'-xanthen]-5-amine (36A) were obtained form racemic 4'-fluoro-7'-(2-fluoropyridin-3-yl)-2'-(2-fluoropyridin-4-yl)-2,6-dihydrospiro[[1,4]oxazine-3,9'-xanthen]-5-amine using similar chiral separation conditions as described herein for intermediate 10.

MS m/z=475.0 [M+H]$^+$. Calculated for $C_{26}H_{17}F_3N_4O_2$: 474.13

$^1$H NMR (400 MHz, DMSO-d$_6$) δ ppm 4.24 (d, J=15.7 Hz, 1 H), 4.30 (d, J=15.7 Hz, 1 H), 6.15 (br. s., 1 H), 7.41 (d, J=8.5 Hz, 1 H), 7.46-7.56 (m, 4 H), 7.59-7.69 (m, 2 H), 7.90 (dd, J=11.7, 2.0 Hz, 1 H), 8.09 (ddd, J=9.9, 7.8, 1.6 Hz, 1 H), 8.25 (d, J=4.6 Hz, 1 H), 8.33 (d, J=5.2 Hz, 1 H)

Example 37A

Method A8

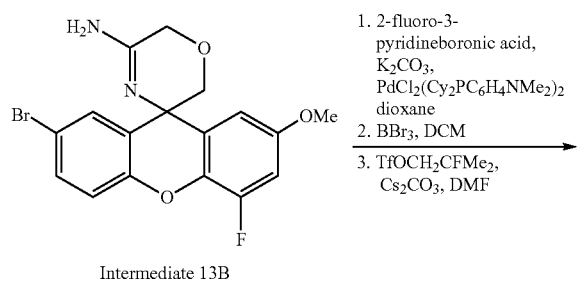

Intermediate 13B 1. 2-fluoro-3-pyridineboronic acid, K$_2$CO$_3$, PdCl$_2$(Cy$_2$PC$_6$H$_4$NMe$_2$)$_2$ dioxane
2. BBr$_3$, DCM
3. TfOCH$_2$CFMe$_2$, Cs$_2$CO$_3$, DMF

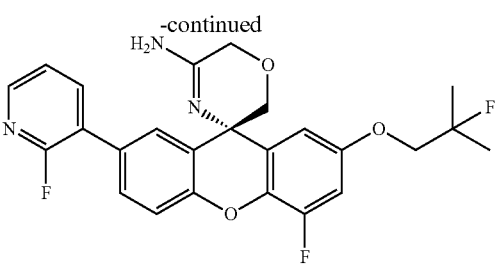

Synthesis of (S)-4'-fluoro-2'-(2-fluoro-2-methylpropoxy)-7'-(2-fluoropyridin-3-yl)-2,6-dihydrospiro[[1,4]oxazine-3,9'-xanthen]-5-amine (37A)

Step 1: A 250 ml RB flask was charged with 7'-bromo-4'-fluoro-2'-methoxy-2,6-dihydrospiro[[1,4]oxazine-3,9'-xanthen]-5-amine (2.73 g, 6.94 mmol), bis(di-tert-butyl(4-dimethylaminophenyl)phosphine)dichloropalladium(II) (0.492 g, 0.694 mmol) and 2-fluoropyridin-3-ylboronic acid (1.467 g, 10.41 mmol). Dioxane (40 mL) and potassium carbonate (1M solution) (20.83 mL, 20.83 mmol) were added and the mixture was flushed with argon and heated at 85° C. for 30 minutes. The mixture was cooled to RT, diluted with EtOAc and the organic layer was separated and concentrated in vacuo to give a yellow semisolid. After trituration with 10 ml of EtOH the solid was filtered, washed with EtOH (2×1 ml) and dried on air overnight to afford 4'-fluoro-7'-(2-fluoropyridin-3-yl)-2'-methoxy-2,6-dihydrospiro[[1,4]oxazine-3,9'-xanthen]-5-amine (2.11 g, 5.15 mmol).

Step 2: To a suspension of 4'-fluoro-7'-(2-fluoropyridin-3-yl)-2'-methoxy-2,6-dihydrospiro[[1,4]oxazine-3,9'-xanthen]-5-amine (1.668 g, 4.07 mmol) in DCM (12 ml) was added boron tribromide (0.963 mL, 10.19 mmol). Stirring was continued for 45 hrs at 0° C. at which point the mixture was removed from the bath and stirred for 2 hrs at RT. The reaction mixture was recooled to 0° C. and quenched by careful addition of saturated aqueous NaHCO$_3$ solution (~10 mL). The mixture became colorless with a white precipitate. The solvent was removed in vacuo, the mixture was diluted with water and filtered. The solid was washed with water and dried on air for 2 hrs, then for 2 hrs in high vacuum at RT to afford 5-amino-4'-fluoro-7'-(2-fluoropyridin-3-yl)-2,6-dihydrospiro[[1,4]oxazine-3,9'-xanthen]-2'-ol (1.53 g, 3.87 mmol, 95% yield).

Step 3: To a solution of 5-amino-4'-fluoro-7'-(2-fluoropyridin-3-yl)-2,6-dihydrospiro[[1,4]oxazine-3,9'-xanthen]-2'-ol (200 mg, 0.506 mmol) in DMF (2529 µL) cesium carbonate (330 mg, 1.012 mmol), KI (25.2 mg, 0.152 mmol) and 2-fluoro-2-methylpropyl trifluoromethanesulfonate (125 mg, 0.556 mmol) were added sequentially and the resulting mixture was stirred overnight at RT. The mixture was diluted with 5 ml of water and stirred for 5 minutes. The solvents were decanted from a precipitated gummy solid. 10 ml of water was added and the mixture was stirred for 1 hr at RT at which point a fine precipitate formed. The solids were filtered, washed with water and dried on air for 3 hr, then overnight in vacuo to afford racemic 4'-fluoro-2'-(2-fluoro-2-methylpropoxy)-7'-(2-fluoropyridin-3-yl)-2,6-dihydrospiro[[1,4]oxazine-3,9'-xanthen]-5-amine (175 mg, 73% yield).

Step 4: The final compound (S)-4'-fluoro-2'-(2-fluoro-2-methylpropoxy)-7'-(2-fluoropyridin-3-yl)-2,6-dihydrospiro[[1,4]oxazine-3,9'-xanthen]-5-amine (37A) was obtained form racemic 4'-fluoro-2'-(2-fluoro-2-methylpropoxy)-7'-(2-fluoropyridin-3-yl)-2,6-dihydrospiro[[1,4]oxazine-3,9'-xanthen]-5-amine using similar chiral separation conditions as described herein for intermediate 10.

MS m/z=470.0 [M+H]+. Calculated for $C_{25}H_{22}F_3N_3O_3$: 469.13

$^1$H NMR (400 MHz, DMSO-d$_6$) δ ppm 1.40 (s, 3 H), 1.45 (s, 3 H), 3.40-3.45 (m, 2 H), 3.90-4.09 (m, 2 H), 4.14-4.25 (m, 2 H), 6.01-6.18 (m, 2 H), 6.66 (dd, J=2.9, 1.6 Hz, 1 H), 7.04 (dd, J=12.5, 2.9 Hz, 1 H), 7.44-7.51 (m, 2 H), 7.57 (ddd, J=8.5, 2.2, 1.6 Hz, 1 H), 8.07 (ddd, J=10.4, 7.5, 1.9 Hz, 1 H), 8.20-8.27 (m, 1 H)

Example 38

Method A9

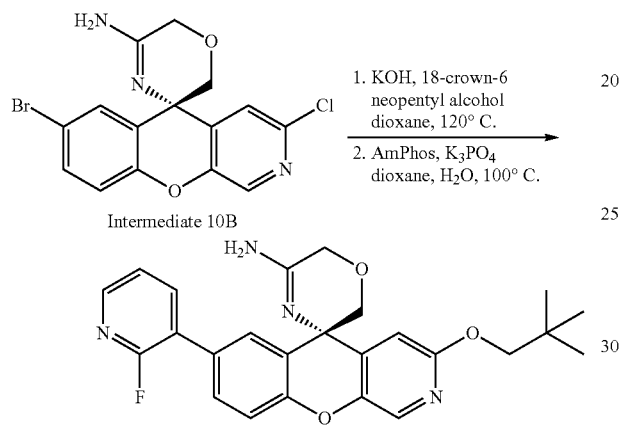

Synthesis of (S)-7-(2-fluoropyridin-3-yl)-3-methoxy-2',6'-dihydrospiro[chromeno[2,3-c]pyridine-5,3'-[1,4]oxazin]-5'-amine Step 1: A microwave vial was charged with (S)-7-bromo-3-chloro-2',6'-dihydrospiro[chromeno[2,3-c]pyridine-5,3'-[1,4]oxazin]-5'-amine (1.2557 g, 3.30 mmol), 2,2-dimethylpropan-1-ol (0.914 g, 10.37 mmol), 18-crown-6 (0.087 g, 0.330 mmol), and potassium hydroxide (0.925 g, 16.50 mmol) (freshly ground). The vial was flushed with Ar (g), then dioxane (6.60 mL) was added. The vial was sealed and placed in a 120° C. oil bath and stirred for 24 hours. The reaction mixture was diluted with water and a small amount of brine. The aq. mixture was then extracted with EtOAc (3×). The combined organic extracts were dried over sodium sulfate, filtered, and concentrated. The residue was purified by chromatography (0-100% EtOAc/hexanes) to afford 0.657 g of (S)-7-bromo-3-methoxy-2',6'-dihydrospiro[chromeno[2,3-c]pyridine-5,3'-[1,4]oxazin]-5'-amine as a yellow solid.

Step 2: A microwave vial was charged with (S)-7-bromo-3-methoxy-2',6'-dihydrospiro[chromeno[2,3-c]pyridine-5,3'-[1,4]oxazin]-5'-amine (0.065 g, 0.173 mmol), 2-fluoropyridin-3-ylboronic acid (0.049 g, 0.346 mmol), potassium phosphate (0.110 g, 0.518 mmol), and bis(di-tert-butyl(4-dimethylaminophenyl)phosphine)dichloropalladium(II) (6.12 mg, 8.64 μmol). The vial was flushed with Ar (g), dioxane (0.648 mL) and water (0.216 mL) were added in sequence. The vial was sealed and heated in a Biotage Initiator microwave reactor for 30 min at 100° C. The reaction was diluted with ethyl acetate and washed with water. The aqueous layer was extracted with EtOAc, and the combined organic layers were washed with brine, dried with sodium sulfate, filtered, and concentrated. The material was purified via column chromatography (0-10% MeOH/EtOAc) to afford 65 mg of (S)-7-(2-fluoropyridin-3-yl)-3-methoxy-2',6'-dihydrospiro[chromeno[2,3-c]pyridine-5,3'-[1,4]oxazin]-5'-amine as a light yellow solid.

Example 39

Method A10

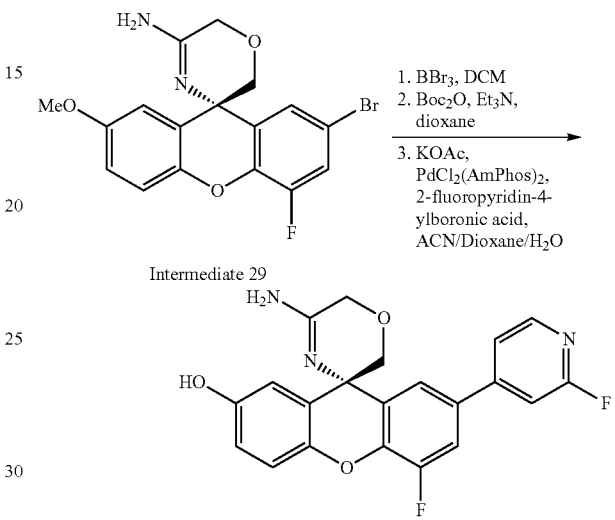

Synthesis of (S)-5-amino-4'-fluoro-2'-(2-fluoropyridin-4-yl)-2,6-dihydrospiro[[1,4]oxazine-3,9'-xanthen]-7'-ol Step 1: In a 500-mL flask, (S)-2'-bromo-4'-fluoro-7'-methoxy-2,6-dihydrospiro[[1,4]oxazine-3,9'-xanthen]-5-amine (0.676 g, 1.719 mmol) was suspended in DCM (50 mL). The suspension was cooled to 0° C., and boron tribromide (1.0 M in DCM; 5.16 mL, 5.16 mmol) was added. After 1.5 h, excess boron tribromide was quenched with saturated aqueous NH$_4$Cl (18 mL) and aqueous NH$_4$OH (2 mL). The aqueous phase was separated and extracted further with 5% MeOH-DCM (3×50 mL). The organics were combined, washed with brine (15 mL), dried over sodium sulfate and concentrated to afford 604 mg of (S)-5-amino-2'-bromo-4'-fluoro-2,6-dihydrospiro[[1,4]oxazine-3,9'-xanthen]-7'-ol which was used in the next step without further purification.

Step 2: A flask was charged with (S)-5-amino-2'-bromo-4'-fluoro-2,6-dihydrospiro[[1,4]oxazine-3,9'-xanthen]-7'-ol (10 mg, 0.026 mmol) and dioxane (0.6 mL). Triethylamine (10.5 μL, 0.076 mmol) and di-tert-butyl dicarbonate (0.017 g, 0.076 mmol) were added, and the solution was stirred at RT for 14 h. The material was taken up in 1 M aqueous HCl (10 mL) and the aqueous phase was extracted with DCM (3×20 mL). The organics were combined, dried over sodium sulfate and concentrated. The material was purified by chromatography (30% ethyl acetate/hexane) to afford 12 mg of (S)-tert-butyl 2'-bromo-4'-fluoro-7'-hydroxy-2,6-dihydrospiro[[1,4]oxazine-3,9'-xanthene]-5-ylcarbamate.

Step 3: A microwave vial was charged with potassium acetate (6.14 mg, 0.063 mmol), bis(di-tert-butyl(4-dimethylaminophenyl)phosphine)dichloropalladium(II) (1.77 mg, 2.504 μmol), and 2-fluoropyridin-4-ylboronic acid (4.23 mg, 0.030 mmol). The (S)-tert-butyl 2'-bromo-4'-fluoro-7'-hydroxy-2,6-dihydrospiro[[1,4]oxazine-3,9'-xanthene]-5-ylcarbamate (0.012 g, 0.025 mmol) was added as a solution in 1:1 acetonitrile/dioxane (1 mL). Water (0.1 mL) was added. Argon was blown through the vessel, which was then sealed and heated in a 100° C. oil bath for 6 h. The mixture was cooled, diluted with brine (10 mL), and the aqueous layer was extracted with 10% MeOH-DCM (3×20 mL). The organics were combined, washed with dilute brine (5 mL), dried over sodium sulfate and concentrated. The residue was purified by preparative TLC (20% MeOH in DCM) to afford 3.8 mg of (S)-5-amino-4'-fluoro-2'-(2-fluoropyridin-4-yl)-2,6-dihydrospiro[[1,4]oxazine-3,9'-xanthen]-7'-ol.

Example 40

Method A11

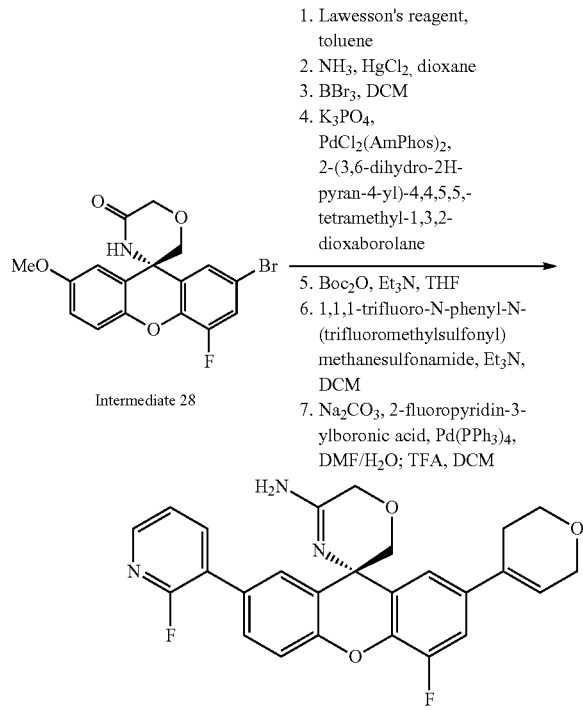

Synthesis of (S)-2'-(3,6-dihydro-2H-pyran-4-yl)-4'-fluoro-7'-(2-fluoropyridin-3-yl)-2,6-dihydrospiro[[1,4]oxazine-3,9'-xanthen]-5-amine Step 1: In a 250-mL flask, Lawesson's reagent (0.577 g, 1.427 mmol) and (S)-2'-bromo-4'-fluoro-7'-methoxyspiro[morpholine-3,9'-xanthene]-5-one (0.978 g, 2.481 mmol) were suspended in toluene (25 mL). An air-cooled condenser was attached, and the flask was heated in a 90° C. oil bath for 3 h. The mixture was then cooled and concentrated to give (S)-2'-bromo-4'-fluoro-7'-methoxyspiro[morpholine-3,9'-xanthene]-5-thione which was used in the next step without further purification.

Step 2: In a 150-mL resealable vessel, the crude (S)-2'-bromo-4'-fluoro-7'-methoxyspiro[morpholine-3,9'-xanthene]-5-thione (1.0 g, 2.437 mmol) was dissolved in a dioxane solution of ammonia (0.5 M, 58.5 mL, 29.2 mmol). Mercury (II) chloride (0.993 g, 3.66 mmol) was added, and the vessel was sealed and heated in a 55° C. oil bath overnight. The mixture was then cooled and concentrated. The residue was filtered through Celite, rinsing with 10% MeOH-DCM (400 mL). The filtrate was concentrated, and the residue was purified through silica gel (150 mL) using 7.5% MeOH-DCM to afford 131 mg of (S)-2'-bromo-4'-fluoro-7'-methoxy-2,6-dihydrospiro[[1,4]oxazine-3,9'-xanthen]-5-amine Step 3: In a 100-mL flask, (S)-2'-bromo-4'-fluoro-7'-methoxy-2,6-dihydrospiro[[1,4]oxazine-3,9'-xanthen]-5-amine (0.233 g, 0.593 mmol) was dissolved in DCM (7.5 mL). The solution was cooled to 0° C., and a DCM solution of boron tribromide (1 M, 1.78 mL, 1.78 mmol) was added. The mixture was stirred at 0° C. for 1 h, then was quenched with saturated aqueous NH$_4$Cl (18 mL) and aqueous NH$_4$OH (2 mL). The aqueous phase was extracted 5% MeOH-DCM (3×40 mL). The organics were combined, washed with dilute brine (15 mL), dried over sodium sulfate and concentrated to afford 187 mg of (S)-5-amino-2'-bromo-4'-fluoro-2,6-dihydrospiro[[1,4]oxazine-3,9'-xanthen]-7'-ol.

Step 4: In a microwave vial, potassium phosphate (0.307 g, 1.448 mmol), PdCl$_2$(AmPhos)$_2$ (0.026 g, 0.036 mmol), (S)-5-amino-2'-bromo-4'-fluoro-2,6-dihydrospiro[[1,4]oxazine-3,9'-xanthen]-7'-ol (0.183 g, 0.483 mmol), and 2-(3,6-dihydro-2H-pyran-4-yl)-4,4,5,5-tetramethyl-1,3,2-dioxaborolane (0.147 g, 0.700 mmol) were suspended in dioxane (4 mL) and water (1.6 mL). Argon was blown through the vessel, which was sealed and heated by microwave at 120° C. for 30 min. The reaction was concentrated, and the residue was neutralized with 1/3 saturated aqueous NH$_4$Cl (15 mL) and the aqueous phase was extracted with 5% MeOH-DCM (3×25 mL). The organics were combined, washed with dilute brine (7 mL), and concentrated to afford (S)-5-amino-2'-(3,6-dihydro-2H-pyran-4-yl)-4'-fluoro-2,6-dihydrospiro[[1,4]oxazine-3,9'-xanthen]-7'-ol which was used in the next step without further purification.

Step 5: In a 100-mL flask, the crude (S)-5-amino-2'-(3,6-dihydro-2H-pyran-4-yl)-4'-fluoro-2,6-dihydrospiro[[1,4]oxazine-3,9'-xanthen]-7'-ol (0.185 g, 0.484 mmol) was suspended in THF (12 mL). Boc$_2$O (0.132 g, 0.605 mmol) was added, followed by TEA (0.088 mL, 0.629 mmol). The mixture was stirred at rt overnight. The mixture was concentrated to afford (S)-tert-butyl 2'-(3,6-dihydro-2H-pyran-4-yl)-4'-fluoro-7'-hydroxy-2,6-dihydrospiro[[1,4]oxazine-3,9'-xanthene]-5-ylcarbamate which was used in the next step without further purification.

Step 6: In a 100-mL flask, the crude (S)-tert-butyl 2'-(3,6-dihydro-2H-pyran-4-yl)-4'-fluoro-7'-hydroxy-2,6-dihydrospiro[[1,4]oxazine-3,9'-xanthene]-5-ylcarbamate (0.233 g, 0.483 mmol) was dissolved in DCM (10 mL). The solution was cooled to 0° C., and TEA (0.157 mL, 1.14 mmol) was added, followed by 1,1,1-trifluoro-N-phenyl-N-(trifluoromethylsulfonyl)methanesulfonamide (0.362 g, 1.01 mmol). After 2 h, the reaction was quenched with aqueous sodium bicarbonate (5 mL). The mixture was diluted with water (10 mL) and the aqueous phase was extracted with 3% MeOH-DCM (3×20 mL). The organics were combined, washed with dilute brine (7 mL), dried over sodium sulfate and concentrated. The residue was purified through silica gel (50 mL) using 30% EtOAc in hexane to afford 166 mg of (S)-5-(tert-butoxycarbonylamino)-2'-(3,6-dihydro-2H-pyran-4-yl)-4'-fluoro-2,6-dihydrospiro[[1,4]oxazine-3,9'-xanthene]-7'-yl trifluoromethanesulfonate.

Step 7: In a microwave vial, 2-fluoropyridin-3-ylboronic acid (0.048 g, 0.338 mmol), (S)-5-(tert-butoxycarbonylamino)-2'-(3,6-dihydro-2H-pyran-4-yl)-4'-fluoro-2,6-dihydrospiro[[1,4]oxazine-3,9'-xanthene]-7'-yl trifluoromethanesulfonate (0.166 g, 0.270 mmol), and Pd(PPh$_3$)$_4$ (0.031 g, 0.027 mmol)

were suspended in DMF (3 mL). Aqueous sodium carbonate (1 M, 0.810 mL, 0.810 mmol) was added. Argon was blown through the vessel, which was sealed and heated in an 85° C. oil bath for 2.5 h. The reaction was cooled and concentrated. The residue was taken up in water (15 mL) and the aqueous phase was extracted with 3% MeOH-DCM (3×25 mL). The organics were combined, washed with dilute brine (7 mL), dried over sodium sulfate and concentrated. The residue was transferred to a microwave vial in DCM (3 mL), and TFA (0.520 mL, 6.75 mmol) was added. The vial was sealed and heated in a 65° C. oil bath for 1.5 h. The mixture was cooled and concentrated, and the residue was neutralized with 0.5 M aqueous $Na_2CO_3$ (15 mL) and the aqueous phase was extracted with 5% MeOH-DCM (3×25 mL). The organics were combined, washed with dilute brine (7 mL), dried over sodium sulfate and concentrated. The residue was purified through silica gel (50 mL) using 8% MeOH-DCM to afford 72 mg of (S)-2'-(3,6-dihydro-2H-pyran-4-yl)-4'-fluoro-7'-(2-fluoropyridin-3-yl)-2,6-dihydrospiro[[1,4]oxazine-3,9'-xanthen]-5-amine. m/z=462.0[M+H]$^+$.

$^1$H NMR (400 MHz, CDCl$_3$) δ ppm; 8.18 (d, 1 H, J=5.0 Hz), 7.89 (m, 1 H), 7.52 (m, 2 H), 7.35 (d, 1 H, J=8.4 Hz), 7.28 (m, 1 H), 7.16 (dd, 1 H, J=11.7, 2.0 Hz), 7.10 (s, 1 H), 6.10 (s, 1 H), 4.33 (m, 4 H), 3.93 (t, 2 H, J=5.5 Hz), 3.59 (d, 2 H, J=5.7 Hz), 2.50 (m, 2 H).

Example 41

Method A12

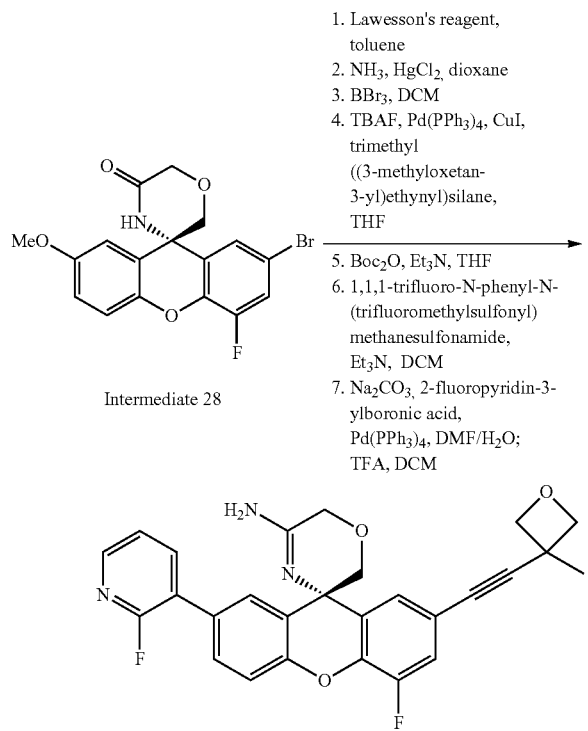

Synthesis of (S)-4'-fluoro-7'-(2-fluoropyridin-3-yl)-2'-((3-methyloxetan-3-yl)ethynyl)-2,6-dihydrospiro[[1,4]oxazine-3,9'-xanthen]-5-amine Step 1: In a 1-L flask, the (S)-2'-bromo-4'-fluoro-7'-methoxyspiro[morpholine-3,9'-xanthen]-5-one (3.16 g, 8.02 mmol) was suspended in toluene (75 mL). Lawesson's reagent (1.864 g, 4.61 mmol) was added. An air-cooled condenser was affixed, and the mixture was heated in a 90° C. oil bath for 2 h. The mixture was cooled and concentrated to afford crude (S)-2'-bromo-4'-fluoro-7'-methoxyspiro[morpholine-3,9'-xanthene]-5-thione which was used in the next step without further purification.

Step 2: In a 350-mL resealable vessel, the (S)-2'-bromo-4'-fluoro-7'-methoxyspiro[morpholine-3,9'-xanthene]-5-thione (3.0 g, 7.31 mmol) was dissolved in a dioxane solution of ammonia (0.5 M, 175 mL, 88 mmol). Mercury (II) chloride (2.98 g, 10.97 mmol) was added, and the vessel was sealed and heated in a 55° C. oil bath overnight. The reaction was cooled and then filtered through Celite, rinsing with 10% MeOH-DCM. The filtrate was concentrated, and the residue was transferred to a resealable vessel with 50 mL of dioxane. A solution of ammonia in dioxane (0.5 M, 100 mL, 50 mmol) was added, followed by mercury (II) chloride (2.0 g, 7.36 mmol). The vessel was sealed and heated in a 60° C. oil bath for 14 h. The mixture was cooled and filtered through Celite, rinsing with 10% MeOH-DCM. The filtrate was concentrated, and the residue was purified through silica gel (300 mL) using 7.5% MeOH-DCM to afford 1.33 g of (S)-2'-bromo-4'-fluoro-7'-methoxy-2,6-dihydrospiro[[1,4]oxazine-3,9'-xanthen]-5-amine Step 3: In a 50-mL flask, the (S)-2'-bromo-4'-fluoro-7'-methoxy-2,6-dihydrospiro[[1,4]oxazine-3,9'-xanthen]-5-amine (0.340 g, 0.864 mmol) was taken up in DCM (15 mL). The suspension was cooled to 0° C., and a DCM solution of boron tribromide (2.59 mL, 2.59 mmol) was added. After 1 h, the reaction was quenched with 18 mL of saturated aqueous NH$_4$Cl and 2 mL of aqueous NH$_4$OH. The mixture was diluted further with water (10 mL), and the aqueous phase was extracted with 5% MeOH-DCM (3×50 mL). The organics were combined, washed with dilute brine (15 mL), dried over sodium sulfate and concentrated to afford 241 mg of (S)-5-amino-2'-bromo-4'-fluoro-2,6-dihydrospiro[[1,4]oxazine-3,9'-xanthen]-7'-ol which was used in the next step without further purification.

Step 4: A microwave vial was charged with tetrabutylammonium fluoride trihydrate (0.301 g, 0.952 mmol), Pd(PPh$_3$)$_4$ (0.073 g, 0.063 mmol), and copper(I) iodide (12.3 mg, 0.065 mmol). The (S)-5-amino-2'-bromo-4'-fluoro-2,6-dihydrospiro[[1,4]oxazine-3,9'-xanthen]-7'-ol (0.241 g, 0.64 mmol) was added as a solution in THF (2.7 mL). Argon was blown through the vessel, and trimethyl((3-methyloxetan-3-yl)ethynyl)silane (0.161 g, 0.951 mmol) was added. The vessel was sealed and heated in an 80° C. oil bath for 1.5 h. The mixture was cooled and concentrated, diluted with water (15 mL), and the aqueous phase was extracted with 5% MeOH-DCM (3×25 mL). The organics were combined, washed with dilute brine (7 mL), dried over sodium sulfate and concentrated to afford (S)-5-amino-4'-fluoro-2'-((3-methyloxetan-3-yl)ethynyl)-2,6-dihydrospiro[[1,4]oxazine-3,9'-xanthen]-7'-ol, which was used in the next step without further purification.

Step 5: In a 50-mL flask, the crude (S)-5-amino-4'-fluoro-2'-((3-methyloxetan-3-yl)ethynyl)-2,6-dihydrospiro[[1,4]oxazine-3,9'-xanthen]-7'-ol (0.251 g, 0.636 mmol) was dissolved in THF (12 mL). Boc$_2$O (0.303 g, 1.39 mmol) and triethylamine (0.204 mL, 1.47 mmol) were added. After 14 h, the reaction mixture was concentrated to afford (S)-tert-butyl 4'-fluoro-7'-hydroxy-2'-((3-methyloxetan-3-yl)ethynyl)-2,6-dihydrospiro[[1,4]oxazine-3,9'-xanthene]-5-ylcarbamate which was used in the next step without further purification.

Step 6: In a 50-mL flask, the crude (S)-tert-butyl 4'-fluoro-7'-hydroxy-2'-((3-methyloxetan-3-yl)ethynyl)-2,6-dihydrospiro[[1,4]oxazine-3,9'-xanthene]-5-ylcarbamate (0.315 g, 0.637 mmol) was dissolved in DCM (12 mL). The solution was cooled to 0° C., and triethylamine (0.175 mL, 1.26 mmol) and 1,1,1-trifluoro-N-phenyl-N-(trifluoromethylsulfonyl) methanesulfonamide (0.400 g, 1.12 mmol) were added. After 2.5 h, the reaction was quenched with dilute aqueous NaHCO₃ (15 mL) and the aqueous phase was extracted with 3% MeOH-DCM (3×20 mL). The organics were combined, dried over sodium sulfate and concentrated. The residue was purified through silica gel (60 mL) using 25% ethyl acetate in hexane to afford 230 mg of (S)-5-(tert-butoxycarbonylamino)-4'-fluoro-2'-((3-methyloxetan-3-yl)ethynyl)-2,6-dihydrospiro[[1,4]oxazine-3,9'-xanthene]-7-yl trifluoromethanesulfonate Step 7: In a microwave vial, 2-fluoropyridin-3-ylboronic acid (0.065 g, 0.459 mmol), Pd(PPh₃)₄ (0.042 g, 0.037 mmol) and (S)-5-(tert-butoxycarbonylamino)-4'-fluoro-2'-((3-methyloxetan-3-yl)ethynyl)-2,6-dihydrospiro[[1,4]oxazine-3,9'-xanthene]-7-yl trifluoromethanesulfonate (0.230 g, 0.367 mmol) were taken up in DMF (3 mL). Aqueous sodium carbonate (1.0 M, 1.10 mL, 1.10 mmol) was added. Argon was blown through the vessel which was then sealed and heated in an 85° C. oil bath for 4 h. The reaction was cooled and concentrated, and the residue was diluted with water (15 mL) and the aqueous phase was extracted with 3% MeOH-DCM (3×25 mL). The organics were combined, washed with dilute brine (7 mL), dried over sodium sulfate and concentrated. The residue was purified through silica gel (33 mL) which had been deactivated with Et₃N (3.3 mL), using 33% EtOAc in hexane. The resulting residue was transferred to a microwave vessel in DCM (3 mL), and TFA (0.283 mL, 3.67 mmol) was added. The vessel was sealed and heated in a 60° C. oil bath for 1.5 h. The reaction was cooled and concentrated, and the residue was neutralized with 0.5 M aqueous Na₂CO₃ (15 mL). The aqueous phase was extracted with 5% MeOH-DCM (3×25 mL). The organics were combined, washed with dilute brine (7 mL) and dried over sodium sulfate. The residue was purified through silica gel (33 mL) using 7.5% MeOH-DCM to afford 27 mg of (S)-4'-fluoro-7'-(2-fluoropyridin-3-yl)-2'-((3-methyloxetan-3-yl)ethynyl)-2,6-dihydrospiro[[1,4]oxazine-3,9'-xanthene]-5-amine. m/z=474.0[M+H]⁺.

¹H NMR (400 MHz, CDCl₃) δ ppm; 8.19 (d, 1 H, J=4.9 Hz), 7.89 (m, 2 H), 7.52 (m, 2 H), 7.34 (d, 1 H, J=8.4 Hz), 7.28 (m, 1 H), 7.16 (m, 2 H), 4.92 (d, 2 H, J=5.3 Hz), 4.48 (d, 2 H, J=5.3 Hz), 4.33 (d, 2 H, J=2.5 Hz), 3.57 (d, 2 H, J=2.7 Hz), 1.71 (s, 3 H).

Example 42

Method A13

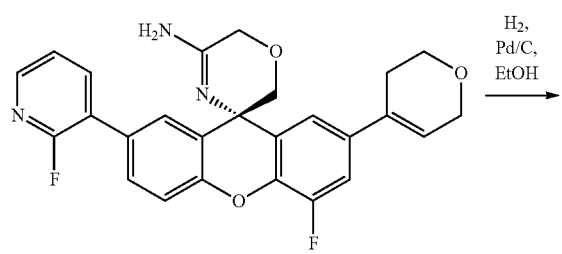

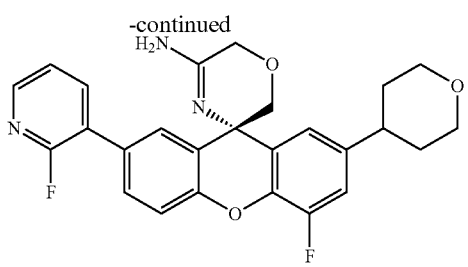

Synthesis of (S)-4'-fluoro-7'-(2-fluoropyridin-3-yl)-2'-(tetrahydro-2H-pyran-4-yl)-2,6-dihydrospiro[[1,4]oxazine-3,9'-xanthen]-5-amine In a microwave vial, (S)-2'-(3,6-dihydro-2H-pyran-4-yl)-4'-fluoro-7'-(2-fluoropyridin-3-yl)-2,6-dihydrospiro[[1,4]oxazine-3,9'-xanthen]-5-amine (0.040 g, 0.087 mmol) and Pd/C (10%, 0.055 g, 0.052 mmol) were suspended in EtOH (1.5 mL). A balloon full of hydrogen (~1 L) was emptied into the vessel, venting through a needle, and the vessel was sealed. After 2 days, the mixture was filtered through Celite, rinsing with 5% MeOH-DCM. The filtrate was concentrated, and the residue was purified by chromatography (7.5% MeOH/DCM) to afford 29 mg of (S)-4'-fluoro-7'-(2-fluoropyridin-3-yl)-2'-(tetrahydro-2H-pyran-4-yl)-2,6-dihydrospiro[[1,4]oxazine-3,9'-xanthen]-5-amine Example 43

Method A14

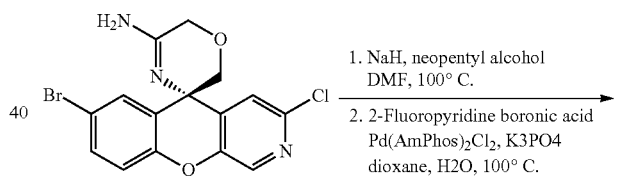

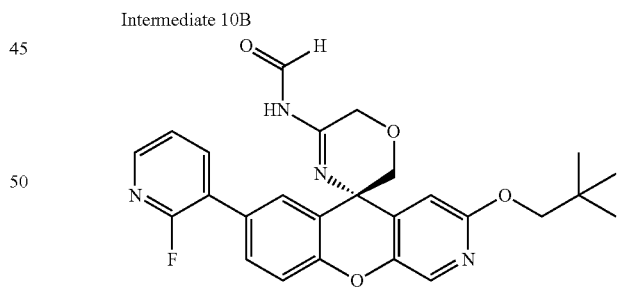

Synthesis of (S)—N-(7-(2-fluoropyridin-3-yl)-3-(neopentyloxy)-2',6'-dihydrospiro[chromeno[2,3-c]pyridine-5,3'-[1,4]oxazine]-5'-yl)formamide Step 1: A vial was charged with neopentyl alcohol (0.579 g, 6.57 mmol) and DMF (6.57 mL). Sodium hydride (60% in mineral oil; 0.263 g, 6.57 mmol) was added and the reaction was stirred for 10 minutes at room temperature. The vial was heated to 100° C. for 5 min. The vial was cooled to rt. (S)-7-bromo-3-chloro-2',6'-dihydrospiro[chromeno[2,3-c]pyridine-5,3'-[1,4]oxazin]-5'-amine (0.500 g, 1.314 mmol) was added in one portion. The vial was sealed and heated to 100° C. three hours. The mixture was diluted with ethyl acetate and water. A small amount of brine was added and the layers were separated. The aq. layer was extracted twice with ethyl acetate. The combined organic extracts were dried over sodium sulfate, filtered, and concentrated. The residue was purified by chromatography (0-100% EtOAc/Hexanes) to give 175 mg of (S)—N-(7-bromo-3-(neopentyloxy)-2',6'-dihydrospiro[chromeno[2,3-c]pyridine-5,3'-[1,4]oxazine]-5'-yl)formamide as a light yellow solid.

Step 2: A microwave vial was charged with (S)—N-(7-bromo-3-(neopentyloxy)-2',6'-dihydrospiro[chromeno[2,3-c]pyridine-5,3'-[1,4]oxazine]-5'-yl)formamide (0.075 g, 0.163 mmol), 2-fluoropyridin-3-ylboronic acid (0.046 g, 0.326 mmol), potassium phosphate (0.104 g, 0.489 mmol), and bis(di-tert-butyl(4-dimethylaminophenyl)phosphine) dichloropalladium(II) (5.77 mg, 8.15 μmol). The vial was flushed with Ar (g), then dioxane (0.611 mL) and water (0.204 mL) were added in sequence. The vial was sealed and heated in a Biotage Initiator microwave reactor for 30 min at 100° C. The reaction was diluted with EtOAc and washed with water. The aqueous layer was extracted with EtOAc, and the combined organic layers were washed with brine, dried with sodium sulfate, filtered, and concentrated. The material was purified via column chromatography (0-10% MeOH: DCM w/1% NH$_4$OH) to afford 32 mg of (S)—N-(7-(2-fluoropyridin-3-yl)-3-(neopentyloxy)-2',6'-dihydrospiro[chromeno[2,3-c]pyridine-5,3'-[1,4]oxazine]-5'-yl)formamide as an off-white solid.

Example 44

Method A15

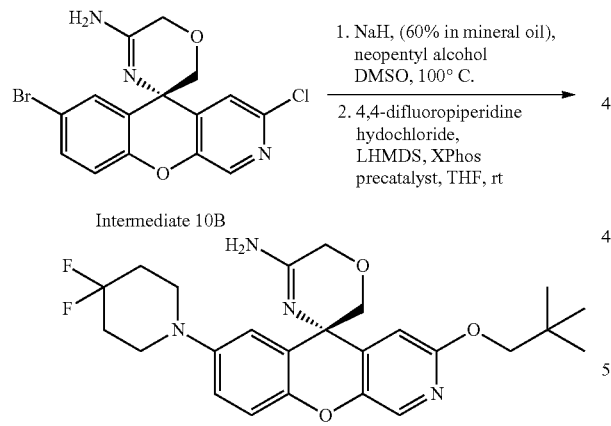

Synthesis of (S)-7-(4,4-difluoropiperidin-1-yl)-3-(neopentyloxy)-2',6'-dihydrospiro[chromeno[2,3-c]pyridine-5,3'-[1,4]oxazin]-5'-amine Step 1: A vial was charged with 2,2-dimethylpropan-1-ol (100 mg, 1.130 mmol) and DMSO (1130 μL) to give a clear solution. Sodium hydride (60% in mineral oil; 45.2 mg, 1.130 mmol) was added and the vial was placed in a 100° C. oil bath for 5 min, then was removed from the heat and cooled to RT. (S)-7-bromo-3-chloro-2',6'-dihydrospiro[chromeno[2,3-c]pyridine-5,3'-[1,4]oxazin]-5'-amine (Intermediate 1B, 86 mg, 0.226 mmol) was added to give an orange solution. The vial was sealed and heated in a 100° C. oil bath for 2 h. The mixture was cooled to room temperature, then diluted with water and EtOAc. Brine was added and the layers were separated. The aq. layer was extracted with EtOAc (2×). The combined organic extracts were dried over sodium sulfate, filtered, and concentrated. The residue was purified by chromatography on silica gel (0-100% EtOAc/Hexane) to give (S)-7-bromo-3-(neopentyloxy)-2',6'-dihydrospiro[chromeno[2,3-c]pyridine-5,3'-[1,4]oxazin]-5'-amine as a light-yellow solid.

Step 2: A vial was charged with (S)-7-bromo-3-(neopentyloxy)-2',6'-dihydrospiro[chromeno[2,3-c]pyridine-5,3'-[1,4]oxazin]-5'-amine (74.0 mg, 0.171 mmol) 4,4-difluoropiperidine hydrochloride (31.1 mg, 0.257 mmol), and chloro(2-dicyclohexylphosphino-2',4',6'-tri-1-propyl-1,1'-biphenyl)[2-(2-aminoethyl)phenyl]palladium(II) methyl-t-butylether adduct (12.02 mg, 0.017 mmol). The vial was flushed with Argon and sealed. Lithium bis(trimethylsilyl)amide (1M in THF) (599 μL, 0.599 mmol) was added in one portion. The resulting mixture was sonicated for 1 min, then stirred for 30 min at rt. The reaction mixture was diluted with saturated aq ammonium chloride solution and extracted with EtOAc (3×). The combined organic extracts were dried over sodium sulfate, filtered, and concentrated. The residue was purified by chromatography (0-10% MeOH/DCM) to give (S)-7-(4,4-difluoropiperidin-1-yl)-3-(neopentyloxy)-2',6'-dihydrospiro[chromeno[2,3-c]pyridine-5,3'-[1,4]oxazin]-5'-amine as an off-white solid. [M+H]$^+$=473.2.

$^1$H NMR (400 MHz, DMSO-d$_6$) δ=8.01 (d, J=0.5 Hz, 1 H), 7.10-6.95 (m, 2 H), 6.83 (d, J=2.8 Hz, 1 H), 6.57 (d, J=0.4 Hz, 1 H), 6.16 (br. s., 2 H), 4.28-4.11 (m, 2 H), 3.98-3.80 (m, 2 H), 3.47-3.27 (m, 2 H), 3.25-3.12 (m, 4 H), 2.21-1.98 (m, 4 H), 0.99 (s, 9 H)

Example 45

Method A16

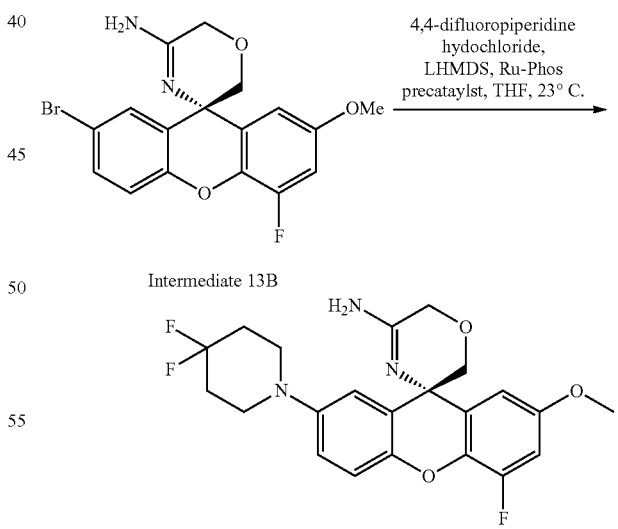

Synthesis of (S)-7'-(4,4-difluoropiperidin-1-yl)-4'-fluoro-2'-methoxy-2,6-dihydrospiro[[1,4]oxazine-3,9'-xanthen]-5-amine A vial was charged with (S)-7'-bromo-4'-fluoro-2'-methoxy-2,6-dihydrospiro[[1,4]oxazine-3,9'-xanthen]-5-amine (200 mg, 0.509 mmol), chloro(2-dicyclohexylphosphino-2', 6'-di-i-propoxy-1,1'-biphenyl)[2-(2-aminoethyl)phenyl]palladium(II) methyl-t-butylether adduct (18.53 mg, 0.025 mmol), 4,4-difluoropiperidine hydrochloride (160 mg, 1.017 mmol) and 1 ml of THF. The mixture was cooled to 0° C. and LHMDS (1M in THF; 2035 µL, 2.035 mmol) was added. The vial was sealed and stirred at room temperature for 2 hr. At this point more chloro(2-dicyclohexylphosphino-2',6'-di-i-propoxy-1,1'-biphenyl)[2-(2-aminoethyl)phenyl]palladium (II) methyl-t-butylether adduct (18.53 mg, 0.025 mmol), (18.53 mg, 0.025 mmol) was added followed by LHMDS solution (1 ml) and stirring was continued for another hour. The mixture was quenched by addition of 2 ml of water and extracted with ethyl acetate. The combined organic layers were concentrated and purified by chromatography (5-50% DCM/MeOH/NH4OH (90:10:1) to afford (S)-7'-(4,4-difluoropiperidin-1-yl)-4'-fluoro-2'-methoxy-2,6-dihydrospiro[[1,4]oxazine-3,9'-xanthen]-5-amine (130 mg, 0.300 mmol, 59.0% yield) as yellowish foam.

Example 46

Method A17

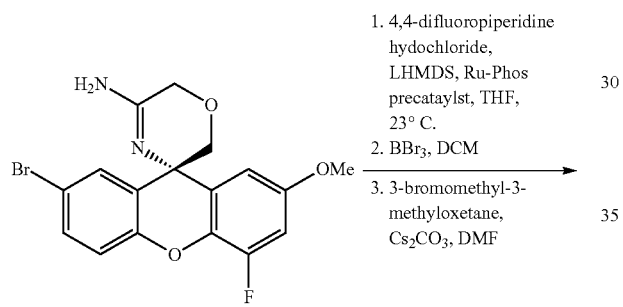

Intermediate 13B

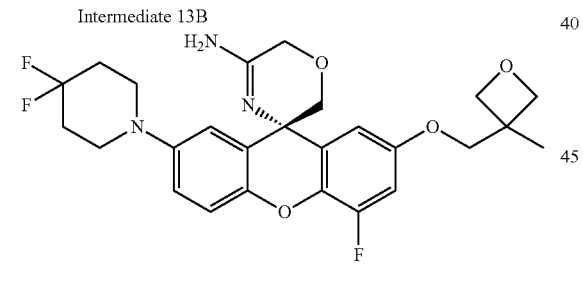

Synthesis of (S)-7'-(4,4-difluoropiperidin-1-yl)-4'-fluoro-2'-((3-methyloxetan-3-yl)methoxy)-2,6-dihydrospiro[[1,4]oxazine-3,9'-xanthen]-5-amine Step 1: A vial was charged with (S)-7'-bromo-4'-fluoro-2'-methoxy-2,6-dihydrospiro[[1,4]oxazine-3,9'-xanthen]-5-amine (200 mg, 0.509 mmol), chloro(2-dicyclohexylphosphino-2',6'-di-i-propoxy-1,1'-biphenyl)[2-(2-aminoethyl)phenyl]palladium(II) methyl-t-butylether adduct (18.53 mg, 0.025 mmol), 4,4-difluoropiperidine hydrochloride (160 mg, 1.017 mmol) and 1 ml of THF. The mixture was cooled to 0° C. and LHMDS (1M in THF) (2035 µL, 2.035 mmol) was added, and the vial was sealed and stirred at RT for 2 hr. At this point more chloro(2-dicyclohexylphosphino-2',6'-di-i-propoxy-1,1'-biphenyl)[2-(2-aminoethyl)phenyl] palladium(II) methyl-t-butylether adduct (18.53 mg, 0.025 mmol), (18.53 mg, 0.025 mmol) was added followed by LHMDS solution (1 ml) and stirring continued for another hour. The mixture was quenched by addition of 2 ml of water and extracted with EtOAc. The combined organic fractions were concentrated and purified by chromatography [5-50% DCM/MeOH/NH4OH (90:10:1)] to afford (S)-7'-(4,4-difluoropiperidin-1-yl)-4'-fluoro-2'-methoxy-2,6-dihydrospiro[[1,4]oxazine-3,9'-xanthen]-5-amine as yellowish foam.

Step 2: To a solution of (S)-7'-(4,4-difluoropiperidin-1-yl)-4'-fluoro-2'-methoxy-2,6-dihydrospiro[[1,4]oxazine-3,9'-xanthen]-5-amine (130 mg, 0.300 mmol) in DCM (3 ml) boron tribromide (0.085 ml, 0.900 mmol) was added dropwise at room temperature and the mixture was stirred for 3 hrs at RT. The reaction was quenched by addition of MeOH (~1 ml), stirred for 10 min, then neutralized by addition of 25% NH4OH. The homogeneous mixture was concentrated in vacuo and extracted with EtOAc. The organic layer was washed with brine and concentrated in vacuo to give after trituration with DCM off white solid. The solid was redissolved in 3 ml of DMF, cesium carbonate (195 mg, 0.600 mmol) and potassium iodide (14.94 mg, 0.090 mmol) were added and then 3-bromomethyl1-3-methyloxetane (0.054 ml, 0.330 mmol) was added dropwise. The mixture was stirred at RT for 4 hrs. The mixture was diluted with water (10 ml) and extracted with EtOAc. The combined organic layers was washed twice with water, then with brine and concentrated in vacuo. The residue was purified by chromatography [10-80% DCM/MeOH/NH4OH (90:10:1) in DCM] to afford (S)-7'-(4,4-difluoropiperidin-1-yl)-4'-fluoro-2'-((3-methyloxetan-3-yl)methoxy)-2,6-dihydrospiro[[1,4]oxazine-3,9'-xanthen]-5-amine Example 47

Method A18

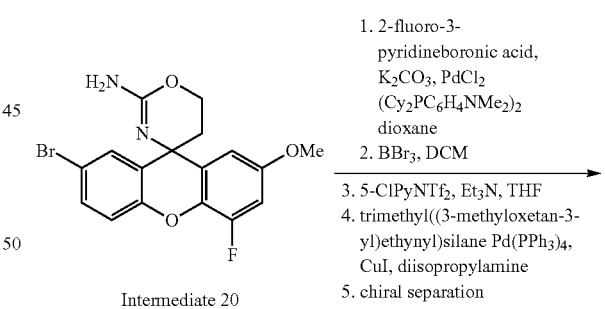

Intermediate 20

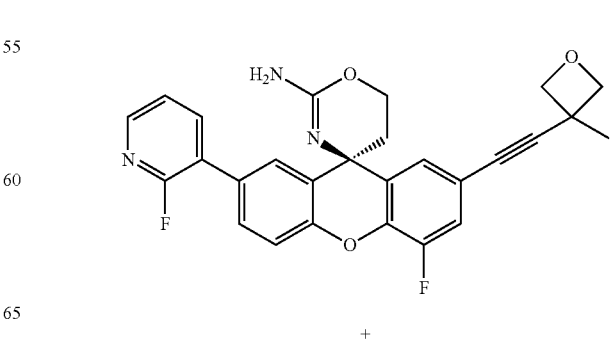

+

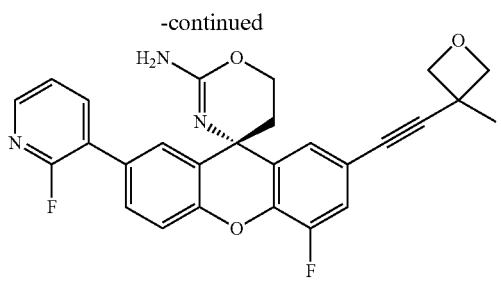

Synthesis of (R)-4'-fluoro-7'-(2-fluoropyridin-3-yl)-2'-((3-methyloxetan-3-yl)ethynyl)-5,6-dihydrospiro[[1,3]oxazine-4,9'-xanthen]-2-amine (Example 47B) and (S)-4'-fluoro-7'-(2-fluoropyridin-3-yl)-2'((3-methyloxetan-3-yl)ethynyl)-5,6-dihydrospiro[[1,3]oxazine-4,9'-xanthen]-2-amine (Example 47A)

Step 1: A 50 ml RB flask was charged with 7'-bromo-4'-fluoro-2'-methoxy-5,6-dihydrospiro[[1,3]oxazine-4,9'-xanthen]-2-amine (806 mg, 2.050 mmol), 2-fluoropyridin-3-ylboronic acid (433 mg, 3.07 mmol), PdCl$_2$(Cy$_2$PC$_6$H$_4$NMe$_2$)$_2$ (72.6 mg, 0.102 mmol), then dioxane (10 ml) and potassium carbonate (1M solution in water; 6.15 ml, 6.15 mmol). The mixture was stirred at 85° C. for 1 hr. The reaction mixture was cooled to RT, diluted with EtOAc and organic layer was separated and concentrated in vacuo. The residue was treated with 3 ml of EtOH and precipitated solid was filtered off, washed with ethanol and dried on air to afford 514 mg (61%) of pure desired product. The filtrate was concentrated and purified by chromatography [5-80% DCM./MeOH/NH$_4$OH (90:10:1) in DCM] to afford additional 300 mg (35%) of the product.

Step 2: To a suspension of 4'-fluoro-7'-(2-fluoropyridin-3-yl)-2'-methoxy-5,6-dihydrospiro[[1,3]oxazine-4,9'-xanthen]-2-amine (2.178 g, 5.32 mmol) in DCM (43 mL) boron tribromide (1.509 mL, 15.96 mmol) was added dropwise at RT. The mixture was stirred 2 hrs at RT, the mixture was cooled to 0° C. and quenched by addition of 5 ml of methanol dropwise. The resulting white suspension was stirred for 20 min at 0° C., then sat. aq. NaHCO$_3$ (~5 ml) was added followed by addition of 25% aq. ammonia (~15 ml). The mixture was stirred for 30 min, then DCM was removed in a stream of nitrogen. The mixture was diluted with water (10 ml) and 25% ammonia (10 ml) and filtered. The white solid was washed with water twice, then dried for 3 hrs on air, then in vacuo overnight to give 2-amino-4'-fluoro-7'-(2-fluoropyridin-3-yl)-5,6-dihydrospiro[[1,3]oxazine-4,9'-xanthen]-2'-ol (2.08 g, 5.26 mmol, 99% yield).

Step 3: To a suspension of 2-amino-4'-fluoro-7'-(2-fluoropyridin-3-yl)-5,6-dihydrospiro[[1,3]oxazine-4,9'-xanthen]-2'-ol (1.91 g, 4.83 mmol) in DCM (24.16 ml) TEA (1.347 ml, 9.66 mmol) and N-(5-chloropyridin-2-yl)-1,1,1-trifluoro-N-((trifluoromethyl)sulfonyl)methanesulfonamide (2.087 g, 5.31 mmol) were added at RT. The mixture was stirred for 1 hr at RT and the mixture became homogeneous. The reaction mixture was washed twice with 2N NaOH solution, brine, filtered through the pad of celite and concentrated to leave 2-amino-5'-fluoro-2'-(2-fluoropyridin-3-yl)-5,6-dihydrospiro[[1,3]oxazine-4,9'-xanthen]-7'-yl trifluoromethanesulfonate (2.04 g, 3.87 mmol, 80% yield) as a creamy solid which was used without further purification.

Step 4: A sealable tube was charged with 2-amino-5'-fluoro-2'-(2-fluoropyridin-3-yl)-5,6-dihydrospiro[[1,3]oxazine-4,9'-xanthen]-7'-yl trifluoromethanesulfonate (500 mg, 0.948 mmol), tetrakis(triphenylphosphine)palladium (0) (219 mg, 0.190 mmol), copper(I) iodide (72.2 mg, 0.379 mmol), DMF (4.5 mL), trimethyl((3-methyloxetan-3-yl)ethynyl)silane (479 mg, 2.84 mmol) and DIPA (1.3 ml, 9.48 mmol). The vial was sealed and stirred at 90° C. for 18 hrs. The mixture was diluted with EtOAc (10 ml) and washed twice with water (5 ml) and brine. The organic layer was concentrated and purified by chromatography (30-50% DCM/MeOH/NH$_4$OH in DCM) to afford racemic 4'-fluoro-7'-(2-fluoropyridin-3-yl)-2'-((3-methyloxetan-3-yl)ethynyl)-5,6-dihydrospiro[[1,3]oxazine-4,9'-xanthen]-2-amine (117 mg, 0.247 mmol, 26.1% yield).

Step 5: The final compounds (R)-4'-fluoro-7'-(2-fluoropyridin-3-yl)-2'-((3-methyloxetan-3-yl)ethynyl)-5,6-dihydrospiro[[1,3]oxazine-4,9'-xanthen]-2-amine and (S)-4'-fluoro-7'-(2-fluoropyridin-3-yl)-2'-((3-methyloxetan-3-yl)ethynyl)-5,6-dihydrospiro[[1,3]oxazine-4,9'-xanthen]-2-amine were obtained from racemic 4'-fluoro-7'-(2-fluoropyridin-3-yl)-2'-((3-methyloxetan-3-yl)ethynyl)-5,6-dihydrospiro[[1,3]oxazine-4,9'-xanthen]-2-amine using similar chiral separation conditions as described herein for intermediate 10.

Example 48

Method A19

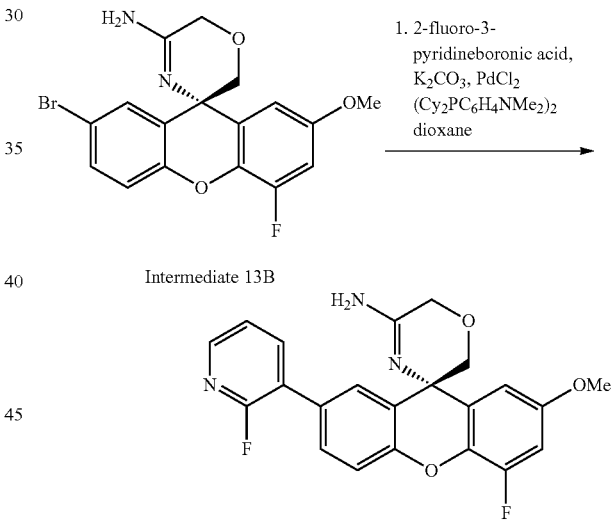

Synthesis of (S)-4'-fluoro-7'-(2-fluoropyridin-3-yl)-2'-methoxy-2,6-dihydrospiro[[1,4]oxazine-3,9'-xanthen]-5-amine A 250 ml RB flask was charged with (S)-7'-bromo-4'-fluoro-2'-methoxy-2,6-dihydrospiro[[1,4]oxazine-3,9'-xanthen]-5-amine (1.0 g, 2.54 mmol), PdCl$_2$(Cy$_2$C$_6$H$_4$NMe$_2$)$_2$ (0.126 g, 0.178 mmol) and 2-fluoropyridin-3-ylboronic acid (0.538 g, 3.81 mmol). Dioxane (12.72 mL) and potassium carbonate (1M solution) (7.63 mL, 7.63 mmol) were added, and the mixture was flushed with argon and heated to 85° C. for 30 min. The mixture was cooled to RT and diluted with EtOAc. The organic layer was separated and concentrated under reduced pressure to give a yellow foam. The residue was purified by chromatography (5-50% of EtOAc/MeOH/NH$_4$OH 90:10:1 in EtOAc) to afford (S)-4'-fluoro-7'-(2-fluoropyridin-3-yl)-2'-methoxy-2,6-dihydrospiro[[1,4]oxazine-3,9'-xanthen]-5-amine (0.82 g, 2.003 mmol, 79% yield).

Example 49

Method A20

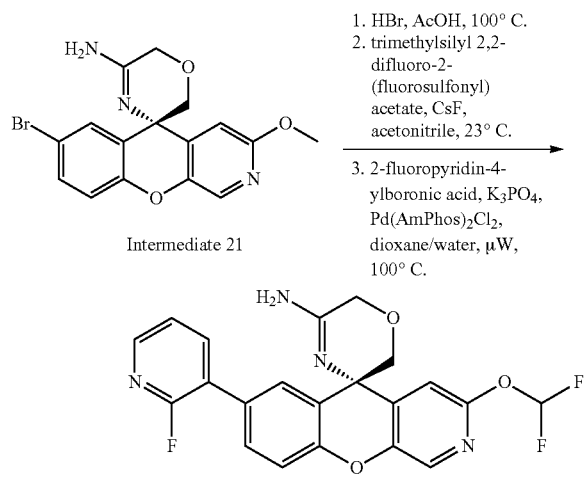

Synthesis of (S)-3-(difluoromethoxy)-7-(2-fluoropyridin-3-yl)-2',6'-dihydrospiro[chromeno[2,3-c]pyridine-5,3'-[1,4]oxazin]-5'-amine Step 1: (S)-7-bromo-3-methoxy-2',6'-dihydrospiro[chromeno[2,3-c]pyridine-5,3'-[1,4]oxazin]-5'-amine (0.611 g, 1.624 mmol) was dissolved in HOAc (6.14 mL, 107 mmol). Hydrobromic acid (48% aq.; 6.06 mL, 53.6 mmol) was added and the reaction was stirred at 100° C. for two hours. The reaction was diluted with water, slowly neutralized to pH 7 with 6N NaOH, and stirred overnight, during which a light pink solid crashed out of solution. The solution was filtered, and the solid was air dried to afford (S)-5'-amino-7-bromo-2',6'-dihydrospiro[chromeno[2,3-c]pyridine-5,3'-[1,4]oxazin]-3-ol (0.554 g, 1.530 mmol, 94% yield) as an off-white solid. [M+H]+=363.9

Step 2: A flask was charged with (S)-5'-amino-7-bromo-2',6'-dihydrospiro[chromeno[2,3-c]pyridine-5,3'-[1,4]oxazin]-3-ol (0.250 g, 0.690 mmol), cesium fluoride (9.17 mg, 0.069 mmol), and acetonitrile (6.90 mL). Trimethylsilyl 2,2-difluoro-2-(fluorosulfonyl)acetate (0.272 mL, 1.381 mmol) was added slowly and the reaction was stirred for 15 minutes. The reaction was diluted with EtOAc and washed with water. The aqueous layer was extracted with EtOAc, and the combined organic layers were washed with brine, dried with sodium sulfate, filtered, and concentrated. The material was purified via column chromatography (0-10% MeOH/DCM), to afford (S)-7-bromo-3-(difluoromethoxy)-2',6'-dihydrospiro[chromeno[2,3-c]pyridine-5,3'-[1,4]oxazin]-5'-amine (0.056 g, 0.136 mmol, 19.68% yield) as a light yellow solid. [M+H]+=411.9

Step 3: A microwave vial was charged with (S)-7-bromo-3-(difluoromethoxy)-2',6'-dihydrospiro[chromeno[2,3-c]pyridine-5,3'-[1,4]oxazin]-5'-amine (0.056 g, 0.136 mmol). 2-fluoropyridin-3-ylboronic acid (0.038 g, 0.272 mmol), potassium phosphate (0.087 g, 0.408 mmol), and bis(di-tert-butyl(4-dimethylaminophenyl)phosphine)dichloropalladium(II) (4.81 mg, 6.79 µmol) were added. The vial was flushed with Ar (g), then dioxane (0.509 mL) and water (0.170 mL) were added in sequence. The vial was sealed and heated in a Biotage Initiator microwave reactor for 30 min at 100° C. The reaction was diluted with EtOAc and washed with water. The aqueous layer was extracted with EtOAc, and the combined organic layers were washed with brine, dried with sodium sulfate, filtered, and concentrated. The material was purified via column chromatography (0-10% MeOH/DCM) to afford (S)-3-(difluoromethoxy)-7-(2-fluoropyridin-3-yl)-2',6'-dihydrospiro[chromeno[2,3-c]pyridine-5,3'-[1,4]oxazin]-5'-amine (0.042 g, 0.098 mmol) as a light yellow solid. [M+H]+=429.0

Example 50

Method A21

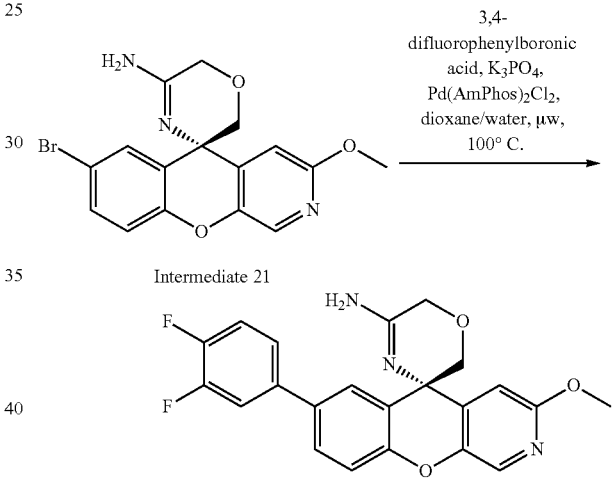

Synthesis of (S)-7-(3,4-difluorophenyl)-3-methoxy-2',6'-dihydrospiro[chromeno[2,3-c]pyridine-5,3'-[1,4]oxazin]-5'-amine A microwave vial was charged with (S)-7-bromo-3-methoxy-2',6'-dihydrospiro[chromeno[2,3-c]pyridine-5,3'-[1,4]oxazin]-5'-amine (0.075 g, 0.199 mmol). 3,4-difluorophenylboronic acid (0.063 g, 0.399 mmol), potassium phosphate (0.127 g, 0.598 mmol), and bis(di-tert-butyl(4-dimethylaminophenyl)phosphine)dichloropalladium(II) (7.06 mg, 9.97 µmol) were added. The vial was flushed with Ar (g), then dioxane (0.748 mL) and water (0.249 mL) were added in sequence. The vial was sealed and heated in a Biotage Initiator microwave reactor for 30 min at 100° C. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (0-100% EtOAc/Hexanes) to afford (S)-7-(3,4-difluorophenyl)-3-methoxy-2',6'-dihydrospiro[chromeno[2,3-c]pyridine-5,3'-[1,4]oxazin]-5'-amine (0.073 g, 0.178 mmol, 89% yield) as an off-white solid. [M+H]+=410.4

Example 51

Method A22

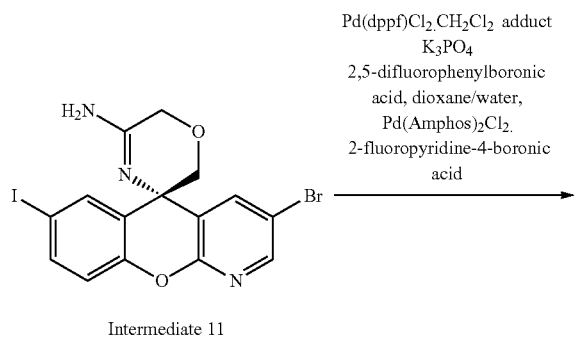

Intermediate 11

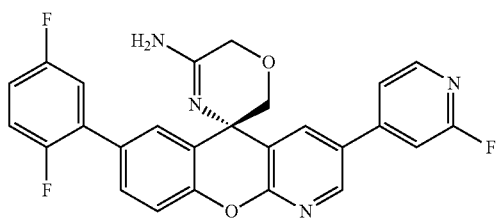

Synthesis of (S)-7-(2,5-difluorophenyl)-3-(2-fluoro-pyridin-4-yl)-2',6'-dihydrospiro[chromeno[2,3-b]pyridine-5,3'-[1,4]oxazin]-5'-amine A vial was charged with 2,5-difluorophenylboronic acid (0.035 g, 0.222 mmol), PdCl₂(dppf)-CH₂Cl₂ adduct (8.65 mg, 10.59 μmol), (S)-3-bromo-7-iodo-2',6'-dihydrospiro[chromeno[2,3-b]pyridine-5,3'-[1,4]oxazin]-5'-amine (0.100 g, 0.212 mmol), and potassium phosphate (0.450 g, 2.118 mmol). Dioxane (2 mL) and water (1 mL) were added, the vial was flushed with argon, sealed and heated to 80° C. 1 hour. The reaction mixture was cooled to rt and bis(di-tert-butyl(4-dimethylaminophenyl)phosphine)dichloropalladium(II) (7.50 mg, 10.59 μmol) was added, followed by 2-fluoropyridin-4-ylboronic acid (0.045 g, 0.318 mmol). The reaction mixture was again capped under argon and was heated to 80° C. for and additional hour. The reaction mixture was then diluted with 2-MeTHF, dried over MgSO₄ and concentrated. Purification of the crude residue by column chromatography [0-100% (95:5 EtOAc/MeOH)/DCM] gave (S)-7-(2,5-difluorophenyl)-3-(2-fluoropyridin-4-yl)-2',6'-dihydrospiro[chromeno[2,3-b]pyridine-5,3'-[1,4]oxazin]-5'-amine (0.028 g, 0.059 mmol, 27.9% yield) as a light yellow solid. [M+H]+=475.0

Example 52

Method A23

1. Pd(dppf)Cl₂·CH₂Cl₂ adduct, K₂CO₃
2-fluoropyridine-3-boronic acid, dioxane/water,
2. tBuXPhos palladacycle, Cs₂CO₃ 3,3-dimethyl-1-butyne, DMF

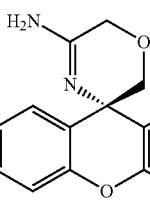

Intermediate 11

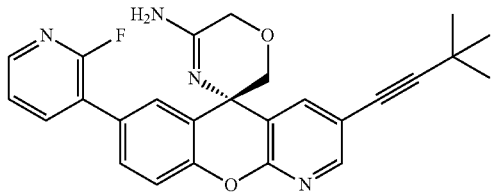

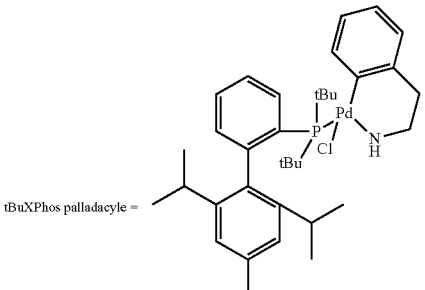

tBuXPhos palladacyle =

Synthesis of (S)-3-(3,3-dimethylbut-1-ynyl)-7-(pyridin-3-yl)-2',6'-dihydrospiro[chromeno[2,3-b]pyridine-5,3'-[1,4]oxazin]-5'-amine Step 1: A vial was charged with pyridin-3-ylboronic acid (0.027 g, 0.222 mmol), PdCl₂(dppf)-CH₂Cl₂-adduct (8.65 mg, 10.59 μmol), (S)-3-bromo-7-iodo-2',6'-dihydrospiro[chromeno[2,3-b]pyridine-5,3'-[1,4]oxazin]-5'-amine (0.100 g, 0.212 mmol), and potassium carbonate (0.117 g, 0.847 mmol). Dioxane (5 mL) and water (0.5 mL) were added. The vial was flushed with argon, and heated to 100° C. for 1 hour. An additional portion of pyridin-3-ylboronic acid (0.027 g, 0.222 mmol) was added, and the reaction mixture was heated to 100° C. for an additional hour. The reaction mixture was diluted with 2-MeTHF, dried over MgSO₄ and concentrated under reduced pressure. The crude residue was used without purification.

Step 2: The crude residue from step 1 was dissolved in 2 mL DMF, treated with 3,3-dimethyl-1-butyne (0.130 mL, 1.059 mmol), cesium carbonate (0.345 g, 1.059 mmol), and tBu-XPhos palladacycle (7.27 mg, 10.59 μmol). The reaction mixture was capped under argon, and was heated to 90° C. for 2 hours. The reaction mixture was then diluted with 2-MeTHF and washed with water. The organics were dried over MgSO₄ and concentrated. Purification of the crude residue by column chromatography [0-100% (95:5 EtOAc/MeOH)/DCM] gave (S)-3-(3,3-dimethylbut-1-ynyl)-7-(pyridin-3-yl)-2',6'-dihydrospiro[chromeno[2,3-b]pyridine-5,3'-[1,4]oxazin]-5'-amine (0.018 g, 0.042 mmol, 20.02% yield) as a grey solid. [M+H]+=425.0

Example 53

Method A24

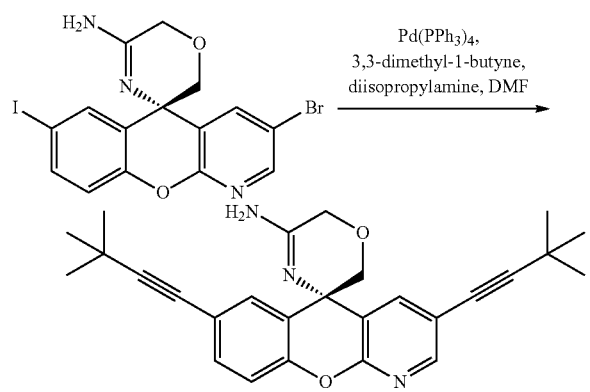

Synthesis of (S)-3,7-bis(3,3-dimethylbut-1-ynyl)-2',6'-dihydrospiro[chromeno[2,3-b]pyridine-5,3'-[1,4]oxazin]-5'-amine Step 1: A vial was charged with (S)-3-bromo-7-iodo-2',6'-dihydrospiro[chromeno[2,3-b]pyridine-5,3'-[1,4]oxazin]-5'-amine (0.520 g, 1.102 mmol), DIPA (0.785 mL, 5.51 mmol), Pd(PPh₃)₄ (0.127 g, 0.110 mmol), copper(I) iodide (0.021 g, 0.110 mmol), and 3,3-dimethyl-1-butyne (0.203 mL, 1.652 mmol) DMF (3 ml) was added, the vial was sealed under argon, and was heated to 90° C. for 60 minutes. The reaction mixture was diluted with 2-MeTHF then washed with water. The organics were dried over MgSO₄ and concentrated. Purification of the crude residue by column chromatography gave (S)-3,7-bis(3,3-dimethylbut-1-ynyl)-2',6'-dihydrospiro[chromeno[2,3-b]pyridine-5,3'-[1,4]oxazin]-5'-amine (0.180 g, 0.421 mmol) as a white solid. [M+H]+=428.0

Example 54

Method A25

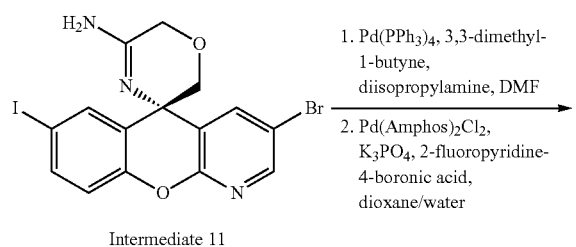

Intermediate 11

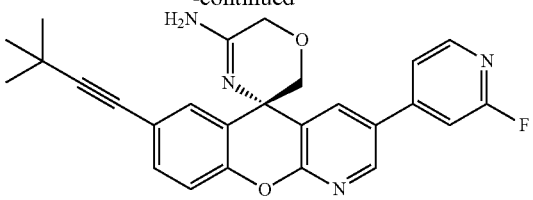

Synthesis of (S)-7-(3,3-dimethylbut-1-ynyl)-3-(2-fluoropyridin-4-yl)-2',6'-dihydrospiro[chromeno[2,3-b]pyridine-5,3'-[1,4]oxazin]-5'-amine Step 1: A vial was charged with (S)-3-bromo-7-iodo-2',6'-dihydrospiro[chromeno[2,3-b]pyridine-5,3'-[1,4]oxazin]-5'-amine, diisopropylamine (0.785 mL, 5.51 mmol), Pd(PPh₃)₄ (0.127 g, 0.110 mmol), copper(I) iodide (0.021 g, 0.110 mmol), and 3,3-dimethyl-1-butyne (0.203 mL, 1.652 mmol). DMF (3 mL) were added, the vial was sealed under argon and heated to 90° C. for 60 minutes. The reaction mixture was diluted with 2-MeTHF then washed with water. The organics were dried over MgSO4 and concentrated. Purification of the crude residue by column chromatography gave (S)-3-bromo-7-(3,3-dimethylbut-1-ynyl)-2',6'-dihydrospiro[chromeno[2,3-b]pyridine-5,3'-[1,4]oxazin]-5'-amine (0.120 g, 0.281 mmol, 25.6% yield) as a white solid.

Step 2: A vial was charged with (S)-3-bromo-7-(3,3-dimethylbut-1-ynyl)-2',6'-dihydrospiro[chromeno[2,3-b]pyridine-5,3'-[1,4]oxazin]-5'-amine (0.060 g, 0.141 mmol), 2-fluoropyridin-4-ylboronic acid (0.050 g, 0.352 mmol), potassium phosphate (0.299 g, 1.407 mmol) and bis(di-tert-butyl(4-dimethylaminophenyl)phosphine)dichloropalladium(II) (4.98 mg, 7.04 µmol) Dioxane (2 mL) and water (0.5 mL) were added, the vial was sealed under argon and heated to 80° C. for 1 hour. The reaction mixture was then diluted with 2-MeTHF, dried over MgSO4 and concentrated. Purification of the crude residue by column chromatography [0-100% (95:5 EtOAc/MeOH)/DCM] gave (S)-7-(3,3-dimethylbut-1-ynyl)-3-(2-fluoropyridin-4-yl)-2',6'-dihydrospiro[chromeno[2,3-b]pyridine-5,3'-[1,4]oxazin]-5'-amine (0.029 g, 0.066 mmol, 46.6% yield) as a yellow solid. [M+H]+=443.0

Example 55

Method A26

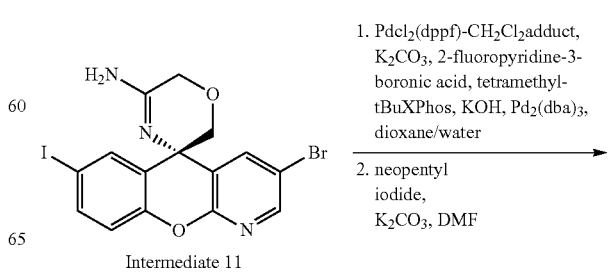

Intermediate 11

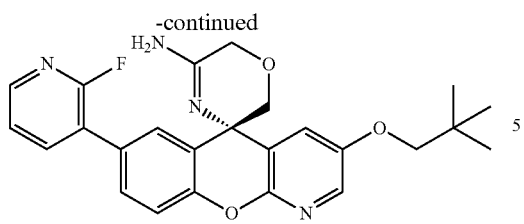

Synthesis of (S)-7-(2-fluoropyridin-3-yl)-3-(neopentyloxy)-2',6'-dihydrospiro[chromeno[2,3-b]pyridine-5,3'-[1,4]oxazin]-5'-amine Step 1: A vial charged with a solution of (S)-3-bromo-7-iodo-2',6'-dihydrospiro[chromeno[2,3-b]pyridine-5,3'-[1,4]oxazin]-5'-amine (0.880 g, 1.864 mmol), 2-fluoropyridin-3-ylboronic acid (0.276 g, 1.957 mmol), PdCl$_2$(dppf)-CH$_2$Cl$_2$-adduct (0.038 g, 0.047 mmol), and potassium carbonate (1.031 g, 7.46 mmol). Dioxane (10 mL) and water (5 mL) were added, and the vial was flushed with argon and heated to 100° C. for 90 minutes. Pd$_2$(dba)$_3$ (0.171 g, 0.186 mmol), di-tert-butyl(2',4',6'-triisopropyl-3,4,5,6-tetramethylbiphenyl-2-yl)phosphine (0.224 g, 0.466 mmol), and potassium hydroxide (1.046 g, 18.64 mmol) were added to the reaction mixture. The vial was sealed and heated to 120° C. for an additional 3 hours. The reaction mixture was then neutralized to pH 7 with 1N HCl, and was diluted with 2-MeTHF. The organics were dried over MgSO4 and concentrated. Purification of the crude residue by column chromatography [0-100% (90:10:1 DCM/MeOH/NH$_4$OH)/DCM] gave (S)-5'-amino-7-(2-fluoropyridin-3-yl)-2',6'-dihydrospiro[chromeno[2,3-b]pyridine-5,3'-[1,4]oxazin]-3-ol (0.133 g, 0.352 mmol).

Step 2: A solution of (S)-5'-amino-7-(2-fluoropyridin-3-yl)-2',6'-dihydrospiro[chromeno[2,3-b]pyridine-5,3'-[1,4]oxazin]-3-ol (0.133 g, 0.352 mmol), potassium carbonate (0.194 g, 1.406 mmol), and neopentyl iodide (0.093 mL, 0.703 mmol) in 1.5 mL DMF was heated to 115° C. overnight. The reaction mixture was then diluted with 2-MeTHF and washed with water. The organics were dried over MgSO$_4$ and concentrated. Purification of the crude residue by column chromatography [0-100% (9:1 EtOAc/MeOH)/DCM] gave (S)-7-(2-fluoropyridin-3-yl)-3-(neopentyloxy)-2',6'-dihydrospiro[chromeno[2,3-b]pyridine-5,3'-[1,4]oxazin]-5'-amine (0.025 g, 0.056 mmol, 15.86% yield). MS m/z=449.20 [M+H]$^+$. Calculated for C$_{25}$H$_{25}$FN$_4$O$_3$: 448.49.

$^1$H NMR (400 MHz, MeCN) δ ppm 1.05 (s, 9 H) 3.48 (s, 2 H) 3.72 (s, 2 H) 4.21-4.31 (m, 2 H) 7.26-7.30 (m, 2 H) 7.35-7.39 (m, 1 H) 7.48-7.50 (m, 1 H) 7.55-7.58 (m, 1 H) 7.91 (d, J=4.0 Hz, 1 H) 7.96-8.01 (m, 1 H) 8.16-8.19 (m, 1 H)

Example 56

Method A27

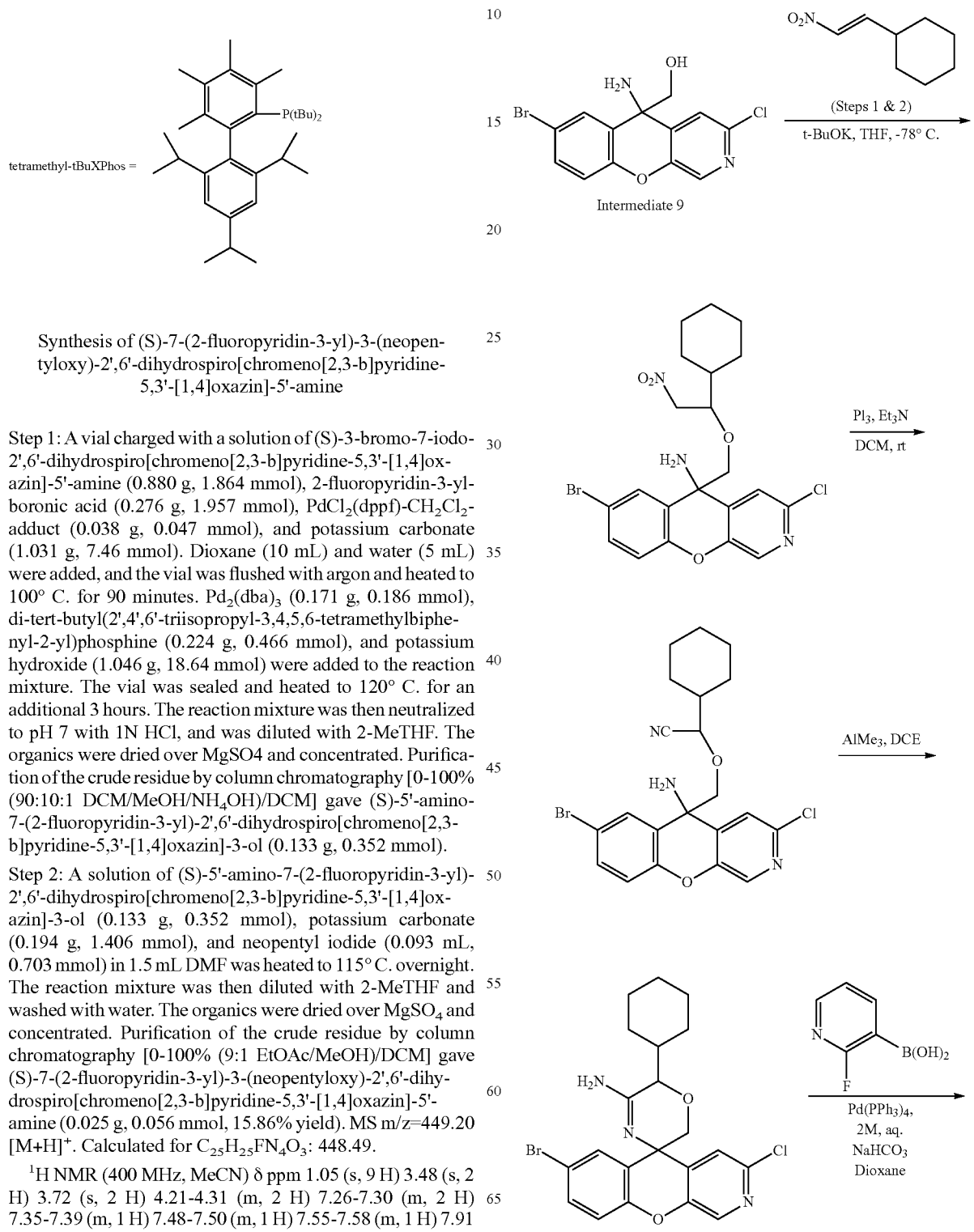

-continued

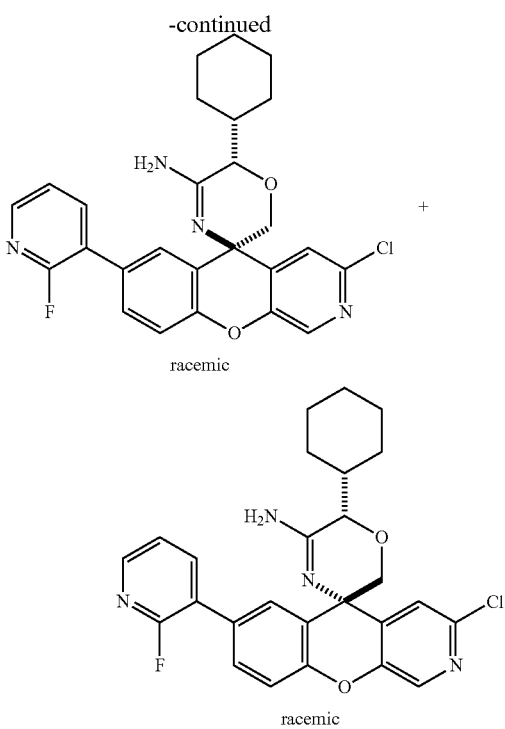

Synthesis of (3'R,6'S)-3-chloro-6'-cyclohexyl-7-(2-fluoropyridin-3-yl)-2',6'-dihydrospiro[chromeno[2,3-c]pyridine-5,3'-[1,4]oxazin]-5'-amine (Example 56B) and racemic (3'S,6'S)-3-chloro-6'-cyclohexyl-7-(2-fluoropyridin-3-yl)-2',6'-dihydrospiro[chromeno[2,3-c]pyridine-5,3'-[1,4]oxazin]-5'-amine (Example 56A)

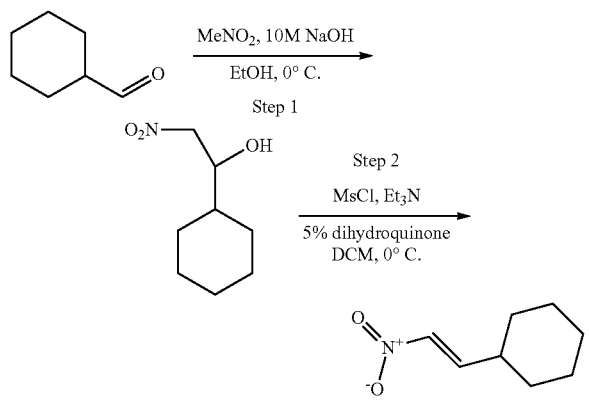

Steps 1 and 2: Synthesis of (E)-(2-nitrovinyl)cyclohexane

Step 1: 10 M aqueous NaOH (8.31 mL, 83 mmol) was added dropwise via addition funnel to a solution of nitromethane (4.46 mL, 83 mmol) and cyclohexanecarboxaldehyde (10 mL, 83 mmol) in EtOH (20 mL) at 0° C. with vigorous stirring. The resulting white slurry was stirred 10 minutes and became a white solid. Acetic acid (4.76 mL, 83 mmol) was added and the reaction was partitioned between diethyl ether and water. The layers were separated and the aqueous layer was extracted with diethyl ether. The combined organic extracts were washed with water, saturated aqueous sodium chloride, and dried over magnesium sulfate. The solution was filtered and concentrated in vacuo and dried under vacumm to afford 1-cyclohexyl-2-nitroethanol. The product was used directly for the next step without further purification.

Step 2: Methanesulfonyl chloride (2.83 mL, 36.4 mmol) was added via syringe to a solution of (E)-(2-nitrovinyl)cyclohexane and hydroquinone (0.200 g, 1.819 mmol) in DCM (35 mL) at 0° C. Next, triethylamine (10.14 mL, 72.7 mmol) was added dropwise and the solution was stirred 20 minutes (precipitate forms) before being transferred to a separatory funnel with DCM and water. The layers were separated and the organics were washed with water, 1N HCl, saturated aqueous sodium chloride, and dried over sodium sulfate. The solution was filtered and concentrated in vacuo to give (E)-(2-nitrovinyl)cyclohexane. The product was used directly for the next step without further purification.

Step 3: Potassium t-butoxide (0.517 g, 4.61 mmol) was added in one portion to a solution of (5-amino-7-bromo-3-chloro-5H-chromeno[2,3-c]pyridin-5-yl)methanol (Intermediate X, 1.5 g, 4.39 mmol) in THF (30 mL) at −78° C. After stirring for 45 minutes, (E)-(2-nitrovinyl)cyclohexane (0.716 g, 4.61 mmol) in THF (15.00 mL) was added slowly via syringe. The reaction was stirred at −78° C. for 20 minutes and was quenched with acetic acid (0.502 mL, 8.78 mmol) at −78° C., diluted with saturated aqueous ammonium chloride, water and EtOAc. After warming to RT, the layers were separated and the aqueous layer was extracted with EtOAc. The combined organic extracts were washed with water, saturated aqueous sodium chloride, and dried over sodium sulfate. The solution was filtered and concentrated in vacuo to give the crude material. The crude material was purified by silica gel chromatography by eluting with 1:6 to 1:4 EtOAc in hexane, to provide 7-bromo-3-chloro-5-((1-cyclohexyl-2-nitroethoxy)methyl)-5H-chromeno[2,3-c]pyridin-5-amine as a yellow oil. [M+H]$^+$=496.1.

Step 4: TEA (1.263 ml, 9.06 mmol) and triiodophosphine (1.243 g, 3.02 mmol) were added to 7-bromo-3-chloro-5-((1-cyclohexyl-2-nitroethoxy)methyl)-5H-chromeno[2,3-c]pyridin-5-amine (1.5 g, 3.02 mmol) in DCM (30.2 ml) at 0° C. The reaction was stirred 10 minutes before the ice water bath was removed and the reaction was allowed to come to RT. After 1.5 hours, the solution is cooled to 0° C. and quenched with saturated aqueous sodium bicarbonate, diluted with water, and extracted with DCM. The combined organic extracts were washed with 1N NaOH, water, saturated aqueous NaCl, and dried over sodium sulfate. The solution was filtered and concentrated in vacuo to give the crude material. The crude material was purified by silica gel chromatography by eluting with 1:4 EtOAc in hexane, to provide 2-((5-amino-7-bromo-3-chloro-5H-chromeno[2,3-c]pyridin-5-yl)methoxy)-2-cyclohexylacetonitrile, [M+H]=462.0.

Step 5: Trimethylaluminum, as a 2 M solution in toluene, (0.973 ml, 1.947 mmol) was added dropwise via syringe to a solution of 2-((5-amino-7-bromo-3-chloro-5H-chromeno[2,3-c]pyridin-5-yl)methoxy)-2-cyclohexylacetonitrile (0.563 g, 1.217 mmol) in DCE (12 ml) at RT. After stirring 14 hours, the reaction was cooled to 0° C. and 1 N aq. HCl (12 ml, 12 mmol) was added dropwise via syringe (slowly at first until vigorous reaction subsided) and the mixture was stirred at 0° C. for 10 minutes and then at RT before being diluted with DCM. The layers were separated and the aqueous layer was extracted with DCM. The combined organic extracts were washed with 1 N aq. NaOH, saturated aqueous sodium chloride, and dried over sodium sulfate. The solution was filtered and concentrated in vacuo to give the crude material. The crude material was purified by silica gel chromatography by eluting with 1:20 MeOH in DCM, to provide 7-bromo-3- chloro-6'-cyclohexyl-2',6'-dihydrospiro[chromeno[2,3-c]pyridine-5,3'-[1,4]oxazin]-5'-amine as a mixture of racemic diastereomers. [M+H]=462.0.

Step 6: A glass microwave reaction vessel was charged with 7-bromo-3-chloro-6'-cyclohexyl-2',6'-dihydrospiro[chromeno[2,3-c]pyridine-5,3'-[1,4]oxazin]-5'-amine (0.075 g, 0.162 mmol), 2 M aqueous sodium carbonate (0.8 mL, 1.600 mmol), and dioxane (1.6 mL). The vessel was capped and the solution was degassed by bubbling nitrogen gas through the solution for 10 minutes. Next, Pd(PPh$_3$)$_4$ (7.49 mg, 6.48 μmol) and (2-fluoropyridin-3-yl)boronic acid (0.027 g, 0.194 mmol) were added and the vessel was sealed. The reaction mixture was stirred and heated in a Initiator microwave reactor (Personal Chemistry, Biotage AB, Inc., Upssala, Sweden) at 120° C. for 20 minutes. The reaction was poured into water and the mixture was extracted with EtOAc. The combined organic extracts were washed with water, saturated aqueous sodium chloride, and dried over sodium sulfate. The solution was filtered and concentrated in vacuo to give the crude material. The crude material was purified by silica gel chromatography by eluting with 1:20 MeOH in DCM, to provide the product as a racemic mixture of diastereomers. The diastereomers were separated by reverse-phase preparative HPLC using a Phenomenex Gemini column, 10 micron, C18, 100 Å, 150×30 mm, 0.1% TFA in CH$_3$CN/H$_2$O, gradient 10% to 70% over 20 min to provide racemic (3'R, 6'S)-3-chloro-6'-cyclohexyl-7-(2-fluoropyridin-3-yl)-2',6'-dihydrospiro[chromeno[2,3-c]pyridine-5,3'-[1,4]oxazin]-5'-amine and racemic (3'S,6'S)-3-chloro-6'-cyclohexyl-7-(2-fluoropyridin-3-yl)-2',6'-dihydrospiro[chromeno[2,3-c]pyridine-5,3'-[1,4]oxazin]-5'-amine each as a white solid after isolating the free base by partitioning between DCM and 1 N NaOH. [M+H]$^+$=479.1 for each racemic diastereomer pair.

Example 57

Method A28

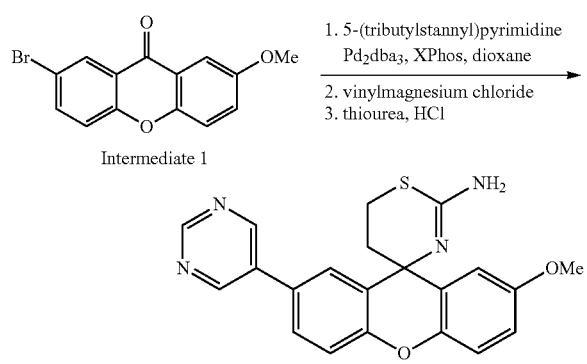

Synthesis of 2'-methoxy-7'-(pyrimidin-5-yl)-5,6-dihydrospiro[[1,3]thiazine-4,9'-xanthen]-2-amine Step 1: A vial charged with Pd$_2$(dba)$_3$ (0.150 g, 0.164 mmol), XPhos (0.391 g, 0.819 mmol), 5-(tributylstannyl)pyrimidine (1.81 g, 4.92 mmol), 2-bromo-7-methoxy-9H-xanthen-9-one (1.000 g, 3.28 mmol) and dioxane (10 mL). The reaction mixture was evacuated and backfilled with nitrogen. The reaction mixture was heated to 100° C. overnight. The reaction mixture was cooled to RT and diluted with water and EtOAc. A grey solid precipitated out, which was filtered off. The solid was washed with EtOAc and water. The grey solid dried under reduced pressure to afford 2-methoxy-7-(pyrimidin-5-yl)-9H-xanthen-9-one) (0.600 g, 60.2% yield).

Step 2: A solution of vinylmagnesium chloride (1.6M solution in THF; 0.82 mL, 1.314 mmol) was added dropwise to a solution of 2-methoxy-7-(pyrimidin-5-yl)-9H-xanthen-9-one (200 mg, 0.657 mmol) in THF (10 mL) at −78° C. After 30 min, the reaction mixture was allowed to warm to −10° C. and was then quenched with saturated aqueous ammonium chloride. The reaction was extracted with EtOAc, and the organic phase was dried over sodium sulfate, and concentrated under reduced pressure. The residue was purified by chromatography to give 2-methoxy-7-(pyrimidin-5-yl)-9-vinyl-9H-xanthen-9-ol as a pale yellow gum.

Step 3: 2 N HCl (3 mL) was added to solution of 2-methoxy-7-(pyrimidin-5-yl)-9-vinyl-9H-xanthen-9-ol (50 mg, 0.150 mmol) and thiourea (9.25 μL, 0.171 mmol) in HOAc (5 mL). The reaction mixture was allowed to stir overnight at rt and concentrated under reduced pressure. The residue was treated with of TFA (4 mL). The reaction mixture was stirred overnight at rt. The reaction mixture was concentrated under reduced pressure and the residue was treated with aqueous, half-saturated sodium bicarbonate, extracted with EtOAc, and concentrated under reduced pressure. The residue was purified by chromatography (DCM/MeOH 20:1 to 5:1) to give 2'-methoxy-7'-(pyrimidin-5-yl)-5,6-dihydrospiro[[1,3]thiazine-4,9'-xanthen]-2-amine as an off-white solid.

Example 58

Method A29

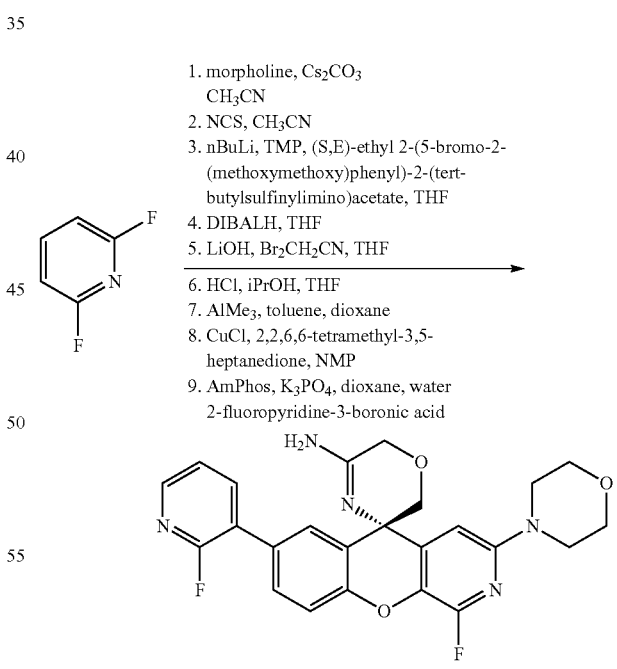

Synthesis of (S)-1-fluoro-7-(2-fluoropyridin-3-yl)-3-morpholino-2',6'-dihydrospiro[chromeno[2,3-c]pyridine-5,3'-[1,4]oxazin]-5'-amine.TFA Step 1: A suspension of cesium carbonate (41.1 g, 126 mmol), 2,6-difluoropyridine (11.01 mL, 121 mmol) and morpholine (10.00 mL, 115 mmol) in ACN (100 mL) was heated to 70° C. for 12 hours in a sealed vessel. The reaction mixture was cooled to RT and filtered. The obtained filtrate was concentrated under reduced pressure. The crude material was purified by silica gel chromatography (5-25% EtOAc/hexanes) to provide 13.7 g, of 4-(6-fluoropyridin-2-yl)morpholine.

Step 2: Chlorosuccinimide (10.29 g, 77 mmol) was added to a solution of 4-(6-fluoropyridin-2-yl)morpholine (11.7 g, 64.2 mmol) in ACN (15 mL). The reaction mixture was heated to 70° C. for 30 min. Water and DCM were added. The organic phase was separated, washed with aqueous $NaHCO_3$, brine and subsequently dried over $MgSO_4$. The solvent was removed under reduced pressure and the residue was purified by silica gel chromatography (5-20% EtOAc/hexanes) to afford 3.11 g of 4-(5-chloro-6-fluoropyridin-2-yl)morpholine.

Step 3: A solution of 2,2,6,6-tetramethylpiperidine (1.897 mL, 11.24 mmol) in THF (45 mL) was cooled to −78° C. and treated with n-BuLi (1.6M in hexanes) (6.77 mL, 10.83 mmol) under nitrogen atmosphere. The solution was warmed to 0° C. and stirred at that temperature for 25 minutes. The solution was cooled back down to −78° C. and treated with a solution of 4-(5-chloro-6-fluoropyridin-2-yl)morpholine (2.165 g, 9.99 mmol) in THF (11.25 mL) under nitrogen atmosphere. The solution was allowed to stir at that temperature for 40 minutes and then added drop wise via cannula to a solution of (S)-ethyl 2-(5-bromo-2-(methoxymethoxy)phenyl)-2-(tert-butylsulfinylimino)acetate (3.5 g, 8.33 mmol) in THF (11.25 mL) also cooled to −78° C. under nitrogen atmosphere. The reaction mixture was allowed to stir at −78° C. for additional 2 hours and then quenched with acetic acid (0.715 mL, 12.49 mmol). The reaction mixture was allowed to warm to RT overnight. The solvent was removed under reduced pressure and the crude material was purified by silica gel chromatography (10-60% EtOAc/hexane) to afford 3.56 g (S)-ethyl 2-(5-bromo-2-(methoxymethoxy)phenyl)-2-(3-chloro-2-fluoro-6-morpholinopyridin-4-yl)-2-((S)-1,1-dimethylethylsulfinamido)acetate.

Step 4: A solution of (S)-ethyl 2-(5-bromo-2-(methoxymethoxy)phenyl)-2-(3-chloro-2-fluoro-6-morpholinopyridin-4-yl)-2-((S)-1,1-dimethylethylsulfinamido)acetate (3.56 g, 5.59 mmol) in THF (60 mL) was cooled to 0° C. and treated drop wise with DIBAL (1M in THF) (22.36 mL, 22.36 mmol) under nitrogen atmosphere. After 1 h additional 10 mL DIBAL solution were added at RT. After 12 h at RT additional 10 mL DIBAL solution were added. After 30 min aqueous saturated solution of potassium sodium tartrate was added, followed by EtOAc. The reaction mixture was allowed to stir vigorously for 1 h. The organic phase was separated, washed with aqueous saturated solution of potassium sodium tartrate and dried over $MgSO_4$. The solvent was removed under reduced pressure and the crude material was purified by silica gel chromatography (20-100% EtOAc/hexane) to provide 1.90 g of (S)—N—((S)-1-(5-bromo-2-(methoxymethoxy)phenyl)-1-(3-chloro-2-fluoro-6-morpholinopyridin-4-yl)-2-hydroxyethyl)-2-methylpropane-2-sulfinamide.

Step 5: Lithium hydroxide hydrate (0.402 g, 9.58 mmol) was added to a solution of (S)—N—((S)-1-(5-bromo-2-(methoxymethoxy)phenyl)-1-(3-chloro-2-fluoro-6-morpholinopyridin-4-yl)-2-hydroxyethyl)-2-methylpropane-2-sulfinamide (1.9 g, 3.19 mmol) in THF (25 mL) at RT, followed by bromoacetonitrile (0.445 mL, 6.39 mmol). The reaction mixture was allowed to stir at RT for 12 h. The reaction mixture was treated with aqueous saturated ammonium chloride, and the mixture was extracted with EtOAc. The organic phase was washed with water, brine, dried over $MgSO_4$ and then concentrated under reduced pressure. The remaining residue was purified by silica gel chromatography (50-100% EtOAc/hexanes) to afford 1.51 g of (S)—N—((S)-1-(5-bromo-2-(methoxymethoxy)phenyl)-1-(3-chloro-2-fluoro-6-morpholinopyridin-4-yl)-2-(cyanomethoxy)ethyl)-2-methylpropane-2-sulfinamide.

Step 6-7: A solution of hydrogen chloride (5-6N in iPrOH; 1.025 mL, 5.12 mmol) was added to a solution of (S)—N—((S)-1-(5-bromo-2-(methoxymethoxy)phenyl)-1-(3-chloro-2-fluoro-6-morpholinopyridin-4-yl)-2-(cyanomethoxy)ethyl)-2-methylpropane-2-sulfinamide (1083 mg, 1.708 mmol) in THF (4 mL) under nitrogen atmosphere. The reaction mixture was stirred for 10 min at RT. The solvent was removed under reduced pressure and the residue was dissolved in DCE (2 mL). A solution of $AlMe_3$ (2M in toluene; 2.56 mL, 5.12 mmol) was added drop wise and the reaction mixture was allowed to stir at 70 C for 3 h. The reaction mixture was cooled to RT and a solution of aqueous saturated solution of potassium sodium tartrate was added, followed by EtOAc. The reaction mixture was allowed to stir vigorously for 1 h. The organic phase was separated, washed with brine and dried over $MgSO_4$. The solvent was removed under reduced pressure and the residue was purified by silica gel chromatography (100% EtOAc) to afford 390 mg of (S)-2-(5-amino-3-(3-chloro-2-fluoro-6-morpholinopyridin-4-yl)-3,6-dihydro-2H-1,4-oxazin-3-yl)-4-bromophenol.

Step 8: A sealable vial was charged with (S)-2-(5-amino-3-(3-chloro-2-fluoro-6-morpholinopyridin-4-yl)-3,6-dihydro-2H-1,4-oxazin-3-yl)-4-bromophenol (234 mg, 0.482 mmol), cesium carbonate (471 mg, 1.445 mmol) and copper chloride (9.54 mg, 0.096 mmol The vial was evacuated and back-filled with nitrogen. NMP (1.5 mL) was added and the vial was evacuated and backfilled with nitrogen. 2,2,6,6-Tetramethyl-3,5-heptanedione (0.080 mL, 0.385 mmol) was added and the reaction mixture was heated to 120° C. for 1 h. The reaction mixture was cooled to room temperature, diluted with EtAOc and filtered through a pad of silica gel. The solvent was removed under reduced pressure and the residue was purified by preparative reversed-phase preparative HPLC using a Phenomenex Gemini column, 10 micron, C18, 110 Å, 100×50 mm, 0.1% TFA in $CH_3CN/H_2O$, gradient 10% to 100% over 20 min to obtain 68 mg of (S)-7-bromo-1-fluoro-3-morpholino-2',6'-dihydrospiro[chromeno[2,3-c]pyridine-5,3'-[1,4]oxazin]-5'-amine.TFA.

Step 9: A sealable vial was charged with (S)-7-bromo-1-fluoro-3-morpholino-2',6'-dihydrospiro[chromeno[2,3-c]pyridine-5,3'-[1,4]oxazin]-5'-amine (50 mg, 0.111 mmol), 2-fluoropyridin-3-ylboronic acid (31.4 mg, 0.223 mmol), bis[di-tert-butyl(4-dimethylaminophenyl)phosphine]dichloropalladium(II) (7.88 mg, 0.011 mmol) and potassium phosphate (0.028 mL, 0.334 mmol). The vial was evacuated and backfilled with nitrogen (procedure was repeated twice). Dioxane (1.3 mL) and water (0.433 mL) were added and the reaction mixture was purged for 1 min with nitrogen. The vial was placed in a preheated oil bath (100° C.) for start 2.5 h. The reaction mixture was cooled to RT and the solvent was removed under reduced pressure. The residue was purified by preparative reversed-phase preparative HPLC using a Phenomenex Gemini column, 10 micron, C18, 110 Å, 100×50 mm, 0.1% TFA in $CH_3CN/H_2O$, gradient 10% to 100% over 20 min to obtain 39 mg of (S)-1-fluoro-7-(2-fluoropyridin-3-yl)-3-morpholino-2',6'-dihydrospiro[chromeno[2,3-c]pyridine-5,3'-[1,4]oxazin]-5'-amine 2,2,2-trifluoroacetate as a light-yellow powder. MS m/z=466.0 [M+H]⁺. Calculated for $C_{24}H_{21}F_2N_5O_3 \cdot C_2HF_3O_2$: 579.48 (TFA salt).

Example 59

Method A30

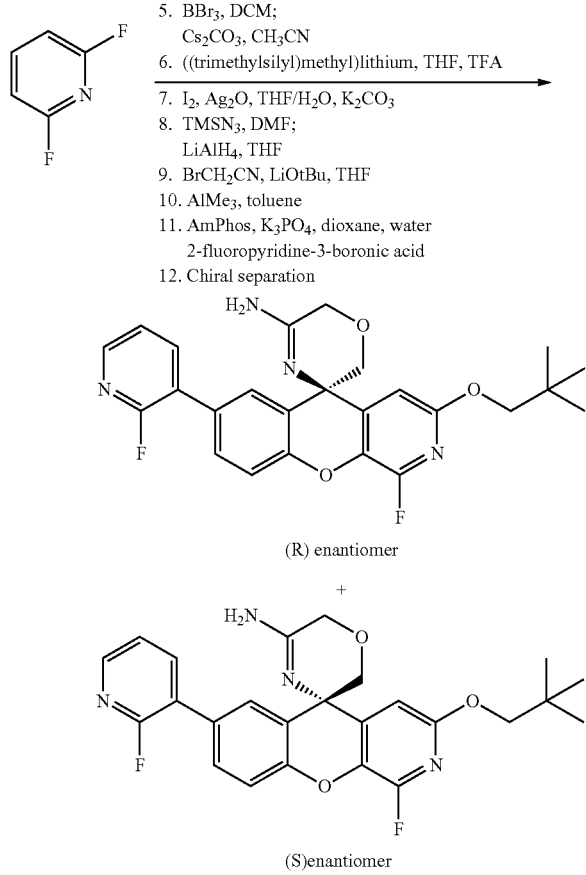

1. neopentylacohol, NaH, DMSO
2. NBS, CH₃CN
3. n-BuLi, B(Oi—Pr)₃;
   H₂O₂, NaOH;
   MOMCl, K₂CO₃, acetone
4. 5-bromo-2-fluorobenzaldehyde, LiTMP, THF;
   TPAP, NMO, DCM
5. BBr₃, DCM;
   Cs₂CO₃, CH₃CN
6. ((trimethylsilyl)methyl)lithium, THF, TFA
7. I₂, Ag₂O, THF/H₂O, K₂CO₃
8. TMSN₃, DMF;
   LiAlH₄, THF
9. BrCH₂CN, LiOtBu, THF
10. AlMe₃, toluene
11. AmPhos, K₃PO₄, dioxane, water
    2-fluoropyridine-3-boronic acid
12. Chiral separation Synthesis of (R)-1-fluoro-7-(2-fluoropyridin-3-yl)-3-(neopentyloxy)-2',6'-dihydrospiro[chromeno[2,3-c]pyridine-5,3'-[1,4]oxazin]-5'-amine and (S)-1-fluoro-7-(2-fluoropyridin-3-yl)-3-(neopentyloxy)-2',6'-dihydrospiro[chromeno[2,3-c]pyridine-5,3'-[1,4]oxazin]-5'-amine Step 1: A solution of neopentyl alcohol (1.065 mL, 9.81 mmol) in DMSO (82 mL) was cooled to 0° C. NaH (60% in mineral oil; 0.490 g, 12.26 mmol) were added in one portion, the reaction mixture was warmed to rt and stirred for 20 minutes. 2,6-Difluoropyridine (0.941 mL, 8.175 mmol) was added and the reaction mixture was stirred at overnight. The reaction mixture was quenched with aqueous, saturated ammonium chloride solution, diluted with water and EtOAc. The organic layer was separated, washed with brine and dried over sodium sulfate. The solvent was removed under reduced pressure to afford 2-fluoro-6-(neopentyloxy)pyridine (1.48 g, 8.08 mmol) as a colorless liquid.

Step 2: N-bromosuccinimide (8.29 g, 46.6 mmol) was added to a solution of 2-fluoro-6-(neopentyloxy)pyridine (7.11 g, 38.8 mmol) in acetonitrile (80 mL) at rt. The reaction mixture was heated to 70° C. overnight. The reaction mixture was cooled to rt and the solvent was removed under reduced pressure. The residue was dissolved in DCM and washed with water. The organic layer was separated, dried over sodium sulfate and concentrated under reduced pressure. The residue was purified by flash chromatography (100% hexanes) to obtain 3-bromo-2-fluoro-6-(neopentyloxy)pyridine (5.27 g, 20.11 mmol) as a white solid.

Step 3: A solution of 3-bromo-2-fluoro-6-(neopentyloxy)pyridine (5.6 g, 21.36 mmol) in THF (50 mL) was cooled to −100° C. and a solution of n-butyllithium (1.6M in hexane; 14.69 mL, 23.50 mmol) was added drop wise. The reaction mixture was allowed to stir for 10 min at −100° C. Triisopropyl borate (7.35 mL, 32.0 mmol) was added and the reaction mixture was allowed to warm to rt. Aqueous NaOH solution (5M; 29.9 mL, 150 mmol) was added, followed by hydrogen peroxide (30%; 15.28 mL, 150 mmol). The reaction mixture was allowed to stir for 30 min at rt. The reaction mixture was acidified with 2N HCl and extracted with EtOAc. The organic phase was separated and dried over MgSO₄. The solvent was removed under reduced pressure, the residue was dissolved in acetone (50 mL) and the solution was cooled to 0° C. K₂CO₃ (3.25 g, 23.50 mmol) was added, followed by chloromethyl methyl ether (1.785 mL, 23.50 mmol). After 30 min, additional K₂CO₃ (3.25 g, 23.50 mmol) and chloromethyl methyl ether (1.785 mL, 23.50 mmol) were added and the reaction mixture was warmed to rt. After 2 h brine and diethyl ether were added. The organic was separated and dried over magnesium sulfate. The solvent was removed under reduced pressure. The residue was purified by flash chromatography (0-20% EtOAc/hexanes) to yield 2-fluoro-3-(methoxymethoxy)-6-(neopentyloxy)pyridine (2.88 g, 11.84 mmol).

Step 4: A solution of n-butyllithium (1.6M in hexanes; 6.52 mL, 10.44 mmol) was added drop wise to a solution of 2,2,6,6-tetramethylpiperidine (1.897 mL, 11.24 mmol) in THF (30 mL) at −78° C. under nitrogen atmosphere. The reaction mixture was warmed to 0° C. and stirred for 25 min. The reaction mixture was cooled down again to −78° C. and a solution of 2-fluoro-3-(methoxymethoxy)-6-(neopentyloxy)pyridine (2.149 g, 8.83 mmol) in THF (5 mL) was added drop wise. The reaction mixture was kept for 1 h at 78° C., after which a solution of 5-bromo-2-fluorobenzaldehyde (1.63 g, 8.03 mmol) in THF (5 mL) was added. The reaction mixture was allowed to warm up to rt. Aqueous, saturated NH₄Cl solution was added, followed by EtOAc. The organic phase was separated and dried over MgSO₄. The solvent was removed under reduced pressure and the residue was dissolved in DCM (75 mL). 4-Methylmorpholine 4-oxide (1.176 g, 10.04 mmol) followed by tetrapropylammonium perruthenate (0.141 g, 0.401 mmol) were added. The reaction mixture was allowed to stir for 2 h at rt. The reaction mixture was filtered through a pad of celite and the solvent was removed under reduced pressure. The residue was purified by flash chromatography (5-20% EtOAc/hexanes) to yield (5-bromo-2-fluorophenyl)(2-fluoro-3-(methoxymethoxy)-6-(neopentyloxy)pyridin-4-yl)methanone as a white solid.

Step 5: A solution of (5-bromo-2-fluorophenyl)(2-fluoro-3-(methoxymethoxy)-6-(neopentyloxy)pyridin-4-yl)methanone (1.89 g, 4.25 mmol) in DCM (20 mL) was cooled to −78° C. under nitrogen atmosphere. Boron tribromide (1.0M in CH₂Cl₂; 4.25 mL, 4.25 mmol) was added drop wise and the reaction mixture was stirred for 5 min at rt. Aqueous, saturated ammonium chloride solution was added, followed by water and DCM. The organic phase was separated and dried over magnesium sulfate. The solvent was removed under reduced pressure to afford a yellow solid, which was dissolved in ACN (20.00 mL). Cesium carbonate (1.386 g, 4.25 mmol) was added in one portion and the reaction mixture was allowed to stir for 5 min. Water was added and the remaining light-yellow solid was filtered off and dried to afford 7-bromo-1-fluoro-3-(neopentyloxy)-5H-chromeno[2,3-c]pyridin-5-one (1.27 g).

Step 6: To a suspension of 7-bromo-1-fluoro-3-(neopentyloxy)-5H-chromeno[2,3-c]pyridin-5-one (1000 mg, 2.63 mmol) in THF (25 mL) at −40° C. was added drop wise ((trimethylsilyl)methyl)lithium (1.0M solution in pentane; 3.95 mL, 3.95 mmol). After 10 min, TFA (0.304 mL, 3.95 mmol) was added drop wise and the reaction mixture was allowed to warm to rt Additional 1 ml of TFA was added and the reaction mixture was allowed to stir for 1 hour at rt. An aqueous, saturated K₂CO₃ solution was added, followed by EtOAc. The organic phase was separated and dried over Na₂SO₄. The solvent was removed under reduced pressure to yield 7-bromo-1-fluoro-5-methylene-3-(neopentyloxy)-5H-chromeno[2,3-c]pyridine as a yellow solid (995 mg), which was used in the next step without further purification.

Step 7: To a solution of 7-bromo-1-fluoro-5-methylene-3-(neopentyloxy)-5H-chromeno[2,3-c]pyridine (995 mg, 2.63 mmol) in THF (60 mL)/Water (10 mL) was added iodine (1335 mg, 5.26 mmol) and silver oxide (1219 mg, 5.26 mmol). The reaction mixture was allowed to stir at rt for 20 min. K₂CO₃ (545 mg, 3.95 mmol) was added in one portion and the reaction mixture was allowed to stir for 30 min. The reaction mixture was filtered through a pad of celite. The reaction mixture was partitioned between water and EtOAc. The organic phase was separated, dried over Na₂SO₄. The solvent was removed under reduced pressure to afford 7-bromo-1-fluoro-3-(neopentyloxy)spiro[chromeno[2,3-c]pyridine-5,2'-oxirane] as a yellow solid (1000 mg) which was taken onto the next step without further purification.

Step 8: 7-Bromo-1-fluoro-3-(neopentyloxy)spiro[chromeno[2,3-c]pyridine-5,2'-oxirane] (1000 mg, 2.54 mmol) was dissolved in DMF (16 mL) and azidotrimethylsilane (2.020 mL, 15.22 mmol) was added drop wise. The reaction mixture was allowed to stir at rt for 1 h. Water and EtOAc were added, the organic layer was separated and dried over MgSO₄. The solvent was removed under reduced pressure to afford an oil which was dissolve in THF (20 mL) and cooled to 0° C. Lithium aluminum hydride (1.0M in THF; 3.27 mL, 3.27 mmol) was added drop wise. After 1 h additional 1.5 mL of LiAlH₄ solution were added and the reaction mixture was allowed to stir for additional 10 min at 0° C. The reaction mixture was quenched with an aqueous, saturated solution of Rochelle's salt. Water and EtOAc were added. The organic phase was separated and dried over Na₂SO₄. The solvent was removed under reduced pressure and the crude product was taken onto the next step without further purification.

Step 9: To a solution of (5-amino-7-bromo-3-chloro-1-fluoro-5H-chromeno[2,3-c]pyridin-5-yl)methanol (1 g, 2.78 mmol) in THF (2 mL) was added simultaneously and drop wise lithium tert-butoxide (1.0 M in THF; 4.73 mL, 4.73 mmol) and a solution of bromoacetonitrile (0.329 mL, 4.73 mmol) in THF (2 mL) at RT. Additional lithium tert-butoxide (1.0 M in THF; 4.73 mL, 4.73 mmol) and a solution of bromoacetonitrile (0.329 mL, 4.73 mmol) in THF (2 mL) were added after 1 hour, 2 hours and 3 hours reaction time, respectively. The reaction mixture was quenched with aqueous, saturated NH₄Cl solution and 2M HCl. EtOAc was added and the organic phase was separated and dried over MgSO₄. The solvent was removed under reduced pressure and the residue was taken onto the next step without further purification.

Step 10: 2-((5-Amino-7-bromo-1-fluoro-3-(neopentyloxy)-5H-chromeno[2,3-c]pyridin-5-yl)methoxy)-acetonitrile (1000 mg, 2.221 mmol) was dissolved in DCE (4 mL) and trimethylaluminum solution (2M in toluene; 2.221 mL, 4.44 mmol) was added drop wise. The reaction mixture was heated to 70° C. for 15 min. The reaction mixture was cooled to rt. Aqueous, saturated solution of Rochelle's salt was added, followed by EtOAc. The organic phase was separated, washed with brine and dried over MgSO₄. The solvent was removed under reduced pressure and the residue was purified by flash chromatography (10-100% EtOAc/hexanes) to afford 7-bromo-1-fluoro-3-(neopentyloxy)-2',6'-dihydrospiro[chromeno[2,3-c]pyridine-5,3'-[1,4]oxazin]-5'-amine as a light-brown solid.

Step 11: A sealable vial was charged with 7-bromo-1-fluoro-3-(neopentyloxy)-2',6'-dihydrospiro[chromeno[2,3-c]pyridine-5,3'-[1,4]oxazin]-5'-amine (200 mg, 0.444 mmol), 2-fluoropyridin-3-ylboronic acid (125 mg, 0.888 mmol), bis[di-tert-butyl(4-dimethylaminophenyl)phosphine]dichloropalladium(II) (31.4 mg, 0.044 mmol) and potassium phosphate (283 mg, 1.332 mmol). The vial was evacuated and backfilled with nitrogen (procedure was repeated twice). Dioxane (3 mL) and water (1 mL) were added and the reaction mixture was purged for 1 min with nitrogen. The vial was placed in a preheated oilbath (100° C.) for start 1.5 h. The reaction mixture was cooled to rt and water and EtOAc were added to the reaction mixture. The organic phase was separated and dried over MgSO₄. The solvent was removed under reduced pressure and the residue was purified by column chromatography (1-10% MeOH in DCM) to obtain 1-fluoro-7-(2-fluoropyridin-3-yl)-3-(neopentyloxy)-2',6'-dihydrospiro[chromeno[2,3-c]pyridine-5,3'-[1,4]oxazin]-5'-amine as a beige solid (185 mg).

Step 12: Compounds (R)-1-fluoro-7-(2-fluoropyridin-3-yl)-3-(neopentyloxy)-2',6'-dihydrospiro[chromeno[2,3-c]pyridine-5,3'-[1,4]oxazin]-5'-amine (Example 59B) and (S)-1-fluoro-7-(2-fluoropyridin-3-yl)-3-(neopentyloxy)-2',6'-dihydrospiro[chromeno[2,3-c]pyridine-5,3'-[1,4]oxazin]-5'-amine (Example 59A) were obtained from racemic 1-fluoro-7-(2-fluoropyridin-3-yl)-3-(neopentyloxy)-2',6'-dihydrospiro[chromeno[2,3-c]pyridine-5,3'-[1,4]oxazin]-5'-amine using similar chiral separation conditions as described herein for intermediate 10.

Mass for both peaks m/z=467.0 [M+H]⁺. Calculated for C₂₅H₂₄F₂N₄O₃: 466.18

¹H NMR (400 MHz, CHLOROFORM-d) δ ppm 1.03 (s, 9 H) 3.53-3.61 (m, 1 H) 3.62-3.69 (m, 1 H) 3.86-3.92 (m, 1 H) 3.92-3.98 (m, 1 H) 4.28-4.41 (m, 2 H) 6.58 (s, 1 H) 7.28-7.31 (m, 1 H) 7.33 (d, J=8.41 Hz, 1 H) 7.47-7.57 (m, 2 H) 7.88 (t, J=9.39 Hz, 1 H) 8.19 (d, J=4.50 Hz, 1 H).

Example 60

Method A31

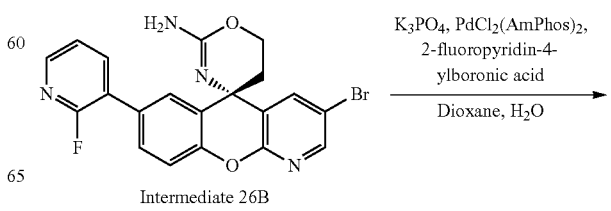

Intermediate 26B

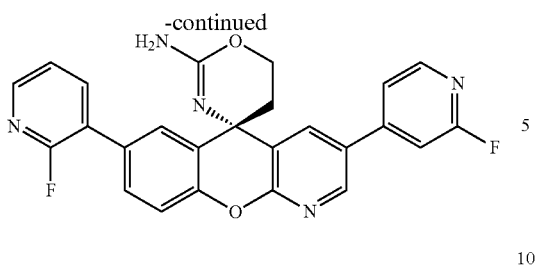

Synthesis of (S)-7-(2-fluoropyridin-3-yl)-3-(2-fluoropyridin-4-yl)-5',6'-dihydrospiro[chromeno[2,3-b]pyridine-5,4'-[1,3]oxazin]-2'-amine In a microwave vial, potassium phosphate (0.084 g, 0.394 mmol), PdCl$_2$(AmPhos)$_2$ (8.38 mg, 0.012 mmol), and 2-fluoropyridin-4-ylboronic acid (0.024 g, 0.171 mmol) were loaded. The (S)-3-bromo-7-(2-fluoropyridin-3-yl)-5',6'-dihydrospiro[chromeno[2,3-b]pyridine-5,4'-[1,3]oxazin]-2'-amine (0.058 g, 0.131 mmol) was added as a solution in dioxane (2.5 mL). Water (1 mL) was added and argon gas was blown through the vessel, which was sealed and heated in a 90° C. oil bath for 1.5 h. The residue was taken up in 5% MeOH/DCM (60 mL) and the organic layer was extracted with dilute brine (2×6 mL), then was dried over sodium sulfate and concentrated. The residue was purified by chromatography (4.5-5.5% MeOH/DCM) to afford (S)-7-(2-fluoropyridin-3-yl)-3-(2-fluoropyridin-4-yl)-5',6'-dihydrospiro[chromeno[2,3-b]pyridine-5,4'-[1,3]oxazin]-2'-amine (Example 60A; 44 mg). MS (m/z) 458 (M+H)$^+$. $^1$H NMR (400 MHz, CDCl$_3$) δ ppm: 8.57 (d, 1 H, J=2.5 Hz), 8.32 (d, 1 H, J=5.3 Hz), 8.22 (d, 1 H, J=4.7 Hz), 8.07 (d, 1 H, J=2.3 Hz), 7.88 (m, 1 H), 7.55 (m, 2 H), 7.43 (m, 2 H), 7.30 (m, 1 H), 7.17 (s, 1 H), 4.39 (br, 2 H), 4.18 (m, 2 H), 2.02 (m, 1 H), 1.90 (m, 1 H).

Example 61

Method A32

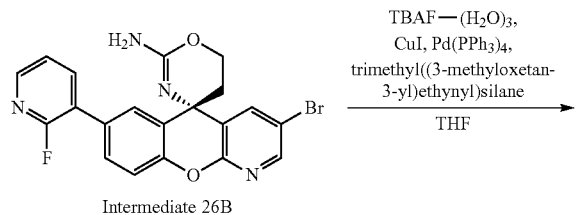

Intermediate 26B

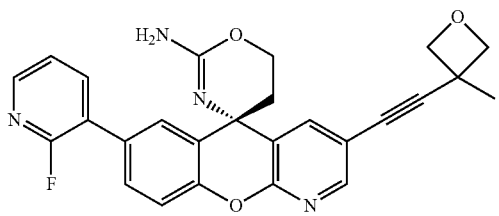

Synthesis of (S)-7-(2-fluoropyridin-3-yl)-3-((3-methyloxetan-3-yl)ethynyl)-5',6'-dihydrospiro[chromeno[2,3-b]pyridine-5,4'-[1,3]oxazin]-2'-amine In a microwave vial, tetrabutylammonium fluoride trihydrate (0.059 g, 0.187 mmol), trimethyl((3-methyloxetan-3-yl)ethynyl)silane (0.031 g, 0.187 mmol), copper(I) iodide (2.374 mg, 0.012 mmol), Pd(PPh$_3$)$_4$ (0.014 g, 0.012 mmol), and (S)-3-bromo-7-(2-fluoropyridin-3-yl)-5',6'-dihydrospiro[chromeno[2,3-b]pyridine-5,4'-[1,3]oxazin]-2'-amine (0.055 g, 0.125 mmol) were suspended in THF (1.25 mL). Argon gas was blown through the vessel, which was sealed and heated in an 80° C. oil bath for 1.5 h. The mixture was taken up in 10% MeOH-EtOAc (60 mL) and the organic layer was extracted with dilute brine (8 mL) then with saturated brine (8 mL), dried over sodium sulfate and concentrated. The residue was purified by chromatography (5% MeOH/DCM), to afford (S)-7-(2-fluoropyridin-3-yl)-3-(3-methyloxetan-3-yl)ethynyl)-5',6'-dihydrospiro[chromeno[2,3-b]pyridine-5,4'-[1,3]oxazin]-2'-amine (41 mg, 0.09 mmol). MS (m/z) 457 (M+H)$^+$. $^1$H NMR (400 MHz, CDCl$_3$) δ ppm: 8.32 (d, 1 H, J=2.0 Hz), 8.20 (d, 1 H, J=4.9 Hz), 7.90 (m, 1 H), 7.78 (s, 1 H), 7.53 (m, 2 H), 7.38 (d, 1 H, J=8.4 Hz), 7.27 (m, 1 H), 4.94 (d, 2 H, J=5.3 Hz), 4.50 (d, 2 H, J=5.5 Hz), 4.44 (br, 2 H), 4.28 (m, 2 H), 1.95 (m, 1 H), 1.85 (m, 1 H), 1.74 (s, 3 H).

Example 62

Method A33

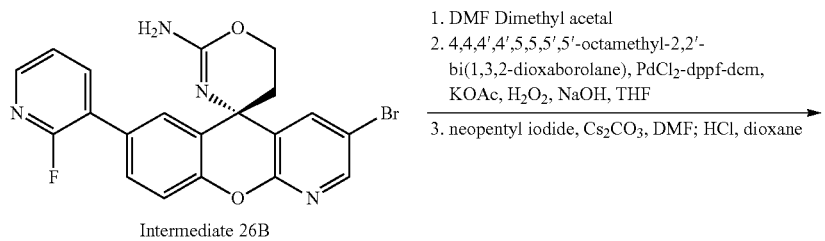

Intermediate 26B

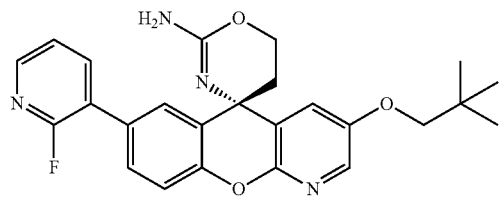

Synthesis of (S)-7-(2-fluoropyridin-3-yl)-3-(neopentyloxy)-5',6'-dihydrospiro[chromeno[2,3-b]pyridine-5,4'-[1,3]oxazin]-2'-amine Step 1: In a 25-mL flask, the (R)-3-bromo-7-(2-fluoropyridin-3-yl)-5',6'-dihydrospiro[chromeno[2,3-b]pyridine-5,4'-[1,3]oxazin]-2'-amine (0.350 g, 0.793 mmol) was suspended in 1,1-dimethoxy-N,N-dimethylmethanamine (5.29 mL, 39.7 mmol). The reaction mixture was heated to 100° C. for 1 h. The reaction was concentrated, and the residue was taken up in 5% MeOH/DCM (60 mL) and the organic phase was extracted with dilute brine (2×8 mL), then was dried over sodium sulfate and concentrated. The residue was purified by chromatography (3.5% MeOH/DCM) to afford (R,E)-N'-(3-bromo-7-(2-fluoropyridin-3-yl)-5',6'-dihydrospiro[chromeno[2,3-b]pyridine-5,4'-[1,3]oxazin]-2'-yl)-N,N-dimethylformimidamide (394 mg, 0.793 mmol).

Step 2: In a 100-mL resealable vessel, the potassium acetate (0.234 g, 2.381 mmol), PdCl$_2$-dppf-DCM (0.065 g, 0.079 mmol), 4,4,4',4',5,5,5',5'-octamethyl-2,2'-bi(1,3,2-dioxaborolane) (0.242 g, 0.953 mmol), (R,E)-N'-(3-bromo-7-(2-fluoropyridin-3-yl)-5',6'-dihydrospiro[chromeno[2,3-b]pyridine-5,4'-[1,3]oxazin]-2'-yl)-N,N-dimethylformimidamide (0.394 g, 0.794 mmol) was suspended in THF (8 mL). Argon was blown through the vessel, which was then sealed and heated in an 85° C. oil bath for 14 h. The vessel was removed from the oil bath and cooled to 0° C., and aqueous NaOH (2.5 M, 1.905 mL, 4.76 mmol) was added, followed by aqueous 30% hydrogen peroxide (0.811 mL, 7.94 mmol). The ice bath was removed, and the mixture was stirred for 45 min. The mixture was concentrated to remove most of the THF. The residue was taken up in 10% MeOH/DCM (600 mL), and the organic layer was extracted with dilute brine (2×15 mL). The organic layer was dried with magnesium sulfate, filtered, and concentrated. The crude (R,E)-N'-(7-(2-fluoropyridin-3-yl)-3-hydroxy-5',6'-dihydrospiro[chromeno[2,3-b]pyridine-5,4'-[1,3]oxazin]-2'-yl)-N,N-dimethylformimidamide was used in the next step without further purification.

Step 3: In a 35-mL resealable vessel, cesium carbonate (0.621 g, 1.905 mmol), 1-iodo-2,2-dimethylpropane (0.211 mL, 1.587 mmol), and crude (S,E)-N'-(7-(2-fluoropyridin-3-yl)-3-hydroxy-5',6'-dihydrospiro[chromeno[2,3-b]pyridine-5,4'-[1,3]oxazin]-2'-yl)-N,N-dimethylformimidamide (0.344 g, 0.794 mmol) were taken up in DMF (8 mL). The vessel was sealed and heated in a 100° C. oil bath. After 6 h, the reaction was concentrated. The residue was taken up in 10% MeOH/DCM (120 mL) and the organic layer was extracted with water (2×10 mL). The organic layer was dried over MgSO$_4$, filtered and concentrated. The residue was taken up in dioxane (8 mL), and a dioxane solution of HCl (4 M, 2 mL) was added. The vessel was sealed and heated in a 60° C. oil bath. After 1 h, the reaction was concentrated. The residue was diluted with water (30 mL) and the aqueous phase was extracted with 10% MeOH/DCM (3×50 mL). The organics were dried over magnesium sulfate, filtered, and concentrated. The material was purified by chromatography using 65:35:0.5:1 EtOAc-hexane-MeOH-Et$_3$N to afford (5)-7-(2-fluoropyridin-3-yl)-3-(neopentyloxy)-5',6'-dihydrospiro[chromeno[2,3-b]pyridine-5,4'-[1,3]oxazin]-2'-amine (4.5 mg, 0.010 mmol). MS (m/z) 449 (M+H)$^+$.

Example 63

Method A34

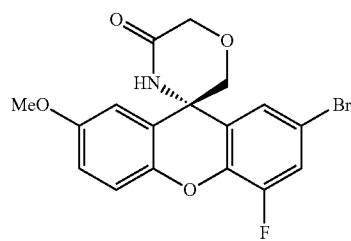

1. Lawesson's reagent, toluene
2. NH$_3$, HgCl$_2$, dioxane
3. BBr$_3$, DCM
4. K$_3$PO$_4$, PdCl$_2$(AmPhos)$_2$
   2-(5,6-dihydro-2H-pyran-3-yl)-4,4,5,5-tetramethyl-1,3,2-dioxaborolane, dioxane H$_2$O
5. Et$_3$N, N-(5-chloropyridin-2-yl)-1,1,1-trifluoro-N-(trifluoromethylsulfonyl)methanesulfonamide, DCM
6. Pd(PPh$_3$)$_4$, Na$_2$CO$_3$, pyridin-3-ylboronic acid, DMF, H$_2$O Intermediate 28

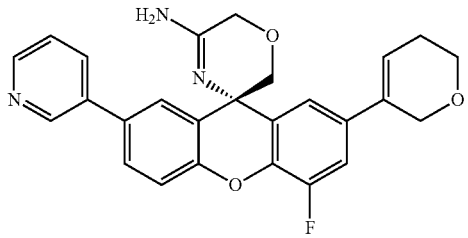

Synthesis of (S)-2'-(5,6-dihydro-2H-pyran-3-yl)-4'-fluoro-7'-(pyridin-3-yl)-2,6-dihydrospiro[[1,4]oxazine-3,9'-xanthen]-5-amine Step 1: In a 250-mL flask, Lawesson's reagent (0.577 g, 1.427 mmol) and (S)-2'-bromo-4'-fluoro-7'-methoxyspiro[morpholine-3,9'-xanthen]-5-one (0.978 g, 2.481 mmol) were suspended in toluene (25 mL). An air-cooled condenser was attached, and the flask was heated in a 90° C. oil bath for 3 h. The mixture was then cooled and concentrated to give (S)-2'-bromo-4'-fluoro-7'-methoxyspiro[morpholine-3,9'-xanthene]-5-thione which was used in the next step without further purification.

Step 2: In a 150-mL resealable vessel, the crude (S)-2'-bromo-4'-fluoro-7'-methoxyspiro[morpholine-3,9'-xanthene]-5-thione (1.0 g, 2.437 mmol) was dissolved in a dioxane solution of ammonia (0.5 M, 58.5 mL, 29.2 mmol). Mercury (II) chloride (0.993 g, 3.66 mmol) was added, and the vessel was sealed and heated in a 55° C. oil bath overnight. The mixture was then cooled and concentrated. The residue was filtered through Celite, rinsing with 10% MeOH-DCM (400 mL). The filtrate was concentrated, and the residue was purified through silica gel (150 mL) using 7.5% MeOH-DCM to afford 131 mg of (S)-2'-bromo-4'-fluoro-7'-methoxy-2,6-dihydrospiro[[1,4]oxazine-3,9'-xanthen]-5-amine Step 3: In a 500-mL flask, the (S)-2'-bromo-4'-fluoro-7'-methoxy-2,6-dihydrospiro[[1,4]oxazine-3,9'-xanthen]-5-amine (0.595 g, 1.513 mmol) was dissolved in DCM (45 mL). The orange solution was cooled to 0° C. and a DCM solution of boron tribromide (1.0 M, 4.54 mL, 4.54 mmol) was added. After 2 h, the reaction mixture was quenched with 20 mL of 9:1 NH$_4$Cl/NH$_4$OH. The mixture was diluted further with water (10 mL) and the aqueous phase was extracted with 5% MeOH-dcm (3×60 mL). The organics were combined, washed with brine (20 mL), dried over sodium sulfate and concentrated to afford crude (S)-5-amino-2'-bromo-4'-fluoro-2,6-dihydrospiro[[1,4]oxazine-3,9'-xanthen]-7'-ol (0.574 g, 1.21 mmol) which was used directly in the next step.

Step 4: In a microwave vial, the potassium phosphate (0.771 g, 3.63 mmol), PdCl$_2$(AmPhos)$_2$ (0.064 g, 0.091 mmol) and 2-(5,6-dihydro-2H-pyran-3-yl)-4,4,5,5-tetramethyl-1,3,2-dioxaborolane (0.356 g, 1.695 mmol) were loaded. The (S)-5-amino-2'-bromo-4'-fluoro-2,6-dihydrospiro[[1,4]oxazine-3,9'-xanthen]-7'-ol (0.459 g, 1.211 mmol) was added as a solution in dioxane (6 mL). Water (2.4 mL) was added and argon gas was blown through the vessel, which was sealed and heated by microwave at 120° C. for 30 min. The residue was taken up in half-saturated aqueous NH$_4$Cl (30 mL) and the aqueous phase was extracted with 5% MeOH/DCM (3×25 mL). The organics were combined, washed with brine (7 mL), dried over sodium sulfate and concentrated to afford crude (S)-5-amino-2'-(5,6-dihydro-2H-pyran-3-yl)-4'-fluoro-2,6-dihydrospiro[[1,4]oxazine-3,9'-xanthen]-7'-ol which was used directly in the next step.

Step 5: Crude (S)-5-amino-2'-(5,6-dihydro-2H-pyran-3-l)-4'-fluoro-2,6-dihydrospiro[[1,4]oxazine-3,9'-xanthen]-7'-ol (0.463 g, 1.211 mmol) was dissolved in DCM (35 mL). The solution was cooled to 0° C., and TEA (0.175 mL, 1.27 mmol) was added, followed by N-(5-chloropyridin-2-yl)-1,1,1-trifluoro-N-(trifluoromethylsulfonyl)methanesulfonamide (0.427 g, 1.09 mmol). The solution was allowed to warm naturally. After 9 h, the reaction was quenched with 1 M aqueous NaOH (15 mL). The aqueous layer was separated and extracted further with 5% MeOH-DCM (3×20 mL). The organics were combined, washed with brine (7 mL), dried over sodium sulfate and concentrated. The residue was partially purified by chromatography (5% MeOH/DCM) to afford (S)-5-amino-2'-(5,6-dihydro-2H-pyran-3-yl)-4'-fluoro-2,6-dihydrospiro[[1,4]oxazine-3,9'-xanthene]-7'-yl trifluoromethanesulfonate (393 mg, 0.764 mmol).

Step 6: In a microwave vial, the pyridin-3-ylboronic acid (0.061 g, 0.495 mmol), (S)-5-amino-2'-(5,6-dihydro-2H-pyran-3-yl)-4'-fluoro-2,6-dihydrospiro[[1,4]oxazine-3,9'-xanthene]-7'-yl trifluoromethanesulfonate (0.196 g, 0.381 mmol), and Pd(PPh$_3$)$_4$ (0.044 g, 0.038 mmol) were suspended in dmf (4.1 mL). Aqueous sodium carbonate (1.0 M, 1.143 mL, 1.143 mmol) was added. Argon was blown through the vessel, which was sealed and heated in an 85° C. oil bath (11:40). After 1.5 h the reaction was concentrated. The residue was taken up in EtOAc (100 mL) and the organic layer was extracted with water (15 mL), brine (, then was dried over sodium sulfate and concentrated. The residue was purified by chromatography (7.5% MeOH/DCM) to afford (S)-2'-(5,6-dihydro-2H-pyran-3-yl)-4'-fluoro-7'-(pyridin-3-yl)-2,6-dihydrospiro[[1,4]oxazine-3,9'-xanthen]-5-amine (99 mg, 0.22 mmol). MS (m/z) 444 (M+H)+. $^1$H NMR (400 MHz, CDCl$_3$) δ ppm; 8.85 (s, 1 H), 8.57 (d, 1 H, J=4.5 Hz), 7.86 (d, 1 H, J=8.0 Hz), 7.50 (m, 2 H), 7.36 (m, 2 H), 7.08 (dd, 1 H, J=11.7, 2.0 Hz), 6.99 (s, 1 H), 6.17 (s, 1 H), 4.46 (m, 2 H), 4.33 (s, 2 H), 3.85 (t, 2 H, J=5.7 Hz), 3.57 (m, 2 H), 2.33 (m, 2 H).

Example 64

Method A35

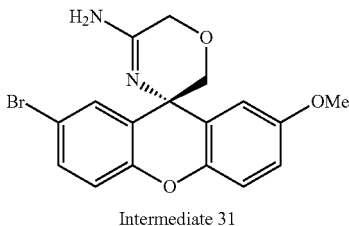

Intermediate 31

1. BBr$_3$, DCM
2. K$_3$PO$_4$, PdCl$_2$(AmPhos)$_2$
   2-fluoropyridin-3-ylboronic acid, dioxane H$_2$O
3. Boc$_2$O, Et$_3$N, THF
4. 1,1,1-trifluoro-N-phenyl-N-(trifluoromethylsulfonyl)methanesulfonamide, Et$_3$N, DCM
5. Pd(PPh$_3$)$_4$, Na$_2$CO$_3$, 2-(3,6-dihydro-2H-pyran-4-yl)-4,4,5,5-tetramethyl-1,3,2-dioxaborolane, DMF, H$_2$O; TFA, DCM

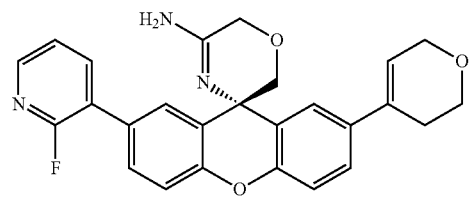

Synthesis of (R)-2'-(3,6-dihydro-2H-pyran-4-yl)-7'-(2-fluoropyridin-3-yl)-2,6-dihydrospiro[[1,4]oxazine-3,9'-xanthen]-5-amine Step 1: In a 250-mL flask, the (R)-2'-bromo-7'-methoxy-2,6-dihydrospiro[[1,4]oxazine-3,9'-xanthen]-5-amine (0.393 g, 1.047 mmol) was dissolved in dcm (10 mL). The solution was cooled to 0° C. A DCM solution of boron tribromide (1.0 M, 3.14 mL, 3.14 mmol) was added. After 1.5 h, the mixture was quenched with 9:1 saturated aqueous NH$_4$Cl/NH$_4$OH (10 mL). The mixture was diluted further with water (10 mL) and the aqueous phase was extracted with 5% MeO/DCM (3×50 mL). The organics were combined, washed with dilute brine (10 mL), dried over sodium sulfate and concentrated to afford crude (R)-5-amino-2'-bromo-2,6-dihydrospiro[[1,4]oxazine-3,9'-xanthen]-7'-ol (349 mg, 0.966 mmol), which was used directly in the next step.

Step 2: In a microwave vial, potassium phosphate (0.615 g, 2.90 mmol), bis[di-tert-butyl(4-dimethylaminophenyl)phosphine]dichloropalladium(II) (0.068 g, 0.097 mmol), 2-fluoropyridin-3-ylboronic acid (0.170 g, 1.208 mmol) and (R)-5-amino-2'-bromo-2,6-dihydrospiro[[1,4]oxazine-3,9'-xanthen]-7'-ol (0.349 g, 0.966 mmol) were suspended in dioxane (8 mL). Water (2 mL) was added, and argon gas was blown through the vessel, which was then sealed and heated in a 100° C. oil bath for 3 h. The reaction was concentrated to remove the dioxane. The residue was diluted with aqueous NH$_4$Cl (15 mL) and the aqueous phase was extracted with 5% MeOH/DCM (3×33 mL). The organics were combined, washed with dilute brine (8 mL), dried over sodium sulfate and concentrated to afford crude (S)-5-amino-2'-(2-fluoropyridin-3-yl)-2,6-dihydrospiro[[1,4]oxazine-3,9'-xanthen]-7'-ol which was used directly in the next step.

Step 3: In a 250-mL flask, the crude (S)-5-amino-2'-(2-fluoropyridin-3-yl)-2,6-dihydrospiro[[1,4]oxazine-3,9'-xanthen]-7'-ol (0.365 g, 0.967 mmol) was dissolved in THF (10 mL). Boc$_2$o (0.232 g, 1.06 mmol) was added, followed by TEA (0.148 mL, 1.06 mmol). After 1 h The reaction was concentrated to afford crude (S)-tert-butyl 2'-(2-fluoropyridin-3-yl)-7'-hydroxy-2,6-dihydrospiro[[1,4]oxazine-3,9'-xanthene]-5-ylcarbamate, which was used directly in the next step.

Step 4: In a 100-mL flask, crude (S)-tert-butyl 2'-(2-fluoropyridin-3-yl)-7'-hydroxy-2,6-dihydrospiro[[1,4]oxazine-3,9'-xanthene]-5-ylcarbamate (0.462 g, 0.968 mmol) was dissolved in DCM (10 mL). The solution was cooled to 0° C., and 1,1,1-trifluoro-N-phenyl-N-(trifluoromethylsulfonyl)methanesulfonamide (0.513 g, 1.43 mmol) and triethylamine (0.243 mL, 1.74 mmol) were added. After 3 h, the reaction was concentrated and material was purified by chromatography (33% EtOAc/hexanes) to afford (S)-5-(tert-butoxycarbonylamino)-2'-(2-fluoropyridin-3-yl)-2,6-dihydrospiro[[1,4]oxazine-3,9'-xanthene]-7'-yl trifluoromethanesulfonate (0.293 g, 0.481 mmol).

Step 5: In a microwave vial, 2-(3,6-dihydro-2H-pyran-4-yl)-4,4,5,5-tetramethyl-1,3,2-dioxaborolane (0.062 g, 0.297 mmol), (S)-5-(tert-butoxycarbonylamino)-2'-(2-fluoropyridin-3-yl)-2,6-dihydrospiro[[1,4]oxazine-3,9'-xanthene]-7'-yl trifluoromethanesulfonate (0.145 g, 0.238 mmol) and tetrakis(triphenylphosphine)palladium(0) (0.027 g, 0.024 mmol) were taken up in DMF (3 mL). Aqueous sodium carbonate (1.0 M, 0.714 mL, 0.714 mmol) was added. Argon was blown through the vessel which was sealed and placed in an 85° C. oil bath. After 3 h, the reaction was concentrated. The residue was diluted with water (15 mL) and the aqueous phase was extracted with 3% MeOH/DCM (3×25 mL). The organics were combined, washed with brine (7 mL), dried over sodium sulfate and concentrated. The residue was transferred to a microwave vial with 3 mL of DCMm and tfa (0.275 mL, 3.57 mmol) was added. The vial was sealed and the reaction was stirred in a 65° C. oil bath for 2 h. The reaction was concentrated. The residue was neutralized with 0.5 M Na$_2$CO$_3$ (13 mL). The aqueous phase was extracted with 5% MeOH/DCM (3×25 mL). The organics were combined, washed with dilute brine (8 mL), dried over sodium sulfate and concentrated. The residue was purified by chromatography (7%-8% MeOH/DCM) to afford (R)-2'-(3,6-dihydro-2H-pyran-4-yl)-7'-(2-fluoropyridin-3-yl)-2,6-dihydrospiro[[1,4]oxazine-3,9'-xanthen]-5-amine (65 mg, 0.146 mmol).

MS (m/z) 444 (M+H)$^+$.

$^1$H NMR (400 MHz, CDCl$_3$) δ ppm; 8.17 (d, 1 H, J=4.5 Hz), 7.89 (m, 1 H), 7.52 (m, 2 H), 7.34 (m, 2 H), 7.27 (m, 2 H), 7.15 (d, 1 H, J=8.4 Hz), 6.08 (s, 1 H), 4.40 (s, 2 H), 4.33 (m, 2 H), 3.94 (t, 2 H, J=5.5 Hz), 3.64 (d, 1 H, J=11.5 Hz), 3.59 (d, 1 H, J=11.5 Hz), 2.53 (m, 2 H).

Example 65

Method A36

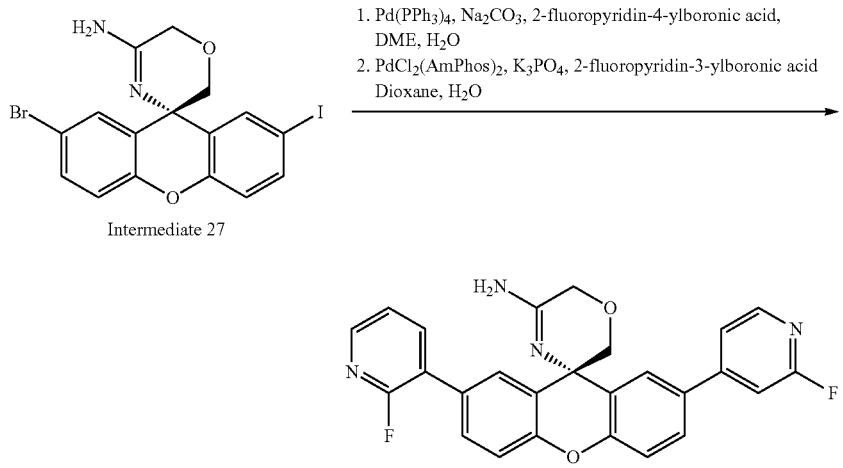 [SMILES: NC1=N[C@@]2(COC1)c1cc(Br)ccc1Oc1ccc(I)cc12 ; NC1=N[C@]2(COC1)c1cc(-c3ccnc(F)c3)ccc1Oc1ccc(-c3cccnc3F)cc12]

Intermediate 27

Synthesis of (R)-2'-(2-fluoropyridin-3-yl)-7'-(2-fluoropyridin-4-yl)-2,6-dihydrospiro[[1,4]oxazine-3,9'-xanthen]-5-amine Step 1: In a microwave vial, sodium carbonate (0.094 g, 0.885 mmol), 2-fluoropyridin-4-ylboronic acid (0.048 g, 0.339 mmol), Pd(PPh$_3$)$_4$ (0.034 g, 0.030 mmol), and (S)-2'-bromo-7'-iodo-2,6-dihydrospiro[[1,4]oxazine-3,9'-xanthen]-5-amine (0.139 g, 0.295 mmol) were suspended in DME (2.5 mL) and water (0.5 mL). Argon gas was blown through the vessel which was sealed and heated in an 80° C. oil bath. After 6 h, the reaction mixture was diluted with brine (10 mL) and the aqueous phase was extracted with 7.5% MeOH-dcm (3×25 mL). The organics were combined, washed with dilute brine (5 mL), dried over sodium sulfate and concentrated. The material was purified through silica gel (33 mL) using 3.5 to 4.5 to 7% MeOH-DCM to afford (R)-2'-bromo-7'-(2-fluoropyridin-4-yl)-2,6-dihydrospiro[[1,4]oxazine-3,9'-xanthen]-5-amine Step 2: In a microwave vial, the potassium phosphate (0.071 g, 0.334 mmol), PdCl$_2$(AmPhos)$_2$ (7.88 mg, 0.011 mmol), 2-fluoropyridin-3-ylboronic acid (0.020 g, 0.139 mmol), and (R)-2'-bromo-7'-(2-fluoropyridin-4-yl)-2,6-dihydrospiro[[1,4]oxazine-3,9'-xanthen]-5-amine (0.049 g, 0.111 mmol) were suspended in dioxane (2 mL) and water (0.5 mL). Argon gas was blown through the vessel, which was sealed and heated by microwave at 120° C. for 30 min. The mixture was concentrated, and the residue was diluted with brine (15 mL), and the aqueous phase was extracted with 5% MeOH-dcm (3×25 mL). The organics were combined, dried over sodium sulfate and concentrated. The residue was purified by chromatography (3.5%-4.5% MeOH/DCM) to afford (R)-2'-(2-fluoropyridin-3-yl)-7'-(2-fluoropyridin-4-yl)-2,6-dihydrospiro[[1,4]oxazine-3,9'-xanthen]-5-amine (35 mg, 0.076 mmol). MS $(m/z)$ 457 (M+H)$^+$.

$^1$H NMR (400 MHz, CDCl$_3$) δ ppm; 8.25 (d, 1 H, J=5.3 Hz), 8.19 (d, 1 H, J=8.2 Hz), 7.89 (m, 1 H), 7.56 (m, 4 H), 7.40 (d, 1 H, J=5.1 Hz), 7.29 (m, 4 H), 7.13 (s, 1 H), 4.60 (br, 2 H), 4.34 (s, 2 H), 3.59 (m, 2 H).

Example 66

Method A37

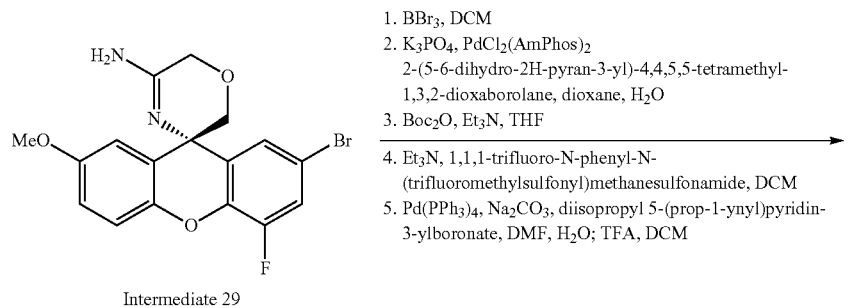

Intermediate 29

1. BBr$_3$, DCM
2. K$_3$PO$_4$, PdCl$_2$(AmPhos)$_2$
   2-(5-6-dihydro-2H-pyran-3-yl)-4,4,5,5-tetramethyl-1,3,2-dioxaborolane, dioxane, H$_2$O
3. Boc$_2$O, Et$_3$N, THF
4. Et$_3$N, 1,1,1-trifluoro-N-phenyl-N-(trifluoromethylsulfonyl)methanesulfonamide, DCM
5. Pd(PPh$_3$)$_4$, Na$_2$CO$_3$, diisopropyl 5-(prop-1-ynyl)pyridin-3-ylboronate, DMF, H$_2$O; TFA, DCM

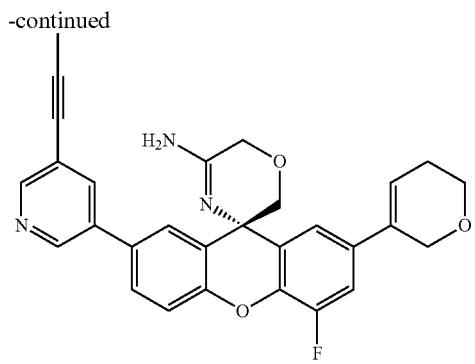

Synthesis of (S)-2'-(5,6-dihydro-2H-pyran-3-yl)-4'-fluoro-7'-(5-(prop-1-ynyl)pyridin-3-yl)-2,6-dihydrospiro[[1,4]oxazine-3,9'-xanthen]-5-amine Step 1: In a 500-mL flask, the (S)-2'-bromo-4'-fluoro-7'-methoxy-2,6-dihydrospiro[[1,4]oxazine-3,9'-xanthen]-5-amine (0.676 g, 1.719 mmol) was suspended in dcm (50 mL). The suspension was cooled to 0° C., and a DCM solution of tribromoborane (1.0 M, 5.16 mL, 5.16 mmol) was added. After 1.5 h, the reaction was quenched with 9:1 aqueous NH₄Cl/NH₄OH (20 mL). The aqueous phase was extracted with 5% MeOH/DCM (3×50 mL). The organics were combined, washed with brine (15 mL), dried over sodium sulfate and concentrated to afford crude (S)-5-amino-2'-bromo-4'-fluoro-2,6-dihydrospiro[[1,4]oxazine-3,9'-xanthen]-7'-ol (604 mg, 1.593 mmol) which was used directly in the next step.

Step 2: In a microwave vial, the potassium phosphate (1.014 g, 4.78 mmol), PdCl₂(AmPhos)₂ (0.085 g, 0.119 mmol), (S)-5-amino-2'-bromo-4'-fluoro-2,6-dihydrospiro[[1,4]oxazine-3,9'-xanthen]-7'-ol (0.604 g, 1.593 mmol), and 2-(5,6-dihydro-2H-pyran-3-yl)-4,4,5,5-tetramethyl-1,3,2-dioxaborolane (0.485 g, 2.310 mmol) were suspended in dioxane (6.5 mL) and water (2.5 mL). Argon gas was blown through the vessel, which was sealed and heated by microwave at 120° C. for 30 min. The mixture was concentrated. The residue was neutralized with half-saturated aqueous NH₄Cl (35 mL). The aqueous phase was extracted with 5% MeOH/DCM (3×35 mL). The organics were combined, washed with dilute brine (15 mL), dried over sodium sulfate and concentrated to afford crude (S)-5-amino-2'-(5,6-dihydro-2H-pyran-3-yl)-4'-fluoro-2,6-dihydrospiro[[1,4]oxazine-3,9'-xanthen]-7'-ol which was used directly in the next step.

Step 3: In a 250-mL flask, the crude (S)-5-amino-2'-(5,6-dihydro-2H-pyran-3-yl)-4'-fluoro-2,6-dihydrospiro[[1,4]oxazine-3,9'-xanthen]-7'-ol (0.609 g, 1.593 mmol) was suspended in THF (30 mL). Boc₂O (0.564 g, 2.58 mmol) was added, followed by triethylamine (0.373 mL, 2.69 mmol). The mixture was stirred at rt. After 1.5 h, the reaction was concentrated to afford crude (S)-tert-butyl 2'-(5,6-dihydro-2H-pyran-3-yl)-4'-fluoro-7'-hydroxy-2,6-dihydrospiro[[1,4]oxazine-3,9'-xanthene]-5-ylcarbamate which was used directly in the next step.

Step 4: In a 250-mL flask, the (S)-tert-butyl 2'-(5,6-dihydro-2H-pyran-3-yl)-4'-fluoro-7'-hydroxy-2,6-dihydrospiro[[1,4]oxazine-3,9'-xanthene]-5-ylcarbamate (0.768 g, 1.592 mmol) was dissolved in DCM (25 mL). The solution was cooled to 0° C. TEA (0.533 mL, 3.85 mmol) was added, followed by 1,1,1-trifluoro-N-phenyl-N-(trifluoromethylsulfonyl)methanesulfonamide (1.25 g, 3.50 mmol). After 2 h, the reaction was concentrated. Without working it up, the residue was purified by chromatography (25% EtOAc/hexanes) to afford (S)-5-(tert-butoxycarbonylamino)-2'-(5,6-dihydro-2H-pyran-3-yl)-4'-fluoro-2,6-dihydrospiro[[1,4]oxazine-3,9'-xanthene]-7'-yl trifluoromethanesulfonate (436 mg, 0.709 mmol).

Step 5: In a microwave vial, diisopropyl 5-(prop-1-ynyl)pyridin-3-ylboronate (0.109 g, 0.443 mmol), (S)-5-(tert-butoxycarbonylamino)-2'-(5,6-dihydro-2H-pyran-3-yl)-4'-fluoro-2,6-dihydrospiro[[1,4]oxazine-3,9'-xanthene]-7'-yl trifluoromethanesulfonate (0.218 g, 0.355 mmol), and Pd(PPh₃)₄ (0.041 g, 0.035 mmol) were taken up in DMF (3.7 mL). Aqueous sodium carbonate (1.0 M, 1.064 mL, 1.064 mmol) was added. Argon gas was blown through the vessel, which was sealed and heated in an 85° C. oil bath for 1.5 h. The reaction was concentrated. The residue was taken up in water (10 mL) and the aqueous phase was extracted with 5% MeOH/DCM (3×20 mL). The organics were combined, washed with dilute brine (5 mL), dried over sodium sulfate and concentrated. The residue was transferred to a microwave vial in DCM (2 mL), and TFA (0.683 mL, 8.87 mmol) was added. The vessel was sealed and heated in a 50° C. oil bath for 1.5 h. The reaction was concentrated, and the residue was neutralized with 0.5 M aqueous Na₂CO₃ (15 mL). The aqueous phase was extracted with 5% MeOH/DCM (3×20 mL). The organics were combined, washed with dilute brine (6 mL), dried over sodium sulfate and concentrated. The residue was purified by chromatography (7% MeOH/DCM) to afford (S)-2'-(5,6-dihydro-2H-pyran-3-yl)-4'-fluoro-7'-(5-(prop-1-ynyl)pyridin-3-yl)-2,6-dihydrospiro[[1,4]oxazine-3,9'-xanthen]-5-amine (98 mg, 0.203 mmol).

MS (m/z) 482 (M+H)⁺.

Example 67

Method A38

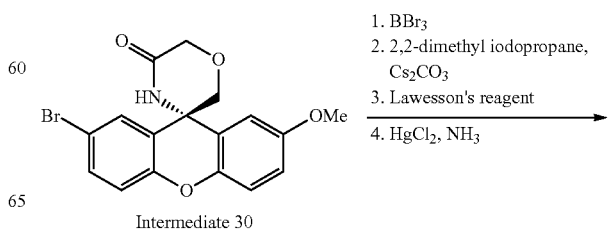

Intermediate 30

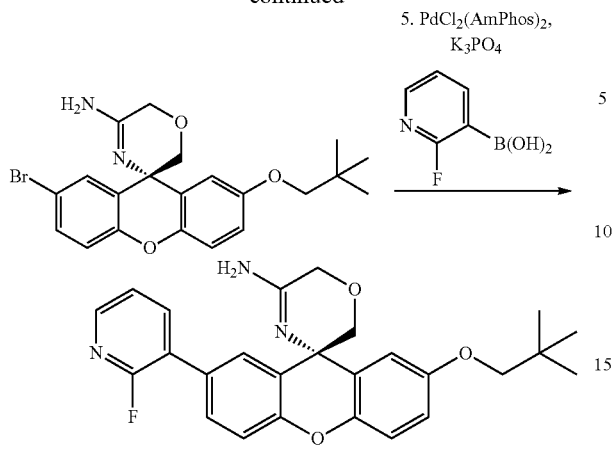

Synthesis of (3S)-2'-(2,2-dimethylpropoxy)-7'-(2-fluoro-3-pyridinyl)-6H-spiro[1,4-oxazine-3,9'-xanthen]-5-amine Step 1: In a 25-mL flask, the 2'-bromo-7'-methoxyspiro[morpholine-3,9'-xanthen]-5-one (0.094 g, 0.250 mmol) was dissolved in DCM (5 mL). The solution was cooled to −78° C., and a solution of boron tribromide (1.0 M, 0.750 mL, 0.750 mmol) in DCM was added. The mixture was warmed to 0° C. and held at that temperature for 2 h. The reaction was diluted with water (20 mL) and the aqueous phase was extracted with 3% MeOH/DCM (3×25 mL). The organics were combined, washed with dilute brine (5 mL), dried over sodium sulfate, and concentrated. The residue was purified by chromatography (70:30:1 EtOAc/hexane/MeOH) to afford(R)-2'-bromo-7'-hydroxyspiro[morpholine-3,9'-xanthen]-5-one.

Step 2: In a 25-ml flask, 2'-bromo-7'-hydroxyspiro[morpholine-3,9'-xanthen]-5-one (0.020 g, 0.055 mmol) was dissolved in DMF (1 mL). Cesium carbonate (0.043 g, 0.133 mmol) was added, followed by 1-iodo-2,2-dimethylpropane (0.022 g, 0.110 mmol). The reaction was heated in a 115° C. oil bath for 10 h. The reaction was cooled to ambient temperature and concentrated. The residue was taken up in 0.3 M aqueous HCl (15 mL) and the aqueous layer was extracted with EtOAc (3×20 mL). The organic layers were combined, washed with saturated brine (5 mL), dried over sodium sulfate, and concentrated. The residue was purified by chromatography (25% EtOAc/hexane) to afford (R)-2'-bromo-7'-(neopentyloxy)spiro[morpholine-3,9'-xanthen]-5-one.

Steps 3 and 4: (R)-2'-Bromo-7'-(neopentyloxy)spiro[morpholine-3,9'-xanthen]-5-one (0.0068 g, 0.016 mmol) was converted to (3R)-2'-bromo-7'-(2,2-dimethylpropoxy)-6H-spiro[1,4-oxazine-3,9'-xanthen]-5-amine using procedures analogous to that described in steps 1 and 2 in method A12 (Example 67a).

Step 5: In a microwave vessel, potassium phosphate (0.012 g, 0.056 mmol), bis[di-tert-butyl(4-dimethylaminophenyl)phosphine]dichloropalladium(II) (0.985 mg, 1.391 µmol) and 2-fluoropyridin-3-ylboronic acid (5.23 mg, 0.037 mmol) were loaded as solids, and (3R)-2'-bromo-7'-(2,2-dimethylpropoxy)-6H-spiro[1,4-oxazine-3,9'-xanthen]-5-amine (0.008 g, 0.019 mmol) was added via cannula as a solution in dioxane (1 mL). Water (0.25 mL) was added to the vessel, and the mixture was purged with argon gas, then the vessel was sealed and heated in microwave radiation at 135° C. for 30 min. The material was taken up in water (10 mL) and the aqueous phase was extracted with DCM (3×20 mL). The organics were combined, washed with dilute brine (5 mL), dried over sodium sulfate, and concentrated. The material was purified by preparative TLC (13% MeOH/DCM) to afford (3S)-2'-(2,2-dimethylpropoxy)-7'-(2-fluoro-3-pyridinyl)-6H-spiro[1,4-oxazine-3,9'-xanthen]-5-amine.

Example 68

Method A39

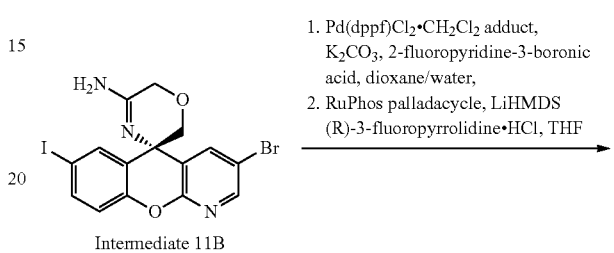

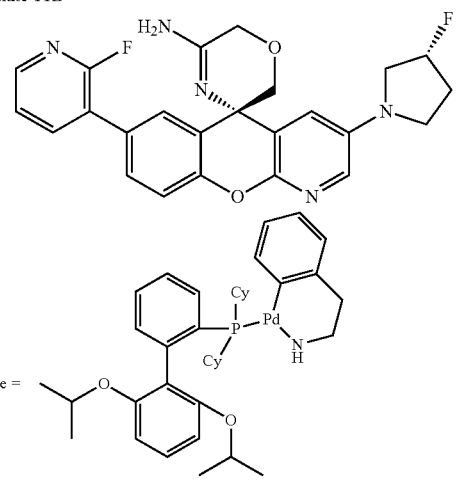

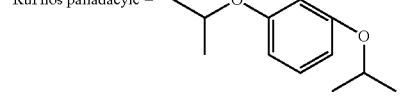

Synthesis of (S)-7-(2-fluoropyridin-3-yl)-3-((R)-3-fluoropyrrolidin-1-yl)-2',6'-dihydrospiro[chromeno[2,3-b]pyridine-5,3'-[1,4]oxazin]-5'-amine Step 1: A vial was charged with 2-fluoropyridin-3-ylboronic acid (0.094 g, 0.667 mmol), PdCl$_2$(dppf)-CH$_2$Cl$_2$-adduct (0.026 g, 0.032 mmol), (S)-3-bromo-7-iodo-2',6'-dihydrospiro[chromeno[2,3-b]pyridine-5,3'-[1,4]oxazin]-5'-amine (0.300 g, 0.635 mmol), and potassium carbonate (0.351 g, 2.54 mmol). Dioxane (3.5 mL) and water (1.5 mL) were added. The vial was flushed with argon, sealed and heated to 80° C. for 1 hour. The reaction mixture was then diluted with EtOAc, dried over MgSO$_4$ and concentrated. Purification of the crude residue by column chromatography [0-80% (90:10:1 DCM/MeOH/NH4OH)/DCM] gave (S)-3-bromo-7-(2-fluoropyridin-3-yl)-2',6'-dihydrospiro[chromeno[2,3-b]pyridine-5,3'-[1,4]oxazin]-5'-amine (0.202 g, 0.458 mmol)

Step 2: A vial was charged with (R)-3-fluoropyrrolidine HCl (0.021 g, 0.170 mmol), (S)-3-bromo-7-(2-fluoropyridin-3-yl)-2',6'-dihydrospiro[chromeno[2,3-b]pyridine-5,3'-[1,4]oxazin]-5'-amine (0.050 g, 0.113 mmol) and RuPhos palladacycle (9.05 mg, 0.011 mmol). THF (1 mL) and LiHMDS (1N in THF; 0.567 mL, 0.567 mmol) were added, and the reaction mixture was allowed to stir at RT overnight. Additional RuPhos palladacycle (9.05 mg, 0.011 mmol) and LiHMDS solution (0.567 mL, 0.567 mmol) were added, and the reaction mixture was heated to 45° C. for 2 hours. The reaction mixture was then quenched with MeOH and concentrated under reduced pressure. Purification of the crude residue by column chromatography [0-100% (90:10:1 DCM/MeOH/NH4OH)/DCM] gave (S)-7-(2-fluoropyridin-3-yl)-3-((R)-3-fluoropyrrolidin-1-yl)-2',6'-dihydrospiro[chromeno[2,3-b]pyridine-5,3'-[1,4]oxazin]-5'-amine (0.018 g, 0.040 mmol, 35.3% yield).

The following compounds in Table I are additional representative examples of compounds of Formulas I, I-A, I-A-1 through I-A-7, I-B, II, II-A and II-B provided by the present invention. The methods and intermediates used to prepare each compound are also included in the Table, along with the mass found and biological data (average nM $IC_{50}$'s for the enzyme and cell assays) where available. The names of the compounds were generated using the naming convention of the ChemDraw Ultra software, version 11 and above. Where the example is a racemic mixture, the name for that example includes both enantiomers. Individual enantiomers of examples are as indicated in the name.

TABLE I

| Ex. No. | Compound Name | Observed Mass | Method | Intermediate used | BACE 1 FRET assay (uM) | HEK cell assay (uM) |
| --- | --- | --- | --- | --- | --- | --- |
| 9 | (5R)-7-bromo-3-chloro-6'H-spiro[chromeno[2,3-c]pyridine-5,3'-[1,4]oxazin]-5'-amine, (5S)-7-bromo-3-chloro-6'H-spiro[chromeno[2,3-c]pyridine-5,3'-[1,4]oxazin]-5'-amine | 380 | Procedure I | Intermediate 2 | 4.1333 | 10 |
| 69 | (5R)-7-(2-fluoro-3-pyridinyl)-3-(2-fluoro-4-pyridinyl)-6'H-spiro[chromeno[2,3-c]pyridine-5,3'-[1,4]oxazin]-5'-amine, (5S)-7-(2-fluoro-3-pyridinyl)-3-(2-fluoro-4-pyridinyl)-6'H-spiro[chromeno[2,3-c]pyridine-5,3'-[1,4]oxazin]-5'-amine | 458.1 | A1 | Intermediate 10 | 0.0009 | 0.0055 |
| 9B | (5R)-7-bromo-3-chloro-6'H-spiro[chromeno[2,3-c]pyridine-5,3'-[1,4]oxazin]-5'-amine | 380 | Procedure I | Intermediate 2 | 23.128 | 10 |
| 9A | (5S)-7-bromo-3-chloro-6'H-spiro[chromeno[2,3-c]pyridine-5,3'-[1,4]oxazin]-5'-amine | 380 | Procedure I | Intermediate 2 | 4.1525 | 10 |
| 70 | (5R)-7-(2-fluoro-3-pyridinyl)-3-(2-fluoro-4-pyridinyl)-6'H-spiro[chromeno[2,3-c]pyridine-5,3'-[1,4]oxazin]-5'-amine | 458.2 | A1 | Intermediate 10A | 0.0524 | 0.2676 |
| 30 | (5S)-7-(2-fluoro-3-pyridinyl)-3-(2-fluoro-4-pyridinyl)-6'H-spiro[chromeno[2,3-c]pyridine-5,3'-[1,4]oxazin]-5'-amine | 458.2 | A1 | Intermediate 10A | 0.0003 | 0.0017 |
| 71 | (5S)-3-(3,6-dihydro-2H-pyran-4-yl)-7-(2-fluoro-3-pyridinyl)-6'H-spiro[chromeno[2,3-c]pyridine-5,3'-[1,4]oxazin]-5'-amine | 445.2 | A1 | Intermediate 10B | 0.0004 | 0.0012 |
| 72 | (5S)-3-(5,6-dihydro-2H-pyran-3-yl)-7-(2-fluoro-3-pyridinyl)-6'H-spiro[chromeno[2,3-c]pyridine-5,3'-[1,4]oxazin]-5'-amine | 445.2 | A1 | Intermediate 10B | 0.0004 | 0.0006 |
| 31 | (5S)-7-(2-fluoro-3-pyridinyl)-3-((3-methyl-3-oxetanyl)ethynyl)-6'H-spiro[chromeno[2,3-c]pyridine-5,3'-[1,4]oxazin]-5'-amine | 457.2 | A2 | Intermediate 10B | 0.0007 | 0.0015 |
| 73 | (5S)-3-(3,4-difluorophenyl)-7-(2-fluoro-3-pyridinyl)-6'H-spiro[chromeno[2,3-c]pyridine-5,3'-[1,4]oxazin]-5'-amine | 475.2 | A1 | Intermediate 10b | 0.0003 | 0.0027 |
| 74 | (5S)-3-(3,3-difluoro-1-pyrrolidinyl)-7-(2-fluoro-3-pyridinyl)-6'H-spiro[chromeno[2,3-c]pyridine-5,3'-[1,4]oxazin]-5'-amine | 468.2 | A3 | Intermediate 10b | 0.0004 | 0.0008 |
| 32 | (5S)-3-(4,4-difluoro-1-piperidinyl)-7-(2-fluoro-3-pyridinyl)-6'H-spiro[chromeno[2,3-c]pyridine-5,3'-[1,4]oxazin]-5'-amine | 482.1 | A3 | Intermediate 10B | 0.0006 | 0.0012 |
| 33 | (5S)-3-(2,2-dimethylpropoxy)-7-(2-fluoro-3-pyridinyl)-6'H-spiro[chromeno[2,3-c]pyridine-5,3'-[1,4]oxazin]-5'-amine | 449.2 | A4 | Intermediate 10B | 0.0004 | 0.0011 |
| 75 | (5S)-3-(2-fluoro-4-pyridinyl)-7-(5-(1-propyn-1-yl)-3-pyridinyl)-6'H-spiro[chromeno[2,3-c]pyridine-5,3'-[1,4]oxazin]-5'-amine | 478.2 | A1 | Intermediate 10B | 0.0005 | 0.0028 |
| 76 | (5S)-3-(6,6-dimethyl-3,6-dihydro-2H-pyran-4-yl)-7-(2-fluoro-3-pyridinyl)-6'H-spiro[chromeno[2,3-c]pyridine-5,3'-[1,4]oxazin]-5'-amine | 474.2 | A1 | Intermediate 10B | 0.0006 | 0.0007 |
| 77 | (5S)-3-(2,2-dimethyl-3,6-dihydro-2H-pyran-4-yl)-7-(2-fluoro-3-pyridinyl)-6'H-spiro[chromeno[2,3-c]pyridine-5,3'-[1,4]oxazin]-5'-amine | 474.2 | A1 | Intermediate 10b | 0.0007 | 0.0005 |
| 34 | (5S)-7-(2-fluoro-3-pyridinyl)-3-(tetrahydro-2H-pyran-4-yl)-6'H-spiro[chromeno[2,3-c]pyridine-5,3'-[1,4]oxazin]-5'-amine | 447.2 | A5 | Intermediate 10B | 0.0007 | 0.0009 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 78 | (5S)-3-(2-fluoro-4-pyridinyl)-7-(5-pyrimidinyl)-6'H-spiro[chromeno[2,3-c]pyridine-5,3'-[1,4]oxazin]-5'-amine | 441.2 | A1 | Intermediate 10B | 0.0005 | 0.0011 |
| 79 | (5S)-3-(3,4-difluorophenyl)-7-(5-pyrimidinyl)-6'H-spiro[chromeno[2,3-c]pyridine-5,3'-[1,4]oxazin]-5'-amine | 458.2 | A1 | Intermediate 10B | 0.0003 | 0.0008 |
| 80 | (5S)-7-(2-fluoro-3-pyridinyl)-3-((3R)-tetrahydro-2H-pyran-3-yl)-6'H-spiro[chromeno[2,3-c]pyridine-5,3'-[1,4]oxazin]-5'-amine | 447.2 | A5 | Intermediate 10B | 0.0039 | 0.0058 |
| 81 | (5S)-7-(2-fluoro-3-pyridinyl)-3-((3S)-tetrahydro-2H-pyran-3-yl)-6'H-spiro[chromeno[2,3-c]pyridine-5,3'-[1,4]oxazin]-5'-amine | 447.2 | A5 | Intermediate 10B | 0.0037 | 0.0041 |
| 36B | (3R)-4'-fluoro-7'-(2-fluoro-3-pyridinyl)-2'-(2-fluoro-4-pyridinyl)-6H-spiro[1,4-oxazine-3,9'-xanthen]-5-amine | 475 | A7 | Intermediate 13A | 0.1403 | 0.628 |
| 36A | (3S)-4'-fluoro-7'-(2-fluoro-3-pyridinyl)-2'-(2-fluoro-4-pyridinyl)-6H-spiro[1,4-oxazine-3,9'-xanthen]-5-amine | 475 | A7 | Intermediate 13A | 0.0004 | 0.0029 |
| 35A | (3S)-4'-fluoro-7'-(2-fluoro-3-pyridinyl)-2'-(4-morpholinyl)-6H-spiro[1,4-oxazine-3,9'-xanthen]-5-amine | 465 | A6 | Intermediate 13B | 0.0005 | 0.0019 |
| 35B | (3R)-4'-fluoro-7'-(2-fluoro-3-pyridinyl)-2'-(4-morpholinyl)-6H-spiro[1,4-oxazine-3,9'-xanthen]-5-amine | 465 | A6 | Intermediate 13A | 0.211 | 0.0862 |
| 82 | (3R)-4'-fluoro-7'-(2-fluoro-3-pyridinyl)-2'-((3-methyl-3-oxetanyl)methoxy)-6H-spiro[1,4-oxazine-3,9'-xanthen]-5-amine | 480 | A8 | Intermediate 13A | 0.043 | 0.1212 |
| 83 | (3S)-4'-fluoro-7'-(2-fluoro-3-pyridinyl)-2'-((3-methyl-3-oxetanyl)methoxy)-6H-spiro[1,4-oxazine-3,9'-xanthen]-5-amine | 480 | A8 | Intermediate 13B | 0.0004 | 0.0004 |
| 37A | (3S)-4'-fluoro-2'-(2-fluoro-2-methylpropoxy)-7'-(2-fluoro-3-pyridinyl)-6H-spiro[1,4-oxazine-3,9'-xanthen]-5-amine | 470 | A8 | Intermediate 13B | 0.0002 | 0.0013 |
| 37B | (3R)-4'-fluoro-2'-(2-fluoro-2-methylpropoxy)-7'-(2-fluoro-3-pyridinyl)-6H-spiro[1,4-oxazine-3,9'-xanthen]-5-amine | 470 | A8 | Intermediate 13A | 0.1096 | 0.0641 |
| 84 | (3R)-4'-fluoro-7'-(2-fluoro-3-pyridinyl)-2'-((3R)-3-fluoro-1-pyrrolidinyl)-6H-spiro[1,4-oxazine-3,9'-xanthen]-5-amine | 467 | A6 | Intermediate 13A | 0.0004 | 0.0022 |
| 85 | (3S)-4'-fluoro-7'-(2-fluoro-3-pyridinyl)-2'-((3R)-3-fluoro-1-pyrrolidinyl)-6H-spiro[1,4-oxazine-3,9'-xanthen]-5-amine | 467 | A6 | Intermediate 13B | 0.0397 | 0.1008 |
| 86 | (3R)-2'-(4,4-difluoro-1-piperidinyl)-4'-fluoro-7'-(2-fluoro-3-pyridinyl)-6H-spiro[1,4-oxazine-3,9'-xanthen]-5-amine | 499 | A6 | Intermediate 13A | 0.0005 | 0.0026 |
| 87 | (5S)-7-(2-fluoro-3-pyridinyl)-3-((3-methyl-3-oxetanyl)ethynyl)-6'H-spiro[chromeno[2,3-b]pyridine-5,3'-[1,4]oxazin]-5'-amine | 457 | A2 | Intermediate 11B | 0.002 | 0.0013 |
| 88 | (5R)-7-(2-fluoro-3-pyridinyl)-3-((3-methyl-3-oxetanyl)ethynyl)-6'H-spiro[chromeno[2,3-b]pyridine-5,3'-[1,4]oxazin]-5'-amine | 457 | A2 | Intermediate 11A | 0.3318 | 0.1975 |
| 89 | (5S)-3-(3,3-dimethyl-1-butyn-1-yl)-7-(2-fluoro-3-pyridinyl)-6'H-spiro[chromeno[2,3-b]pyridine-5,3'-[1,4]oxazin]-5'-amine | 443 | A2 | Intermediate 11B | 0.0007 | 0.0004 |
| 90 | (5S)-7-(2-fluoro-3-pyridinyl)-3-(4-methylphenyl)-6'H-spiro[chromeno[2,3-b]pyridine-5,3'-[1,4]oxazin]-5'-amine | 453 | A22 | Intermediate 11B | 0.0006 | 0.0012 |
| 91 | (5S)-3-(4-fluorophenyl)-7-(2-fluoro-3-pyridinyl)-6'H-spiro[chromeno[2,3-b]pyridine-5,3'-[1,4]oxazin]-5'-amine | 457 | A22 | Intermediate 11B | 0.0005 | 0.0007 |
| 68 | (5S)-7-(2-fluoro-3-pyridinyl)-3-((3R)-3-fluoro-1-pyrrolidinyl)-6'H-spiro[chromeno[2,3-b]pyridine-5,3'-[1,4]oxazin]-5'-amine | 450 | A39 | Intermediate 11B | 0.0014 | 0.0012 |
| 92 | (5S)-7-(5-chloro-2-fluorophenyl)-3-((3R)-3-fluoro-1-pyrrolidinyl)-6'H-spiro[chromeno[2,3-b]pyridine-5,3'-[1,4]oxazin]-5'-amine | 483 | A39 | Intermediate 11B | 0.0006 | 0.0019 |
| 93 | (5S)-7-(5-chloro-2-fluorophenyl)-3-(4-morpholinyl)-6'H-spiro[chromeno[2,3-b]pyridine-5,3'-[1,4]oxazin]-5'-amine | 481 | A39 | Intermediate 11B | 0.0007 | 0.0039 |
| 94 | (5S)-7-(5-chloro-2-fluorophenyl)-3-(8-oxa-3-azabicyclo[3.2.1]oct-3-yl)-6'H-spiro[chromeno[2,3-b]pyridine-5,3'-[1,4]oxazin]-5'-amine | 507 | A39 | Intermediate 11B | 0.0013 | 0.0013 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 95 | (5S)-7-(5-chloro-2-fluorophenyl)-3-((3-methyl-3-oxetanyl)ethynyl)-6'H-spiro[chromeno[2,3-b]pyridine-5,3'-[1,4]oxazin]-5'-amine | 490 | A2 | Intermediate 11B | 0.0005 | 0.0012 |
| 96 | (5S)-3-(3,3-dimethyl-1-butyn-1-yl)-8-fluoro-7-(5-pyrimidinyl)-6'H-spiro[chromeno[2,3-b]pyridine-5,3'-[1,4]oxazin]-5'-amine | 444 | A2 | Intermediate 12 | 0.0012 | 0.0006 |
| 97 | (5R)-3-(3,3-dimethyl-1-butyn-1-yl)-8-fluoro-7-(5-pyrimidinyl)-6'H-spiro[chromeno[2,3-b]pyridine-5,3'-[1,4]oxazin]-5'-amine | 444 | A2 | Intermediate 12 | 0.4186 | 0.273 |
| 13 | (4R)-2'-bromo-7'-iodo-5,6-dihydrospiro[1,3-thiazine-4,9'-xanthen]-2-amine, (4S)-2'-bromo-7'-iodo-5,6-dihydrospiro[1,3-thiazine-4,9'-xanthen]-2-amine | 487, 489 | Procedure M | | 9.9592 | 10 |
| 98 | 2',7'-di-5-pyrimidinyl-5,6-dihydrospiro[1,3-thiazine-4,9'-xanthen]-2-amine | 439 | A1 | Intermediate 14 | 0.2572 | 0.6346 |
| 99 | 2',7'-di-3-pyridinyl-5,6-dihydrospiro[1,3-thiazine-4,9'-xanthen]-2-amine | 437 | A1 | Intermediate 14 | 0.0818 | 0.1184 |
| 100 | (5R)-3,7-bis(2-fluoro-3-pyridinyl)-5',6'-dihydrospiro[chromeno[2,3-c]pyridine-5,4'-[1,3]oxazin]-2'-amine, (5S)-3,7-bis(2-fluoro-3-pyridinyl)-5',6'-dihydrospiro[chromeno[2,3-c]pyridine-5,4'-[1,3]oxazin]-2'-amine | 458.1 | A1 | Intermediate 18 | 0.0496 | 0.184 |
| 101 | (5R)-1-fluoro-3,7-bis(2-fluoro-3-pyridinyl)-5',6'-dihydrospiro[chromeno[2,3-c]pyridine-5,4'-[1,3]oxazin]-2'-amine, (5S)-1-fluoro-3,7-bis(2-fluoro-3-pyridinyl)-5',6'-dihydrospiro[chromeno[2,3-c]pyridine-5,4'-[1,3]oxazin]-2'-amine | 476.1 | A1 | Intermediate 15 | 0.0146 | 0.0459 |
| 102 | (5R)-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine, (5S)-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine | 457.9 | A1 | Intermediate 18 | 0.025 | 0.0366 |
| 103 | (5R)-1-fluoro-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine, (5S)-1-fluoro-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine | 475.9 | A1 | Intermediate 15 | 0.0022 | 0.0069 |
| 104 | (5R)-1-fluoro-3,7-bis(2-fluoro-3-pyridinyl)-5',6'-dihydrospiro[chromeno[2,3-c]pyridine-5,4'-[1,3]oxazin]-2'-amine | 475.9 | A1 | Intermediate 15A | 1.7445 | 1.9035 |
| 105 | (5S)-1-fluoro-3,7-bis(2-fluoro-3-pyridinyl)-5',6'-dihydrospiro[chromeno[2,3-c]pyridine-5,4'-[1,3]oxazin]-2'-amine | 475.9 | A1 | Intermediate 15B | 0.0206 | 0.0242 |
| 106 | (5R)-1-fluoro-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine | 475.9 | A1 | Intermediate 15A | 1.7387 | 2.639 |
| 107 | (5S)-1-fluoro-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine | 475.9 | A1 | Intermediate 15B | 0.0005 | 0.0018 |
| 108 | (5S)-3-(3,6-dihydro-2H-pyran-4-yl)-1-fluoro-7-(2-fluoro-3-pyridinyl)-5',6'-dihydrospiro[chromeno[2,3-c]pyridine-5,4'-[1,3]oxazin]-2'-amine | 463 | A1 | Intermediate 15B | 0.0006 | 0.0006 |
| 109 | (5R)-3-(3,6-dihydro-2H-pyran-4-yl)-7-(2-fluoro-3-pyridinyl)-5',6'-dihydrospiro[chromeno[2,3-c]pyridine-5,4'-[1,3]oxazin]-2'-amine | 445.1 | A1 | Intermediate 18A | 2.8157 | 0.5792 |
| 110 | (5S)-3-(5,6-dihydro-2H-pyran-3-yl)-1-fluoro-7-(2-fluoro-3-pyridinyl)-5',6'-dihydrospiro[chromeno[2,3-c]pyridine-5,4'-[1,3]oxazin]-2'-amine | 463 | A1 | Intermediate 15B | 0.0005 | 0.0005 |
| 111 | (5S)-3-(3,6-dihydro-2H-pyran-4-yl)-7-(2-fluoro-3-pyridinyl)-5',6'-dihydrospiro[chromeno[2,3-c]pyridine-5,4'-[1,3]oxazin]-2'-amine | 445.1 | A1 | Intermediate 18B | 0.0018 | 0.0021 |
| 112 | (5S)-3,7-bis(5-fluoro-3-pyridinyl)-6'H-spiro[chromeno[2,3-c]pyridine-5,3'-[1,4]oxazin]-5'-amine | 458.4 | A1 | Intermediate 10B | 0.0005 | 0.0015 |
| 113 | (5S)-3-(2-fluoro-4-pyridinyl)-7-(5-fluoro-3-pyridinyl)-6'H-spiro[chromeno[2,3-c]pyridine-5,3'-[1,4]oxazin]-5'-amine | 458.4 | A1 | Intermediate 10B | 0.0005 | 0.001 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 114 | (5S)-3-(3,4-difluorophenyl)-7-(5-fluoro-3-pyridinyl)-6'H-spiro[chromeno[2,3-c]pyridine-5,3'-[1,4]oxazin]-5'-amine | 475.2 | A1 | Intermediate 10B | 0.0004 | 0.0023 |
| 115 | (5S)-3-(3,4-difluorophenyl)-7-(3-pyridinyl)-6'H-spiro[chromeno[2,3-c]pyridine-5,3'-[1,4]oxazin]-5'-amine | 457.2 | A1 | Intermediate 10B | 0.0004 | 0.0016 |
| 116 | (5S)-3-(2-fluoro-4-pyridinyl)-7-(3-pyridinyl)-6'H-spiro[chromeno[2,3-c]pyridine-5,3'-[1,4]oxazin]-5'-amine | 440.4 | A1 | Intermediate 10B | 0.0006 | 0.0008 |
| 117 | (5S)-3-(3,4-difluorophenyl)-7-(4-fluoro-3-pyridinyl)-6'H-spiro[chromeno[2,3-c]pyridine-5,3'-[1,4]oxazin]-5'-amine | 475.2 | A1 | Intermediate 10B | 0.0003 | 0.0016 |
| 118 | (5S)-3-(2-fluoro-4-pyridinyl)-7-(4-fluoro-3-pyridinyl)-6'H-spiro[chromeno[2,3-c]pyridine-5,3'-[1,4]oxazin]-5'-amine | 458.4 | A1 | Intermediate 10B | 0.0004 | 0.0006 |
| 43 | N-((5S)-3-(2,2-dimethylpropoxy)-7-(2-fluoro-3-pyridinyl)-6'H-spiro[chromeno[2,3-c]pyridine-5,3'-[1,4]oxazin]-5'-yl)formamide | 477.3 | A14 | Intermediate 10B | 0.0174 | 0.0012 |
| 119 | (5S)-3-(2,2-dimethylpropoxy)-7-(3-pyridinyl)-6'H-spiro[chromeno[2,3-c]pyridine-5,3'-[1,4]oxazin]-5'-amine | 431.4 | A4 | Intermediate 10B | 0.0006 | 0.0004 |
| 120 | (5S)-3-(2,2-dimethylpropoxy)-7-(5-fluoro-3-pyridinyl)-6'H-spiro[chromeno[2,3-c]pyridine-5,3'-[1,4]oxazin]-5'-amine | 449.4 | A4 | Intermediate 10B | 0.0006 | 0.0007 |
| 121 | (5S)-3-(5,6-dihydro-2H-pyran-3-yl)-7-(5-fluoro-3-pyridinyl)-6'H-spiro[chromeno[2,3-c]pyridine-5,3'-[1,4]oxazin]-5'-amine | 445.2 | A1 | Intermediate 10B | 0.0005 | 0.0002 |
| 122 | (5S)-3-(3,3-difluoro-1-pyrrolidinyl)-7-(5-fluoro-3-pyridinyl)-6'H-spiro[chromeno[2,3-c]pyridine-5,3'-[1,4]oxazin]-5'-amine | 468.3 | A3 | Intermediate 10B | 0.0006 | 0.0003 |
| 123 | (5S)-7-(2-fluoro-3-pyridinyl)-3-methoxy-6'H-spiro[chromeno[2,3-c]pyridine-5,3'-[1,4]oxazin]-5'-amine | 393.3 | A21 | Intermediate 21 | 0.0022 | 0.0033 |
| 124 | (5S)-3-methoxy-7-(3-pyridinyl)-6'H-spiro[chromeno[2,3-c]pyridine-5,3'-[1,4]oxazin]-5'-amine | 375.2 | A21 | Intermediate 21 | 0.0068 | 0.0051 |
| 125 | (5S)-7-(2-chloro-5-fluorophenyl)-3-methoxy-6'H-spiro[chromeno[2,3-c]pyridine-5,3'-[1,4]oxazin]-5'-amine | 426.3 | A21 | Intermediate 21 | 0.0022 | 0.0124 |
| 126 | 3-(((5S)-5'-amino-7-(3-fluorophenyl)-6'H-spiro[chromeno[2,3-c]pyridine-5,3'-[1,4]oxazin]-3-yl)oxy)-2,2-dimethylpropanenitrile | 459.3 | A4 | Intermediate 10B | 0.0004 | 0.0015 |
| 127 | 3-(((5S)-5'-amino-7-(5-chloro-2-fluorophenyl)-6'H-spiro[chromeno[2,3-c]pyridine-5,3'-[1,4]oxazin]-3-yl)oxy)-2,2-dimethylpropanenitrile | 493.2 | A4 | Intermediate 10B | 0.0003 | 0.0014 |
| 128 | (5S)-7-bromo-3-(4,4-difluoro-1-piperidinyl)-1-fluoro-6'H-spiro[chromeno[2,3-c]pyridine-5,3'-[1,4]oxazin]-5'-amine | 482.9 | A29 | | 0.0173 | 0.1094 |
| 129 | (5S)-3-(4,4-difluoro-1-piperidinyl)-1-fluoro-7-(2-fluoro-3-pyridinyl)-6'H-spiro[chromeno[2,3-c]pyridine-5,3'-[1,4]oxazin]-5'-amine | 500 | A29 | | 0.0009 | 0.0049 |
| 39 | (3S)-5-amino-5'-fluoro-7'-(2-fluoro-4-pyridinyl)-6H-spiro[1,4-oxazine-3,9'-xanthen]-2'-ol | 396 | A10 | Intermediate 29 | 0.3682 | 2.5925 |
| 65 | (3R)-2'-(2-fluoro-3-pyridinyl)-7'-(2-fluoro-4-pyridinyl)-6H-spiro[1,4-oxazine-3,9'-xanthen]-5-amine | 457 | A36 | Intermediate 27 | 0.0016 | 0.0182 |
| 64 | (3R)-2'-(3,6-dihydro-2H-pyran-4-yl)-7'-(2-fluoro-3-pyridinyl)-6H-spiro[1,4-oxazine-3,9'-xanthen]-5-amine | 444 | A35 | Intermediate 31 | 0.0006 | 0.0052 |
| 40 | (3S)-2'-(3,6-dihydro-2H-pyran-4-yl)-4'-fluoro-7'-(2-fluoro-3-pyridinyl)-6H-spiro[1,4-oxazine-3,9'-xanthen]-5-amine | 462 | A11 | Intermediate 28 | 0.0003 | 0.003 |
| 130 | (3R)-2'-(5,6-dihydro-2H-pyran-3-yl)-7'-(2-fluoro-3-pyridinyl)-6H-spiro[1,4-oxazine-3,9'-xanthen]-5-amine | 444 | A35 | Intermediate 31 | 0.0007 | 0.0122 |
| 41 | (3S)-4'-fluoro-7'-(2-fluoro-3-pyridinyl)-2'-((3-methyl-3-oxetanyl)ethynyl)-6H-spiro[1,4-oxazine-3,9'-xanthen]-5-amine | 474 | A12 | Intermediate 28 | 0.0005 | 0.0019 |
| 131 | (3S)-2'-(3,6-dihydro-2H-pyran-4-yl)-4'-fluoro-7'-(5-(1-propyn-1-yl)-3-pyridinyl)-6H-spiro[1,4-oxazine-3,9'-xanthen]-5-amine | 482 | A37 | Intermediate 29 | 0.0007 | 0.0025 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 66 | (3S)-2'-(5,6-dihydro-2H-pyran-3-yl)-4'-fluoro-7'-(5-(1-propyn-1-yl)-3-pyridinyl)-6H-spiro[1,4-oxazine-3,9'-xanthen]-5-amine | 482 | A37 | Intermediate 29 | 0.0005 | 0.0015 |
| 132 | (3S)-2'-(5,6-dihydro-2H-pyran-3-yl)-4'-fluoro-7'-(2-fluoro-3-pyridinyl)-6H-spiro[1,4-oxazine-3,9'-xanthen]-5-amine | 462 | A37 | Intermediate 29 | 0.0003 | 0.0013 |
| 42 | (3S)-4'-fluoro-7'-(2-fluoro-3-pyridinyl)-2'-(tetrahydro-2H-pyran-4-yl)-6H-spiro[1,4-oxazine-3,9'-xanthen]-5-amine | 464 | A13 | | 0.0004 | 0.0024 |
| 63 | (3S)-2'-(5,6-dihydro-2H-pyran-3-yl)-4'-fluoro-7'-(3-pyridinyl)-6H-spiro[1,4-oxazine-3,9'-xanthen]-5-amine | 444 | A34 | Intermediate 28 | 0.0003 | 0.0005 |
| 133 | (3S)-2'-(5,6-dihydro-2H-pyran-3-yl)-4'-fluoro-7'-(5-pyrimidinyl)-6H-spiro[1,4-oxazine-3,9'-xanthen]-5-amine | 445 | A34 | Intermediate 28 | 0.0003 | 0.0004 |
| 134 | (3R)-2'-bromo-7'-methoxy-6H-spiro[1,4-oxazine-3,9'-xanthen]-5-amine | 375/377 | Procedure ZZ | | 7.1087 | 10 |
| 135 | (3R)-2'-bromo-7'-(2,2-dimethylpropoxy)-6H-spiro[1,4-oxazine-3,9'-xanthen]-5-amine | 431/433 | A38 | Intermediate 30 | 0.1017 | 0.5873 |
| 67 | (3S)-2'-(2,2-dimethylpropoxy)-7'-(2-fluoro-3-pyridinyl)-6H-spiro[1,4-oxazine-3,9'-xanthen]-5-amine | 448 | A38 | Intermediate 30 | 0.002 | 0.0155 |
| 136 | (4R/S)-2'-bromo-7'-methoxy-5,6-dihydrospiro[1,3-thiazine-4,9'-xanthen]-2-amine | 390.9/392.9 | 28 | Intermediate 1 | 23.658 | 10 |
| 137 | (4R/S)-2'-methoxy-7'-(5-pyrimidinyl)-5,6-dihydrospiro[1,3-thiazine-4,9'-xanthen]-2-amine | 391 | 28 | Intermediate 1 | 1.1333 | 1.1404 |
| 138 | (5S)-7-(2-fluoro-3-pyridinyl)-3-phenyl-5',6'-dihydrospiro[chromeno[2,3-c]pyridine-5,4'-[1,3]oxazin]-2'-amine | 439.1 | A1 | 18B | 0.0041 | |
| 139 | (5S)-3-(3,3-dimethyl-1-butyn-1-yl)-7-(5-fluoro-3-pyridinyl)-5',6'-dihydrospiro[chromeno[2,3-c]pyridine-5,4'-[1,3]oxazin]-2'-amine | 443 | A2 | 18B | 0.0128 | 0.0069 |
| 140 | (5S)-7-(5-fluoro-3-pyridinyl)-3-(3-pyridinyl)-5',6'-dihydrospiro[chromeno[2,3-c]pyridine-5,4'-[1,3]oxazin]-2'-amine | 440 | A1 | 18B | 0.0108 | 0.0034 |
| 141 | (5S)-3-(5-chloro-3-pyridinyl)-7-(2-fluoro-3-pyridinyl)-5',6'-dihydrospiro[chromeno[2,3-c]pyridine-5,4'-[1,3]oxazin]-2'-amine | 473.9 | A1 | 18B | 0.0095 | 0.0225 |
| 142 | (5S)-3,7-bis(5-fluoro-3-pyridinyl)-5',6'-dihydrospiro[chromeno[2,3-c]pyridine-5,4'-[1,3]oxazin]-2'-amine | 458 | A1 | 18B | 0.0062 | 0.0042 |
| 143 | (5S)-3-(3,6-dihydro-2H-pyran-4-yl)-7-(5-fluoro-3-pyridinyl)-5',6'-dihydrospiro[chromeno[2,3-c]pyridine-5,4'-[1,3]oxazin]-2'-amine | 445.1 | A1 | 18B | 0.0057 | 0.0037 |
| 144 | (5S)-7-(2-fluoro-3-pyridinyl)-3-(tetrahydro-2H-pyran-4-yl)-5',6'-dihydrospiro[chromeno[2,3-c]pyridine-5,4'-[1,3]oxazin]-2'-amine | 447 | A5 | 18B | 0.0132 | 0.0354 |
| 145 | (5S)-3-(2-fluoro-4-pyridinyl)-7-(5-fluoro-3-pyridinyl)-5',6'-dihydrospiro[chromeno[2,3-c]pyridine-5,4'-[1,3]oxazin]-2'-amine | 458 | A1 | 18B | 0.005 | 0.004 |
| 146 | (5S)-3-(5,6-dihydro-2H-pyran-3-yl)-7-(5-fluoro-3-pyridinyl)-5',6'-dihydrospiro[chromeno[2,3-c]pyridine-5,4'-[1,3]oxazin]-2'-amine | 445.1 | A1 | 18B | 0.0022 | 0.0015 |
| 147 | (5R)-7-(2-fluoro-3-pyridinyl)-3-(3-pyridinyl)-5',6'-dihydrospiro[chromeno[2,3-c]pyridine-5,4'-[1,3]oxazin]-2'-amine | 440 | A1 | 18B | 0.132 | 0.132 |
| 148 | (5S)-7-(2-fluoro-3-pyridinyl)-3-(3-pyridinyl)-5',6'-dihydrospiro[chromeno[2,3-c]pyridine-5,4'-[1,3]oxazin]-2'-amine | 440 | A1 | 18B | 0.0046 | 0.0041 |
| 149 | (5S)-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine | 458 | A1 | 18B | 0.0048 | 0.0038 |
| 150 | 3,7-di-3-pyridinyl-5',6'-dihydrospiro[chromeno[2,3-c]pyridine-5,4'-[1,3]oxazin]-2'-amine | 422 | A1 | 18B | 0.013 | 0.0103 |
| 151 | 3-(3,6-dihydro-2H-pyran-4-yl)-7-(3-pyridinyl)-5',6'-dihydrospiro[chromeno[2,3-c]pyridine-5,4'-[1,3]oxazin]-2'-amine | 427.1 | A1 | 18B | 0.0073 | 0.0034 |
| 152 | (5R)-7-(2-fluoro-3-pyridinyl)-3-(5-fluoro-3-pyridinyl)-5',6'-dihydrospiro[chromeno[2,3-c]pyridine-5,4'-[1,3]oxazin]-2'-amine | 458 | A1 | 18B | 0.2384 | 0.1081 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 153 | (5S)-3-(5,6-dihydro-2H-pyran-3-yl)-7-(2-fluoro-3-pyridinyl)-5',6'-dihydrospiro[chromeno[2,3-c]pyridine-5,4'-[1,3]oxazin]-2'-amine | 445.1 | A1 | 18B | 0.002 | 0.0026 |
| 154 | (5S)-3-(3,3-dimethyl-1-butyn-1-yl)-7-(2-fluoro-3-pyridinyl)-5',6'-dihydrospiro[chromeno[2,3-c]pyridine-5,4'-[1,3]oxazin]-2'-amine | 443 | A2 | 18B | 0.0058 | 0.005 |
| 155 | (5S)-7-(2-fluoro-3-pyridinyl)-3-(5-fluoro-3-pyridinyl)-5',6'-dihydrospiro[chromeno[2,3-c]pyridine-5,4'-[1,3]oxazin]-2'-amine | 458 | A1 | 18B | 0.0038 | 0.0062 |
| 44 | (5S)-7-(4,4-difluoro-1-piperidinyl)-3-(2,2-dimethylpropoxy)-6'H-spiro[chromeno[2,3-c]pyridine-5,3'-[1,4]oxazin]-5'-amine | 473.2 | A15 | 10B | 0.0105 | 0.0193 |
| 48 | (3S)-4'-fluoro-7'-(2-fluoro-3-pyridinyl)-2'-methoxy-6H-spiro[1,4-oxazine-3,9'-xanthen]-5-amine | 410 | A19 | 13B | 0.0015 | 0.0156 |
| 45 | (3S)-7'-(4,4-difluoro-1-piperidinyl)-4'-fluoro-2'-methoxy-6H-spiro[1,4-oxazine-3,9'-xanthen]-5-amine | 434.2 | A16 | 13B | 0.1578 | 0.4203 |
| 156 | (4S)-2'-(3,6-dihydro-2H-pyran-4-yl)-4'-fluoro-7'-(3-pyridinyl)-5,6-dihydrospiro[1,3-oxazine-4,9'-xanthen]-2-amine | 443.8 | A7 | 20B | 0.0048 | 0.0042 |
| 157 | (4R)-2'-(3,6-dihydro-2H-pyran-4-yl)-4'-fluoro-7'-(3-pyridinyl)-5,6-dihydrospiro[1,3-oxazine-4,9'-xanthen]-2-amine | 443.8 | A7 | 20A | 0.7839 | 0.0781 |
| 158 | (4R)-4'-fluoro-2'-(2-fluoro-2-methylpropoxy)-7'-(3-pyridinyl)-5,6-dihydrospiro[1,3-oxazine-4,9'-xanthen]-2-amine | 452 | A8 | 20A | 0.9406 | 0.393 |
| 159 | (4R)-2'-(5,6-dihydro-2H-pyran-3-yl)-4'-fluoro-7'-(3-pyridinyl)-5,6-dihydrospiro[1,3-oxazine-4,9'-xanthen]-2-amine | 444.2 | A7 | 20A | 0.6156 | 0.0713 |
| 160 | (4S)-4'-fluoro-2'-((3-methyl-3-oxetanyl)methoxy)-7'-(3-pyridinyl)-5,6-dihydrospiro[1,3-oxazine-4,9'-xanthen]-2-amine | 461.9 | A8 | 20A | 0.0063 | 0.0059 |
| 20 | (4R)-7'-bromo-4'-fluoro-2'-methoxy-5,6-dihydrospiro[1,3-oxazine-4,9'-xanthen]-2-amine, '(4S)-7'-bromo-4'-fluoro-2'-methoxy-5,6-dihydrospiro[1,3-oxazine-4,9'-xanthen]-2- | 394.2 | Procedure T | | 15.44 | 10 |
| 161 | (4R)-4'-fluoro-2'-((3-methyl-3-oxetanyl)methoxy)-7'-(3-pyridinyl)-5,6-dihydrospiro[1,3-oxazine-4,9'-xanthen]-2-amine | 461.9 | A8 | 20A | 2.782 | 0.3329 |
| 162 | (4R)-2'-(4,4-difluoro-1-piperidinyl)-4'-fluoro-7'-(2-fluoro-3-pyridinyl)-5,6-dihydrospiro[1,3-oxazine-4,9'-xanthen]-2-amine | 498.9 | A6 | 20A | 0.9582 | 3.0182 |
| 163 | (4S)-2'-(3,6-dihydro-2H-pyran-4-yl)-4'-fluoro-7'-(2-fluoro-3-pyridinyl)-5,6-dihydrospiro[1,3-oxazine-4,9'-xanthen]-2-amine | 461.8 | A7 | 20B | 0.0026 | 0.006 |
| 164 | (4S)-2'-(5,6-dihydro-2H-pyran-3-yl)-4'-fluoro-7'-(3-pyridinyl)-5,6-dihydrospiro[1,3-oxazine-4,9'-xanthen]-2-amine | 444.2 | A7 | 20B | 0.0028 | 0.0027 |
| 17A | (4S)-4'-fluoro-7'-(2-fluoro-3-pyridinyl)-2'-((3-methyl-3-oxetanyl)ethynyl)-5,6-dihydrospiro[1,3-oxazine-4,9'-xanthen]-2-amine | 473.8 | A18 | 20B | 0.0033 | 0.0026 |
| 17B | (4R)-4'-fluoro-7'-(2-fluoro-3-pyridinyl)-2'-((3-methyl-3-oxetanyl)ethynyl)-5,6-dihydrospiro[1,3-oxazine-4,9'-xanthen]-2-amine | 473.8 | A18 | 20A | 0.2243 | 0.4702 |
| 165 | (4R)-4'-fluoro-7'-(2-fluoro-3-pyridinyl)-2'-(4-pyridinyl)-5,6-dihydrospiro[1,3-oxazine-4,9'-xanthen]-2-amine | 456.8 | A7 | 20A | 0.5533 | 0.248 |
| 166 | (4S)-4'-fluoro-7'-(2-fluoro-3-pyridinyl)-2'-(4-pyridinyl)-5,6-dihydrospiro[1,3-oxazine-4,9'-xanthen]-2-amine | 456.8 | A7 | 20B | 0.006 | 0.0082 |
| 167 | (4R)-4'-fluoro-7'-(2-fluoro-3-pyridinyl)-2'-(3-pyridinyl)-5,6-dihydrospiro[1,3-oxazine-4,9'-xanthen]-2-amine | 456.8 | A7 | 20A | 0.1473 | 0.1095 |
| 168 | (4S)-4'-fluoro-7'-(2-fluoro-3-pyridinyl)-2'-(3-pyridinyl)-5,6-dihydrospiro[1,3-oxazine-4,9'-xanthen]-2-amine | 456.8 | A7 | 20B | 0.0035 | 0.0063 |
| 169 | (4R)-2'-(3,6-dihydro-2H-pyran-4-yl)-4'-fluoro-7'-(2-fluoro-3-pyridinyl)-5,6-dihydrospiro[1,3-oxazine-4,9'-xanthen]-2-amine | 461.8 | A7 | 20A | 3.0734 | 3.4016 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 170 | (4R)-4'-fluoro-7'-(2-fluoro-3-pyridinyl)-2'-methoxy-5,6-dihydrospiro[1,3-oxazine-4,9'-xanthen]-2-amine, '(4S)-4'-fluoro-7'-(2-fluoro-3-pyridinyl)-2'-methoxy-5,6-dihydrospiro[1,3-oxazine-4,9'-xanthen]-2-amine | 410 | A19 | 20 | 0.1016 | 0.2721 |
| 171 | (4R)-4'-fluoro-7'-(2-fluoro-3-pyridinyl)-2'-((3-methyl-3-oxetanyl)methoxy)-5,6-dihydrospiro[1,3-oxazine-4,9'-xanthen]-2-amine | 479.8 | A8 | 20A | 0.5247 | 0.2451 |
| 172 | (4R)-2'-(5,6-dihydro-2H-pyran-3-yl)-4'-fluoro-7'-(2-fluoro-3-pyridinyl)-5,6-dihydrospiro[1,3-oxazine-4,9'-xanthen]-2-amine | 461.8 | A7 | 20A | 1.1938 | 1.0675 |
| 173 | (4S)-2'-(5,6-dihydro-2H-pyran-3-yl)-4'-fluoro-7'-(2-fluoro-3-pyridinyl)-5,6-dihydrospiro[1,3-oxazine-4,9'-xanthen]-2-amine | 461.8 | A7 | 20B | 0.0011 | 0.0029 |
| 174 | (4R)-4'-fluoro-7'-(2-fluoro-3-pyridinyl)-2'-methoxy-5,6-dihydrospiro[1,3-oxazine-4,9'-xanthen]-2-amine | 409.9 | A19 | 20A | 4.2221 | 10 |
| 175 | (4S)-4'-fluoro-7'-(2-fluoro-3-pyridinyl)-2'-methoxy-5,6-dihydrospiro[1,3-oxazine-4,9'-xanthen]-2-amine | 409.9 | A19 | 20B | 0.0383 | 0.093 |
| 176 | (4S)-4'-fluoro-2'-(2-fluoro-2-methylpropoxy)-7'-(3-pyridinyl)-5,6-dihydrospiro[1,3-oxazine-4,9'-xanthen]-2-amine | 452 | A8 | 20B | 0.0061 | 0.0085 |
| 177 | (4R)-4'-fluoro-7'-(2-fluoro-3-pyridinyl)-2'-((3R)-3-fluoro-1-pyrrolidinyl)-5,6-dihydrospiro[1,3-oxazine-4,9'-xanthen]-2-amine | 466.8 | A6 | 20A | 0.8922 | 2.5323 |
| 178 | (4S)-4'-fluoro-7'-(2-fluoro-3-pyridinyl)-2'-((3R)-3-fluoro-1-pyrrolidinyl)-5,6-dihydrospiro[1,3-oxazine-4,9'-xanthen]-2-amine | 466.8 | A6 | 20B | 0.004 | 0.0101 |
| 179 | (4R)-4'-fluoro-7'-(2-fluoro-3-pyridinyl)-2'-(4-morpholinyl)-5,6-dihydrospiro[1,3-oxazine-4,9'-xanthen]-2-amine | 464.8 | A6 | 20A | 5.1872 | 2.8172 |
| 46 | (3S)-7'-(4,4-difluoro-1-piperidinyl)-4'-fluoro-2'-((3-methyl-3-oxetanyl)methoxy)-6H-spiro[1,4-oxazine-3,9'-xanthen]-5-amine | 503.8 | A17 | 20B | 0.0094 | 0.0321 |
| 180 | (4S)-4'-fluoro-7'-(2-fluoro-3-pyridinyl)-2'-((3-methyl-3-oxetanyl)methoxy)-5,6-dihydrospiro[1,3-oxazine-4,9'-xanthen]-2-amine | 479.8 | A8 | 20B | 0.0023 | 0.0032 |
| 181 | (4R)-4'-fluoro-2'-(2-fluoro-2-methylpropoxy)-7'-(2-fluoro-3-pyridinyl)-5,6-dihydrospiro[1,3-oxazine-4,9'-xanthen]-2-amine | 469.8 | A8 | 20A | 1.3711 | 1.1607 |
| 182 | (4S)-4'-fluoro-2'-(2-fluoro-2-methylpropoxy)-7'-(2-fluoro-3-pyridinyl)-5,6-dihydrospiro[1,3-oxazine-4,9'-xanthen]-2-amine | 469.8 | A8 | 20B | 0.0025 | 0.0041 |
| 183 | (4R)-4'-fluoro-7'-(2-fluoro-3-pyridinyl)-2'-(2-fluoro-4-pyridinyl)-5,6-dihydrospiro[1,3-oxazine-4,9'-xanthen]-2-amine, '(4S)-4'-fluoro-7'-(2-fluoro-3-pyridinyl)-2'-(2-fluoro-4-pyridinyl)-5,6-dihydrospiro[1,3-oxazine-4,9'-xanthen]-2-amine | 474.9 | A7 | 20 | 0.007 | 0.0154 |
| 184 | (4S)-4'-fluoro-7'-(2-fluoro-3-pyridinyl)-2'-(4-morpholinyl)-5,6-dihydrospiro[1,3-oxazine-4,9'-xanthen]-2-amine, '(4S)-4'-fluoro-7'-(2-fluoro-3-pyridinyl)-2'-(4-morpholinyl)-5,6-dihydrospiro[1,3-oxazine-4,9'-xanthen]-2-amine | 464.8 | A6 | 20 | 0.0048 | 0.0069 |
| 185 | (4S)-2'-(4,4-difluoro-1-piperidinyl)-4'-fluoro-7'-(2-fluoro-3-pyridinyl)-5,6-dihydrospiro[1,3-oxazine-4,9'-xanthen]-2-amine | 498.8 | A6 | 20B | 0.0044 | 0.0096 |
| 186 | (4R)-4'-fluoro-7'-(2-fluoro-3-pyridinyl)-2'-methoxy-5,6-dihydrospiro[1,3-thiazine-4,9'-xanthen]-2-amine | 425.8 | A19 | 23 | 9.5873 | 10 |
| 187 | (4S)-4'-fluoro-7'-(2-fluoro-3-pyridinyl)-2'-methoxy-5,6-dihydrospiro[1,3-thiazine-4,9'-xanthen]-2-amine | 425.8 | A19 | 23 | 0.0299 | 0.159 |
| 188 | (5S)-7-(2-fluoro-3-pyridinyl)-3-(2-fluoro-4-pyridinyl)-5',6'-dihydrospiro[chromeno[2,3-c]pyridine-5,4'-[1,3]thiazin]-2'-amine | 473.8 | A1 | 22 | 0.0026 | 0.0111 |
| 189 | (5R)-7-(2-fluoro-3-pyridinyl)-3-(2-fluoro-4-pyridinyl)-5',6'-dihydrospiro[chromeno[2,3-c]pyridine-5,4'-[1,3]thiazin]-2'-amine | 473.8 | A1 | 22 | 2.3918 | 3.2804 |

TABLE I-continued

| Ex. No. | Compound Name | Observed Mass | Method | Intermediate used | BACE 1 FRET assay (uM) | HEK cell assay (uM) |
| --- | --- | --- | --- | --- | --- | --- |
| 190 | (4R)-2'-(5,6-dihydro-2H-pyran-3-yl)-4'-fluoro-7'-(2-fluoro-3-pyridinyl)-5,6-dihydrospiro[1,3-thiazine-4,9'-xanthen]-2-amine | 477.8 | A7 | 23 | 0.4616 | 0.434 |
| 191 | (4R)-4'-fluoro-7'-(2-fluoro-3-pyridinyl)-2'-methoxy-5,6-dihydrospiro[1,3-thiazine-4,9'-xanthen]-2-amine, '(4S)-4'-fluoro-7'-(2-fluoro-3-pyridinyl)-2'-methoxy-5,6-dihydrospiro[1,3-thiazine-4,9'-xanthen]-2-amine | 425.8 | A19 | 23 | 0.0873 | 0.3745 |
| 192 | (5R)-3-chloro-7-(2-fluoro-3-pyridinyl)-5',6'-dihydrospiro[chromeno[2,3-c]pyridine-5,4'-[1,3]thiazin]-2'-amine | 412.8 | A1 | 22 | 3.3485 | 5.6113 |
| 193 | (5S)-3-(3,6-dihydro-2H-pyran-4-yl)-7-(2-fluoro-3-pyridinyl)-5',6'-dihydrospiro[chromeno[2,3-c]pyridine-5,4'-[1,3]thiazin]-2'-amine | 461.2 | A1 | 22 | 0.0033 | 0.0047 |
| 194 | (5R)-3-(3,6-dihydro-2H-pyran-4-yl)-7-(2-fluoro-3-pyridinyl)-5',6'-dihydrospiro[chromeno[2,3-c]pyridine-5,4'-[1,3]thiazin]-2'-amine | 461.2 | A1 | 22 | 0.4734 | 0.9372 |
| 195 | (5R)-3-(5,6-dihydro-2H-pyran-3-yl)-7-(2-fluoro-3-pyridinyl)-5',6'-dihydrospiro[chromeno[2,3-c]pyridine-5,4'-[1,3]thiazin]-2'-amine | 461.2 | A1 | 22 | 0.9218 | 1.9675 |
| 196 | (4R)-2'-(3,6-dihydro-2H-pyran-4-yl)-4'-fluoro-7'-(2-fluoro-3-pyridinyl)-5,6-dihydrospiro[1,3-thiazine-4,9'-xanthen]-2-amine | 478.2 | A7 | 23 | 2.5309 | 0.0831 |
| 197 | (4S)-4'-fluoro-7'-(2-fluoro-3-pyridinyl)-2'-((3-methyl-3-oxetanyl)methoxy)-5,6-dihydrospiro[1,3-thiazine-4,9'-xanthen]-2-amine | 495.8 | A8 | 23 | 0.0025 | 0.0048 |
| 198 | (4R)-4'-fluoro-7'-(2-fluoro-3-pyridinyl)-2'-((3-methyl-3-oxetanyl)methoxy)-5,6-dihydrospiro[1,3-thiazine-4,9'-xanthen]-2-amine | 495.8 | A8 | 23 | 0.5633 | 0.6337 |
| 199 | (5S)-3-chloro-7-(2-fluoro-3-pyridinyl)-5',6'-dihydrospiro[chromeno[2,3-c]pyridine-5,4'-[1,3]thiazin]-2'-amine | 412.8 | A1 | 22 | 0.0908 | 0.3922 |
| 200 | (4S)-2'-(3,6-dihydro-2H-pyran-4-yl)-4'-fluoro-7'-(2-fluoro-3-pyridinyl)-5,6-dihydrospiro[1,3-thiazine-4,9'-xanthen]-2-amine | 478.2 | A7 | 23 | 0.0027 | 0.0123 |
| 201 | (4S)-2'-(5,6-dihydro-2H-pyran-3-yl)-4'-fluoro-7'-(2-fluoro-3-pyridinyl)-5,6-dihydrospiro[1,3-thiazine-4,9'-xanthen]-2-amine | 477.8 | A7 | 23 | 0.0014 | 0.0097 |
| 202 | (4R)-4'-fluoro-2'-(2-fluoro-2-methylpropoxy)-7'-(2-fluoro-3-pyridinyl)-5,6-dihydrospiro[1,3-thiazine-4,9'-xanthen]-2-amine | 485.8 | A8 | 23 | 0.8631 | 2.4276 |
| 204 | (5S)-3-(5,6-dihydro-2H-pyran-3-yl)-7-(2-fluoro-3-pyridinyl)-5',6'-dihydrospiro[chromeno[2,3-c]pyridine-5,4'-[1,3]thiazin]-2'-amine | 461.2 | A1 | 22 | 0.0016 | 0.0027 |
| 204 | (4S)-4'-fluoro-2'-(2-fluoro-2-methylpropoxy)-7'-(2-fluoro-3-pyridinyl)-5,6-dihydrospiro[1,3-thiazine-4,9'-xanthen]-2-amine | 485.8 | A8 | 23 | 0.0028 | 0.0112 |
| 56A | (5R,6'R)-3-chloro-6'-cyclohexyl-7-(2-fluoro-3-pyridinyl)-6'H-spiro[chromeno[2,3-c]pyridine-5,3'-[1,4]oxazin]-5'-amine, '(5S,6'S)-3-chloro-6'-cyclohexyl-7-(2-fluoro-3-pyridinyl)-6'H-spiro[chromeno[2,3-c]pyridine-5,3'-[1,4]oxazin]-5'-amine | 479.1 | A27 | 9 | 0.0307 | 0.1383 |
| 205 | (5S,6'S)-7-bromo-3-chloro-6'-(trifluoromethyl)-6'H-spiro[chromeno[2,3-c]pyridine-5,3'-[1,4]oxazin]-5'-amine, '(5R,6'R)-7-bromo-3-chloro-6'-(trifluoromethyl)-6'H-spiro[chromeno[2,3-c]pyridine-5,3'-[1,4]oxazin]-5'-amine, '(5R,6'S)-7-bromo-3-chloro-6'-(trifluoromethyl)-6'H-spiro[chromeno[2,3-c]pyridine-5,3'-[1,4]oxazin]-5'-amine, '(5S,6'R)-7-bromo-3-chloro-6'-(trifluoromethyl)-6'H-spiro[chromeno[2,3-c]pyridine-5,3'-[1,4]oxazin]-5'-amine | 450.0 | A27 | 9 | 19.967 | 10 |
| 206 | (5S,6'R)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine, '(5R,6'S)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine | 481.2 | A27 | 9 | 0.3333 | 0.0687 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 207 | (5R,6'R)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine, '(5S,6'S)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine | 481.2 | A27 | 9 | 0.0115 | 0.0213 |
| 208 | (5S,6'R)-3-chloro-7-(2-fluoro-3-pyridinyl)-6'-phenyl-6'H-spiro[chromeno[2,3-c]pyridine-5,3'-[1,4]oxazin]-5'-amine, '(5R,6'S)-3-chloro-7-(2-fluoro-3-pyridinyl)-6'-phenyl-6'H-spiro[chromeno[2,3-c]pyridine-5,3'-[1,4]oxazin]-5'-amine, '(5R,6'R)-3-chloro-7-(2-fluoro-3-pyridinyl)-6'-phenyl-6'H-spiro[chromeno[2,3-c]pyridine-5,3'-[1,4]oxazin]-5'-amine, '(5S,6'S)-3-chloro-7-(2-fluoro-3-pyridinyl)-6'-phenyl-6'H-spiro[chromeno[2,3-c]pyridine-5,3'-[1,4]oxazin]-5'-amine | 473.2 | A27 | 9 | 0.0883 | 0.1344 |
| 56B | (5R,6'S)-3-chloro-6'-cyclohexyl-7-(2-fluoro-3-pyridinyl)-6'H-spiro[chromeno[2,3-c]pyridine-5,3'-[1,4]oxazin]-5'-amine, '(5S,6'R)-3-chloro-6'-cyclohexyl-7-(2-fluoro-3-pyridinyl)-6'H-spiro[chromeno[2,3-c]pyridine-5,3'-[1,4]oxazin]-5'-amine | 479.1 | A27 | 9 | 1.2766 | 0.4516 |
| 209 | (5S,6'R)-3-chloro-7-(2-fluoro-3-pyridinyl)-6'-(3-pyridinyl)-6'H-spiro[chromeno[2,3-c]pyridine-5,3'-[1,4]oxazin]-5'-amine, '(5R,6'S)-3-chloro-7-(2-fluoro-3-pyridinyl)-6'-(3-pyridinyl)-6'H-spiro[chromeno[2,3-c]pyridine-5,3'-[1,4]oxazin]-5'-amine, '(5S,6'S)-3-chloro-7-(2-fluoro-3-pyridinyl)-6'-(3-pyridinyl)-6'H-spiro[chromeno[2,3-c]pyridine-5,3'-[1,4]oxazin]-5'-amine | 474.0 | A27 | 9 | 0.1044 | 0.6644 |
| 210 | (5R,6'S)-3-chloro-7-(2-fluoro-3-pyridinyl)-6'-methyl-6'H-spiro[chromeno[2,3-c]pyridine-5,3'-[1,4]oxazin]-5'-amine, '(5R,6'R)-3-chloro-7-(2-fluoro-3-pyridinyl)-6'-methyl-6'H-spiro[chromeno[2,3-c]pyridine-5,3'-[1,4]oxazin]-5'-amine, '(5S,6'R)-3-chloro-7-(2-fluoro-3-pyridinyl)-6'-methyl-6'H-spiro[chromeno[2,3-c]pyridine-5,3'-[1,4]oxazin]-5'-amine, '(5S,6'S)-3-chloro-7-(2-fluoro-3-pyridinyl)-6'-methyl-6'H-spiro[chromeno[2,3-c]pyridine-5,3'-[1,4]oxazin]-5'-amine | 411.1 | A27 | 9 | 0.0908 | 0.2053 |
| 211 | (5S,6'R)-7-bromo-3-chloro-6'-(tetrahydro-2H-pyran-4-yl)-6'H-spiro[chromeno[2,3-c]pyridine-5,3'-[1,4]oxazin]-5'-amine, '(5R,6'S)-7-bromo-3-chloro-6'-(tetrahydro-2H-pyran-4-yl)-6'H-spiro[chromeno[2,3-c]pyridine-5,3'-[1,4]oxazin]-5'-amine, '(5R,6'R)-7-bromo-3-chloro-6'-(tetrahydro-2H-pyran-4-yl)-6'H-spiro[chromeno[2,3-c]pyridine-5,3'-[1,4]oxazin]-5'-amine, '(5S,6'S)-7-bromo-3-chloro-6'-(tetrahydro-2H-pyran-4-yl)-6'H-spiro[chromeno[2,3-c]pyridine-5,3'-[1,4]oxazin]-5'-amine | 466.0 | A27 | 9 | 2.55 | 2.4526 |
| 212 | (5S,6'R)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine, '(5R,6'S)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine, '(5R,6'R)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine, '(5S,6'S)-3-chloro-7-(2-fluoro-3-pyridinyl)-6'-(tetrahydro-2H-pyran-4-yl)-6'H-spiro[chromeno[2,3-c]pyridine-5,3'-[1,4]oxazin]-5'-amine | 481.2 | A27 | 9 | 0.0241 | 0.0327 |
| 213 | (5S)-7-(2-fluoro-3-pyridinyl)-3-(3-methyl-1-butyn-1-yl)-6'H-spiro[chromeno[2,3-b]pyridine-5,3'-[1,4]oxazin]-5'-amine | 429 | A23 | 11B | 0.0006 | 0.001 |
| 52 | (5S)-3-(3,3-dimethyl-1-butyn-1-yl)-7-(3-pyridinyl)-6'H-spiro[chromeno[2,3-b]pyridine-5,3'-[1,4]oxazin]-5'-amine | 425 | A23 | 11B | 0.0004 | 0.0003 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 53 | (5S)-3,7-bis(3,3-dimethyl-1-butyn-1-yl)-6'H-spiro[chromeno[2,3-b]pyridine-5,3'-[1,4]oxazin]-5'-amine | 428 | A24 | 11B | 0.0054 | 0.0251 |
| 214 | (5S)-3-(3,6-dihydro-2H-pyran-4-yl)-7-(3,3-dimethyl-1-butyn-1-yl)-6'H-spiro[chromeno[2,3-b]pyridine-5,3'-[1,4]oxazin]-5'-amine | 430 | A25 | 11B | 0.0032 | 0.0061 |
| 215 | (5S)-7-(2,5-difluorophenyl)-3-(tetrahydro-2H-pyran-4-yl)-6'H-spiro[chromeno[2,3-b]pyridine-5,3'-[1,4]oxazin]-5'-amine | 464 | A2 & A13 | 11B | 0.0037 | 0.0032 |
| 216 | (5S)-7-(2,5-difluorophenyl)-3-(3-pyridinyl)-6'H-spiro[chromeno[2,3-b]pyridine-5,3'-[1,4]oxazin]-5'-amine | 457 | A22 | 11B | 0.0023 | 0.0028 |
| 217 | (5S)-7-(2,5-difluorophenyl)-3-(4-pyridinyl)-6'H-spiro[chromeno[2,3-b]pyridine-5,3'-[1,4]oxazin]-5'-amine | 457 | A22 | 11B | 0.0036 | 0.0043 |
| 218 | (5S)-7-(2,5-difluorophenyl)-3-(3,6-dihydro-2H-pyran-4-yl)-6'H-spiro[chromeno[2,3-b]pyridine-5,3'-[1,4]oxazin]-5'-amine | 462 | A22 | 11B | 0.0013 | 0.0026 |
| 219 | (5S)-7-(3,3-dimethyl-1-butyn-1-yl)-3-(2-fluoro-4-pyridinyl)-6'H-spiro[chromeno[2,3-b]pyridine-5,3'-[1,4]oxazin]-5'-amine | 443 | A25 | 11B | 0.0059 | 0.0248 |
| 220 | (5S)-7-(2,5-difluorophenyl)-3-(2-fluoro-4-pyridinyl)-6'H-spiro[chromeno[2,3-b]pyridine-5,3'-[1,4]oxazin]-5'-amine | 475 | A22 | 11B | 0.002 | 0.0044 |
| 55 | (5S)-3-(2,2-dimethylpropoxy)-7-(2-fluoro-3-pyridinyl)-6'H-spiro[chromeno[2,3-b]pyridine-5,3'-[1,4]oxazin]-5'-amine | 449.2 | A26 | 11B | 0.0008 | 0.0004 |
| 221 | (5R)-7-(2-fluoro-3-pyridinyl)-1-methoxy-3-(3-pyridinyl)-5',6'-dihydrospiro[chromeno[2,3-c]pyridine-5,4'-[1,3]oxazin]-2'-amine, '(5S)-7-(2-fluoro-3-pyridinyl)-1-methoxy-3-(3-pyridinyl)-5',6'-dihydrospiro[chromeno[2,3-c]pyridine-5,4'-[1,3]oxazin]-2'-amine | 470 | A1 | Int 16 | 0.0498 | 0.1186 |
| 222 | 3-((5R)-2'-amino-1-fluoro-3-(2-fluoro-4-pyridinyl)-5',6'-dihydrospiro[chromeno[2,3-c]pyridine-5,4'-[1,3]oxazin]-7-yl)benzonitrile | 482 | A1 | Int 15B | 0.1704 | 1.5776 |
| 223 | 3-((5S)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)benzonitrile | 469.1 | A1 | Int 15B | 0.0008 | 0.0014 |
| 224 | 3-((5R)-2'-amino-3-(5,6-dihydro-2H-pyran-3-yl)-1-fluoro-5',6'-dihydrospiro[chromeno[2,3-c]pyridine-5,4'-[1,3]oxazin]-7-yl)benzonitrile | 469.1 | A1 | Int 15B | 0.5412 | 0.9816 |
| 225 | 3-((5S)-2'-amino-1-fluoro-3-(2-fluoro-4-pyridinyl)-5',6'-dihydrospiro[chromeno[2,3-c]pyridine-5,4'-[1,3]oxazin]-7-yl)benzonitrile | 482 | A1 | Int 15B | 0.0007 | 0.003 |
| 226 | (5S)-1-fluoro-3-(2-fluoro-4-pyridinyl)-7-(5-fluoro-3-pyridinyl)-5',6'-dihydrospiro[chromeno[2,3-c]pyridine-5,4'-[1,3]oxazin]-2'-amine | 476 | A1 | Int 15B | 0.0014 | 0.0016 |
| 227 | (5R)-1-fluoro-7-(2-fluoro-3-pyridinyl)-3-(3-pyridinyl)-5',6'-dihydrospiro[chromeno[2,3-c]pyridine-5,4'-[1,3]oxazin]-2'-amine | 458 | A1 | Int 15B | 0.4894 | 0.1006 |
| 228 | (5S)-3-(3,6-dihydro-2H-pyran-4-yl)-1-fluoro-7-(5-fluoro-3-pyridinyl)-5',6'-dihydrospiro[chromeno[2,3-c]pyridine-5,4'-[1,3]oxazin]-2'-amine | 463.1 | A1 | Int 15B | 0.0003 | 0.0007 |
| 229 | (5R)-3-(3,6-dihydro-2H-pyran-4-yl)-1-fluoro-7-(5-fluoro-3-pyridinyl)-5',6'-dihydrospiro[chromeno[2,3-c]pyridine-5,4'-[1,3]oxazin]-2'-amine | 463.1 | A1 | Int 15B | 0.1489 | 0.1268 |
| 230 | (5S)-1-fluoro-7-(2-fluoro-3-pyridinyl)-3-phenyl-5',6'-dihydrospiro[chromeno[2,3-c]pyridine-5,4'-[1,3]oxazin]-2'-amine | 457.1 | A1 | Int 15B | 0.002 | |
| 231 | (5S)-1-fluoro-3-(5-fluoro-3-pyridinyl)-7-(3-pyridinyl)-5',6'-dihydrospiro[chromeno[2,3-c]pyridine-5,4'-[1,3]oxazin]-2'-amine | 458 | A1 | Int 15B | 0.0008 | 0.0003 |
| 232 | (5R)-3-(5,6-dihydro-2H-pyran-3-yl)-1-fluoro-7-(5-fluoro-3-pyridinyl)-5',6'-dihydrospiro[chromeno[2,3-c]pyridine-5,4'-[1,3]oxazin]-2'-amine | 463.1 | A1 | Int 15A | 0.7925 | 0.1641 |
| 233 | 3-((5R)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)benzonitrile | 469.1 | A1 | Int 15A | 1.5787 | 0.1085 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 234 | 3-((5S)-2'-amino-3-(3,6-dihydro-2H-pyran-4-yl)-1-fluoro-5',6'-dihydrospiro[chromeno[2,3-c]pyridine-5,4'-[1,3]oxazin]-7-yl)benzonitrile | 469 | A1 | Int 15B | 0.0007 | 0.0007 |
| 235 | (5R)-1-fluoro-7-(2-fluoro-3-pyridinyl)-3-phenyl-5',6'-dihydrospiro[chromeno[2,3-c]pyridine-5,4'-[1,3]oxazin]-2'-amine | 457 | A1 | Int 15A | 0.1755 | |
| 236 | (5S)-3-(5,6-dihydro-2H-pyran-3-yl)-1-fluoro-7-(5-fluoro-3-pyridinyl)-5',6'-dihydrospiro[chromeno[2,3-c]pyridine-5,4'-[1,3]oxazin]-2'-amine | 463.1 | A1 | Int 15B | 0.0008 | 0.0005 |
| 237 | (5R)-3,7-di-3-pyridinyl-5',6'-dihydrospiro[chromeno[2,3-c]pyridine-5,4'-[1,3]oxazin]-2'-amine, '(5S)-3,7-di-3-pyridinyl-5',6'-dihydrospiro[chromeno[2,3-c]pyridine-5,4'-[1,3]oxazin]-2'-amine | 422 | A1 | Int 18A | 0.0616 | 0.0342 |
| 238 | (5R)-3-(5,6-dihydro-2H-pyran-3-yl)-1-fluoro-7-(2-fluoro-3-pyridinyl)-5',6'-dihydrospiro[chromeno[2,3-c]pyridine-5,4'-[1,3]oxazin]-2'-amine | 463.1 | A1 | Int 15A | 0.2931 | 0.1714 |
| 239 | (5S)-1-fluoro-3-(2-fluoro-4-pyridinyl)-7-(3-pyridinyl)-5',6'-dihydrospiro[chromeno[2,3-c]pyridine-5,4'-[1,3]oxazin]-2'-amine | 458 | A1 | Int 15B | 0.035 | 0.0161 |
| 240 | (5R)-1-fluoro-3-(2-fluoro-4-pyridinyl)-7-(3-pyridinyl)-5',6'-dihydrospiro[chromeno[2,3-c]pyridine-5,4'-[1,3]oxazin]-2'-amine | 458 | A1 | Int 15A | 0.1525 | 0.2065 |
| 241 | (5S)-1-fluoro-7-(2-fluoro-3-pyridinyl)-3-(3-pyridinyl)-5',6'-dihydrospiro[chromeno[2,3-c]pyridine-5,4'-[1,3]oxazin]-2'-amine | 458 | A1 | Int 15B | 0.0006 | 0.0009 |
| 242 | (5S)-3-chloro-1-fluoro-7-(2-fluoro-3-pyridinyl)-6'H-spiro[chromeno[2,3-c]pyridine-5,3'-[1,4]oxazin]-5'-amine | 415 | A1 | Int 17B | 0.0012 | 0.016 |
| 243 | (5S)-1-fluoro-7-(2-fluoro-3-pyridinyl)-3-(3-pyridinyl)-6'H-spiro[chromeno[2,3-c]pyridine-5,3'-[1,4]oxazin]-5'-amine | 458 | A1 | Int 17B | 0.0003 | 0.0005 |
| 244 | (5R)-3-chloro-1-fluoro-7-(2-fluoro-3-pyridinyl)-6'H-spiro[chromeno[2,3-c]pyridine-5,3'-[1,4]oxazin]-5'-amine | 415 | A1 | Int 17B | 0.4812 | 3.1458 |
| 245 | (5S)-1-fluoro-7-(2-fluoro-3-pyridinyl)-3-(5-fluoro-3-pyridinyl)-6'H-spiro[chromeno[2,3-c]pyridine-5,3'-[1,4]oxazin]-5'-amine | 476 | A1 | Int 17B | 0.0003 | 0.0003 |
| 246 | (5S)-3-(5,6-dihydro-2H-pyran-3-yl)-1-fluoro-7-(3-pyridinyl)-6'H-spiro[chromeno[2,3-c]pyridine-5,3'-[1,4]oxazin]-5'-amine | 445.1 | A1 | Int 17B | 0.0004 | 0.0001 |
| 247 | (5S)-3-(3,6-dihydro-2H-pyran-4-yl)-1-fluoro-7-(2-fluoro-3-pyridinyl)-6'H-spiro[chromeno[2,3-c]pyridine-5,3'-[1,4]oxazin]-5'-amine | 463.1 | A1 | Int 17B | 0.0006 | 0.0008 |
| 248 | (5S)-1-fluoro-7-(2-fluoro-3-pyridinyl)-3-(2-methyl-4-pyridinyl)-6'H-spiro[chromeno[2,3-c]pyridine-5,3'-[1,4]oxazin]-5'-amine | 472.1 | A1 | Int 17B | 0.0006 | 0.0007 |
| 249 | (5S)-3-(5,6-dihydro-2H-pyran-3-yl)-1-fluoro-7-(2-fluoro-3-pyridinyl)-6'H-spiro[chromeno[2,3-c]pyridine-5,3'-[1,4]oxazin]-5'-amine | 463.1 | A1 | Int 17B | 0.0004 | 0.0004 |
| 250 | (5S)-3-(2,2-dimethylpropoxy)-1-fluoro-7-(2-fluoro-3-pyridinyl)-6'H-spiro[chromeno[2,3-c]pyridine-5,3'-[1,4]oxazin]-5'-amine | 467 | | A30 | 0.0006 | 0.0028 |
| 50 | (5S)-7-(3,4-difluorophenyl)-3-methoxy-6'H-spiro[chromeno[2,3-c]pyridine-5,3'-[1,4]oxazin]-5'-amine | 410.4 | A21 | Int 21 | 0.0309 | 0.1065 |
| 49 | (5S)-3-(difluoromethoxy)-7-(2-fluoro-3-pyridinyl)-6'H-spiro[chromeno[2,3-c]pyridine-5,3'-[1,4]oxazin]-5'-amine | 429 | A20 | Int 21 | 0.0067 | 0.0115 |
| 251 | (5S)-7-bromo-3-(2,2-dimethylpropoxy)-6'H-spiro[chromeno[2,3-c]pyridine-5,3'-[1,4]oxazin]-5'-amine | 432.3 | A4 | Int 10B | 0.0196 | 0.0625 |
| 252 | (5S)-7-(3-fluorophenyl)-3-methoxy-6'H-spiro[chromeno[2,3-c]pyridine-5,3'-[1,4]oxazin]-5'-amine | 392.4 | A21 | Int 21 | 0.0106 | 0.05 |
| 253 | (5S)-7-(5-chloro-3-pyridinyl)-3-ethoxy-6'H-spiro[chromeno[2,3-c]pyridine-5,3'-[1,4]oxazin]-5'-amine | 423.3 | A4 | Int 10B | 0.001 | 0.0015 |
| 254 | (5S)-7-(5-fluoro-3-pyridinyl)-3-(2-methylpropoxy)-6'H-spiro[chromeno[2,3-c]pyridine-5,3'-[1,4]oxazin]-5'-amine | 435.3 | A4 | Int 10B | 0.0005 | 0.0009 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 255 | (5S)-7-(2-fluoro-3-pyridinyl)-3-(2-methylpropoxy)-6'H-spiro[chromeno[2,3-c]pyridine-5,3'-[1,4]oxazin]-5'-amine | 435.3 | A4 | Int 10B | 0.0005 | 0.001 |
| 256 | (5S)-3-ethoxy-7-(3-fluorophenyl)-6'H-spiro[chromeno[2,3-c]pyridine-5,3'-[1,4]oxazin]-5'-amine | 406.5 | A4 | Int 10B | 0.0043 | 0.0255 |
| 257 | (5S)-3-chloro-7-(5-fluoro-3-pyridinyl)-6'H-spiro[chromeno[2,3-c]pyridine-5,3'-[1,4]oxazin]-5'-amine | 397.2 | A1 | Int 10B | 0.0328 | 0.042 |
| 258 | (5S)-3-(1-methylethoxy)-7-(3-pyridinyl)-6'H-spiro[chromeno[2,3-c]pyridine-5,3'-[1,4]oxazin]-5'-amine | 403.5 | A4 | Int 1 | 0.0027 | 0.0042 |
| 259 | (5S)-7-(2-fluoro-3-pyridinyl)-3-(1-methylethoxy)-6'H-spiro[chromeno[2,3-c]pyridine-5,3'-[1,4]oxazin]-5'-amine | 421.5 | A4 | Int 1 | 0.0012 | 0.004 |
| 260 | (5S)-3-ethoxy-7-(2-fluoro-3-pyridinyl)-6'H-spiro[chromeno[2,3-c]pyridine-5,3'-[1,4]oxazin]-5'-amine | 407.4 | A4 | Int 10B | 0.0016 | 0.0021 |
| 261 | (5R)-3-(5,6-dihydro-2H-pyran-3-yl)-7-(2-fluoro-3-pyridinyl)-5'-methyl-5',6'-dihydrospiro[chromeno[2,3-c]pyridine-5,4'-[1,3]oxazin]-2'-amine | 459 | A1 | 19 | 0.8895 | |
| 262 | (4'S,5'S)-3-(5,6-dihydro-2H-pyran-3-yl)-7-(2-fluoropyridin-3-yl)-5'-methyl-5',6'-dihydrospiro[chromeno[2,3-c]pyridine-5,4'-[1,3]oxazin]-2'-amine | 459 | A1 | 19 | 0.0041 | |
| 263 | (4'R,5'R)-3-(5,6-dihydro-2H-pyran-3-yl)-7-(2-fluoropyridin-3-yl)-5'-methyl-5',6'-dihydrospiro[chromeno[2,3-c]pyridine-5,4'-[1,3]oxazin]-2'-amine | 459 | A1 | 19 | 0.4495 | |
| 59B | (5R)-3-(2,2-dimethylpropoxy)-1-fluoro-7-(2-fluoro-3-pyridinyl)-6'H-spiro[chromeno[2,3-c]pyridine-5,3'-[1,4]oxazin]-5'-amine | 467 | A30 | | 0.0849 | 0.3696 |
| 264 | (5S)-3-(5,6-dihydro-2H-pyran-3-yl)-7-(2-fluoro-3-pyridinyl)-5'-methyl-5',6'-dihydrospiro[chromeno[2,3-c]pyridine-5,4'-[1,3]oxazin]-2'-amine | 459 | A1 | 19 | 0.0037 | |
| 17A | (5S)-7-bromo-3-chloro-1-fluoro-6'H-spiro[chromeno[2,3-c]pyridine-5,3'-[1,4]oxazin]-5'-amine | 399.8 | Procedure Q | | 0.5711 | 1.5917 |
| 17B | (5R)-7-bromo-3-chloro-1-fluoro-6'H-spiro[chromeno[2,3-c]pyridine-5,3'-[1,4]oxazin]-5'-amine | 399.8 | Procedure Q | | 5.9968 | 10 |
| 58 | (5S)-1-fluoro-7-(2-fluoro-3-pyridinyl)-3-(4-morpholinyl)-6'H-spiro[chromeno[2,3-c]pyridine-5,3'-[1,4]oxazin]-5'-amine | 466 | A29 | | 0.0005 | 0.0007 |
| 265 | (3R)-2'-bromo-7'-methoxy-6H-spiro[1,4-oxazine-3,9'-xanthen]-5-amine | 375/377 | Procedure ZZ | | 7.1087 | 10 |
| 67 | (3S)-2'-(2,2-dimethylpropoxy)-7'-(2-fluoro-3-pyridinyl)-6H-spiro[1,4-oxazine-3,9'-xanthen]-5-amine | 448 | A38 | 30 | 0.0007 | 0.0131 |
| 266 | (5R)-7-(2-fluoro-3-pyridinyl)-3-(2-fluoro-4-pyridinyl)-5',6'-dihydrospiro[chromeno[2,3-b]pyridine-5,4'-[1,3]oxazin]-2'-amine, '(5S)-7-(2-fluoro-3-pyridinyl)-3-(2-fluoro-4-pyridinyl)-5',6'-dihydrospiro[chromeno[2,3-b]pyridine-5,4'-[1,3]oxazin]-2'-amine | 458 | A31 | 26B | 0.0199 | 0.017 |
| 267 | (5R)-7-(2-fluoro-3-pyridinyl)-3-(2-fluoro-4-pyridinyl)-5',6'-dihydrospiro[chromeno[2,3-b]pyridine-5,4'-[1,3]oxazin]-2'-amine | 458 | A31 | 26B | 6.6658 | 3.5589 |
| 268 | (5S)-3-(5,6-dihydro-2H-pyran-3-yl)-7-(2-fluoro-3-pyridinyl)-5',6'-dihydrospiro[chromeno[2,3-b]pyridine-5,4'-[1,3]oxazin]-2'-amine | 445 | A31 | 26B | 0.0116 | 0.0217 |
| 60 | (5S)-7-(2-fluoro-3-pyridinyl)-3-(2-fluoro-4-pyridinyl)-5',6'-dihydrospiro[chromeno[2,3-b]pyridine-5,4'-[1,3]oxazin]-2'-amine | 458 | A31 | 26B | 0.0122 | 0.011 |
| 67a | (3R)-2'-bromo-7'-(2,2-dimethylpropoxy)-6H-spiro[1,4-oxazine-3,9'-xanthen]-5-amine | 431/433 | A38 | 30 | 0.1017 | 0.5873 |
| 62 | (5S)-3-(2,2-dimethylpropoxy)-7-(2-fluoro-3-pyridinyl)-5',6'-dihydrospiro[chromeno[2,3-b]pyridine-5,4'-[1,3]oxazin]-2'-amine | 449 | A33 | 26B | 0.0025 | 0.0048 |
| 61 | (5S)-7-(2-fluoro-3-pyridinyl)-3-((3-methyl-3-oxetanyl)ethynyl)-5',6'-dihydrospiro[chromeno[2,3-b]pyridine-5,4'-[1,3]oxazin]-2'-amine | 457 | A32 | 26B | 0.0028 | 0.0024 |

TABLE I-continued

| Ex. No. | Compound Name | Observed Mass | Method | Intermediate used | BACE 1 FRET assay (uM) | HEK cell assay (uM) |
|---|---|---|---|---|---|---|
| 269 | (S)-3-(3,6-dihydro-2H-pyran-4-yl)-7-(2-fluoropyridin-3-yl)-5',6'-dihydrospiro[chromeno[2,3-b]pyridine-5,4'-[1,3]oxazin]-2'-amine | 445 | A31 | 26B | 0.012 | 0.0056 |
| 25 | (5R)-3-bromo-7-iodo-5',6'-dihydrospiro[chromeno[2,3-b]pyridine-5,4'-[1,3]oxazin]-2'-amine, '(5S)-3-bromo-7-iodo-5',6'-dihydrospiro[chromeno[2,3-b]pyridine-5,4'-[1,3]oxazin]-2'-amine | 472/474 | Procedure Y | | 15.959 | 10 |
| 270 | (5S)-3-(3,3-dimethyl-1-butyn-1-yl)-7-(2-fluoro-3-pyridinyl)-5',6'-dihydrospiro[chromeno[2,3-b]pyridine-5,4'-[1,3]oxazin]-2'-amine | 443 | A32 | 26B | 0.0031 | 0.0049 |
| 271 | (5R)-3-(5,6-dihydro-2H-pyran-3-yl)-7-(2-fluoro-3-pyridinyl)-5',6'-dihydrospiro[chromeno[2,3-b]pyridine-5,4'-[1,3]thiazin]-2'-amine | 461 | A22 | 24 | 1.040 | 2.540 |
| 272 | (5S)-3-(5,6-dihydro-2H-pyran-3-yl)-7-(2-fluoro-3-pyridinyl)-5',6'-dihydrospiro[chromeno[2,3-b]pyridine-5,4'-[1,3]thiazin]-2'-amine | 461 | A22 | 24 | 0.004 | 0.011 |

Various of the compounds in Table I above were prepared and characterized as follows:

Example 107

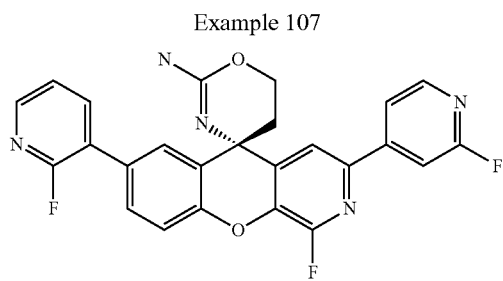

Synthesis (S)-1-fluoro-7-(2-fluoropyridin-3-yl)-3-(2-fluoropyridin-4-yl)-5',6'-dihydrospiro[chromeno[2,3-c]pyridine-5,4'-[1,3]oxazin]-2'-amine The title compound was synthesized by steps analogous to those described in method A1 above, but using intermediate 15B, 2-fluoropyridin-3-ylboronic acid and 2-fluoropyridin-4-ylboronic acid. MS m/z=476.0 [M+H]$^+$. Calculated for $C_{25}H_{16}F_3N_5O_3$: 475.13

$^1$H NMR (300 MHz, MeOH) δ ppm 2.33-2.49 (m, 2 H) 4.51-4.60 (m, 2 H) 7.33-7.40 (m, 1 H) 7.49 (d, J=9.21 Hz, 1 H) 7.68-7.74 (m, 3 H) 7.94 (td, J=3.22, 1.50 Hz, 1 H) 8.05 (ddd, J=10.01, 7.53, 2.00 Hz, 1 H) 8.13-8.16 (m, 1 H) 8.15 (br. s, 1 H) 8.23 (d, J=5.41 Hz, 1 H).

Example 110

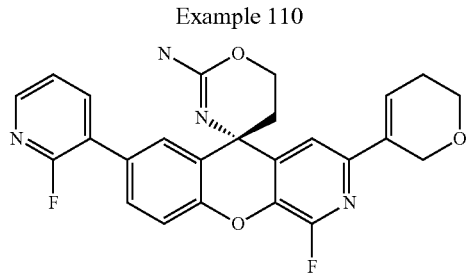

Synthesis of (S)-3-(5,6-dihydro-2H-pyran-3-yl)-1-fluoro-7-(2-fluoropyridin-3-yl)-5',6'-dihydrospiro[chromeno[2,3-c]pyridine-5,4'-[1,3]oxazin]-2'-amine The title compound was synthesized by steps analogous to those described in method A1 above, but using intermediate 15B, 2-fluoropyridin-3-ylboronic acid and 2-(5,6-dihydro-2H-pyran-3-yl)-4,4,5,5-tetramethyl-1,3,2-dioxaborolane.

MS m/z=463.0 [M+H]$^+$. Calculated for $C_{25}H_{20}F_2N_4O_3$: 462.15

$^1$H NMR (300 MHz, CHLOROFORM-d) δ ppm 1.80-2.02 (m, 2 H) 2.26-2.43 (m, 2 H) 3.84 (t, J=5.55 Hz, 2 H) 4.03-4.24 (m, 2 H) 4.42-4.68 (m, 3 H) 6.66-6.76 (m, 1 H) 7.19-7.31 (m, 1 H) 7.36 (d, J=8.33 Hz, 1 H) 7.48-7.59 (m, 2 H) 7.86 (ddd, J=9.79, 7.60, 1.90 Hz, 1 H) 8.14-8.23 (m, 1 H).

Example 111

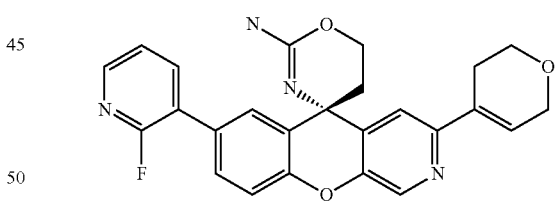

Synthesis of (S)-3-(3,6-dihydro-2H-pyran-4-yl)-7-(2-fluoro dihydrospiro[chromeno[2,3-c]pyridine-5,4'-[1,3]oxazin]-2'-amine The title compound was synthesized by steps analogous to those described in method A1 above, but using intermediate 18B, 2-fluoropyridin-3-ylboronic acid and 2-(3,6-dihydro-2H-pyran-4-yl)-4,4,5,5-tetramethyl-1,3,2-dioxaborolane.

MS m/z=445.1 [M+H]$^+$. Calculated for $C_{25}H_{21}FN_4O_3$: 444.16

$^1$H NMR (400 MHz, CHLOROFORM-d) δ ppm 1.86-1.94 (m, 2 H) 3.92-3.99 (m, 2 H) 4.08-4.19 (m, 2 H) 4.23-4.30 (m, 2 H) 4.35-4.41 (m, 2 H) 6.59-6.65 (m, 1 H) 7.26 (s, 2 H) 7.43

(s, 1 H) 7.49-7.54 (m, 1 H) 7.54-7.58 (m, 1 H) 7.86 (ddd, J=10.00, 7.40, 2.0 Hz, 1 H) 8.20 (d, J=4.69 Hz, 1 H) 8.50 (s, 1 H).

Example 239

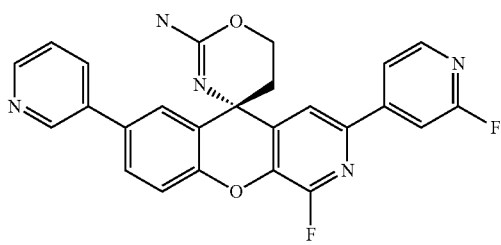 [SMILES: NC1=N[C@@]2(CCO1)c1cc(-c3cccnc3)ccc1Oc1c2cc(-c2ccnc(F)c2)nc1F]

Synthesis of (S)-1-fluoro-3-(2-fluoropyridin-4-yl)-7-(pyridin-3-yl)-5',6'-dihydrospiro[chromeno[2,3-c]pyridine-5,4'-[1,3]oxazin]-2'-amine The title compound was synthesized by steps analogous to those described in method A1 above, but using intermediate 15B, 3-pyridylboronic acid and 2-fluoropyridine-4-boronic acid. MS m/z=458.0 [M+H]$^+$. Calculated for $C_{25}H_{17}F_2N_5O_2$: 457.14

$^1$H NMR (300 MHz, MeOH) δ ppm 2.01-2.09 (m, 2 H) 4.23 (m, 2 H) 7.50 (d, J=1.00 Hz, 1 H) 7.53-7.60 (m, 1 H) 7.67-7.79 (m, 3 H) 7.94-7.98 (m, 1 H) 8.00 (s, 1 H) 8.11-8.17 (m, 1 H) 8.30-8.35 (m, 1 H) 8.53-8.59 (m, 1 H) 8.82-8.86 (m, 1 H).

Example 226

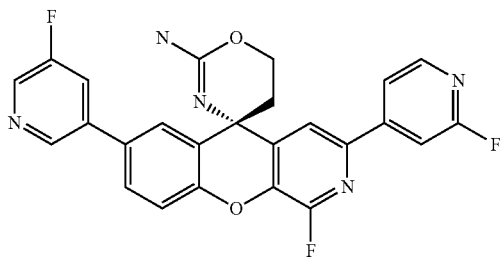 [SMILES: NC1=N[C@@]2(CCO1)c1cc(-c3cncc(F)c3)ccc1Oc1c2cc(-c2ccnc(F)c2)nc1F]

Synthesis of (S)-1-fluoro-7-(5-fluoropyridin-3-yl)-3-(2-fluoropyridin-4-yl)-5',6'-dihydrospiro[chromeno[2,3-c]pyridine-5,4'-[1,3]oxazin]-2'-amine The title compound was synthesized by steps analogous to those described in method A1 above, but using intermediate 15B, 5-fluoropyridin-3-ylboronic acid and 2-fluoropyridine-4-boronic acid.

MS m/z=476.0 [M+H]$^+$. Calculated for $C_{25}H_{16}F_3N_5O_2$: 475.13

$^1$H NMR (300 MHz, CHLOROFORM-d) δ ppm 1.93-2.02 (m, 2 H) 4.12-4.21 (m, 2 H) 7.41-7.47 (m, 1 H) 7.53 (br. s, 1 H) 7.57 (m, J=2.30 Hz, 3 H) 7.74-7.81 (m, 2 H) 8.29-8.34 (m, 1 H) 8.46-8.50 (m, 1 H) 8.66-8.71 (m, 1 H).

Example 241

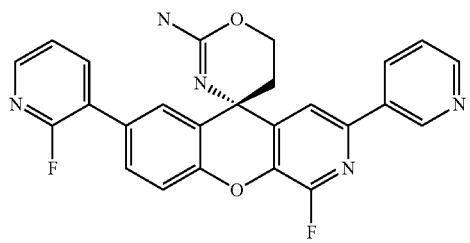 [SMILES: NC1=N[C@@]2(CCO1)c1cc(-c3cccnc3F)ccc1Oc1c2cc(-c2cccnc2)nc1F]

Synthesis of (S)-1-fluoro-7-(2-fluoropyridin-3-yl)-3-(pyridin-3-yl)-5',6'-dihydrospiro[chromeno[2,3-c]pyridine-5,4'-[1,3]oxazin]-2'-amine The title compound was synthesized by steps analogous to those described in method A1 above, but using intermediate 15B, 2-fluoropyridin-3-ylboronic acid and 3-pyridylboronic acid. MS m/z=458.0 [M+H]$^+$. Calculated for $C_{25}H_{17}F_2N_5O_2$: 457.14

$^1$H NMR (300 MHz, CHLOROFORM-d) δ ppm 1.90-2.07 (m, 2 H) 4.10-4.27 (m, 2 H) 7.24-7.33 (m, 1 H) 7.35-7.45 (m, 2 H) 7.51-7.63 (m, 2 H) 7.74 (s, 1 H) 7.87 (ddd, J=9.76, 7.64, 1.90 Hz, 1 H) 8.21 (d, J=4.68 Hz, 1 H) 8.29 (dt, J=8.04, 1.90 Hz, 1 H) 8.63 (dd, J=4.75, 1.39 Hz, 1 H) 9.20 (d, J=1.90 Hz, 1 H).

Example 249

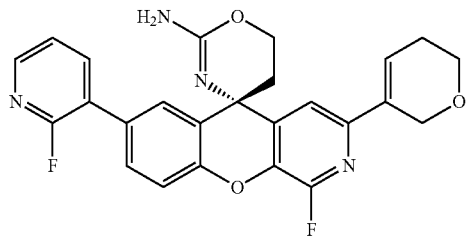

Synthesis of (S)-3-(5,6-dihydro-2H-pyran-3-yl)-1-fluoro-7-(2-fluoropyridin-3-yl)-2',6'-dihydrospiro[chromeno[2,3-c]pyridine-5,3'-[1,4]oxazin]-5'-amine The titled compound was synthesized by steps analogous to those described in method A1 above, but using (Intermediate 17B), 2-fluoropyridin-3-ylboronic acid and 2-(5,6-dihydro-2H-pyran-3-yl)-4,4,5,5-tetramethyl-1,3,2-dioxaborolane.

MS m/z=463.1 [M+H]$^+$. Calculated for $C_{25}H_{20}F_2N_4O_3$: 462.15.

$^1$H NMR (300 MHz, MeOH) δ ppm 2.31-2.42 (m, 2 H) 3.57-3.69 (m, 2 H) 3.80-3.86 (m, 2 H) 4.33-4.47 (m, 2 H)

4.53-4.58 (m, 2 H) 6.69-6.76 (m, 1 H) 7.27 (s, 1 H) 7.35-7.46 (m, 2 H) 7.57-7.60 (m, 1 H) 7.61-7.66 (m, 1 H) 8.03-8.11 (m, 1 H) 8.17-8.21 (m, 1 H)

(d, J=8.61 Hz, 1 H) 7.55 (s, 1 H) 7.62 (d, J=9.19 Hz, 1 H) 7.91 (t, J=8.02 Hz, 1 H) 8.02 (br. s., 1 H) 8.13-8.23 (m, 1 H) 11.22 (br. s., 1 H) 12.31 (br. s., 1 H)

Example 248

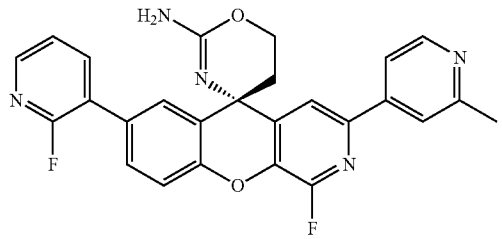 [SMILES: Cc1cc(-c2cc3c(c(F)n2)Oc2ccc(-c4cccnc4F)cc2[C@@]32CCOC(N)=N2)ccn1]

Synthesis of (S)-1-fluoro-7-(2-fluoropyridin-3-yl)-3-(2-methylpyridin-4-yl)-2',6'-dihydrospiro[chromeno[2,3-c]pyridine-5,3'-[1,4]oxazin]-5'-amine The titled compound was synthesized by steps analogous to those described in method A1 above, but using (Intermediate 17B), 2-fluoropyridin-3-ylboronic acid and 2-methylpyridine-4-boronic acid pinacol ester.

MS m/z=472.1 [M+H]$^+$. Calculated for $C_{25}H_{20}F_2N_4O_3$: 471.15.

$^1$H NMR (300 MHz, MeOH) δ ppm 2.63 (s, 3 H) 3.65-3.79 (m, 2 H) 4.38-4.58 (m, 3 H) 7.41-7.47 (m, 3 H) 7.62-7.70 (m, 3 H) 7.81-7.87 (m, 2 H) 7.90-7.94 (m, 1 H) 8.05-8.14 (m, 2 H) 8.18-8.23 (m, 1 H) 8.49-8.53 (m, 1 H)

Example 129

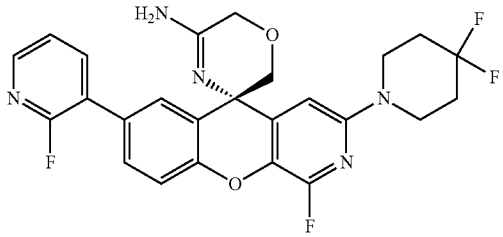 [SMILES: NC1=N[C@@]2(COC1)c1cc(-c3cccnc3F)ccc1Oc1c2cc(N2CCC(F)(F)CC2)nc1F]

Synthesis of (S)-3-(4,4-difluoropiperidin-1-yl)-1-fluoro-7-(2-fluoropyridin-3-yl)-2',6'-dihydrospiro[chromeno[2,3-c]pyridine-5,3'-[1,4]oxazin]-5'-amine 2,2,2-trifluoroacetate The titled compound was synthesized by steps analogous to those described in method 29 above, but using 4,4-difluoropiperidine in step 1.

MS m/z=500.0 [M+H]$^+$. Calculated for $C_{25}H_{21}F_4N_5O_2 \cdot C_2HF_3O_2$: 613.48 (TFA salt).

$^1$H NMR (400 MHz, CHLOROFORM-d) δ ppm 1.95-2.12 (m, 4 H) 3.59-3.68 (m, 2 H) 3.68-3.76 (m, 2 H) 3.88 (s, 2 H) 4.80 (m, 2 H) 6.47 (s, 1 H) 7.31 (dd, J=7.43, 4.50 Hz, 1 H) 7.41

Example 155

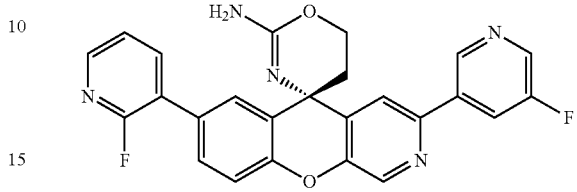

Synthesis of (S)-7-(2-fluoropyridin-3-yl)-3-(5-fluoro dihydrospiro[chromeno[2,3-c]pyridine-5,4'-[1,3] oxazin]-2'-amine The titled compound was synthesized by steps analogous to those described in method A1 above, but using intermediate 18B, 2-fluoropyridin-3-ylboronic acid and 5-fluoropyridin-3-ylboronic acid. MS m/z=458.0 [M+H]$^+$. Calculated for $C_{25}H_{17}F_2N_5O_2$: 457.43

$^1$H NMR (300 MHz, CHLOROFORM-d) δ ppm 1.90-2.00 (m, 2 H) 4.12-4.21 (m, 2 H) 7.29 (ddd, J=7.23, 5.04, 1.75 Hz, 1 H) 7.35 (d, J=8.33 Hz, 1 H) 7.49-7.63 (m, 2 H) 7.81-7.95 (m, 2 H) 8.05-8.13 (m, 1 H) 8.21 (dt, J=4.75, 1.50 Hz, 1 H) 8.49 (d, J=2.63 Hz, 1 H) 8.64 (s, 1 H) 9.03 (t, J=1.61 Hz, 1 H)

Example 153

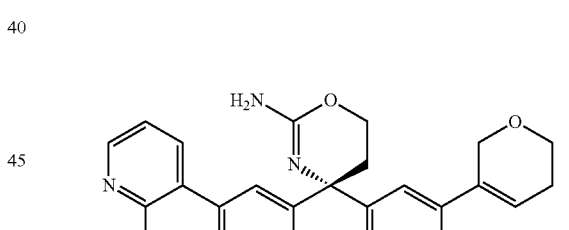

Synthesis of (S)-3-(5,6-dihydro-2H-pyran-3-yl)-7-(2-fluoropyridin-3-yl)-5',6'-dihydrospiro[chromeno[2,3-c]pyridine-5,4'-[1,3]oxazin]-2'-amine The titled compound was synthesized by steps analogous to those described in method A1 above, but using intermediate 18B, 2-fluoropyridin-3-ylboronic acid and 2-(5,6-dihydro-2H-pyran-3-yl)-4,4,5,5-tetramethyl-1,3,2-dioxaborolane.

MS m/z=445.0 [M+H]$^+$. Calculated for $C_{25}H_{21}FN_4O_3$: 444.46

$^1$H NMR (300 MHz, CHLOROFORM-d) δ ppm 2.33-2.42 (m, 2 H) 3.86 (s, 2 H) 4.10-4.17 (m, 2 H) 4.28-4.51 (m, 2 H) 4.55-4.76 (m, 2 H) 6.62-6.68 (m, 1 H) 7.26 (s, 2 H) 7.42 (s, 1

H) 7.48-7.54 (m, 1 H) 7.54-7.58 (m, 1 H) 7.81-7.91 (m, 1 H) 8.17-8.22 (m, 1 H) 8.45 (s, 1 H)

Example 154

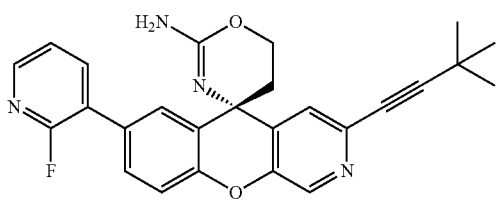 [SMILES: CC(C)(C)C#Cc1cc2c(cn1)Oc1ccc(-c3cccnc3F)cc1[C@@]21CCOC(N)=N1]

Synthesis of (S)-3-(3,3-dimethylbut-1-ynyl)-7-(2-fluoropyridin-3-yl)-5',6'-dihydrospiro[chromeno[2,3-c]pyridine-5,4'-[1,3]oxazin]-2'-amine The titled compound was synthesized by steps analogous to those described in method A2 above, but using intermediate 18B, 2-fluoropyridin-3-ylboronic acid and 3,3-dimethyl-but-1-yne. MS m/z=443.0 [M+H]$^+$. Calculated for $C_{26}H_{23}FN_4O_2$: 442.48

$^1$H NMR (300 MHz, CHLOROFORM-d) δ ppm 1.36 (s, 9 H) 1.84-1.93 (m, 2 H) 4.09-4.20 (m, 2 H) 7.27-7.31 (m, 2 H) 7.41-7.56 (m, 3 H) 7.80-7.95 (m, 1 H) 8.15-8.26 (m, 1 H) 8.40-8.51 (m, 1 H)

Example 149

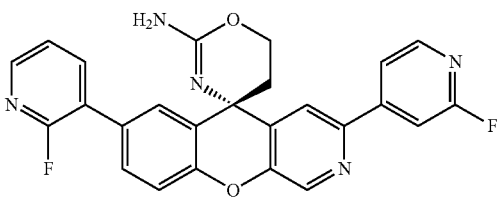 [SMILES: NC1=N[C@@]2(CCO1)c1cc(-c3cccnc3F)ccc1Oc1cnc(-c3ccnc(F)c3)cc12]

Synthesis of (S)-7-(2-fluoropyridin-3-yl)-3-(2-fluoropyridin-4-yl)-5',6'-dihydrospiro[chromeno[2,3-c]pyridine-5,4'-[1,3]oxazin]-2'-amine The titled compound was synthesized by steps analogous to those described in method A1 above, but using intermediate 18B, 2-fluoropyridin-3-ylboronic acid and 2-fluoropyridin-4-ylboronic acid. MS m/z=458.0 [M+H]$^+$. Calculated for $C_{25}H_{17}F_2N_5O_2$: 457.43

$^1$H NMR (300 MHz, CHLOROFORM-d) δ ppm 1.95 (d, J=6.14 Hz, 2 H) 4.17 (d, J=4.53 Hz, 2 H) 4.29-4.49 (m, 2 H) 7.30 (s, 1 H) 7.35 (d, J=8.33 Hz, 1 H) 7.51-7.60 (m, 3 H) 7.80 (d, J=5.12 Hz, 1 H) 7.88 (s, 2 H) 8.22 (d, J=4.38 Hz, 1 H) 8.31 (d, J=5.41 Hz, 1 H) 8.66 (s, 1 H)

Example 145

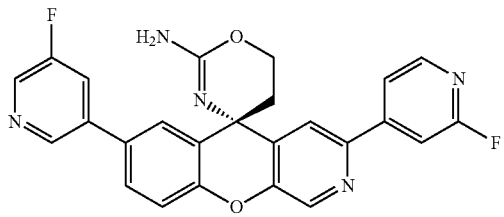 [SMILES: NC1=N[C@@]2(CCO1)c1cc(-c3cncc(F)c3)ccc1Oc1cnc(-c3ccnc(F)c3)cc12]

Synthesis of (S)-7-(5-fluoropyridin-3-yl)-3-(2-fluoropyridin-4-yl)-5',6'-dihydrospiro[chromeno[2,3-c]pyridine-5,4'-[1,3]oxazin]-2'-amine The titled compound was synthesized by steps analogous to those described in method A1 above, but using intermediate 18B, 5-fluoropyridin-3-ylboronic acid and 2-fluoropyridin-4-ylboronic acid. MS m/z=458.0 [M+H]$^+$. Calculated for $C_{25}H_{17}F_2N_5O_2$: 457.43

$^1$H NMR (300 MHz, CHLOROFORM-d) δ ppm 1.95 (q, J=5.07 Hz, 2 H) 4.12-4.20 (m, 2 H) 7.35-7.42 (m, 1 H) 7.54-7.67 (m, 4 H) 7.81 (dt, J=5.26, 1.61 Hz, 1 H) 7.87 (s, 1 H) 8.31 (d, J=5.26 Hz, 1 H) 8.46 (d, J=2.63 Hz, 1 H) 8.63-8.70 (m, 2 H)

Example 146

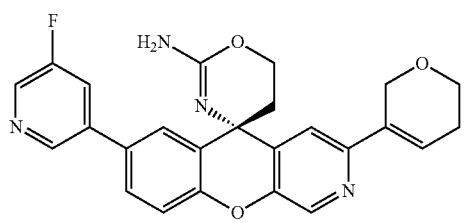 [SMILES: NC1=N[C@@]2(CCO1)c1cc(-c3cncc(F)c3)ccc1Oc1cnc(C3=CCCOC3)cc12]

Synthesis of (S)-3-(5,6-dihydro-2H-pyran-3-yl)-7-(5-fluoropyridin-3-yl)-5',6'-dihydrospiro[chromeno[2,3-c]pyridine-5,4'-[1,3]oxazin]-2'-amine The titled compound was synthesized by steps analogous to those described in method A1 above, but using intermediate 18B, 5-fluoropyridin-3-ylboronic acid and 2-(5,6-dihydro-2H-pyran-3-yl)-4,4,5,5-tetramethyl-1,3,2-dioxaborolane.

MS m/z=445.1 [M+H]$^+$. Calculated for $C_{25}H_{17}F_2N_5O_2$: 444.56

$^1$H NMR (300 MHz, MeOH) δ ppm 1.87-1.99 (m, 2 H) 2.28-2.48 (m, 2 H) 3.85 (s, 2 H) 4.13-4.21 (m, 2 H) 4.63 (d, J=1.90 Hz, 2 H) 6.50-6.79 (m, 1 H) 7.40 (s, 1 H) 7.52 (s, 1 H 7.68 (d, J=2.63 Hz, 2 H) 7.85-7.97 (m, 1 H) 8.41 (s, 1 H) 8.45 (d, J=2.63 Hz, 1 H) 8.69 (s, 1 H)

Example 86

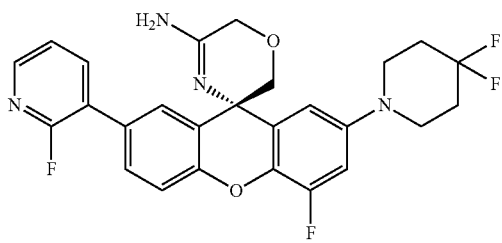 [SMILES: NC1=N[C@@]2(COC1)c1cc(-c3cccnc3F)ccc1Oc1c(F)cc(N3CCC(F)(F)CC3)cc12]

Synthesis of (S)-2'-(4,4-difluoropiperidin-1-yl)-4'-fluoro-7'-(2-fluoropyridin-3-yl)-2,6-dihydrospiro[[1,4]oxazine-3,9'-xanthen]-5-amine The title compound was synthesized by steps analogous to those described in method A6 above, but using intermediate 13A, 2-fluoropyridin-3-ylboronic acid and 4,4-difluoropiperidine. MS m/z=499.0 [M+H]$^+$. Calculated for $C_{26}H_{22}F_4N_4O_2$: 498.17

$^1$H NMR (400 MHz, DMSO-d$_6$) δ ppm 2.01-2.15 (m, 4 H), 3.40 (d, J=11.2 Hz, 1 H), 3.43 (d, J=11.2 Hz, 1 H), 4.19 (s, 2 H), 6.08 (br. s., 1 H), 6.65 (dd, J=2.7, 1.2 Hz, 1 H), 7.31 (d, J=8.4 Hz, 1 H), 7.43-7.51 (m, 2 H), 7.56 (ddd, J=8.4, 2.2, 1.6 Hz, 1 H), 8.06 (ddd, J=10.3, 7.5, 1.9 Hz, 1 H), 8.23 (ddd, J=4.8, 1.5, 1.4 Hz, 1 H)

Example 178

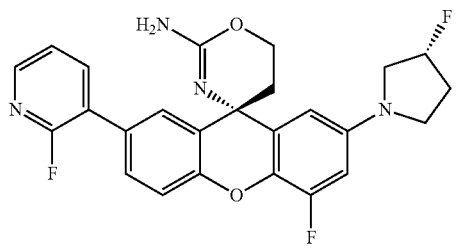 [SMILES: NC1=N[C@@]2(CCO1)c1cc(-c3cccnc3F)ccc1Oc1c(F)cc(N3CC[C@@H](F)C3)cc12]

Synthesis of (S)-4'-fluoro-7'-(2-fluoropyridin-3-yl)-2'-((R)-3-fluoropyrrolidin-1-yl)-2,6-dihydrospiro[[1,4]oxazine-3,9'-xanthen]-5-amine The title compound was synthesized by steps analogous to those described in method A6 above, but using intermediate 20B, 2-fluoropyridin-3-ylboronic acid and (R)-3-fluoropyrrolidine. MS m/z=467.0 [M+H]$^+$. Calculated for $C_{25}H_{21}F_3N_4O_2$: 466.16

$^1$H NMR (400 MHz, DMSO-d$_6$) δ ppm 2.10-2.31 (m, 2 H), 3.23-3.62 (m, 4 H), 4.18 (m, 2 H), 5.45 (dm, J=54.9 Hz, 1 H, HCF), 5.98-6.20 (m, 2 H), 6.23-6.27 (m, 2 H), 6.53 (dd, J=13.4, 2.8 Hz, 1 H), 7.30 (d, J=8.4 Hz, 2 H), 7.46 (s, 2 H), 7.54 (ddd, J=8.4, 2.2, 1.5 Hz, 1 H), 8.07 (ddd, J=10.3, 7.5, 2.0 Hz, 1 H), 8.23 (ddd, J=4.8, 1.7, 1.4 Hz, 1 H)

Example 84

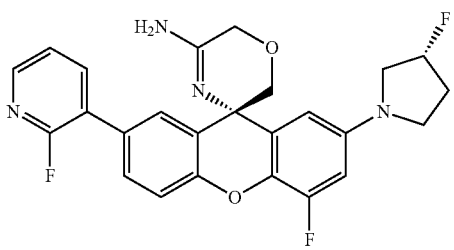 [SMILES: NC1=N[C@@]2(COC1)c1cc(-c3cccnc3F)ccc1Oc1c(F)cc(N3CC[C@@H](F)C3)cc12]

Synthesis of (S)-4'-fluoro-2'-(2-fluoro-2-methylpropoxy)-7'-(2-fluoropyridin-3-yl)-5,6-dihydrospiro[[1,3]oxazine-4,9'-xanthen]-2-amine The title compound was synthesized by steps analogous to those described in method A6 above, but using intermediate 20B, 2-fluoropyridin-3-ylboronic acid and (R)-3-fluoropyrrolidine. MS m/z=467.0 [M+H]$^+$. Calculated for $C_{25}H_{21}F_3N_4O_2$: 466.16

$^1$H NMR (400 MHz, DMSO-d$_6$) δ ppm 1.75 (m, J=3.6 Hz, 2 H), 2.08-2.33 (m, 2 H), 3.29-3.62 (m, 4 H), 3.89-4.09 (m, 2 H), 5.44 (dm, J=55.0 Hz, 1 H, HCF), 5.74 (br. s, 2 H), 6.31 (m, 1 H), 6.50 (dd, J=13.4, 2.8 Hz, 1 H), 7.32 (d, J=9.0 Hz, 1 H), 7.47 (ddd, J=7.2, 4.8, 1.9 Hz, 1 H), 7.50-7.56 (m, 2 H), 8.07 (ddd, J=10.3, 7.5, 1.9 Hz, 1 H), 8.22 (ddd, J=4.8, 1.6, 1.4 Hz, 1 H)

Example 163

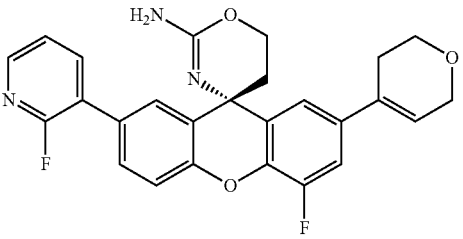 [SMILES: NC1=N[C@@]2(CCO1)c1cc(-c3cccnc3F)ccc1Oc1c(F)cc(C3=CCOCC3)cc12]

Synthesis of (S)-2'-(3,6-dihydro-2H-pyran-4-yl)-4'-fluoro-7'-(2-fluoropyridin-3-yl)-5,6-dihydrospiro[[1,3]oxazine-4,9'-xanthen]-2-amine The title compound was synthesized by steps analogous to those described in method A7 above, but using intermediate 20B, 2-fluoropyridin-3-ylboronic acid and 2-(3,6-dihydro-2H-pyran-4-yl)-4,4,5,5-tetramethyl-1,3,2-dioxaborolane.

MS m/z=462.0 [M+H]$^+$. Calculated for $C_{26}H_{21}F_2N_3O_3$: 461.16

$^1$H NMR (400 MHz, DMSO-d$_6$) δ ppm 1.73-1.81 (m, 2 H), 2.39-2.47 (m, 2 H), 3.81-3.86 (m, 2 H), 3.94-4.02 (m, 2 H), 4.24 (d, J=2.8 Hz, 2 H), 5.82 (s, 2 H), 6.23-6.27 (m, 1 H), 7.21-7.23 (m, 1 H), 7.40 (m, 2 H), 7.49 (ddd, J=7.4, 4.9, 2.0

Hz, 1 H), 7.55 (m, 2 H), 8.10 (ddd, J=10.4, 7.4, 2.0 Hz, 1 H), 8.25 (ddd, J=4.8, 1.9, 1.4 Hz, 1 H).

Example 173

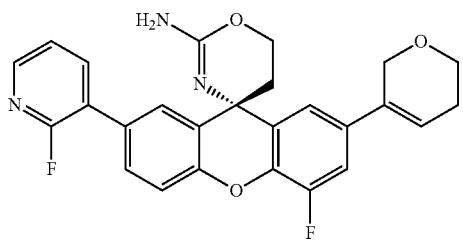 [SMILES: NC1=N[C@@]2(CCO1)c1cc(-c3cccnc3F)ccc1Oc1c(F)cc(C3=CCCOC3)cc12]

Synthesis of (S)-2'-(5,6-dihydro-2H-pyran-3-yl)-4'-fluoro-7'-(2-fluoropyridin-3-yl)-5,6-dihydrospiro[[1,3]oxazine-4,9'-xanthen]-2-amine The title compound was synthesized by steps analogous to those described in method A7 above, but using intermediate 20B, 2-fluoropyridin-3-ylboronic acid and 2-(5,6-dihydro-2H-pyran-3-yl)-4,4,5,5-tetramethyl-1,3,2-dioxaborolane.

MS m/z=462.0 [M+H]$^+$. Calculated for $C_{26}H_{21}F_2N_3O_3$: 461.16

$^1$H NMR (400 MHz, DMSO-d$_6$) δ ppm 1.77 (m, 2 H), 2.20-2.33 (m, 2 H), 3.74 (m, 2 H), 3.91-4.05 (m, 2 H), 4.33-4.48 (m, 2 H), 5.83 (br. s., 2 H), 6.27 (s, 1 H), 7.11-7.14 (m, 1 H), 7.33 (dd, J=12.2, 2.1 Hz, 1 H), 7.40 (d, J=8.3 Hz, 1 H), 7.49 (ddd, J=7.4, 4.9, 1.9 Hz, 1 H), 7.53-7.56 (m, 1 H), 7.58 (ddd, J=8.4, 2.2, 1.4 Hz, 1 H), 8.09 (ddd, J=10.3, 7.5, 2.0 Hz, 1 H), 8.25 (ddd, J=4.8, 1.9, 1.5 Hz, 1 H)

Example 182

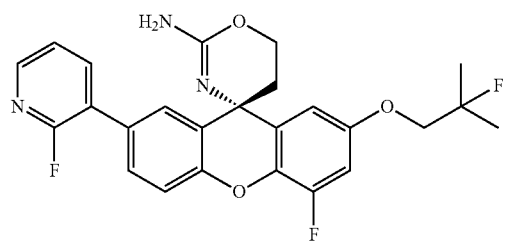

Synthesis of (S)-4'-fluoro-2'-(2-fluoro-2-methylpropoxy)-7'-(2-fluoropyridin-3-yl)-5,6-dihydrospiro[[1,3]oxazine-4,9'-xanthen]-2-amine The title compound was synthesized by steps analogous to those described in method A8 above, but using intermediate 20B, 2-fluoropyridin-3-ylboronic acid and 2-fluoro-2-methylpropyl trifluoromethanesulfonate.

MS m/z=470.0 [M+H]$^+$. Calculated for $C_{25}H_{22}F_3N_3O_3$: 469.16

$^1$H NMR (400 MHz, DMSO-d$_6$) δ ppm 1.40 (s, 3 H), 1.46 (s, 3 H), 1.77 (dd, J=6.4, 4.8 Hz, 2 H), 3.94-4.10 (m, 4 H), 5.82 (s, 2 H), 6.74 (dd, J=2.9, 1.5 Hz, 1 H), 7.02 (dd, J=12.3, 2.9 Hz, 1 H), 7.37 (d, J=8.4 Hz, 1 H), 7.49 (ddd, J=7.4, 4.9, 1.9 Hz, 1 H), 7.51-7.54 (m, 1 H), 7.56 (ddd, J=8.3, 2.2, 1.4 Hz, 1 H), 8.09 (ddd, J=10.4, 7.4, 2.0 Hz, 1 H), 8.24 (ddd, J=4.8, 1.7, 1.4 Hz, 1 H)

Example 168

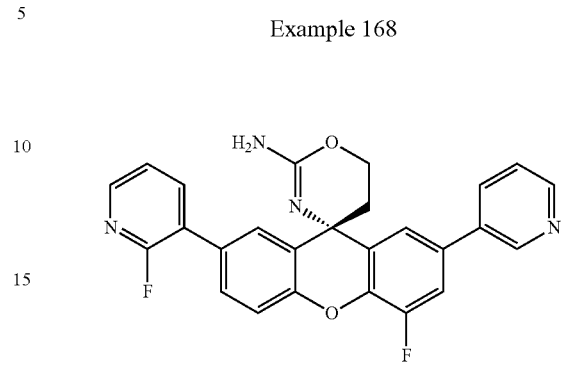

Synthesis of ((S)-4'-fluoro-7'-(2-fluoropyridin-3-yl)-2'-(pyridin-3-yl)-5,6-dihydrospiro[[1,3]oxazine-4,9'-xanthen]-2-amine The title compound was synthesized by steps analogous to those described in method A7 above, but using intermediate 20B, 2-fluoropyridin-3-ylboronic acid and 3-pyridineboronic acid. MS m/z=457.0 [M+H]$^+$. Calculated for $C_{26}H_{18}F_2N_4O_2$: 456.14

$^1$H NMR (400 MHz, DMSO-d$_6$) δ ppm 1.78-1.91 (m, 2 H), 4.03 (m, 2 H), 5.86-6.10 (m, 2 H), 7.42-7.65 (m, 6 H), 7.76 (dd, J=11.6, 2.2 Hz, 1 H), 8.07 (d, J=8.6 Hz, 1 H), 8.09-8.15 (m, 1 H), 8.26 (d, J=4.7 Hz, 1 H), 8.60 (dd, J=4.7, 1.6 Hz, 1 H), 8.89 (d, J=1.9 Hz, 1 H)

Example 184

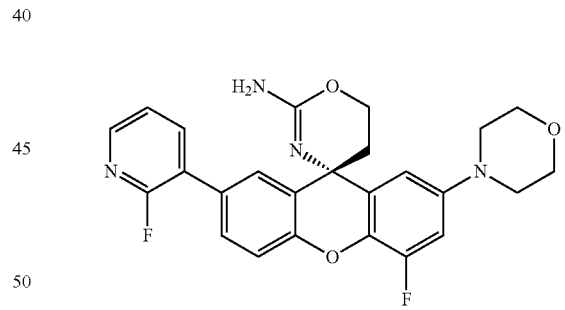

Synthesis of (S)-4'-fluoro-7'-(2-fluoropyridin-3-yl)-2'-morpholino-5,6-dihydrospiro[[1,3]oxazine-4,9'-xanthen]-2-amine The title compound was synthesized by steps analogous to those described in method A6 above, but using intermediate 20, 2-fluoropyridin-3-ylboronic acid and morpholine.

MS m/z=464.8 [M+H]$^+$. Calculated for $C_{25}H_{22}F_2N_4O_3$: 464.17

$^1$H NMR (400 MHz, DMSO-d$_6$) δ ppm 1.70-1.80 (m, 2 H), 3.07 (m, 4 H), 3.71-3.78 (m, 4 H), 3.95-4.02 (m, 2 H), 5.79 (s, 2 H), 6.66-6.70 (m, 1 H), 6.92 (dd, J=13.7, 2.8 Hz, 1 H), 7.32-7.37 (m, 1 H), 7.49 (ddd, J=7.4, 4.9, 1.9 Hz, 1 H), 7.53 (m, 2 H), 8.08 (ddd, J=10.3, 7.5, 1.9 Hz, 1 H), 8.24 (ddd, J=4.8, 1.6, 1.4 Hz, 1 H)

Example 166

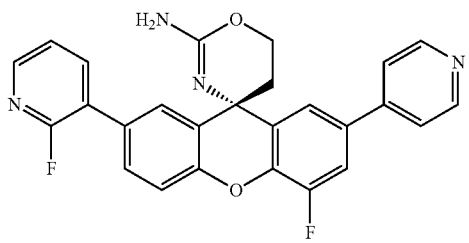 [SMILES: NC1=N[C@@]2(CCO1)c1cc(-c3cccnc3F)ccc1Oc1c(F)cc(-c3ccncc3)cc12]

Synthesis of ((S)-4'-fluoro-7'-(2-fluoropyridin-3-yl)-2'-(pyridin-4-yl)-5,6-dihydrospiro[[1,3]oxazine-4,9'-xanthen]-2-amine The title compound was synthesized by steps analogous to those described in method A7 above, but using intermediate 20B, 2-fluoropyridin-3-ylboronic acid and 4-pyridineboronic acid. MS m/z=456.8 [M+H]$^+$. Calculated for $C_{26}H_{18}F_2N_4O_2$: 456.14

$^1$H NMR (400 MHz, DMSO-d$_6$) δ ppm 1.78-1.91 (m, 2 H), 4.03 (m, 2 H), 5.90 (br. s., 2 H), 7.45 (d, J=8.3 Hz, 1 H), 7.50 (ddd, J=7.3, 5.0, 1.9 Hz, 1 H), 7.54-7.58 (m, 1 H), 7.59-7.64 (m, 1 H), 7.66-7.71 (m, 1 H), 7.82 (dd, J=11.7, 2.2 Hz, 1 H), 8.11 (ddd, J=10.3, 7.5, 1.9 Hz, 1 H), 8.25 (ddd, J=4.8, 18, 1.5 Hz, 1 H), 8.63-8.69 (m, 1 H)

Example 176

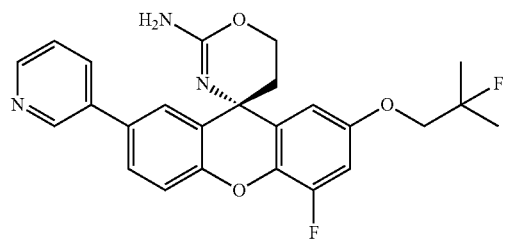 [SMILES: CC(C)(F)COc1cc(F)c2c(c1)[C@]1(CCOC(N)=N1)c1cc(-c3cccnc3)ccc1O2]

Synthesis of (S)-4'-fluoro-2'-(2-fluoro-2-methylpropoxy)-7'-(pyridin-3-yl)-5,6-dihydrospiro[[1,3]oxazine-4,9'-xanthen]-2-amine The title compound was synthesized by steps analogous to those described in method A8 above, but using intermediate 20B, pyridin-3-ylboronic acid and 2-fluoro-2-methylpropyl trifluoromethanesulfonate.

MS m/z=451.8 [M+H]$^+$. Calculated for $C_{25}H_{23}F_2N_3O_3$: 451.17

$^1$H NMR (400 MHz, DMSO-d$_6$) δ ppm 1.41 (s, 3 H), 1.46 (s, 3 H), 1.78 (m, 2 H), 3.92-4.11 (m, 4 H), 5.85 (br. s., 2 H), 6.74 (dd, J=2.9, 1.5 Hz, 1 H), 7.02 (dd, J=12.3, 2.9 Hz, 1 H), 7.36 (d, J=8.4 Hz, 1 H), 7.50 (ddd, J=8.0, 4.7, 0.9 Hz, 1 H), 7.58 (d, J=2.3 Hz, 1 H), 7.67 (dd, J=8.4, 2.3 Hz, 1 H), 7.97-8.03 (m, 1 H), 8.57 (dd, J=4.7, 1.6 Hz, 1 H), 8.83 (dd, J=2.4, 0.8 Hz, 1 H)

Example 164

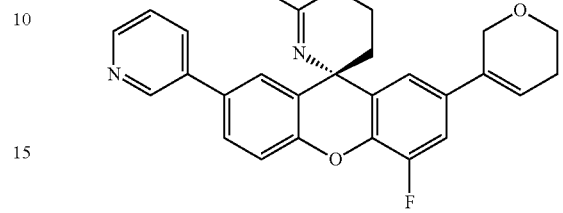

Synthesis of (S)-2'-(5,6-dihydro-2H-pyran-3-yl)-4'-fluoro-7'-(pyridin-3-yl)-5,6-dihydrospiro[[1,3]oxazine-4,9'-xanthen]-2-amine The title compound was synthesized by steps analogous to those described in method A7 above, but using intermediate 20B, pyridin-3-ylboronic acid and 2-(5,6-dihydro-2H-pyran-3-yl)-4,4,5,5-tetramethyl-1,3,2-dioxaborolane.

MS m/z=443.8.0 [M+H]$^+$. Calculated for $C_{26}H_{22}FN_3O_3$: 443.16

$^1$H NMR (400 MHz, DMSO-d$_6$) δ ppm 1.75-1.82 (m, 2 H), 2.23-2.31 (m, 2 H), 3.72-3.77 (m, 2 H), 3.93-4.04 (m, 2 H), 4.37-4.44 (m, 2 H), 5.82-5.88 (m, 2 H), 6.25-6.29 (m, 1 H), 7.10-7.13 (m, 1 H), 7.33 (dd, J=12.1, 2.2 Hz, 1 H), 7.39 (d, J=8.4 Hz, 1 H), 7.51 (ddd, J=7.9, 4.8, 0.9 Hz, 1 H), 7.60 (d, J=2.2 Hz, 1 H), 7.68 (dd, J=8.4, 2.3 Hz, 1 H), 8.01 (m, J=2.4, 1.6 Hz, 1 H), 8.58 (dd, J=4.7, 1.6 Hz, 1 H), 8.84 (dd, J=2.4, 0.8 Hz, 1 H)

Example 156

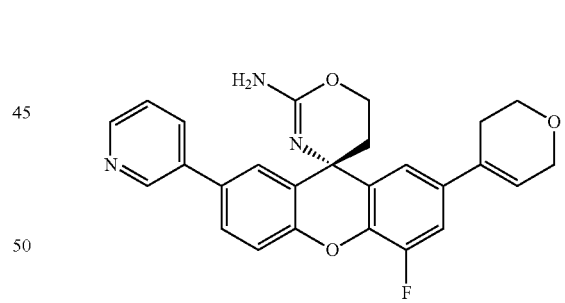

Synthesis of (S)-2'-(3,6-dihydro-2H-pyran-4-yl)-4-'-fluoro-7'-(pyridin-3-yl)-5,6-dihydrospiro[[1,3]oxazine-4,9'-xanthen]-2-amine The title compound was synthesized by steps analogous to those described in method A7 above, but using intermediate 20B, pyridin-3-ylboronic acid and 2-(3,6-dihydro-2H-pyran-4-yl)-4,4,5,5-tetramethyl-1,3,2-dioxaborolane.

MS m/z=443.8 [M+H]$^+$. Calculated for $C_{26}H_{22}FN_3O_3$: 443.16

$^1$H NMR (400 MHz, DMSO-d$_6$) δ ppm 1.79 (m, 2 H), 2.44 (m, 2 H), 3.84 (m, 2 H), 3.94-4.08 (m, 2 H), 4.24 (m, 2 H), 5.84 (m, 2 H), 6.25 (m, 1 H), 7.21 (s, 1 H), 7.35-7.44 (m, 2 H), 7.47-7.56 (m, 1 H), 7.60 (d, J=2.2 Hz, 1 H), 7.68 (dd, J=8.4, 2.3 Hz, 1 H), 7.97-8.06 (m, 1 H), 8.58 (dd, J=4.7, 1.5 Hz, 1 H), 8.84 (d, J=1.7 Hz, 1 H).

Example 126

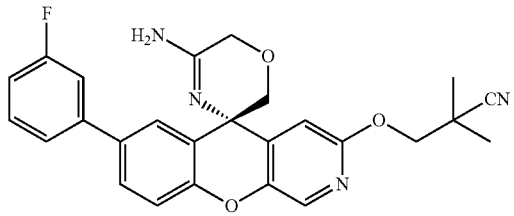 [SMILES: CC(C)(C#N)COc1cc2c(cn1)Oc1ccc(-c3cccc(F)c3)cc1[C@@]21COCC(N)=N1]

Synthesis of (S)-3-(5'-amino-7-(3-fluorophenyl)-2',6'-dihydrospiro[chromeno[2,3-c]pyridine-5,3'-[1,4]oxazine]-3-yloxy)-2,2-dimethylpropanenitrile The title compound was synthesized by steps analogous to those described in Method A4, but using Intermediate 10B, 3-hydroxy-2,2-dimethylpropanenitrile, and 3-fluorophenylboronic acid. MS m/z=459.3 [M+H]$^+$. Calculated for $C_{26}H_{23}FN_4O_3$: 458.18.

$^1$H NMR (400 MHz, DMSO-d$_6$) δ=8.13 (s, 1 H), 7.66 (dd, J=2.3, 8.5 Hz, 1 H), 7.55-7.49 (m, J=5.8 Hz, 2 H), 7.48-7.40 (m, 2 H), 7.28 (d, J=8.4 Hz, 1 H), 7.22-7.15 (m, 1 H), 6.71 (s, 1 H), 6.16 (s, 2 H), 4.32-4.20 (m, 5 H), 3.52-3.42 (m, 2 H), 1.42 (d, J=5.4 Hz, 6 H)

Example 122

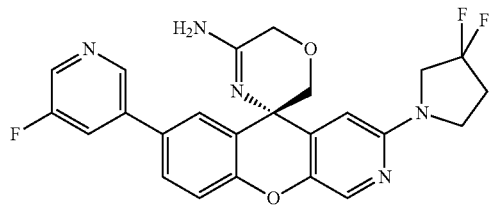 [SMILES: NC1=N[C@@]2(COC1)c1cc(-c3cncc(F)c3)ccc1Oc1cnc(N3CCC(F)(F)C3)cc12]

Synthesis of (S)-3-(3,3-difluoropyrrolidin-1-yl)-7-(5-fluoropyridin-3-yl)-2',6'-dihydrospiro[chromeno[2,3-c]pyridine-5,3'-[1,4]oxazin]-5'-amine The title compound was synthesized by steps analogous to those described in Method A3, but using Intermediate 10B, 5-fluoropyridin-3-ylboronic acid, and 3,3-difluoropyrrolidine hydrochloride. MS m/z=468.3 [M+H]$^+$. Calculated for $C_{24}H_{20}FN_5O_2$: 467.16.

1 H NMR (400 MHz, DMSO-d$_6$) δ=8.73 (t, J=1.7 Hz, 1 H), 8.56 (d, J=2.7 Hz, 1 H), 8.12 (s, 1 H), 7.98 (td, J=2.3, 10.3 Hz, 1 H), 7.72 (dd, J=2.4, 8.5 Hz, 1 H), 7.57 (d, J=2.2 Hz, 1 H), 7.29 (d, J=8.4 Hz, 1 H), 6.35 (s, 1 H), 6.11 (br. s., 2 H), 4.25 (s, 2 H), 3.90-3.73 (m, 2 H), 3.67-3.51 (m, 2 H), 3.49-3.40 (m, 2 H), 2.61-2.53 (m, 2 H)

Example 120

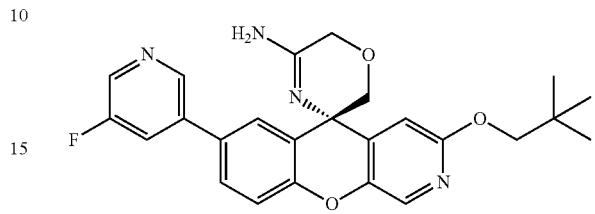

Synthesis of (S)-7-(5-fluoropyridin-3-yl)-3-(neopentyloxy)-2',6'-dihydrospiro[chromeno[2,3-c]pyridine-5,3'-[1,4]oxazin]-5'-amine The title compound was synthesized by steps analogous to those described in Method A4, but using Intermediate 10B, neopentyl alcohol, and 5-fluoropyridin-3-ylboronic acid.

MS m/z=449.4 [M+H]$^+$. Calculated for $C_{25}H_{25}FN_4O_3$: 448.19.

$^1$H NMR (400 MHz, DMSO-d$_6$) δ=8.74 (t, J=1.8 Hz, 1 H), 8.57 (d, J=2.7 Hz, 1 H), 8.10 (d, J=0.5 Hz, 1 H), 8.02-7.96 (m, 1 H), 7.74 (dd, J=2.4, 8.5 Hz, 1 H), 7.58 (d, J=2.3 Hz, 1 H), 7.31 (d, J=8.5 Hz, 1 H), 6.63 (d, J=0.5 Hz, 1 H), 6.14 (s, 2 H), 4.25 (s, 2 H), 3.98-3.87 (m, 2 H), 3.52-3.42 (m, 2 H), 1.00 (s, 9 H)

Example 119

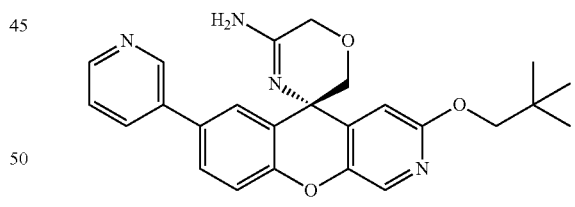

Synthesis of (S)-3-(neopentyloxy)-7-(pyridin-3-yl)-2',6'-dihydrospiro[chromeno[2,3-c]pyridine-5,3'-[1,4]oxazin]-5'-amine The title compound was synthesized by steps analogous to those described in Method A4, but using Intermediate 10B, neopentyl alcohol, and pyridin-3-ylboronic acid.

MS m/z=431.4 [M+H]$^+$. Calculated for $C_{25}H_{26}N_4O_3$: 430.20.

$^1$H NMR (400 MHz, DMSO-d$_6$) δ=8.84 (dd, J=0.7, 2.4 Hz, 1 H), 8.56 (dd, J=1.6, 4.7 Hz, 1 H), 8.09 (s, 1 H), 8.04-7.97 (m, 1 H), 7.72-7.65 (m, 1 H), 7.53 (d, J=2.2 Hz, 1 H), 7.50 (ddd, J=0.8, 4.8, 7.9 Hz, 1 H), 7.30 (d, J=8.4 Hz, 1 H), 6.63 (s, 1 H), 6.15 (s, 2 H), 4.24 (s, 2 H), 3.98-3.87 (m, 2 H), 3.52-3.40 (m, 2 H), 1.00 (s, 9 H)

Example 114

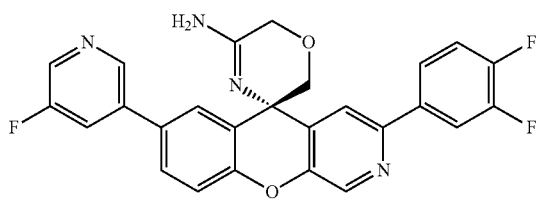 [SMILES: NC1=N[C@@]2(COC1)c1cc(-c3cncc(F)c3)ccc1Oc1cnc(-c3ccc(F)c(F)c3)cc12]

Synthesis of (S)-3-(3,4-difluorophenyl)-7-(5-fluoropyridin-3-yl)-2',6'-dihydrospiro[chromeno[2,3-c]pyridine-5,3'-[1,4]oxazin]-5'-amine The title compound was synthesized by steps analogous to those described in Method A1, but using Intermediate 10B, 5-fluoropyridin-3-ylboronic acid, and 3,4-difluorophenylboronic acid.

MS m/z=475.2 [M+H]$^+$. Calculated for $C_{26}H_{17}F_3N_4O_2$: 474.13.

$^1$H NMR (400 MHz, DMSO-d$_6$) δ=8.75 (t, J=1.8 Hz, 1 H), 8.61 (s, 1 H), 8.58 (d, J=2.6 Hz, 1 H), 8.06-7.97 (m, 2 H), 7.83 (br. s., 1 H), 7.80-7.76 (m, 1 H), 7.74 (s, 1 H), 7.63 (s, 1 H), 7.56 (td, J=8.5, 10.6 Hz, 1 H), 7.38 (d, J=8.4 Hz, 1 H), 6.15 (br. s., 2 H), 4.34 (br. s., 2 H), 3.58 (br. s., 2 H)

Example 115

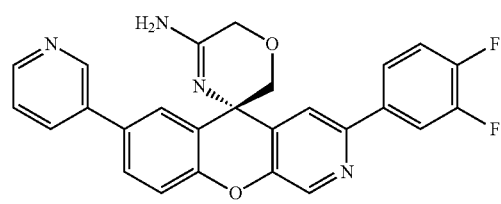 [SMILES: NC1=N[C@@]2(COC1)c1cc(-c3cccnc3)ccc1Oc1cnc(-c3ccc(F)c(F)c3)cc12]

Synthesis of (S)-3-(3,4-difluorophenyl)-7-(pyridin-3-yl)-2',6'-dihydrospiro[chromeno[2,3-c]pyridine-5,3'-[1,4]oxazin]-5'-amine The title compound was synthesized by steps analogous to those described in Method A1, but using Intermediate 10B, pyridin-3-ylboronic acid, and 3,4-difluorophenylboronic acid. MS m/z=457.2 [M+H]$^+$. Calculated for $C_{26}H_{18}F_2N_4O_2$: 456.14.

$^1$H NMR (400 MHz, DMSO-d$_6$) δ=8.86 (dd, J=0.7, 2.4 Hz, 1 H), 8.62 (s, 1 H), 8.58 (dd, J=1.6, 4.7 Hz, 1 H), 8.06-7.99 (m, 2 H), 7.88-7.81 (m, 1 H), 7.74 (s, 1 H), 7.72 (dd, J=2.4, 8.5 Hz, 1 H), 7.61-7.53 (m, 2 H), 7.53-7.49 (m, 1 H), 7.38 (d, J=8.4 Hz, 1 H), 6.16 (s, 2 H), 4.39-4.27 (m, 2 H), 3.60-3.52 (m, 2 H)

Example 156

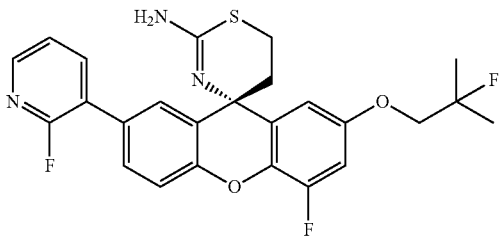 [SMILES: CC(C)(F)COc1cc(F)c2c(c1)[C@]1(CCSC(N)=N1)c1cc(-c3cccnc3F)ccc1O2]

Synthesis of (S)-4'-fluoro-2'-(2-fluoro-2-methylpropoxy)-7'-(2-fluoropyridin-3-yl)-5,6-dihydrospiro[[1,3]thiazine-4,9'-xanthen]-2-amine The titled compound was synthesized by steps analogous to those described in method A8 above, but using intermediate 23 and obtained from racemic 4'-fluoro-2'-(2-fluoro-2-methylpropoxy)-7'-(2-fluoropyridin-3-yl)-5,6-dihydrospiro[[1,3]thiazine-4,9'-xanthen]-2-amine using similar chiral separation conditions as described herein for intermediate 10.

MS m/z=485.8 [M+H]$^+$. Calculated for $C_{25}H_{22}F_3N_3O_2S$: 485.14.

$^1$H NMR (400 MHz, DMSO-d$_6$) δ ppm 1.41 (s, 3 H) 1.47 (s, 3 H) 1.65-1.78 (m, 2 H) 2.76-2.83 (m, 2 H) 3.95-4.09 (m, 2 H) 6.32 (s, 2 H) 6.71 (dd, J=2.9, 1.6 Hz, 1 H) 7.05 (dd, J=12.3, 2.9 Hz, 1 H) 7.38 (d, J=8.4 Hz, 1 H) 7.46-7.53 (m, 2 H) 7.59 (ddd, J=8.4, 2.3, 1.4 Hz, 1 H) 8.03-8.12 (m, 1 H) 8.19-8.29 (m, 1 H

Example 201

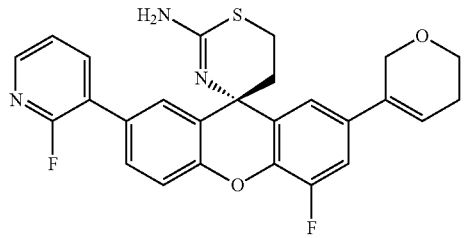

Synthesis of (S)-2'-(5,6-dihydro-2H-pyran-3-yl)-4'-fluoro-7'-(2-fluoropyridin-3-yl)-5,6-dihydrospiro[[1,3]thiazine-4,9'-xanthen]-2-amine The titled compound was synthesized by steps analogous to those described in method A7 above, but using intermediate 23 and 2-(5,6-dihydro-2H-pyran-3-yl)-4,4,5,5-tetramethyl-1,3,2-dioxaborolane. (S)-2'-(5,6-dihydro-2H-pyran-3-yl)-4'-fluoro-7'-(2-fluoropyridin-3-yl)-5,6-dihydrospiro[[1,3]thiazine-4,9'-xanthen]-2-amine (>99% ee) was obtained from racemic 2'-(5,6-dihydro-2H-pyran-3-yl)-4'-fluoro-7'-(2-fluoropyridin-3-yl)-5,6-dihydrospiro[[1,3]thiazine-4,9'-xanthen]-2-amine using similar chiral separation conditions as described herein for intermediate 10.

MS m/z=477.8 [M+H]⁺. Calculated for C₂₆H₂₁F₂N₃O₂S: 477.13.

¹H NMR (400 MHz, DMSO-d₆) δ ppm 1.68-1.80 (m, 2 H) 2.21-2.34 (m, 2 H) 2.69-2.89 (m, 2 H) 3.71-3.80 (m, 2 H) 4.37-4.45 (m, 2 H) 6.26-6.31 (m, 1 H) 6.33 (s, 2 H) 7.08-7.12 (m, 1 H) 7.35 (dd, J=12.2, 2.2 Hz, 1 H) 7.41 (d, J=8.5 Hz, 1 H) 7.47-7.55 (m, 2 H) 7.60 (ddd, J=8.4, 2.3, 1.4 Hz, 1 H) 8.10 (ddd, J=10.3, 7.4, 1.9 Hz, 1 H) 8.26 (ddd, J=4.8, 2.4 Hz, 1 H)

Example 89

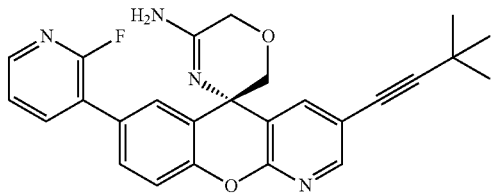 [SMILES: CC(C)(C)C#Cc1cnc2c(c1)[C@]1(COCC(N)=N1)c1cc(-c3cccnc3F)ccc1O2]

Synthesis of (S)-3-(3,3-dimethylbut-1-yn-1-yl)-7-(2-fluoropyridin-3-yl)-2',6'-dihydrospiro[chromeno[2,3-b]pyridine-5,3'-[1,4]oxazin]-5'-amine The titled compound was synthesized as described in Method A2

MS m/z=443.0 [M+H]⁺. Calculated for C₂₆H₂₃FN₄O₂: 442.48.

¹H NMR (400 MHz, MeCN) δ ppm 1.33 (s, 12 H) 3.48 (s, 2 H) 4.26 (m, 2 H) 7.32 (d, J=8.0 Hz, 1 H) 7.36-7.39 (m, 1 H) 7.50-7.51 (m, 1 H) 7.56-7.60 (m, 1 H) 7.65 (d, J=2.4 Hz, 1 H) 7.97-8.02 (m, 1 H) 8.17-8.19 (m, 1 H) 8.22 (d, J=2.4 Hz, 1 H)

Example 91

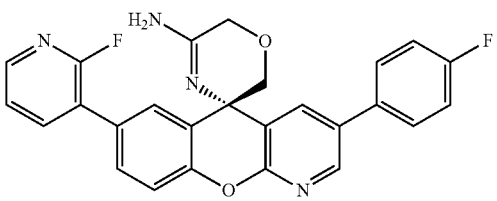 [SMILES: NC1=N[C@@]2(COC1)c1cc(-c3cccnc3F)ccc1Oc1ncc(-c3ccc(F)cc3)cc12]

Synthesis of (S)-3-(4-fluorophenyl)-7-(2-fluoropyridin-3-yl)-2',6'-dihydrospiro[chromeno[2,3-b]pyridine-5,3'-[1,4]oxazin]-5'-amine The titled compound was synthesized by steps analogous to those described in method 22 above, but using 4-fluorophenylboronic acid.

MS m/z=457.0 [M+H]⁺. Calculated for C₂₆H₁₈F₂N₄O₂: 456.44.

¹H NMR (400 MHz, MeCN) δ ppm 3.50-3.60 (m, 2 H) 4.27-4.35 (m, 2 H) 7.22-7.26 (m, 2 H) 7.35-7.40 (m, 2 H) 7.51-7.74 (m, 4 H) 7.89 (d, J=2.8 Hz, 1 H) 7.95-8.05 (m, 1 H) 8.18-8.20 (m, 1 H) 8.47 (d, J=2.8 Hz, 1 H)

Example 90

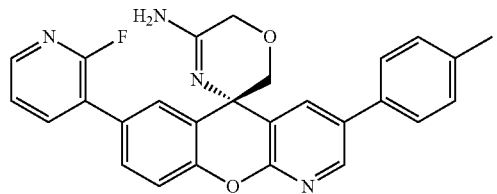 [SMILES: Cc1ccc(-c2cnc3c(c2)[C@]2(COCC(N)=N2)c2cc(-c4cccnc4F)ccc2O3)cc1]

Synthesis of (S)-7-(2-fluoropyridin-3-yl)-3-(p-tolyl)-2',6'-dihydrospiro[chromeno[2,3-b]pyridine-5,3'-[1,4]oxazin]-5'-amine The titled compound was synthesized by steps analogous to those described in method 22 above, but using 4-methylphenylboronic acid.

MS m/z=453.0 [M+H]⁺. Calculated for C₂₇H₂₁FN₄O₂: 452.48.

¹H NMR (400 MHz, MeCN) δ ppm 2.39 (s, 3 H) 3.54 (s, 2 H) 4.25-4.34 (m, 2 H) 7.30-7.40 (m, 4 H) 7.54-7.61 (m, 4 H) 7.90 (d, J=4.0 Hz, 1 H) 7.98-8.03 (m, 1 H) 8.18-8.20 (m, 1 H) 8.48 (d, J=4.0 Hz, 1 H)

Example 220

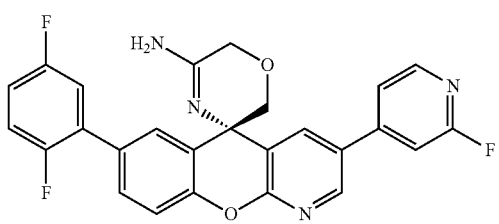 [SMILES: NC1=N[C@@]2(COC1)c1cc(-c3cc(F)ccc3F)ccc1Oc1ncc(-c3ccnc(F)c3)cc12]

Synthesis of (S)-7-(2,5-difluorophenyl)-3-(2-fluoropyridin-4-yl)-2',6'-dihydrospiro[chromeno[2,3-b]pyridine-5,3'-[1,4]oxazin]-5'-amine The titled compound was synthesized by steps analogous to those described in method 22 above, but using 2,5-difluorophenylboronic acid and 2-fluoropyridine-4-boronic acid.

MS m/z=475.0 [M+H]⁺. Calculated for C₂₆H₁₇F₃N₄O₂: 474.43.

¹H NMR (400 MHz, MeCN) δ ppm 3.60 (s, 2 H) 4.34-4.45 (m, 2 H) 7.10-7.16 (m, 1 H) 7.22-7.33 (m, 2 H) 7.35-7.37 (m, 2 H) 7.54-7.61 (m, 3 H) 7.05 (d, J=4 Hz, 1 H) 8.30 (d, J=8 Hz, 1 H) 8.63 (d, J=4.0 Hz, 1 H)

Example 55

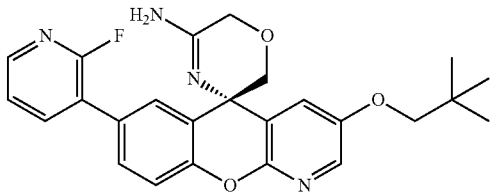 [SMILES: CC(C)(C)COc1cnc2c(c1)[C@]1(COCC(N)=N1)c1cc(-c3cccnc3F)ccc1O2]

Synthesis of (S)-7-(2-fluoropyridin-3-yl)-3-(neopentyloxy)-2',6'-dihydrospiro[chromeno[2,3-b]pyridine-5,3'-[1,4]oxazin]-5'-amine The titled compound was synthesized as described in method 26 above.
MS m/z=449.20 [M+H]$^+$. Calculated for $C_{25}H_{25}FN_4O_3$: 448.49.
$^1$H NMR (400 MHz, MeCN) δ ppm 1.05 (s, 9 H) 3.48 (s, 2 H) 3.72 (s, 2 H) 4.21-4.31 (m, 2 H) 7.26-7.30 (m, 2 H) 7.35-7.39 (m, 1 H) 7.48-7.50 (m, 1 H) 7.55-7.58 (m, 1 H) 7.91 (d, J=4.0 Hz, 1 H) 7.96-8.01 (m, 1 H) 8.16-8.19 (m, 1 H)

Example 72

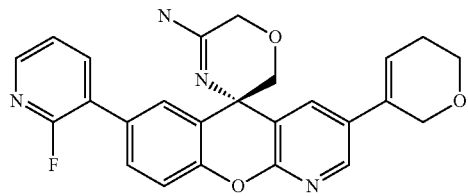 [SMILES: NC1=N[C@@]2(COC1)c1cc(-c3cccnc3F)ccc1Oc1ncc(C3=CCCOC3)cc12]

Synthesis of (5S)-3-(5,6-dihydro-2H-pyran-3-yl)-7-(2-fluoro-3-pyridinyl)-6'H-spiro[chromeno[2,3-c]pyridine-5,3'-[1,4]oxazin]-5'-amine The titled compound was synthesized by steps analogous to those described in method A1. MS m/z=445.2 [M+H]$^+$.
$^1$H NMR (400 MHz, DMSO-d$_6$) δ=8.45 (d, J=0.5 Hz, 1 H), 8.29-8.21 (m, 1 H), 8.09 (ddd, J=1.9, 7.5, 10.4 Hz, 1 H), 7.63-7.57 (m, 1 H), 7.53-7.44 (m, 2 H), 7.41-7.29 (m, 3 H), 6.66-6.55 (m, 1 H), 6.19 (d, J=5.9 Hz, 2 H), 4.58-4.47 (m, 2 H), 4.34-4.15 (m, 2 H), 3.81-3.69 (m, 2 H), 3.53-3.39 (m, 2 H), 2.38-2.23 (m, 2 H).

Example 73

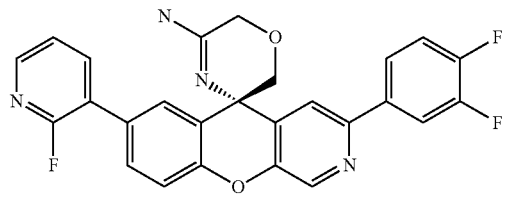 [SMILES: NC1=N[C@@]2(COC1)c1cc(-c3cccnc3F)ccc1Oc1cnc(-c3ccc(F)c(F)c3)cc12]

Synthesis of (5S)-3-(3,4-difluorophenyl)-7-(2-fluoro-3-pyridinyl)-6'H-spiro[chromeno [2,3-c]pyridine-5,3'-[1,4]oxazin]-5'-amine The titled compound was synthesized by steps analogous to those described in method A1. MS m/z=475.2 [M+H]$^+$.
$^1$H NMR (400 MHz, DMSO-d$_6$) δ=8.63 (s, 1 H), 8.25 (td, J=1.5, 4.8 Hz, 1 H), 8.14-7.98 (m, 2 H), 7.86 (dd, J=2.5, 5.5 Hz, 1 H), 7.78 (s, 1 H), 7.65-7.47 (m, 4 H), 7.38 (d, J=8.5 Hz, 1 H), 6.29 (br. s., 2 H), 4.43-4.21 (m, 2 H), 3.66-3.48 (m, 2 H).

Example 74

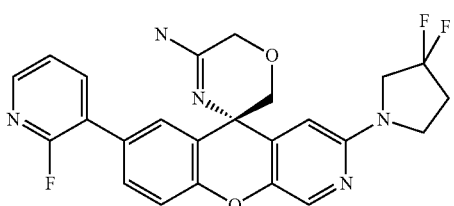

Synthesis of (5S)-3-(3,3-difluoro-1-pyrrolidinyl)-7-(2-fluoro-3-pyridinyl)-6'H-spiro[chromeno[2,3-c]pyridine-5,3'-[1,4]oxazin]-5'-amine The titled compound was synthesized by steps analogous to those described in method A3. MS m/z=468.2[M+H]$^+$.
$^1$H NMR (400 MHz, DMSO-d$_6$) δ=8.23 (td, J=1.5, 4.8 Hz, 1 H), 8.13 (d, J=0.4 Hz, 1 H), 8.07 (ddd, J=2.0, 7.5, 10.4 Hz, 1 H), 7.56 (td, J=1.7, 8.8 Hz, 1 H), 7.51-7.45 (m, 2 H), 7.28 (d, J=8.4 Hz, 1 H), 6.36 (s, 1 H), 6.14 (br. s., 2 H), 4.27-4.13 (m, 2 H), 3.82 (sxt, J=12.9 Hz, 2 H), 3.67-3.51 (m, 2 H), 3.47-3.36 (m, 2 H), 2.62-2.53 (m, 2 H).

Example 132

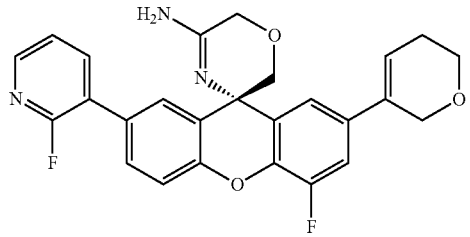 [SMILES: NC1=N[C@@]2(COC1)c1cc(-c3cccnc3F)ccc1Oc1c(F)cc(C3=CCCOC3)cc12]

Synthesis of (S)-2'-(5,6-dihydro-2H-pyran-3-yl)-4'-fluoro-7'-(2-fluoropyridin-3-yl)-2,6-dihydrospiro[[1,4]oxazine-3,9'-xanthen]-5-amine The titled compound was synthesized by steps analogous to those described in method A37 except that 2-fluoropyridin-3-ylboronic acid was used in Step 5, (S)-2'-bromo-4'-fluoro-7'-methoxy-2,6-dihydrospiro[[1,4]oxazine-3,9'-xanthen]-5-amine was converted to (S)-2'-(5,6-dihydro-2H-pyran-3-yl)-4'-fluoro-7'-(2-fluoropyridin-3-yl)-2,6-dihydrospiro[[1,4]oxazine-3,9'-xanthen]-5-amine. MS (m/z) 462 (M+H)$^+$.
$^1$H NMR (400 MHz, CDCl$_3$) δ ppm; 8.19 (d, 1 H, J=4.7 Hz), 7.88 (m, 1 H), 7.52 (m, 2 H), 7.34 (d, 1 H, J=8.4 Hz), 7.28

(m, 1 H), 7.10 (dd, 1 H, J=11.5, 1.9 Hz), 6.99 (s, 1 H), 6.17 (s, 1 H), 4.46 (m, 2 H), 4.34 (s, 3 H), 3.84 (t, 2 H, J=5.6 Hz), 3.58 (m, 2 H), 2.33 (m, 2 H).

Example 270

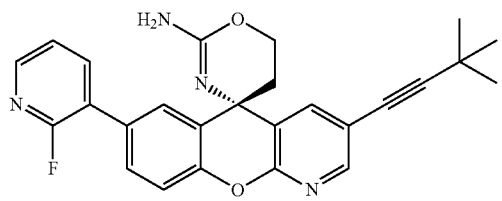 [SMILES: CC(C)(C)C#Cc1cnc2c(c1)[C@]1(CCOC(N)=N1)c1cc(-c3cccnc3F)ccc1O2]

Synthesis of (S)-3-(3,3-dimethylbut-1-ynyl)-7-(2-fluoropyridin-3-yl)-5',6'-dihydrospiro[chromeno[2,3-b]pyridine-5,4'-[1,3]oxazin]-2'-amine The titled compound was synthesized by steps analogous to those described in method A32 (except that 3,3-dimethylbut-1-yne was used, and diisopropylamine was used instead of TBAF-(H$_2$O)$_3$), Intermediate 26B was converted to (S)-3-(3,3-dimethylbut-1-ynyl)-7-(2-fluoropyridin-3-yl)-5',6'-dihydrospiro[chromeno[2,3-b]pyridine-5,4'-[1,3]oxazin]-2'-amine. MS (m/z) 443 (M+H)$^+$.

$^1$H NMR (400 MHz, CDCl$_3$) δ ppm; 8.29 (d, 1 H, J=2.3 Hz), 8.20 (d, 2 H, J=4.9 Hz), 7.86 (t, 1 H, J=9.6 Hz, 7.79 (d, 1 H, J=2.2 Hz), 7.52 (m, 2 H), 7.37 (m, 1 H), 7.28 (m, 1 H), 4.30 (br, 2 H), 4.15 (m, 2 H), 1.94 (m, 1 H), 1.88 (m, 1 H), 1.34 (s, 9H).

The present invention also provides methods for making compounds of Formulas I-II, and sub-formulas thereof. For example, and in addition to the methods described herein, the compounds of the invention may be made by the methods similar to those described in the literature references cited below.

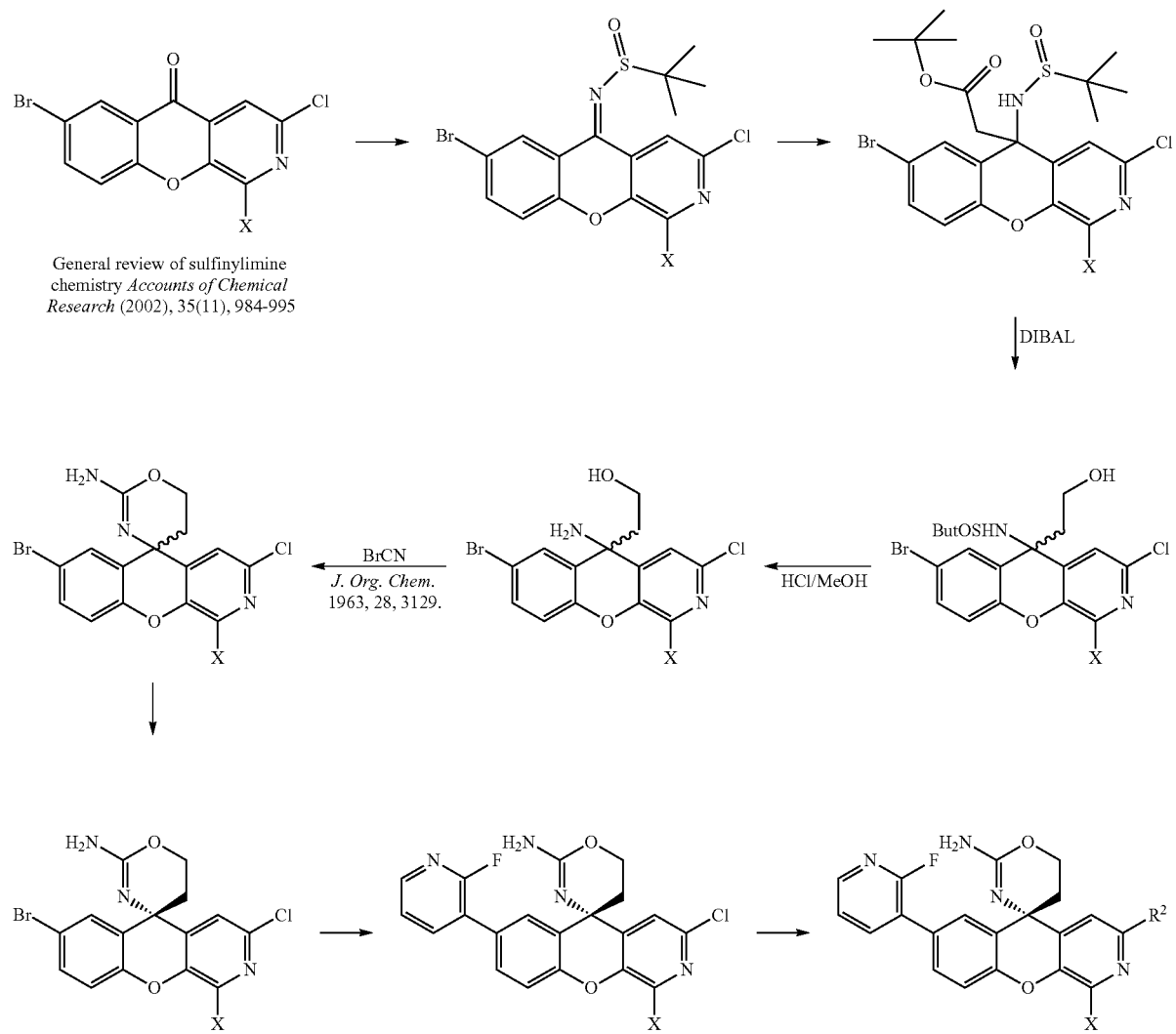

In one embodiment of the invention, there is provided a method of making a compound of Formula I, the method comprising the step of reacting a compound 20

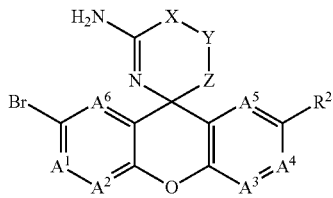

wherein $A^1$, $A^2$, $A^3$, $A^4$, $A^5$, $A^6$, $R^2$, X, Y and Z of Formula I are as defined herein, with a compound having the structure

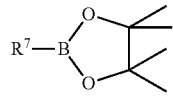

or $R^7$—$B(OH)_2$, wherein $R^7$ is as defined herein, to make a compound of Formula I.

In another embodiment of the invention, there is provided a method of making a compound of Formula I-A, the method comprising the step of reacting a compound 20

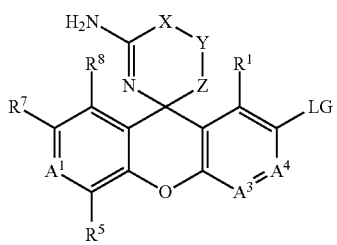

wherein $A^1$, $A^3$, $A^4$, $R^7$, X, Y and Z of Formula I-A are as defined herein and LG is Br, Cl or —OH, with a compound having the structure

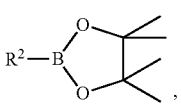

$R^2$—$B(OH)_2$ or $R^2$—Br, wherein $R^2$ is as defined herein, to make a compound of Formula I-A.

In another embodiment of the invention, there is provided a method of making a compound of Formula I-B, the method comprising the step of reacting a compound 20

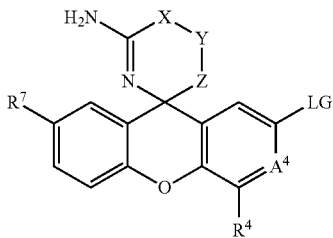

wherein $A^4$, $R^7$, X, Y and Z of Formula I-B are as defined herein and LG is Br, Cl or —OH, with a compound having the structure

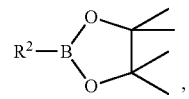

$R^2$—$B(OH)_2$ or $R^2$—Br, wherein $R^2$ is as defined herein, to make a compound of Formula I-B.

In another embodiment of the invention, there is provided a method of making a compound of Formula II, the method comprising the step of reacting a compound 20

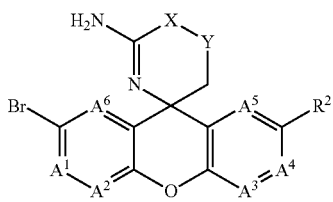

wherein $A^1$, $A^2$, $A^3$, $A^4$, $A^5$, $A^6$, $R^2$, X and Y of Formula II are as defined herein, with a compound having the structure

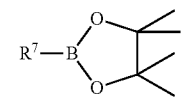

or $R^7$—$B(OH)_2$, wherein $R^7$ is as defined herein, to make a compound of Formula II.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent (s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-II, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H (deuterium), $^3$H (tritium), $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Deuterated ($^2$H), Tritiated ($^3$H) and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-II and sub-Formulas thereof) vary with structural change, in general, activity possessed by compounds of Formulas I-II may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in the Example Table I)

The assay buffer used in this screen is 0.05 M acetate, pH 4.2, 10% DMSO final, 100 uM genapol (which is a nonionic detergent, below its Critical Micelle Concentration). The beta secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Table I.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ40 levels were determined using a sandwich ELISA. The $IC_{50}$ of the compound was calculated from the percent of control or percent inhibition of Aβ40 as a function of the concentration of the test compound.

The sandwich ELISA to detect Aβ40 was performed in 96 well microtiter plates, which were pre-treated with goat anti-rabbit IgG (Pierce). The capture and detecting antibody pair that were used to detect Aβ40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Table I.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76,173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated rats.

Actual vehicles used: Oral: 2% HPMC, 1% Tween80, pH 2.2

IV: 5% EtOH, 45% Propylene glycol in 5% Dextrose

The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Ex. No. | % reduction of rat CSF levels at 10 pmk | % reduction of rat brain levels at 10 mpk |
|---|---|---|
| 30 | 67% | 62% |
| 72 | 38% | 27% |
| 73 | 62% | 42% |
| 74 | 47% | 26% |
| 32 | 37% | 26% |
| 33 | 61% | 48% |
| 36A | 26% | 25% |
| 37A | 44% | 39% |
| 84 | 15% | 17% |
| 86 | 12% | 11% |
| 89 | 50% | 41% |
| 90 | 7% at 3 mpk | 0% at 3 mpk |
| 91 | 29% | 3% |
| 107 | 82% | 72% |
| 110 | 86% | 79% |
| 111 | 81% | 67% |
| 114 | 54% | 34% |
| 115 | 38% | 21% |
| 119 | 5% at 3 mpk | 6% at 3 mpk |
| 120 | 30% at 3 mpk | 24% at 3 mpk |
| 122 | 11% at 3 mpk | 14% at 3 mpk |
| 126 | 25% | 8% |
| 129 | 22% | 17% |
| 65 | 14% | 55% |
| 64 | 8% | 4% |
| 40 | 33% | 15% |
| 41 | 13% | 23% |
| 132 | 38% | 25% |
| 63 | 19% | 16% |
| 145 | 78% | 59% |
| 146 | 75% | 62% |
| 149 | 80% | 62% |
| 153 | 78% | 64% |
| 154 | 57% | 37% |
| 155 | 68% | 53% |
| 156 | 27% | 8% |
| 163 | 52% | 28% |
| 164 | 35% | 12% |
| 17A | 44% | 37% |
| 166 | 42% | 25% |
| 168 | 44% | 18% |
| 173 | 40% | 14% |
| 176 | 30% | 13% |
| 178 | 21% | 14% |
| 182 | 59% | 30% |
| 184 | 19% | 12% |
| 185 | 53% at 30 mpk | 26% at 30 mpk |
| 201 | 80% at 30 mpk | 65% at 30 mpk |
| 204 | 80% at 30 mpk | 66% at 30 mpk |
| 220 | 38% | 2% |
| 55 | 65% | 51% |
| 226 | 83% | 74% |
| 239 | 68% | 48% |
| 248 | 53% | 39% |
| 249 | 72% | 59% |
| 250 | 72% | 72% |
| 60 | 56% | 25% |
| 61 | 70% | 55% |
| 270 | 70% | 52% |

Indications

The compounds of the invention have been shown to modulate, and specifically inhibit the activity of beta-secretase (Memapsin 2) enzyme, thereby reducing the A-beta peptide fragments believed to be responsible for Alzheimer's Disease (AD). Bapineuzamab, a monoclonal amino-terminus specific anti-amyloid antibody is presently in Phase III clinical trials for the treatment of AD. *Alzheimer's Research & Therapy*, 1:2, 2009. Bapineuzumab targets beta amyloid protein involved in AD. It is the most advanced monoclonal antibody in clinical development to stop the disease progression and degradation of cognitive function. The drug has fast track regulatory status with the USFDA (Medpedia, 2011).

Hence, it must clearly show a beneficial and lasting effect through validated biomarker of underlying AD disease mechanism. Clinical trials in AD now measure CSF Aβ levels, brain amyloid load, CSF tau, brain volume by MRI and FDG PET scan. Each of the known genetic causes of AD is linked to A-beta.

Other conditions including dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming more easy. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, Bloomberg News, *The Boston Globe*, 1-7-2010; *Curr. Alzheimer's Res.* 2008, Apr. 5 (2):121-131; *Expert Opin. Drug Discov.* (200( ) 4(4):319-416.

Accordingly, compounds of the invention, and pharmaceutical compositions comprising said compounds, are useful for, but not limited to, the prevention or treatment of beta-secretase related diseases, including Alzheimer's disease, the leading cause of dementia. Particularly, the compounds of the invention are useful to treat various stages of AD, including without limitation mild to moderate AD and prodromal patients pre-disposed to developing AD. The compounds of the invention have the ability to modulate the activity of beta secretase enzyme, thereby regulating the production of amyloid beta (Abeta peptide) and slowing or reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, I-A, I-A-1 through I-A-7, I-B, II, II-A or II-B. In another embodiment, there is provided a method of reducing production of amyloid beta, and of slowing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-II, and sub-Formulas thereof. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-II with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-II with a pharmaceutically acceptable carrier to manufacture the medicament.

COMBINATIONS

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the compounds of the present invention may be administered in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain. Thus, the compounds may be co-administered simultaneously or sequentially along with the other therapeutic agent.

If formulated as a fixed dose, such combination products employ the compounds of this invention within the accepted dosage ranges. Compounds of Formulas I and II may also be administered sequentially with known CNS treating agents when a combination formulation is inappropriate. The invention is not limited in the sequence of administration; compounds of the invention may be administered either prior to, simultaneous with or after administration of the known and used CNS agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

or a stereoisomer, tautomer, hydrate, solvate or pharmaceutically acceptable salt thereof, wherein $A^1$ is $CR^6$;
$A^2$ is $CR^5$;
$A^3$ is $CR^4$;
$A^4$ is N;
$A^5$ is $CR^1$;
$A^6$ is $CR^8$;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

each of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, —Si(CH$_3$)$_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl and ring are optionally substituted, independently, with 1-3 substituents of $R^9$;

$R^6$ is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

each $R^9$, independently, is halo, haloalkyl, haloalkoxyl, CN, OH, $NO_2$, $NH_2$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is —$CR^{10}R^{10}$— or —O—, wherein each $R^{10}$, independently, is H, halo, haloalkyl, $C_{1-6}$alkyl, $C_{2-6}$alkenyl, $C_{2-6}$alkynyl, $C_{3-6}$cycloalkyl or a ring selected from the group consisting of morpholinyl, piperidinyl, piperizinyl, tetrahydrofuranyl, furanyl, thienyl, phenyl, pyrdinyl, pyrimidinyl, pyridazinyl, pyrazinyl, pyranyl, dihydropyranyl, tetrahydropyranyl, pyrrolyl, dihydropyrrolyl, tetrahydropyrrolyl and oxetanyl;

Y is —O—, —S— or —$CH_2$—, provided that (1) when X is —O—, then Y is —$CH_2$—, or (2) when X is —$CR^{10}R^{10}$—, then Y is —O— or —S—; and Z is $CH_2$, CHF, $CF_2$, $CH(CH_3)$, $C(CH_3)_2$ or $CH(CF_3)$.

2. The compound of claim 1 having a Formula II:

or a stereoisomer, tautomer, hydrate, solvate or pharmaceutically acceptable salt thereof, wherein $A^1$ is $CR^6$;
$A^2$ is $CR^5$;
$A^3$ is $CR^4$;
$A^4$ is N;
$A^5$ is $CR^1$;
$A^6$ is $CR^8$;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_oC_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;

$R^2$ is Cl, Br, $C_{1-6}$-alkyl, $C_{2-4}$alkenyl, $C_{2-4}$alkynyl, CN, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl, cyclohexyl or —$Si(CH_3)_3$, wherein the $C_{1-6}$-alkyl, $C_{2-4}$alkenyl, $C_{2-4}$alkynyl, —$OC_{1-6}$alkyl, —$SC_{1-6}$alkyl, —$NHC_{1-6}$alkyl, —$N(C_{1-3}$alkyl$)_2$, —NH-phenyl, —NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3- aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

$R^6$ is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

$R^7$ is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-$NH-phenyl, $-$NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl or cyclohexyl, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-$NH-phenyl, $-$NH-benzyl, phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopentyl and cyclohexyl are optionally substituted, independently, with 1-3 substituents of $R^9$;

each $R^9$, independently, is halo, haloalkyl, CN, OH, $NO_2$, $NH_2$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl, or oxetanyl;

X is $-CH_2-$ or $-O-$; and

Y is $-O-$, $-S-$ or $-CH_2-$, provided that (1) when X is $-O-$, then Y is $-CH_2-$ or (2) when X is $-CH_2-$, then Y is $-O-$ or $-S-$.

3. The compound of claim 1, or a stereoisomer, tautomer or pharmaceutically acceptable salt thereof, wherein $A^1$ is CH or CF;
$A^2$ is CH or CF;
$A^3$ is CH or CF;
$A^4$ is N;
$A^5$ is CH, CF or CBr;
$A^6$ is CH or CF;
X is $-CH_2-$ or $-O-$;
Y is $-O-$, $-S-$ or $-CH_2-$, provided that (1) when X is $-O-$, then Y is $-CH_2-$, or (2) when X is $-CH_2$, then Y is $-O-$ or $-S-$; and
Z is $CH_2$, CHF, $CF_2$, $CH(CH_3)$, $C(CH_3)_2$ or $CH(CF_3)$.

4. The compound of claim 1, or a stereoisomer or pharmaceutically acceptable salt thereof, wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$;

one of $R^2$ and $R^7$, independently, is F, Cl, Br, I, haloalkyl, haloalkoxyl, $C_{1-6}$-alkyl, $C_{2-6}$alkenyl, $C_{2-6}$alkynyl, CN, $-OC_{1-6}$alkyl, $-SC_{1-6}$alkyl, $-NHC_{1-6}$alkyl, $-N(C_{1-3}$alkyl$)_2$, $-$NH-phenyl, $-$NH-benzyl, $-$Si$(CH_3)_3$ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl, $-OC_{1-6}$alkyl, $-SC_{1-6}$alkyl, $-NHC_{1-6}$alkyl, $-N(C_{1-3}$alkyl$)_2$, $-$NH-phenyl, $-$NH-benzyl and ring are optionally substituted, independently, with 1-3 substituents of $R^9$;

the other of $R^2$ and $R^7$, independently, is $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-$NH-phenyl or $-$NH-benzyl, phenyl, pyridyl, pyrimidyl or thienyl, wherein the $C_{1-6}$-alkyl, $C_{2-4}$alkenyl, $C_{2-4}$alkynyl, CN, $-OC_{1-6}$alkyl, $-SC_{1-6}$alkyl, $-NHC_{1-6}$alkyl, $-N(C_{1-3}$alkyl$)_2$, $-$NH-phenyl, $-$NH-benzyl, phenyl, pyridyl, pyrimidinyl and thienyl are optionally substituted, independently, with 1-3 substituents of $R^9$;

$R^6$ is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

X is $-CH_2-$ or $-O-$;
Y is $-O-$, $-S-$ or $-CH_2-$, provided that (1) when X is $-O-$, then Y is $-CH_2-$, or (2) when X is $-CH_2$, then Y is $-O-$ or $-S-$; and
Z is $CH_2$, $CF_2$ or $CH(CH_3)$.

5. The compound of claim 1 wherein $R^7$ is a ring selected from the group consisting of phenyl, pyridyl, pyrimidyl, pyrazinyl, pyridazinyl, pyrazolyl, isoxazolyl, thiazolyl, pyranyl, dihydropyranyl, tetrahydropyranyl, furanyl, dihydrofuranyl, tetrahydrofuranyl, pyrrolidinyl, piperidinyl, piperazinyl and morpholinyl, said ring optionally substituted, independently, with 1-3 substituents of $R^9$.

6. The compound of claim 1, or a stereoisomer or pharmaceutically acceptable salt thereof, wherein $R^2$ is halo, haloalkyl, haloalkoxyl, $C_{1-6}$-alkyl, $C_{2-6}$alkenyl, $C_{2-6}$alkynyl, CN, $-OC_{1-6}$alkyl, $-SC_{1-6}$alkyl, wherein the $C_{1-6}$-alkyl, $C_{2-4}$alkenyl, $C_{2-4}$alkynyl and $C_{3-8}$-cycloalkyl are optionally substituted, independently, with 1-3 substituents of $R^9$;

each of $R^1$, $R^4$, $R^5$ and $R^8$, independently, is H, F, methyl, CN or OH;

$R^6$ is H, F, Cl, $CF_3$, methyl, CN, OH, $OCH_3$, $SCH_3$ or $NHCH_3$;

$R^7$ is a ring selected from the group consisting of phenyl, pyridyl, pyrimidyl, pyridazinyl, pyrazinyl, triazinyl and thienyl, said ring optionally substituted, independently, with 1-3 substituents of $R^9$;

X is $-CH_2-$ or $-O-$;
Y is $-O-$, $-S-$ or $-CH_2-$, provided that (1) when X is $-O-$, then Y is $-CH_2-$, or (2) when X is $-CH_2$, then Y is $-O-$ or $-S-$; and
Z is $CH_2$.

7. The compound of claim 1, or a stereoisomer or pharmaceutically acceptable salt thereof, selected from $A^1$ is CH;
$A^2$ is CH;

A³ is CH or CF;
A⁴ is N;
A⁵ is CH;
A⁶ is CH;
R² is F, Cl, Br, I, C₁₋₆-alkyl, C₂₋₆alkenyl, C₂₋₆alkynyl, CN, —OC₁₋₆alkyl, —SC₁₋₆alkyl, —NHC₁₋₆alkyl, —N(C₁₋₃alkyl)₂, —NH-phenyl, —NH-benzyl, —Si(CH₃)₃ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C₁₋₆-alkyl, C₂₋₄alkenyl, C₂₋₄alkynyl, —OC₁₋₆alkyl, —SC₁₋₆alkyl, —NHC₁₋₆alkyl, —N(C₁₋₃alkyl)₂, —NH-phenyl, —NH-benzyl and ring are optionally substituted, independently, with 1-3 substituents of R⁹;

R⁷ is a ring selected from the group consisting of phenyl, pyridyl, pyrimidyl, pyridazinyl, pyrazinyl, triazinyl and thienyl, said ring optionally substituted, independently, with 1-3 substituents of R⁹;

each R⁹, independently, is F, Cl, Br, CH₂F, CHF₂, CF₃, CN, OH, NO₂, NH₂, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolidinyl, piperazinyl, oxetanyl or dioxolyl, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, C₁₋₃alkylamino-, C₁₋₃dialkylamino, C₁₋₃thioalkoxyl, or oxetanyl;

X is —CH₂— or —O—;
Y is —O—, —S— or —CH₂—, provided that (1) when X is —O—, then Y is —CH₂—, or (2) when X is —CH₂, then Y is —O— or —S—; and
Z is CH₂.

8. The compound of claim 7 wherein R² is F, Cl, Br, I, C₁₋₆-alkyl, C₂₋₆alkenyl, C₂₋₆alkynyl, CN, —OC₁₋₆alkyl, —SC₁₋₆alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the C₁₋₆-alkyl, C₂₋₄alkenyl, C₂₋₄alkynyl, —OC₁₋₆alkyl, —SC₁₋₆alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cyano-propoxyl, 2-fluoro-2-methyl-propoxyl and ring are optionally substituted, independently, with 1-3 substituents of R⁹.

9. The compound of claim 1, or a stereoisomer, tautomer or pharmaceutically acceptable salt thereof, having a general formula I-A

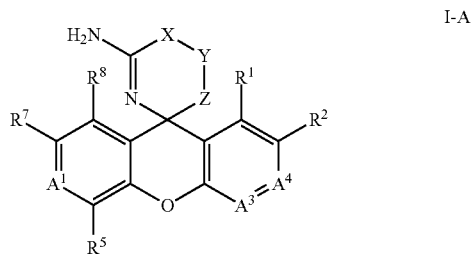

I-A wherein
A¹ is CR⁶;
A³ is CR⁴;
A⁴ is N;
each of R¹, R³, R⁴, R⁵, R⁶ and R⁸, independently, is H, F, Cl, CF₃, OCF₃, methyl, ethyl, CN, OH, OCH₃, SCH₃, NHCH₃ or C(O)CH₃;
one of R² and R⁷, independently, is F, Cl, Br, I, haloalkyl, haloalkoxyl, C₁₋₆-alkyl, C₂₋₆alkenyl, C₂₋₆alkynyl, CN, —OC₁₋₆alkyl, —SC₁₋₆alkyl, —NHC₁₋₆alkyl, —N(C₁₋₃alkyl)₂, —NH-phenyl, —NH-benzyl, —Si(CH₃)₃ or a ring selected from the group consisting of phenyl, pyridyl, pyrimidyl, pyrazinyl, pyridazinyl, triazinyl, thienyl, pyrazolyl, imidazolyl, oxazolyl, isoxazolyl, thiazolyl, isothiazolyl, diazolyl, triazolyl, tetrazolyl, pyranyl, dihydropyranyl, tetrahydropyranyl, furanyl, dihydrofuranyl, tetrahydrofuranyl, pyrrolyl, dihydropyrrolyl, pyrrolidinyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C₁₋₆-alkyl, C₂₋₄alkenyl, C₂₋₄alkynyl, —OC₁₋₆alkyl, —SC₁₋₆alkyl, —NHC₁₋₆alkyl, —N(C₁₋₃alkyl)₂, —NH-phenyl, —NH-benzyl and ring are optionally substituted, independently, with 1-3 substituents of R⁹;
the other of R² and R⁷, independently, is C₁₋₆-alkyl, C₂₋₄alkenyl, C₂₋₄alkynyl, CN, —OC₁₋₆alkyl, —SC₁₋₆alkyl, —NHC₁₋₆alkyl, —N(C₁₋₃alkyl)₂, —NH-phenyl or —NH-benzyl, phenyl, pyridyl, pyrimidyl or thienyl, wherein the C₁₋₆-alkyl, C₂₋₄alkenyl, C₂₋₄alkynyl, CN, —OC₁₋₆alkyl, —SC₁₋₆alkyl, —NHC₁₋₆alkyl, —N(C₁₋₃alkyl)₂, —NH-phenyl, —NH-benzyl, phenyl, pyridyl, pyrmidinyl and thienyl are optionally substituted, independently, with 1-3 substituents of R⁹;
each R⁹, independently, is halo, haloalkyl, CN, OH, NO₂, NH₂, acetyl, —C(O)NHCH₃, oxo, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolidinyl, piperazinyl, oxetanyl or dioxolyl, wherein each of the C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$di-alkylamino, $C_{1-3}$thioalkoxyl, or oxetanyl;

X is —$CH_2$— or —O—;

Y is —O—, —S— or —$CH_2$—, provided that (1) when X is —O—, then Y is —$CH_2$—, or (2) when X is —$CH_2$, then Y is —O— or —S—; and Z is $CH_2$, $CF_2$ or $CH(CH_3)$.

10. The compound of claim 9, or a pharmaceutically acceptable salt thereof, wherein $A^1$ is $CR^6$;

$A^3$ is CH, CF;

$A^4$ is N, each of $R^1$, $R^5$, $R^6$ and $R^8$, independently, is H, F, $CF_3$, methyl or CN;

$R^2$ is F, Cl, Br, I, $C_{1-6}$-alkyl, $C_{2-6}$alkenyl, $C_{2-6}$alkynyl, CN, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cy-ano-propoxyl, 2-fluoro-2-methyl-propoxyl, or a ring selected from the group consisting of phenyl, 2-pyridyl, 3-pyridyl, 4-pyridyl, dihydro-2H-pyran-4-yl, dihydro-2H-pyran-3-yl, tetrahydropyran-4-yl, dihydrofuranyl, tetrahydrofuranyl, pyrrolidin-1-yl, piperidin-1-yl, morpholinyl, 8-oxo-3-aza-bicyclo[3.2.1]oct-3-yl, aza-bicyclo[2.2.1]hept-5-yl and 2-oxo-7-aza-[3,5]-spironon-7-yl, wherein the $C_{1-6}$-alkyl, $C_2$alkenyl, $C_{2-4}$alkynyl, —$OC_{1-6}$alkyl, —$SC_{1-6}$alkyl, 3-methyl-3-oxetanyl-ethynyl, 3-methyl-3-oxetanyl-methoxyl, 3,3-dimethyl-butyn-1-yl, 3-methyl-3-butyn-1-yl, 2,2-dimethyl-3-cy-ano-propoxyl, 2-fluoro-2-methyl-propoxyl and ring are optionally substituted, independently, with 1-3 substituents of $R^9$;

$R^7$ is a ring selected from the group consisting of phenyl, pyridyl, pyrimidyl, pyridazinyl, pyrazinyl, triazinyl and thienyl, said ring optionally substituted, independently, with 1-3 substituents of $R^9$;

each $R^9$, independently, is halo, haloalkyl, CN, OH, $NO_2$, $NH_2$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, piperazinyl, oxetanyl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetanyl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$di-alkylamino, $C_{1-3}$thioalkoxyl, or oxetanyl;

X is —$CH_2$— or —O—;

Y is —O—, —S— or —$CH_2$—, provided that (1) when X is —O—, then Y is —$CH_2$—, or (2) when X is —$CH_2$, then Y is —O— or —S—; and Z is $CH_2$ or $CH(CH_3)$.

11. The compound of claim 1, or a stereoisomer or pharmaceutically acceptable salt thereof, selected from (5S)—7-(2-fluoro-3-pyridinyl)-3-(2-fluoro-4-pyridinyl)-6'H-spiro[chromeno[2,3-c]pyridine-5,3'-[1,4]oxazin]-5'-amine;

(5S)—3-(5,6-dihydro-2H-pyran-3-yl)-7-(2-fluoro-3-pyridinyl)-6'H-spiro[chromeno[2,3-c]pyridine-5,3'-[1,4]oxazin]-5'-amine;

(5S)—3-(3,4-difluorophenyl)-7-(2-fluoro-3-pyridinyl)-6'H-spiro[chromeno[2,3-c]pyridine-5,3'-[1,4]oxazin]-5'-amine;

(5S)—3-(3,3-difluoro-1-pyrrolidinyl)-7-(2-fluoro-3-pyridinyl)-6'H-spiro[chromeno[2,3-c]pyridine-5,3'-[1,4]oxazin]-5'-amine;

(5S)—3-(4,4-difluoro-1-piperidinyl)-7-(2-fluoro-3-pyridinyl)-6'H-spiro[chromeno[2,3-c]pyridine-5,3'-[1,4]oxazin]-5'-amine;

(5S)—3-(2,2-dimethylpropoxy)-7-(2-fluoro-3-pyridinyl)-6'H-spiro[chromeno[2,3-c]pyridine-5,3'-[1,4]oxazin]-5'-amine;

(5S)—1-fluoro-7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine;

(5S)—3-(5,6-dihydro-2H-pyran-3-yl)-1-fluoro-7-(2-fluoro-3-pyridinyl)-5',6'-dihydrospiro[chromeno[2,3-c]pyridine-5,4'-[1,3]oxazin]-2'-amine;

(5S)—3-(3,6-dihydro-2H-pyran-4-yl)-7-(2-fluoro-3-pyridinyl)-5',6'-dihydrospiro[chromeno[2,3-c]pyridine-5,4'-[1,3]oxazin]-2'-amine;

(5S)—3-(3,4-difluorophenyl)-7-(5-fluoro-3-pyridinyl)-6'H-spiro[chromeno[2,3-c]pyridine-5,3'-[1,4]oxazin]-5'-amine;

(5S)—3-(3,4-difluorophenyl)-7-(3-pyridinyl)-6'H-spiro[chromeno[2,3-c]pyridine-5,3'-[1,4]oxazin]-5'-amine;

(5S)—3-(2,2-dimethylpropoxy)-7-(3-pyridinyl)-6'H-spiro[chromeno[2,3-c]pyridine-5,3'-[1,4]oxazin]-5'-amine;

(5S)—3-(2,2-dimethylpropoxy)-7-(5-fluoro-3-pyridinyl)-6'H-spiro[chromeno[2,3-c]pyridine-5,3'-[1,4]oxazin]-5'-amine;

(5S)—3-(3,3-difluoro- 1-pyrrolidinyl)-7-(5-fluoro-3-pyridinyl)-6'H-spiro[chromeno[2,3-c] pyridine-5,3'-[1,4]oxazin]-5'-amine;

3-(((5S)—5'-amino-7-(3-fluorophenyl)-6'H-spiro[chromeno[2,3-c]pyridine-5,3'-[1,4]oxazin]-3-yl)oxy)-2,2-dimethylpropanenitrile;

(5S)—3-(2-fluoro-4-pyridinyl)-7-(5-fluoro-3-pyridinyl)-5',6'-dihydrospiro[chromeno[2,3-c]pyridine-5,4'-[1,3]oxazin]-2'-amine;

(5S)—3-(5,6-dihydro-2H-pyran-3-yl)-7-(5-fluoro-3-pyridinyl)-5',6'-dihydrospiro[chromeno[2,3-c]pyridine-5,4'-[1,3]oxazin]-2'-amine;

(5S)—7-(2-fluoro-3-pyridinyl)-3-(2-fluoro-4-pyridinyl)-5',6'-dihydrospiro[chromeno[2,3-c]pyridine-5,4'-[1,3]oxazin]-2'-amine;

(5S)—3-(5,6-dihydro-2H-pyran-3-yl)-7-(2-fluoro-3-pyridinyl)-5',6'-dihydrospiro[chromeno[2,3-c]pyridine-5,4'-[1,3]oxazin]-2'-amine;

(5S)—3-(3,3-dimethyl-1-butyn-1-yl)-7-(2-fluoro-3-pyridinyl)-5',6'-dihydrospiro[chromeno[2,3-c]pyridine-5,4'-[1,3]oxazin]-2'-amine;

(5S)—7-(2-fluoro-3-pyridinyl)-3-(5-fluoro-3-pyridinyl)-5',6'-dihydrospiro[chromeno[2,3-c]pyridine-5,4'-[1,3]oxazin]-2'-amine;

(5S)—1-fluoro-3-(2-fluoro-4-pyridinyl)-7-(5-fluoro-3-pyridinyl)-5',6'-dihydrospiro[chromeno[2,3-c]pyridine-5,4'-[1,3]oxazin]-2'-amine;

(5S)—1-fluoro-3-(2-fluoro-4-pyridinyl)-7-(3-pyridinyl)-5',6'-dihydrospiro[chromeno[2,3-c]pyridine-5,4'-[1,3]oxazin]-2'-amine;

(5S)—1-fluoro-7-(2-fluoro-3-pyridinyl)-3-(3-pyridinyl)-5',6'-dihydrospiro[chromeno[2,3-c]pyridine-5,4'-[1,3]oxazin]-2'-amine;

(5S)—1-fluoro-7-(2-fluoro-3-pyridinyl)-3-(2-methyl-4-pyridinyl)-6'H-spiro[chromeno[2,3-c]pyridine-5,3'-[1,4]oxazin]-5'-amine;

(5S)—3-(5,6-dihydro-2H-pyran-3-yl)-1-fluoro-7-(2-fluoro-3-pyridinyl)-6'H-spiro[chromeno[2,3-c]pyridine-5,3'-[1,4]oxazin]-5'-amine; and (5S)—3-(2,2-dimethylpropoxy)-1-fluoro-7-(2-fluoro-3-pyridinyl)-6'H-spiro[chromeno[2,3-c]pyridine-5,3'-[1,4]oxazin]-5'-amine.

12. A pharmaceutical composition comprising a compound according to claim 1 and a pharmaceutically acceptable excipient.

13. A pharmaceutical composition comprising a compound according to claim 11 and a pharmaceutically acceptable excipient.

14. A method of reducing the levels of beta amyloid peptide in the cerebral spinal fluid of a subject, the method comprising administering to the subject an effective dosage amount of a compound according to claim 1.

15. A method of treating Alzheimer's disease, cognitive impairment or a combination thereof in a subject, the method comprising administering to the subject an effective dosage amount of a compound of claim 1.

16. A method of treating Alzheimer's disease, cognitive impairment or a combination thereof in a subject, the method comprising administering to the subject an effective dosage amount of a pharmaceutical composition of claim 12.

17. A method of claim treating a neurological disorder selected from the group consisting of mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof, in a subject, the method comprising administering to the subject an effective dosage amount of a compound of claim 1.

18. A method of slowing the formation of plaque on the brain of a subject, the method comprising administering to the subject an effective dosage amount of a compound according to claim 11.

19. A method of slowing the formation of plaque on the brain of a subject, the method comprising administering to the subject an effective dosage amount of a pharmaceutical composition according to claim 13.

20. A process for preparing a compound of claim 1, the process comprising the step of reacting a compound 20

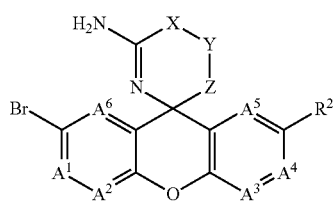

wherein $A^1$, $A^2$, $A^3$, $A^4$, $A^5$, $A^6$, $R^2$, X, Y and Z of Formula I are as defined in claim 1, with a compound having the structure

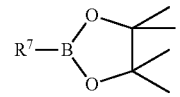

or $R^7$-$B(OH)_2$, wherein $R^7$ is as defined in claim 1 to prepare the compound of claim 1.

* * * * *